US008828928B2

(12) United States Patent
Dittrich et al.

(10) Patent No.: US 8,828,928 B2
(45) Date of Patent: Sep. 9, 2014

(54) AMPHIPHILIC PEPTIDES AND PEPTIDE PARTICLES

(75) Inventors: Christian Dittrich, Winterthur (CH); Gaudenz Danuser, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/592,733

(22) Filed: Aug. 23, 2012

(65) Prior Publication Data

US 2013/0064895 A1    Mar. 14, 2013

Related U.S. Application Data

(60) Provisional application No. 61/526,526, filed on Aug. 23, 2011.

(51) Int. Cl.
| | |
|---|---|
| *A61K 38/10* | (2006.01) |
| *C07K 7/06* | (2006.01) |
| *A61K 9/48* | (2006.01) |
| *C07K 19/00* | (2006.01) |
| *A61K 48/00* | (2006.01) |
| *C07K 7/08* | (2006.01) |
| *C07K 14/00* | (2006.01) |

(52) U.S. Cl.
CPC ... *C07K 7/06* (2013.01); *C07K 7/08* (2013.01); *C07K 14/001* (2013.01); *A61K 9/4825* (2013.01); *C07K 19/00* (2013.01)
USPC ............ 514/3.2; 424/491; 530/327; 530/328; 514/395

(58) Field of Classification Search
CPC .... A61K 9/4825; C07K 14/001; C07K 19/00; C07K 7/06; C07K 7/08
See application file for complete search history.

(56) References Cited

FOREIGN PATENT DOCUMENTS

WO     2009109428 A2    9/2009

OTHER PUBLICATIONS

Torchilin and Lukyanov (Peptide and protein drug delivery to and into tumors: challenges and solutions, Drug Discovery Today, vol. 8, No. 6, Mar. 2003).*
Ouboter (Rational design of purely peptidic amphiphiles for drug delivery applications, Dissertation, published Apr. 26, 2011).*
Dittrich et al., "Solid peptide nanoparticles—structural characterization and quantification of cargo encapsulation", Macromolecular Bioscience, vol. 10, 2010, pp. 1406-1415.
Collins et al., "Self-assembly of peptides into spherical nanoparticles for delivery of hydrophilic moieties to the cytosol", ACS NANO, vol. 4, No. 5, 2010 pp. 2856-2864.
Dittrich et al., "Delivery of membrane impermeable cargo into CHO cells by peptide nanoparticles targeted by a protein corona", Biomaterials, vol. 33, No. 9, Jan. 2012, pp. 2746-2753.
Chen et al. "Solution structure of a parallel left-handed double-helical gramicidin-A determined by 2D 1H NMR." J Mol Biol. Dec. 13, (1996);264(4):757-69.
Dagastine et al. "Dynamic Forces Between Two Deformable Oil Droplets in Water." Science (2006) 313, 210-213.
De Bruyn Ouboter et al. "Hierarchical organization of purely peptidic amphiphiles into peptide beads." J. Phys. Chem. C, (2011) 115 (30), pp. 14583-14590.
De Bruyn Ouboter, et al. "Self-Assembled Peptide Microspheres." European Cells and Materials Journal (Nov. 2010) vol. 20. Suppl 3 (for 3rd International NanoBio Conference 2010, ETH Zurich, Switzerland, Aug. 24-27, 2010).
Dittrich et al. "Delivery of membrane impermeable cargo into CHO cells by peptide nanoparticles targeted by a protein corona." Biomaterials. Mar. (2012);33(9):2746-53. Epub Jan. 9, 2012.
Dittrich et al. "Solid Peptide Nanoparticles: Structural Characterization and Quantification of Cargo Encapsulation." Macromolecular Bioscience (2010) 10, 1406-1415.
Dittrich, C. "Controlled self-assembly of short beta-helical peptides." PhD Thesis, University of BASEL, Faculty of Science (2007). doi: 10.5451/unibas-004198852.
Doyle et al. "Crystal structure of the gramicidin/potassium thiocyanate complex." J Mol Biol. Mar. 14, (1997);266 (5):963-77.
Ehrlich et al. "Endocytosis by random initiation and stabilization of clathrin-coated pits." Cell (2004) 118, 591-605.
Eidenschink et al. "Very short peptides with stable folds: building on the interrelationship of Trp/Trp, Trp/cation, and Trp/backbone-amide interaction geometries." Proteins. May 1, (2009);75(2):308-22.
Fleck et al.. "Electrostatic colloid-membrane binding." Europhys. Lett. (2004) 67, 314-320.
Harding et al. "Receptor-mediated endocytosis of transferrin and recycling of the transferrin receptor in rat reticulocytes." JCB (1983) 97, 329-339.
Heitz et al. "Conformations of gramicidin A and its 9,11,13,15-phenylalanyl analog in dimethyl sulfoxide and chloroform." Biophys Chem. Jul (1986);24(2):149-60.
Hotchkiss et al. "Chemical properties of bactericidal substances isolated from cultures of a soil bacillus." J. Biol. Chem. (1940) 132, 793-794 (1940).
Hotchkiss et al. "Fractionation of the bactericidal agent from cultures of a soil bacillus." J. Biol. Chem. (1940) 132, 791-792.
Kelkar et al. "The gramicidin ion channel: a model membrane protein." Biochim Biophys Acta. Sep. 2007; 1768 (9):2011-25. Epub May 18, 2007.
Kimura et al. "Vesicular Self-Assembly of a Helical Peptide in Water." Langmuir (1999) 15, 4461-4463.

(Continued)

*Primary Examiner* — James H Alstrum Acevedo
*Assistant Examiner* — Tara Martinez
(74) *Attorney, Agent, or Firm* — Nixon Peabody LLP; David S. Resnick

(57) ABSTRACT

The inventions provided herein relate to amphiphilic peptides and particles comprising the amphiphilic peptides. Such amphiphilic peptides and particles described herein can be used as a delivery system, e.g., for therapeutic or diagnostic purposes, or as cell penetration vehicles or cell transfection agents.

31 Claims, 47 Drawing Sheets
(33 of 47 Drawing Sheet(s) Filed in Color)

(56) References Cited

OTHER PUBLICATIONS

Kita et al. "Drug delivery vehicles with improved encapsulation efficiency: taking advantage of specific drug-carrier interactions" Expert Opin. Drug Deliv (2011) 8(3):329-342.
Min et al. "The role of interparticle and external forces in nanoparticle assembly." Nat. Mater. (2008) 7, 527-538.
Monopoli et al. "Physical-Chemical Aspects of Protein Corona: Relevance to in Vitro and in Vivo Biological Impacts of Nanoparticles." J. Am. Chem. Soc. (2011) 133, 2525-2534.
Nel et al. "Understanding biophysicochemical interactions at the nano-bio interface." Nat Mater (2009) 8, 543-557.
Parhi et al. "Volumetric interpretation of protein adsorption: Capacity scaling with adsorbate molecular weight and adsorbent surface energy." Biomaterials (2009) 30, 6814-6824.
Schuster Th. B. "Vesicular Structures Using Short Amphiphilic Peptides." European Cells and Materials Journal (Nov. 2010) vol. 20. Suppl 3 (for 3rd International NanoBio Conference 2010, ETH Zurich, Switzerland, Aug. 24-27, 2010).
Schuster Th. B., de Bruyn Ouboter D., Bordignon E., Jeschke G., Meier W. "Reversible peptide particle formation using a mini amino acid sequence." Soft Matter (2010) 6, 5596-5604.
Sitnikova, N. L., Sprik, R., Wegdam, G. & Eiser, E. "Spontaneously formed trans-anethol/water/alcohol emulsions: mechanism of formation and stability." LANGMUIR (2005) 21, 7083-7089.
Soussan et al. "Drug delivery by soft matter: matrix and vesicular carriers." Angew Chem Int Ed Engl. 2009;48 (2):274-88.
Stark, WJ. "Nanoparticles in biological systems." Angew Chem Int Ed Engl. (Feb. 7, 2011); 50(6):1242-58. Epub Jan. 10, 2011.
Stewart et al. "Cell-penetrating peptides as delivery vehicles for biology and medicine." Org Biomol Chem (2008) 6, 2242-2255.
Sychev et al. "The solution conformations of gramicidin A and its analogs" Bioorganic Chemistry (1980) vol. 9, Issue 1, Mar. 1980, pp. 121-151.
Torchilin, VP. "Multifunctional nanocarriers." Adv Drug Deliv Rev. (Dec. 1, 2006); 58(14):1532-55. Epub Sep. 28, 2006.
Urry et al. "Spectroscopic studies on the conformation of gramicidin A'. Evidence for a new helical conformation." Biochemistry. Feb. 15, (1972); 11(4):487-93.
Veatch et al. "The conformation of gramicidin A" Biochemistry (1974) 13, 5249-56.

* cited by examiner

Before trypsination

After trypsination

Before trypsination

After trypsination

Before trypsination

After trypsination

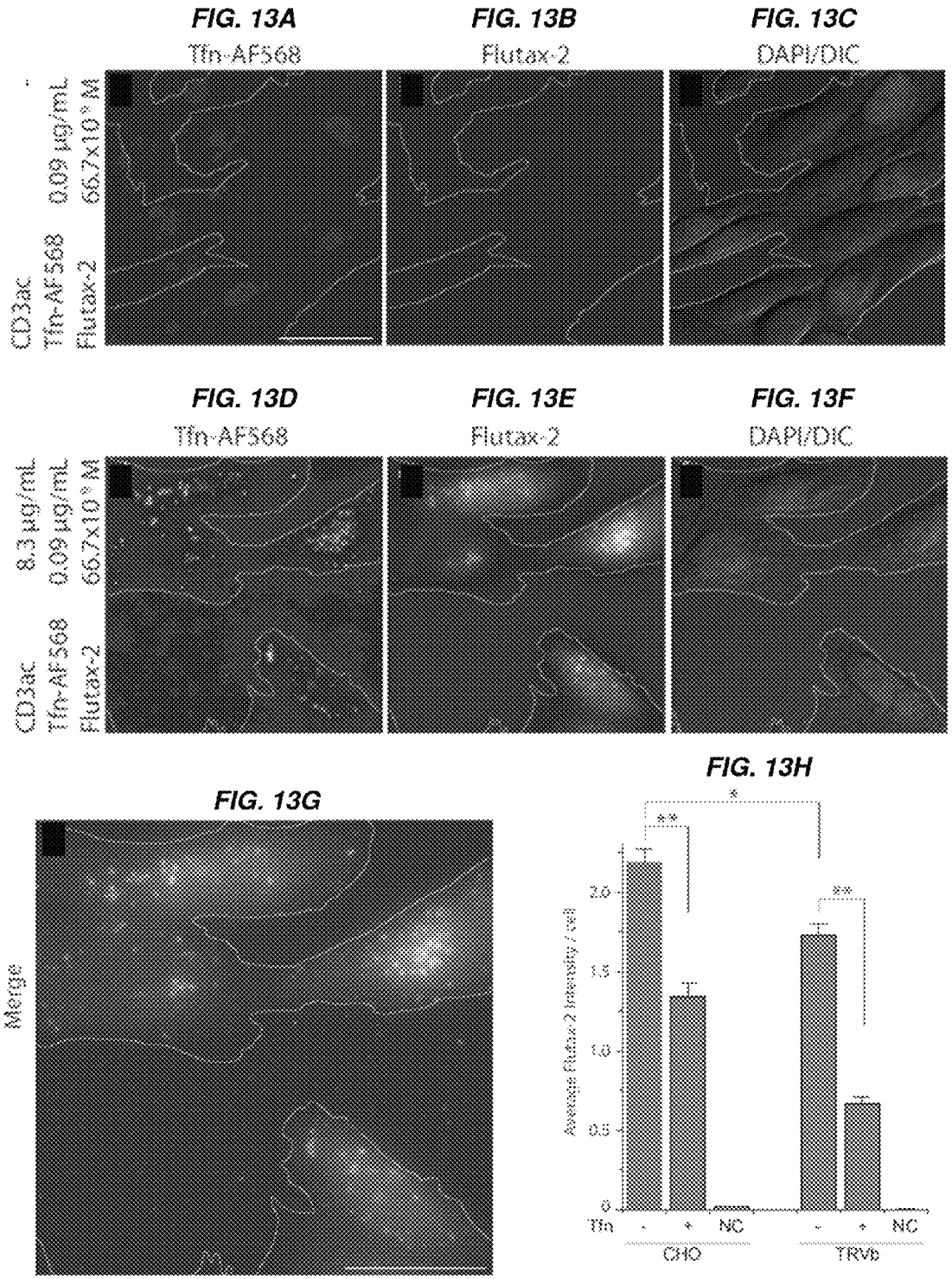

- 21 µM CD3ac (Ac-LK(Ac)-LK(Ac)-LK(Ac)-LW-DL-LW-DL-LW-DL-LW-NH₂)
- 2 µg/mL EGF_TR (Invitrogen E-3480)

■ Biotin
■ Texas Red

MW ~ 60'000

PB1e

- 21 μM CD3ac (Ac-LK(Ac)-LK(Ac)-LK(Ac)-LW-DL-LW-DL-LW-DL-LW-NH$_2$)
- 2 ug/mL EGF labeled with Texas_Red (EGF_TR)
- 20 uM Nocodazole
- DMEM/PBS

Negative control (NC)

- DMEM/PBS

PB1e Supernatant Control (PB1e_sup)

- 21 μM CD3ac (Ac-LK(Ac)-LK(Ac)-LK(Ac)-LW-DL-LW-DL-LW-DL-LW-NH$_2$)
- 2 μg/mL EGF_TR
- 20 uM Nocodazole
- DMEM/PBS
- Incubate for 5 h at 37 °C
- Spin down 16,000g, 30 min
- Apply supernatant to cells

Nocodazole (NOC)

- 20 uM Nocodazole
- DMEM/PBS 1 h incubation at 37 C

PB1e

- 21 μM CD3ac (Ac-LK(Ac)-LK(Ac)-LK(Ac)-LW-DL-LW-DL-LW-DL-LW-NH$_2$)
- 2 ug/mL EGF labeled with Texas_Red (EGF_TR)
- 40 uM Nocodazole
- DMEM/PBS

Negative control (NC)

- DMEM/PBS

PB1e Supernatant Control (PB1e_sup)

- 21 μM CD3ac (Ac-LK(Ac)-LK(Ac)-LK(Ac)-LW-DL-LW-DL-LW-DL-LW-NH$_2$)
- 2 μg/mL EGF_TR
- 40 uM Nocodazole
- DMEM/PBS
- Incubate for 5 h at 37 °C
- Spin down 16,000g, 30 min
- Apply supernatant to cells

Nocodazole (NOC)

- 40 uM Nocodazole
- DMEM/PBS 4 h incubation at 37°C, 10x 4 h incubation at 37°C, 60x 24 h incubation at 37°C, 10x 24 h incubation at 37°C, 60x CD3ac & Primary antibody
(e.g., rabbit anti-transferrin IgG)

CD3ac & secondary antibody
(e.g., donkey anti-rabbit IgG
(optionally labeled with a fluorescent
molecule such as Alexa 555))

• 21 μM CD3 (H-LK-LK-LK-LW-DL-LW-DL-LW-DL-LW-NH$_2$)$^{4+}$
• 5.4 μM (5'-TTGTGCCGCCTTTGCAGGTGTATC-3')$^{24-}$
• 0.24 μM (AF$_{488}$-5'-TTGTGCCGCCTTTGCAGGTGTATC-3')$^{24-}$

- 5.4μM (5'-TTGTGCCGCCTTTGCAGGTGTATC-3')$^{24-}$
- 0.24 μM (AF$_{488}$-5'-TTGTGCCGCCTTTGCAGGTGTATC-3')$^{24-}$ 5.13 µM CD3ac (Ac-LK(Ac)-LK(Ac)-LK(Ac)-LW-DL-LW-DL-LW-DL-LW-NH$_2$)
0.83 µM CD3 (H-LK-LK-LK-LW-DL-LW-DL-LW-DL-LW-NH$_2$)$^{4+}$
0.45 µM (5'-TTGTGCCGCCTTTGCAGGTGTATC-3')$^{24-}$
20 nM (AF488-5'-TTGTGCCGCCTTTGCAGGTGTATC-3')$^{24-}$
4.14 ug/mL Tfn-AF568

AMPHIPHILIC PEPTIDES AND PEPTIDE PARTICLES

CROSS REFERENCE TO RELATED APPLICATIONS

This Application claims the benefit under 35 U.S.C §119 (e) of U.S. Provisional Application Nos. 61/526,526 filed Aug. 23, 2011, the content of which is herein incorporated by reference in its entirety.

GOVERNMENT SUPPORT

This invention was made with government support under grant no. R01 GM090317 awarded by National Institutes of Health. The government has certain rights in this invention.

SEQUENCE LISTING

The instant application contains a Sequence Listing which has been submitted in ASCII format via EFS-Web and is hereby incorporated by reference in its entirety. Said ASCII copy, created on Oct. 9, 2012, is named 002806US.txt and is 43,037 bytes in size.

TECHNICAL FIELD

The present invention relates to amphiphilic peptides and particles comprising the amphiphilic peptides.

BACKGROUND

Nanoparticles are useful in the stabilization and delivery of drugs: they improve solubility, extend shelf lives, reduce side effects and sustain drug exposure for a prolonged therapeutic effect. The matrix used for targeted drug delivery is usually composed of lipids, polymers or metals and assembled into vesicles, micelles or particles. See Torchilin V. (2006) Adv Drug Deliv. 58:1532; Stark W (2011) Angew Chem Int Ed. 50: 1242; Sous san E et al. (2009) ACIE. 48: 274. The main independent particle variables that determine the in vivo applicability include size, surface charge, and dispersibility, mainly governed by the hydrophobic effect. Nel A et al. (2009) Nat. Matter. 8: 543. In contrast to these classical carrier materials, it is exceedingly difficult to design a colloidal delivery system exclusively from amino acids, mainly due to solubility issues of short hydrophobic peptides.

The dissolution of hydrophobic peptides is tedious and thus often requires elaborate protocols of solvent addition [14]. Despite all efforts, many hydrophobic peptides are not soluble at all and consequently difficult to synthesize by Fmoc- or Boc-protection group chemistry: peptide precipitation on the solid phase during synthesis leads to small yields and dominant quantities of by-products.

Yet a particle matrix composed of peptides is desirable as it can degrade into single amino acids. In addition, unlike other matrix materials, e.g., polymer, products of peptide synthesis can be purified to up to 98%, avoiding molecular polydispersity and thus issues with the reproducibility of physicochemical properties. Further, properties of peptide structure can be readily modulated, e.g., by introduction of amino acid point mutations. Accordingly, there is still a strong need for engineering a degradable drug carrier, which can be synthesized and purified in a simple process.

SUMMARY

Various aspects and embodiments provided herein relate to amphiphilic peptides, peptide particles comprising one or more embodiments of the amphiphilic peptides described herein, and uses of the amphiphilic peptides or peptide particles described herein. The net charges of the amphiphilic peptides described herein can be adjusted by controlling the number of charged groups present on amino acid residues of the amphiphilic peptides, e.g., by masking one or more charged amino groups, e.g., with acetylation. Therefore, the amphiphilic peptides and peptide particles described herein can be used as delivery carriers or vehicles for different types of active agents, e.g., charged or uncharged molecules, or polar or non-polar molecules. In addition, the peptide particles described herein can be adjusted for their solubilities, e.g., at a physiological condition, by controlling the ratios of two or more embodiments of the amphiphilic peptides present in the peptide particles. For example, fully-masked (e.g., fully-acetylated) amphiphilic peptides can generally form insoluble peptide particles, while particles formed from partially-masked (e.g., partially-acetylated) or non-masked (e.g., non-acetylated) peptides generally have a higher solubility than the fully-masked (e.g., fully-acetylated) amphiphilic peptides, e.g., at a physiological condition. Thus, in some embodiments, the solubility of the peptide particles described herein, e.g., at a physiological condition, can be controlled by forming the peptide particles with a mixture of these amphiphilic peptides with distinct solubilities and varying their amounts in the peptide particles accordingly.

One aspect provided herein relates to an amphiphilic peptide comprising a hydrophobic peptidyl segment and a hydrophilic peptide segment. The inventor has discovered that by modulating the hydrophilicity of the hydrophilic segment, they can control the type of particle formed by the self-aggregation of the amphiphilic peptides.

Accordingly, one aspect of the inventions provides an amphiphilic peptide comprising a hydrophobic peptidyl segment and a hydrophilic peptidyl segment, wherein the hydrophobic peptidyl segment comprises a sequence of 2 to 10 alternating D- and L-amino acids selected from alanine, valine, isoleucine, leucine (Leu), phenylalanine, tyrosine or tryptophan (Trp), and wherein the hydrophilic peptidyl segment comprises charged, or uncharged but polar amino acids, or derivatives thereof.

In certain embodiments of this aspect and all other aspects described herein, the hydrophobic peptidyl segment can comprise an amino acid sequence of $(Trp\text{-}Leu)_m\text{-}(Trp)_n$ (SEQ ID NO: 1) or $(Leu\text{-}Trp)_p\text{-}(Leu)_q$ (SEQ ID NO: 2), wherein each Trp is D-Trp or L-Trp and each Leu is D-Leu or L-Leu, m and p are independently an integer from 1 to 20, and n and q are independently 0 or 1, provided that when Trp is D-Trp then Leu is L-Leu, and when Trp is L-Trp then Leu is D-Leu, or vice versa.

In some embodiments, the hydrophilic peptidyl segment can comprise at least one charge present either on the N-terminus or an amino acid residue. In such embodiments, the at least one charge can be either a cationic or an anionic charge. In some embodiments, the at least one cationic charge can be in an amino acid residue selected from the group consisting of Lys, Arg, His, and any combinations thereof. In some embodiments, the at least one anionic charge can be in an amino acid residue selected from the group consisting of Asp or Glu, and any combinations thereof.

In alternative embodiments, the hydrophilic peptidyl segment can comprise uncharged but polar amino acids. In other embodiments, the hydrophilic peptidyl segment can comprise at least one charge and at least one uncharged but polar amino acid. In various embodiments, the at least one uncharged but polar amino acid residue can be selected from the group consisting of Ser, Thr, Asn or Gln, and any combinations thereof.

In particular embodiments of this aspect and all other aspects described herein, the hydrophilic peptidyl segment can comprise an amino acid sequence of (Lys)$_r$ (SEQ ID NO: 9), wherein r is an integer from 1 to 15. In some embodiments, r can be an integer from 2 to 5. In some embodiments, r can be equal to 3.

In some embodiments of this aspect and all other aspects described herein, the hydrophobic peptidyl segment can comprise a polymer. In some embodiments, the linked to the hydrophobic peptidyl segment can be adapted to link covalently to the polymer. In certain embodiments, the polymer can be biocompatible and/or biodegradable polymer. Examples of the polymer include, but are not limited to, PEG, PGG, PEO, polycaprolactone, polylactic acid, polyglycolic acid, polyhydroxyalkaboates, dextrans, polyanhydrides, PLA-PGA, polyorthoester, polyfumarate, hydrogels, any art-recognized biocompatible and/or biodegradable polymers, and any combinations thereof.

In certain embodiments of this aspect and all other aspects described herein, at least one amino group in the amphiphilic peptide can be masked, e.g., by acetylation. In such embodiments, the at least one amino group can be a N-terminus amino group of the amphiphilic peptide. In other embodiments, the at least one amino group can be on a Lys residue of the hydrophilic peptidyl segment.

In some embodiments of this aspect and all other aspects described herein, all of the amino groups in the hydrophilic peptidyl segment can be masked, e.g., acetylated. In other embodiments, the N-terminus amino group of the amphiphilic peptide and at least one of the amino groups in the hydrophilic peptidyl segment can be masked, e.g., acetylated. In yet another embodiment, the N-terminus amino group of the amphiphilic peptide and all of the amino groups in the hydrophilic peptidyl segment can be masked, e.g., acetylated. In some embodiments where the hydrophilic peptidyl segment comprises an amino acid sequence of (Lys)$_r$, the N-terminus amino group of the amphiphilic peptide and at least one (including at least 2, at least 3, or more) of the Lys residues of hydrophilic peptidyl segment are masked, e.g., acetylated. In one embodiment where the hydrophilic peptidyl segment comprises an amino acid sequence of (Lys)$_r$, the N-terminus amino group of the amphiphilic peptide and all of the Lys residues of hydrophilic peptidyl segment are masked, e.g., acetylated.

In various embodiments, the hydrophobic peptidyl segment can be linked to the C-terminus of the hydrophilic peptidyl segment.

In certain embodiments, Leu is D-Leu. In some embodiments, Trp is L-Trp. In some embodiments, Lys is L-Lys. In some embodiments, m or p can be independently between 1 and 3. In one embodiment, m or p is 3. In one embodiment, n or q is 1. Accordingly, one embodiment of the amphiphilic peptide comprises the amino acid sequence of (L-Lys)-(L-Lys)-(L-Lys)-(L-Trp)-(D-Leu)-(L-Trp)-(D-Leu)-(L-Trp)-(D-Leu)-(L-Trp) (SEQ ID NO: 3), wherein at least one of the L-Lys residues is acetylated.

In some embodiments, the amphiphilic peptide can comprise the amino acid sequence of Ac-(L-Lys)-(L-Lys)-(L-Lys)-(L-Trp)-(D-Leu)-(L-Trp)-(D-Leu)-(L-Trp)-(D-Leu)-(L-Trp) (SEQ ID NO: 4). In such embodiments, at least one of the L-Lys residues can be acetylated.

In other embodiments, the amphiphilic peptide can comprise the amino acid sequence of Ac-(L-Lys(Ac))-(L-Lys(Ac))-(L-Lys(Ac))-(L-Trp)-(D-Leu)-(L-Trp)-(D-Leu)-(L-Trp)-(D-Leu)-(L-Trp)-X (SEQ ID NO: 5), wherein X is absent or NH$_2$.

The amphiphilic peptide can have an amino acid sequence of any length. In some embodiments, the amphiphilic peptide can have a length of about 5 to about 25 amino acid residues.

The hydrophobic peptidyl segment or hydrophilic peptidyl segment of the amphiphilic peptide can be modified. For example, at least one of the hydrophobic peptidyl segment or the hydrophilic peptidyl segment can comprise at least one point mutation. In various embodiments, at least one backbone amide linkage can include an amide replacement linkage. In other embodiments, the amphiphilic peptide can comprise at least one β-amino acid, γ-amino acid, or any combinations thereof.

In some embodiments, the amphiphilic peptide comprises a hydrophobic peptidyl segment and a hydrophilic peptidyl segment, wherein the hydrophobic peptidyl segment comprises the amino acid sequence $(AA^{11}-AA^{12})_b-(AA^{13})_d$, wherein $AA^{11}$, $AA^{12}$ and $AA^{13}$ are independently selected hydrophobic amino acids residues for each occurrence, b is an integer from 1 to 20, and d is 0 or 1, provided that $AA^{11}$ and $AA^{12}$ have the opposite (i.e., D- and L-) configuration and $A^{12}$ and $A^{13}$ have the opposite (i.e., D- and L-) configuration; the hydrophilic peptidyl segment comprises one or more hydrophilic amino acids or derivatives thereof; and the amphiphilic peptide is partially or fully masked.

In some embodiments, an amphiphilic peptide comprises the amino acid sequence (L-Lys)$_{r'}$-((L-Trp)-(D-Leu))$_{m'}$-(L-Trp) (SEQ ID NO: 6), wherein r' is an integer from 3-21 and m' is an integer from 3-20, and wherein at least one of N-terminus amino group or a side chain amino group of at least one Lys residue is conjugated with a nitrogen- or amino-protecting group.

The inventor has discovered that some embodiments of the amphiphilic peptides described herein can have cell penetration ability. Thus, in some embodiments, amphiphilic peptides described herein can be used as cell penetration and/or transfection agents. In these embodiments, the amphiphilic peptides can be designed to be positively-charged. Accordingly, use of a composition comprising a positively-charged amphiphilic peptide as a cell-penetrating agent or transfection agent is provided herein, wherein the positive-charged amphiphilic peptide comprises a hydrophobic peptidyl segment and a hydrophilic peptidyl segment. The hydrophobic peptidyl segment of the positive-charged amphiphilic peptide comprises an amino acid sequence of (Trp-Leu)$_m$-(Trp)$_n$ (SEQ ID NO: 7) or (Leu-Trp)$_p$-(Leu)$_q$ (SEQ ID NO: 8), wherein each Trp is D-Trp or L-Trp and each Leu is D-Leu or L-Leu, m and p are independently an integer from 1 to 5, and n and q are independently 0 or 1, provided that when Trp is D-Trp then Leu is L-Leu, and when Trp is L-Trp then Leu is D-Leu, or vice versa; while the hydrophilic peptidyl segment comprises an amino acid sequence of (Lys)$_r$ (SEQ ID NO: 9), wherein r is an integer from 1 to 15. Additionally, in the positively-charged amphiphilic peptide, at least one of the Lys residues or the N-terminus amino group of the amphiphilic peptide is not acetylated. In some embodiments, all of the Lys residues and the N-terminus amino group of the positively-charged amphiphilic peptide are not acetylated.

In some embodiments, the positively-charged amphiphilic peptide can comprise an amino acid sequence of (L-Lys)-(L-Lys)-(L-Lys)-(L-Trp)-(D-Leu)-(L-Trp)-(D-Leu)-(L-Trp)-(D-Leu)-(L-Trp)-X (SEQ ID NO: 10), wherein X is absent or NH$_2$.

In some embodiments, the composition can further comprise a nucleic acid molecule (e.g., DNA or RNA) to be delivered into a cell.

Additionally, amphiphilic peptides described herein can also be used, either alone or as part of a delivery system for delivering a compound of interest, e.g., an active agent, to a cell. The delivery system can be a targeted delivery system. Compounds to be delivered can include therapeutic agents, diagnostic agents and any combinations thereof. Accordingly, one aspect of the inventions provides a method of using an amphiphilic peptide as a delivery system, the method comprising complexing an active agent with an amphiphilic peptide and contacting a cell with the complex. In some embodiments, the method can be used for therapeutic or diagnostic purposes.

In another aspect the invention provides particles comprising an amphiphilic peptide described herein. The inventor has discovered inter alfa that the particles formed by the amphiphilic peptides described herein differ from the particles described in C. Dittrich, Ph. D. Thesis, Universität Basel, 2007. To clarify, the particles fabricated from the amphiphilic peptides described herein are different from those described in Dittrich (2007). The peptides described in Dittrich (2007) do not comprise masked amino groups. As such, the particles formed from such peptides are micelles, e.g., hollow particles, and not solid particles as described herein. Accordingly, in certain embodiments, the peptide particles described herein are not micelles, e.g., hollow particles. Stated another way, in certain embodiments, the peptide particles described herein are solid particles.

In some embodiments, the particle comprising an amphiphilic peptide described herein can further comprise a ligand. Accordingly, in one embodiment, a peptide particle described herein comprises an amphiphilic peptide, the amphiphilic peptide comprising a hydrophobic peptidyl segment and a hydrophilic peptidyl segment, wherein the hydrophobic peptidyl segment comprises an amino acid sequence of $(Trp-Leu)_m-(Trp)_n$ (SEQ ID NO: 7) or $(Leu-Trp)_p-(Leu)_q$ (SEQ ID NO: 8), wherein each Trp is D-Trp or L-Trp and each Leu is D-Leu or L-Leu, m and p are independently an integer from 1 to 5, and n and q are independently 0 or 1, provided that when Trp is D-Trp then Leu is L-Leu, and when Trp is L-Trp then Leu is D-Leu, or vice versa; and wherein the hydrophilic peptidyl segment comprises an amino acid sequence of $(Lys)_r$ (SEQ ID NO: 9), wherein r is an integer from 1 to 15, and wherein the peptide particle further comprises on its outer surface a ligand.

In one embodiment, the ligand can be a cell surface receptor ligand or an antibody. Exemplary cell surface receptor ligands include, but not limited to, transferrin, EGF, folate and any combinations thereof. In certain embodiments, the ligand can be present on an outer surface of the particle. For example, the ligand can be adsorbed on the outer surface of the particle described herein. In alternative embodiments, the ligand can be covalently linked to the amphiphilic peptide. In one embodiment, the ligand is covalently linked to the hydrophilic peptidyl segment of the amphiphilic peptide.

The thickness of the ligand present on the outer surface of the particle described herein depends, in part, on the size of ligand molecule. In some embodiments, the thickness of the ligand present on the outer surface of the particle can range from about 1 nm to about 100 nm. In one embodiment, the thickness of the ligand present on the outer surface of the particle is about 10 nm. In some embodiments, a ratio of the ligand to the amphiphilic peptides can range from about 1:10 to about 1:1,000,000.

The ligand present on the peptide particle can be selected based on types of targets (e.g., but not limited to, cells, bacteria, proteins, and/or nucleic acids) to which the peptide particles will be delivered. For example, to facilitate delivery of a peptide particle described herein to a cell, a ligand specific for the cell surface receptor can be selected. Hence, some embodiments of the peptide particles described herein can be used for targeted delivery of an active agent using the peptide particles as delivery carriers or vehicles. In such embodiments, the peptide particles can be used to deliver to a cell an active agent that is cell-impermeable when delivered by itself.

Accordingly, in various embodiments of this aspect and all other aspects described herein, the peptide particle can comprise one or more active agents. In such embodiments, the active agent can be dispersed within the particle. The active agent can have no net charge or a net charge. In some embodiments, the active agent can comprise at least one aromatic group. Examples of the active agent include, without limitations, proteins, peptides, antigens, antibodies or portions thereof, antibody-like molecules, enzymes, nucleic acids, aptamers, small molecules, antibiotics, pharmaceutically active agents, therapeutic agents, contrast agents, and any combinations thereof. In one embodiment, the active agent is a pharmaceutically active agent or a therapeutic agent. In one embodiment, the active agent is a nucleic acid molecule, including, but not limited to, siRNA miRNA, shRNA, DNA and any combinations thereof. In particular embodiments, the ratio of the active agent to the amphiphilic peptides can range from about 1:1 to about 1:100,000, from about 1:1: to about 1:10,000, from about 1:1 to about 1:1,000, from about 1:1 to about 1:100, or from about 1:1 to about 1:10.

The peptide particle of this aspect and all other aspects described herein can be of any size. In some embodiments, the peptide particle can have a size of about 5 nm to about 5,000 nm. In some embodiments, the particle can have a size of about 30 nm to about 150 nm.

In some embodiments, the peptide particle can comprise a mixture of fully-masked (e.g., fully-acetylated) and partially-masked (e.g., partially-acetylated) amphiphilic peptides described herein. In those embodiments, the ratio of the fully-acetylated to the partially-masked amphiphilic peptides can range from about 95:5 to about 1:1. In certain embodiments, the particle can further comprise non-masked (e.g., non-acetylated) amphiphilic peptides.

Accordingly, a mixed peptide particle comprising a fully-acetylated amphiphilic peptide and a partially-acetylated or non-acetylated amphiphilic peptide is also provided herein. In specific embodiments, the mixed peptide particle comprises a first amphiphilic peptide and a second amphiphilic peptide, wherein the first and the second amphiphilic peptide each independently comprises a hydrophobic peptidyl segment and a hydrophilic peptidyl segment, wherein the hydrophobic peptidyl segment comprises an amino acid sequence of $(Trp-Leu)_m-(Trp)_n$ (SEQ ID NO: 7) or $(Leu-Trp)_p-(Leu)_q$ (SEQ ID NO: 8), wherein each Trp is D-Trp or L-Trp and each Leu is D-Leu or L-Leu, m and p are independently an integer from 1 to 5, and n and q are independently 0 or 1, provided that when Trp is D-Trp then Leu is L-Leu, and when Trp is L-Trp then Leu is D-Leu, or vice versa; while the hydrophilic peptidyl segment comprises an amino acid sequence of $(Lys)_r$ (SEQ ID NO: 9), wherein r is an integer from 1 to 15. Additionally, the N-terminus amino group and all of the Lys residues of the first amphiphilic peptide are acetylated; while at least the N-terminus amino group or one of the Lys residues of the second amphiphilic peptide is not acetylated. In some embodiments, none of the N-terminus amino group and the Lys residues of the second amphiphilic peptide is acetylated.

In particular embodiments, the first and second amphiphilic peptide can each independently comprise an amino acid sequence of (L-Lys)-(L-Lys)-(L-Lys)-(L-Trp)-(D-Leu)-(L-Trp)-(D-Leu)-(L-Trp)-(D-Leu)-(L-Trp)-X (SEQ ID NO: 10), wherein X is absent or $NH_2$.

The ratio of the first amphiphilic peptide to the second amphiphilic peptide can be varied based on a number of factors, e.g., but not limited to, desirable solubility and/or stability of the peptide particle, and/or properties of the active agent to be loaded therein. In some embodiments, the ratio of the first amphiphilic peptide to the second amphiphilic peptide can be in a range of about 1:1 to about 1000:1. In other embodiments, the ratio of the first amphiphilic peptide to the second amphiphilic peptide can be in a range of about 5:1 to about 100:1.

In some embodiments, the mixed peptide particle can further comprise an active agent described herein. The active agent can be present in the mixed peptide particle in any amounts, e.g., depending on the loading capacity of the peptide particle and/or binding capacity of the first or second amphiphilic peptide. In some embodiments, the ratio of the active agent to the second amphiphilic peptides can be in a range of about 1:1000 to 1:1, or about 1:100 to about 1:10. In some embodiments, the ratio of the active agent to the second amphiphilic peptide can be in a range of about 1:10 to about 1:2.

Without wishing to be bound by theory, the presence of the second amphiphilic peptide in the mixed peptide particle can provide a cationic charge for binding with anionic nucleic acid molecules. Thus, in some embodiments, the active agent can include a nucleic acid molecule.

In some embodiments, the mixed peptide particle can further comprise on its outer surface a ligand. As described earlier, selection of a ligand can be determined based on a target molecule (e.g., but not limited to, cells, bacteria, proteins, nucleic acids) to which the mixed peptide particle binds. Non-limiting examples of a ligand can include a cell surface receptor ligand or a protein such as an antibody. In some embodiments, the ligand can be covalently linked to at least one of the first and the second amphiphilic peptide, e.g., the hydrophilic peptidyl segment of at least one of the first and the second amphiphilic peptide.

The mixed peptide particle described herein can be used to encapsulate any active agent described herein. In a specific embodiment, the mixed peptide particle can be used to encapsulate a nucleic acid molecule. Thus, a further aspect of the inventions provides use of one or more embodiments of the mixed peptide particle comprising a first amphiphilic peptide and a second amphiphilic peptide for delivery of a nucleic acid molecule to a cell. In some embodiments, the nucleic acid molecule can include RNA (e.g., but not limited to, siRNA, miRNA, shRNA), DNA, or any combinations thereof.

Compositions or kits for making one or more embodiments of a peptide particle or a mixed peptide particle are also provided herein. In some embodiments, the composition or kit can comprise an amphiphilic peptide described herein. The amphiphilic peptide provided in the composition or kit can be stored in a container. Depending on a user's choice of a peptide particle or mixed particle described herein to be produced, in some embodiments, the composition or kit can comprise a first amphiphilic peptide and a second amphiphilic peptide described herein. The amphiphilic peptide can be provided in powder or lyophilized powder. In some embodiments, the composition or kit can further comprise at least one reagent, e.g., for reconstitution of the powdered amphiphilic peptide, for emulsification of a particle assembly mixture, or both. In some embodiments, the composition or kit can further comprise a ligand described herein, e.g., provided in a separate container. In some embodiments, the composition or kit can further comprise an active agent to be encapsulated into the peptide particle. The active agent can be provided in a separate container.

BRIEF DESCRIPTION OF THE DRAWINGS

This patent or application file contains at least one drawing executed in color. Copies of this patent or patent application with color drawing(s) will be provided by the Office upon request and payment of necessary fee.

FIG. 1A shows a mass spectrum measured on an orbitrap mass spectrometer. FIG. 1B shows an overlaid RP-HPLC elution profiles of CD3ac and synthesis intermediate CD3 measured by absorption at 280 nm. Product purity exceeds 95% in both cases.

FIGS. 2A-2B show SEM images of lyophilized CD3ac beads. FIG. 2C shows an SEM Image of a CD3ac-bead, broken in the process of freeze-drying. The image reveals the solid property of the peptide precipitates.

FIG. 5A shows an SEM image of precipitated LCD3ac. Spherical assembly as observed in CD3ac particles could not be observed with precipitated LCD3ac. FIG. 5B show circular dichroism spectra of CD3 (straight line) and LCD3 (dashed line), indicating the differences in secondary structure due to the chirality of leucine amino acids. LCD3 exhibits alpha-helical characteristics.

FIG. 6A show confocal microscopy images of CD3ac beads co-assembled with RB. FIG. 6B show confocal microscopy images of CD3ac beads co-assembled with CF. FIG. 6C show CD3ac beads loaded with RB and CF, indicating the ability of the peptide beads to simultaneously encapsulate compounds of high and low solubility in aqueous solution. As shown in FIGS. 6A-6C, RB-containing CD3ac beads are observed as individual spheres, whereas beads containing exclusively CF tend to aggregate. In FIGS. 6A-6C, upper left panels: fluorescence emission of RB; bottom right panels: fluorescence emission of CF; top right panels: phase contrast image; and bottom left panels: co-localization of both fluorescent channels. The width of one panel corresponds to 55 µm.

FIG. 7A show results of co-precipitation efficiency of RB with CD3ac. The x-axis describes the initially dissolved concentration ratio of CD3ac to RB, prior to solvent exchange and assembly. Left y-axis: molar composition of precipitate (O). Right y-axis: molar ratio of encapsulated to overall RB (Δ). As an example, at an initial ratio of RB:CD3ac=1:4, about 15 mol-% of the beads consist of RB and about 33% of initially dissolved RB was encapsulated in the assemblies. FIG. 7B shows tryptophan absorption of pellet (▲) and supernatant fractions (●) containing different amounts of RB, indicating that CD3ac assembly is not compromised by equimolar concentrations of RB cargo.

FIGS. 8A-8C show fluorescence microscopy images of peptide particles' red (FIG. 8A) and green (FIG. 8B) fluorescence before trypsination. The merged image (FIG. 8C) shows differential fluorescence distribution for Tfn-AF-568 (ring) and Flutax-2 (equally distributed). FIGS. 8D-8F show fluorescent images of the same sample after trypsination for 6 hours. The characteristic ring of Tfn-AF-568 fluorescence disappeared (FIG. 8D) and the emission intensity of Flutax-2 increased by a factor of 13.5 (FIG. 8E). FIGS. 8G-8H show averaged gray level profile of n=10 particles in the red (FIG. 8G) and green (FIG. 8H) channel before and after trypsination. FIG. 8I shows a schematic diagram of CD3ac peptide particles with a protein corona (e.g., Tfn-AF568) before and after trypsination.

FIGS. 9A and 9B show quantified composition of peptide particles self-assembled with Tfn-AF568 (FIG. 9A) and Flutax-2 (FIG. 9B), respectively. The x-axis describes the concentration ratio of initially dissolved Tfn-AF568 or Flutax-2 to CD3ac (123 μM), prior to solvent exchange and assembly. Left y-axis (open symbols): molar composition of peptide nanoparticles (PNPs). Right y-axis (closed symbols): molar ratio of encapsulated to overall Tfn-AF568 or Flutax-2. As an example in FIG. 9B, at an initial ratio of Flutax-2:CD3ac=0.1, about 7.5 mol-% of a PNP consists of Flutax-2 and about 80% of initially dissolved Flutax-2 was encapsulated. The consistent encapsulation efficiency of Flutax-2 around 80% corresponds to a logarithmic partition coefficient of 5.25. FIG. 9C shows Tfn-AF568 fluorescence intensity distribution of PNPs before and after competition with Tfn. Particles were assembled in the presence of 10 μg/mL Tfn-568 and imaged immediately after formation. The black bars correspond to intensity distribution of the resulting fluorescence puncta. The distribution represented by gray bars describes the fluorescence intensities of the same PNPs after an incubation period of 24 hours at 37° C. in the presence of 1360 μg/mL Tfn. FIG. 9D shows a cumulative data plot Tfn-AF568 fluorescence intensity distribution of PNPs before and after competition with Tfn as shown in FIG. 9C.

FIGS. 10A-10C show Tfn-AF568 fluorescence on peptide particles assembled from 492 μM, 246 μM and 123 μM CD3ac. Scale bars correspond to 1 μm. FIG. 10D show three overlaid fluorescence intensity profiles, each of which shows the average results of 10 particles. Results are represented by mean+/− standard deviation. FIG. 10E shows a schematic interpretation of intensity profiles illustrating the relation of particle size, corona fluorescence and the limited resolution of light microscopy. FIGS. 10E-10I show negative staining TEM images of CD3ac particles assembled in the absence (FIGS. 10E-10G) and presence (FIGS. 10H-10I) of 10 μg/mL Tfn. Protein-containing (e.g., Tfn-containing) samples can be distinguished by a layer of intermediate contrast around the peptide particles. Occasional holes (indicated by black arrow) were resulted from vacuum applied in the TEM and similar observation has been described in Hyuk I. et al., (2005) Nat Matter 4: 671. FIGS. 10J-10K show that final particle size depends on the presence of Tfn during assembly. Particle formation in the absence of Tfn-AF568 results in an average particle diameter of 100 nm (FIG. 10J) where the presence of protein during particle assembly reduces the diameter to 51 nm (FIG. 10K). The thickness of the protein corona corresponds to 9.0+/−2.1 nm (inset of FIG. 10K).

FIGS. 11A-11C show fluorescence microscopy images of CHO cells incubated with $PNP_{Flutax-2}^{Tfn-AF568}$ for one hour. Co-localization of fluorescent puncta in the green (Flutax-2) and red channel (Tfn-AF568) indicates the identity of particles, which accumulate on cells. FIGS. 11D-11F show CHO cells incubated with $PNP_{Flutax-2}^{Tfn-AF568}$ for one hour in the presence of 17 μM Tfn. PNP association is significantly reduced. Scale bars correspond to 10 μm. FIG. 11G show averaged peptide nanoparticle (PNP) counts per cell (e.g., CHO or TRVb). The value for the negative control (NC) corresponds to false positive fluorescence puncta on CHO cells incubated in the absence of $PNP_{Flutax-2}^{Tfn-AF568}$ but otherwise identical concentrations of Tfn-AF568 and Flutax-2. Results are mean+/−s.e.m., double asterisk indicates P<10$^{-9}$, Kolmogorov-Smirnov. FIG. 11H show a set of images showing CHO cells after 1 hour incubation with $PNP_{Flutax-2}^{Tfn-AF568}$. The upper row and the lower row show cells incubated in the absence and presence of 17 μM Tfn, respectively. The area outlined in a white square is magnified in FIGS. 11A-11F. Scale bars correspond to 20 μm.

FIGS. 12A-12D show fluorescence microscopy images of CHO cells incubated with $PNP_{Flutax-2}^{Tfn-AF568}$ for 1 hour. FIG. 12E shows distributions of Flutax-2/Tfn-AF568 fluorescence of $PNP_{Flutax-2}^{Tfn-AF568}$ (G/R) after 1 hour incubation of CHO cells with $PNP_{Flutax-2}^{Tfn-AF568}$. Grey bars represent G/R on the glass slide, black bars correspond to G/R found within the cell perimeter. FIG. 12F shows schematic of particle association and internalization after 1 hour. FIGS. 12G-12J show fluorescence microscopy images of CHO cells incubated with $PNP_{Flutax-2}^{Tfn-AF568}$ for 6 hours, wherein the shift of particles towards higher G/R values serves as a surrogate of particle internalization. FIG. 12K shows that the distribution of G/R values is significantly increased after a longer incubation period (black bars). In contrast, the distribution of G/R values on the glass slide (grey bars) is statistically indistinguishable from the G/R values of the same subpopulation after 1 hour. FIG. 12L shows schematic of particle association and internalization after 6 hours. For particles in lysosomal compartments, corona is proteolytically digested yielding decreased Tfn-AF568 fluorescence and increased Flutax-2 fluorescence. FIG. 12M shows images indicating color shift of $PNP_{Flutax-2}^{Tfn-AF568}$. The upper row shows CHO cells incubated with $PNP_{Flutax-2}^{Tfn-AF568}$ for 1 hour and contrasts the lower row, where the same cell line was incubated with $PNP_{Flutax-2}^{Tfn-AF568}$ for 6 hours. The area outlined in a white square is magnified in FIGS. 12A-12D and 12G-12J. Scale bars correspond to 20 μm.

FIGS. 13A-13I show release of cargo after incubation with $PNP_{Flutax-2}^{Tfn-AF568}$ for 24 hours. FIGS. 13A-13C show fluorescence microscopy images of CHO cells incubated for 24 hours with 67 nM Flutax-2 and 0.09 μg/mL Tfn-AF568. FIGS. 13D-13G show fluorescence images of CHO cells incubated for 24 hours with the same amount of Flutax-2 and Tfn-AF568 self-assembled with CD3ac to form $PNP_{Flutax-2}^{Tfn-AF568}$. FIG. 13H shows averaged Flutax-2 fluorescence intensity dependent of cell line (CHO, TRVb) and competition with dissolved unlabeled Tfn. The negative control (NC) corresponds to cellular autofluorescence in the green channel. Results are mean+/−s.e.m., single asterisk indicate P<0.01, double asterisk indicates $P<10^{-9}$, Kolmogorov-Smirnov. Scale bars correspond to 10 μm. FIG. 13I shows images of CHO cells after 24 hours incubation with Flutax-2. Both samples (upper and lower row) contain 66.7 nM Flutax-2. The upper row shows a cell culture incubated with Flutax-2 dissolved in the cell culture media, the lower row the same cell line incubated with Flutax-2 previously self-assembled into $PNP_{Flutax-2}^{Tfn-AF568}$. The area outlined in a white square is magnified in FIGS. 13A-13G. Scale bars correspond to 20

FIG. 16A shows a schematic diagram of a CD3ac particle functionalized with EGF molecules, which can be optionally labeled with Texas Red (for visualization purposes). FIG. 16B is a set of fluorescent images showing the EGF-functionalized CD3ac particles uptaken by the cells.

FIG. 17A shows a schematic representation of four different experimental conditions, wherein PB1e represents EGF-functionalized CD3ac nanoparticles encapsulated with 20 μM nocodazole, and the experimental results are shown in FIGS. 17B-17F. FIG. 17B shows a set of fluorescent images showing microtubule structures of the cells after 1 hour of incubation under the conditions indicated in FIG. 17A. The red fluorescent signals inside the cells indicate the PB1e nanoparticles uptaken by the cells. FIG. 17C shows a set of fluorescent images showing PB1e nanoparticles uptaken by the cells after various periods of times as indicated. FIGS. 17D-17F shows fluorescent images of microtubular structures of HeLa cells treated under different conditions as indicated. FIG. 17G shows a schematic representation of four different experimental conditions, wherein PB1e represents EGF-functionalized CD3ac nanoparticles encapsulated with 40 μM nocodazole, and the experimental results are shown in FIGS. 17H-17K. FIGS. 17H-17I shows images of cells after 4 hours of incubation under different conditions as indicated. FIG. 17I shows fluorescent images of microtubular structures (indicated by green) of cells under different conditions. The red signals inside cells indicate the PB1e nanoparticles uptaken by the cells. FIGS. 17J-17K shows images of cells after 24 hours of incubation under different conditions as indicated. FIG. 17K shows fluorescent images of microtubular structures (indicated by green) of cells under different conditions. The red signals inside cells indicate the PB1e nanoparticles uptaken by the cells.

FIG. 18A shows schematic representations of CD3ac nanoparticles functionalized with primary or secondary antibodies. FIG. 18B shows that the CD3ac nanoparticles functionalized with rabbit anti transferrin IgG can bind to transferrin (labeled with A568), and thus shown as bright spots on the right of the figure. FIG. 18C shows that the CD3ac nanoparticles functionalized with rabbit anti transferrin IgG can bind to anti-rabbit IgG (labeled with Alexa555), and thus shown as bright spots on the right of the figure.

FIG. 19A shows that CD3 particles can be used to deliver oligonucleotides inside cells. FIG. 19A discloses SEQ ID NOS 11-12 and 12, respectively, in order of appearance. FIG. 19B shows no cell transfection with oligonucleotides in the absence of CD3 particles. FIG. 19B discloses SEQ ID NOS 12 and 12, respectively, in order of appearance.

FIG. 20A is a set of time-course images showing migration of oligonucleotides and proteins across an agarose gel during electrophoresis. In FIG. 20A, the upper lane was loaded with a mixture containing ~21 μM CD3 peptides (H-LK-LK-LK-LW-DL-LW-DL-LW-DL-LW-$NH_2$) (SEQ ID NO: 11)$^{4+}$, ~5.4 μM ssDNA (5'-TTGTGCCGCCTTTGCAGGTGTATC-3') (SEQ ID NO: 12)$^{24-}$, 0.24 μM AF488-ssDNA (AF488-5'-TTGT-GCCGCCTTTGCAGGTGTATC-3') (SEQ ID NO: 12)$^{24-}$, and ~4.14 ug/mL Tfn-AF568, while the lower (control) lane was loaded with a similar mixture but without CD3 peptides. After about 40-min electrophoresis, excess ssDNA and Tfn migrated across the agarose gel toward the anode, while the peptide particles formed at the loading zone of the agarose gel (as evidenced by co-localization of the AF488 signal and AF568 fluorescence signal) were not able to migrate in the agarose gel due to their larger size. FIG. 20B is a set of HP-WAX (weak anion exchange) chromatography data showing that a majority of CD3 peptides and ssDNA were encapsulated in peptide particles (pellet), and little remained in supernatant. Peak at ~1.5 min: CD3 peptides; Peaks at ~14.5 min and ~15 min: ssDNA separated and partially-hybridized, respectively.

FIG. 21 discloses SEQ ID NOS 17, 11-12 and 12, respectively, in order of appearance.

FIG. 22A shows that the stability of PNP1 particles (ssDNA-containing CD3 peptide particles) in water is temperature-dependent and more PNP1 particles tend to dissociate at a higher temperature. FIG. 22B shows stability data for a time-course study of the PNP1 particles in water, indicating that the stability of PNP1 particles in water is temperature-dependent and the PNP1 particles tend to dissociate faster at a higher temperature, e.g., at a temperature higher than 4° C. FIG. 22C is a set of fluorescent images showing HeLa cells incubated in the presence of PNP1 particles or PNP2 particles (ssDNA-containing CD3/CD3ac peptide particles) at temperatures of about 4° C. and about 37° C. The upper panels of FIG. 22C show that diffuse and stronger Tfn-AF568 fluorescence signal was detected in the cytosol when the cells were incubated with the PNP1 particles at about 37° C., as compared to more punctated Tfn-AF568 fluorescence detected in the cells incubated at about 4° C. However, this contrast was not observed in the cells incubated with the PNP2 particles, as shown in the lower panels of FIG. 22C. Instead, the lower panels of FIG. 22C show that punctated and comparable Tfn-AF568 fluorescence signals were observed in both the cells incubated at about 4° C. and about 37° C., in the presence of the PNP2 particles. These findings indicate that the PNP1 particles tend to dissociate in serum (e.g., ~10% serum) at about 37° C.; while the PNP2 particles appear to be more stable in serum (e.g., ~10% serum) at about 37° C. for at least about 30 mins. FIG. 22D is a fluorescent image of negative control cells (i.e., HeLa cells incubated in the presence of ssDNA without PNP1 or PNP2 particles or corresponding peptides), indicating that much lower fluorescence intensity of AF488-ssDNA is observed in the negative control than that in the cells incubated with the PNP1 or PNP2 particles.

DETAILED DESCRIPTION OF THE INVENTION

Figure 1A:
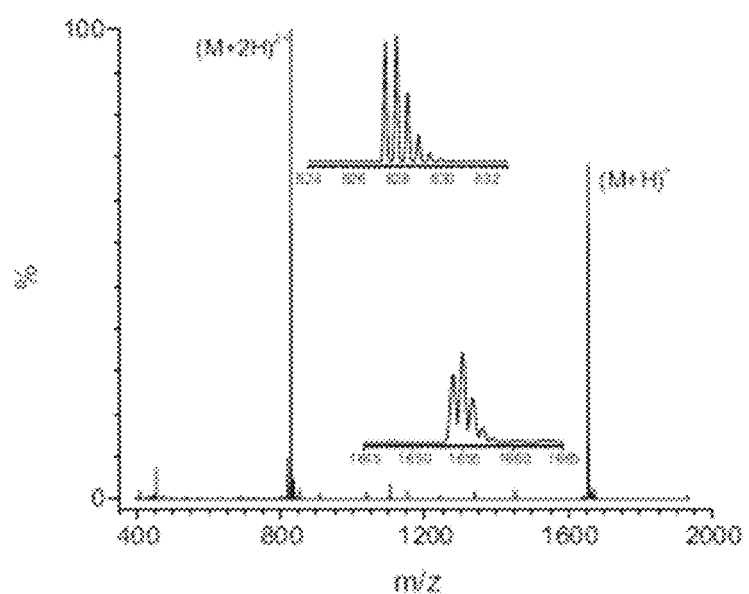
FIGS. 1A-1B show characterization results of purified CD3ac in accordance with one or more embodiments of the invention.

Various aspects and embodiments provided herein relate to amphiphilic peptides, peptide particles comprising one or more embodiments of the amphiphilic peptides described herein, and uses of the amphiphilic peptides or peptide particles described herein. The net charges of the amphiphilic peptides described herein can be adjusted by controlling the number of charged groups present on amino acid residues of the amphiphilic peptides, e.g., by masking one or more charged amino groups, e.g., with acetylation. Therefore, the amphiphilic peptides and peptide particles described herein can be used as delivery carriers or vehicles for different types of active agents, e.g., charged or uncharged molecules, or polar or non-polar molecules. In addition, the peptide particles described herein can be adjusted for their solubilities, e.g., at a physiological condition, by controlling the ratios of two or more embodiments of the amphiphilic peptides present in the peptide particles. For example, fully-masked (e.g., fully-acetylated) amphiphilic peptides can generally form insoluble peptide particles, while particles formed from partially-masked (e.g., partially-acetylated) or non-masked (e.g., non-acetylated) peptides generally have a higher solubility (or lower stability) than the fully-masked (e.g., fully-acetylated) amphiphilic peptides, e.g., at a physiological condition. Thus, in some embodiments, the solubility or stability of the peptide particles described herein, e.g., at a physiological condition, can be controlled, e.g., by forming peptide particles with a mixture of amphiphilic peptides with distinct solubilities and varying their amounts in the peptide particles accordingly. Accordingly, verstability and stability of amphiphilic peptides and peptide particles described herein can be tailored for a variety of applications, e.g., drug delivery and/or sustained release of an active agent.

By the term "stability" or "stable" used herein is meant an ability of a peptide particle to retain its original volume (e.g., at least about 50%, at least about 60%, at least about 70%, at least about 80%, at least about 90%, at least about 95%, or more of its original volume) for a period of time, e.g., at least about 30 mins or longer (including at least about 1 hour, at least about 3 hours, at least about 6 hours, at least about 12 hours, at least about 24 hours, or longer), under a specified condition, e.g., a physiological condition. Stability of a peptide particle can be, in part, governed by its solubility under a specified condition. The more soluble is a peptide particle under a specified condition, the less stable is the peptide particle under the specified condition. In one embodiment, the term "stability" or "stable" as used herein refers to a peptide particle being insoluble under a specified condition, e.g., in an aqueous medium at a specified temperature. In some embodiments, the aqueous medium is water. In some embodiments, the aqueous medium is a physiological medium, e.g., with a certain salt concentration, pH and/or protein/serum concentration.

In one aspect, an amphiphilic peptide comprising a hydrophobic peptidyl segment and a hydrophilic peptide segment is provided herein. The inventor has discovered inter alfa that by modulating the hydrophilicity of a hydrophilic amino acid residue of an amphiphilic peptide, the amphiphilicity of the amphiphilic peptide can be modulated such that it unexpectedly leads to self-assembly of the peptides into solid particles. The amphiphilicity can be modulated by conjugating a hydrophilic group to an amino acid in the hydrophilic peptidyl segment, or by masking a hydrophilic group in the hydrophilic peptidyl segment, or masking the N-terminus amino group of the amphiphilic peptide. For example, when the hydrophilic amino acid is a charged amino acid, the hydrophilicity can be modulated by conjugating the charged part of the molecule with a protecting group. Accordingly, in some embodiments, at least one amino group in the amphiphilic peptide is conjugated with a nitrogen- or amino-protecting group.

In some embodiments, the amphiphilic peptide is fully masked. As used herein, a fully masked peptides refers to an amphiphilic peptide in which the N-terminus amino group and all of the side chain amino groups in the hydrophilic peptidyl segment are conjugated with a nitrogen- or amino-protecting group.

In some embodiments, the amphiphilic peptide is partially masked. As used herein, a partially masked peptide refers to an amphiphilic peptide in which one or more of the N-terminus amino group or side chain amino groups in the hydrophilic peptidyl segment is not conjugated with a nitrogen- or amino-protecting group; however, the amphiphilic peptide still comprises at least one amino group conjugated with a nitrogen- or amino-protecting group.

As used herein, a "nitrogen protecting group" or an "amino protecting group" refers to moieties that block or mask the $NH_2$ group. Exemplary amino-protecting groups include, but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Further amino protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991, content of which is herein incorporated by reference in its entirety.

In some embodiments, the nitrogen- or amino-protecting group is acyl or alkyl, e.g., acetyl, ethanoyl, propionyl, t-butanoyl, methyl, ethyl, propyl, butyl, pentyl, or hexanyl.

In some embodiments, the N-terminus amino group of an amphiphilic peptide is conjugated with a nitrogen- or amino-protecting group.

In some embodiments, at least one (e.g., 1, 2, 3, 4, 5, 6, 7, 8, 9, 10 or more) sidechain amino group of an amino acid of the amphiphilic peptide is conjugated with a nitrogen- or amino-protecting group. The amino acid whose side chain amino group is to be conjugated can be present at any position in the amphiphilic peptide. The sidechain conjugated amino acids can be present next to each other or not next to each other. When three or more sidechain conjugated amino acids are present some of the sidechain amino acids can be present next to another sidechain conjugated amino acid while some of the sidechain conjugated amino acids are not next to another sidechain conjugated amino acid. Additionally, when two or more nitrogen- or amino-protecting groups are present, they can all be the same all different or any combination of same and different.

In some embodiments, at least one (e.g., 1, 2, 3, 4, 5, 6, 7, 8, 9, 10 or more) sidechain amino group of an amino acid in the hydrophilic peptidyl segment is conjugated with a nitrogen- or amino-protecting group. Without limitations, the sidechain conjugated amino acid can be present at any position of the hydrophilic peptidyl segment. For example, reading from the N-terminal, at position 1, 2, 3, 4, 5, 6, 7, 8, 9, 10, and so on of the hydrophilic peptidyl segment.

In some embodiments, the N-terminus amino group of the amphiphilic peptide and at least one sidechain amino group (including, e.g., at least one, at least two, at least three or more sidechain amino groups) in the hydrophilic peptidyl segment of the amphiphilic peptide is conjugated with a nitrogen- or amino-protecting group. In some embodiments, the N-terminus amino group of the amphiphilic peptide and at least one sidechain amino group (including, e.g., at least one, at least two, at least three or more sidechain amino groups) in the hydrophilic peptidyl segment of the amphiphilic peptide is acetylated.

In some embodiments, the N-terminus amino group of the amphiphilic peptide and all of the sidechain amino groups in the hydrophilic peptidyl segment of the amphiphilic peptide are conjugated with a nitrogen- or amino-protecting group. In some embodiments, the N-terminus amino group of the amphiphilic peptide and all of the sidechain amino groups in the hydrophilic peptidyl segment of the amphiphilic peptide are acetylated.

Without wishing to be bound by a theory presence of a nitrogen- or amino-protecting group in the amphiphilic peptide modulate the hydrophilicity of the amphiphilic peptide. Thus, amphiphilic nature of the amphiphilic peptide can be tuned by varying the number of nitrogen- or amino-protecting groups in the amphiphilic peptide.

The amphiphilic peptide can have an amino acid sequence of any length. In some embodiments, the amphiphilic peptide can have a length of about 5 to about 25 amino acid residues. In one embodiment, the amphiphilic peptide has a length of about 10 amino acid residues.

Hydrophobic Peptidyl Segment

As used herein, the term "hydrophobic peptidyl segment" refers to a peptidyl segment having a relatively high content of hydrophobic amino acid. For example, a hydrophobic peptidyl segment refers to a peptidyl segment, in which at least about 50% or more (including at least about 50%, at least about 60%, at least about 70%, at least about 80%, at least about 90%, at least about 95% or more) of the amino acid residues are hydrophobic amino acid residues. In one embodiment, a hydrophobic peptidyl segment is a peptidyl segment, in which all of the amino acids are hydrophobic amino acids.

Accordingly, in some embodiments, the hydrophobic peptidyl segment is comprises the amino acid sequence $(AA^{11}\text{-}AA^{12})_b\text{-}(AA^{13})_d$, wherein $AA^{11}$, $AA^{12}$ and $AA^{13}$ are independently selected hydrophobic amino acids residues for each occurrence, b is an integer from 1 to 20, and d is 0 or 1, provided that $AA^{11}$ and $AA^{12}$ have the opposite (i.e., D- and L-) configuration and $A^{12}$ and $A^{13}$ have the opposite configuration. For example, if amino acids represented by $AA^{11}$ have the D-configuration then amino acids represented by $AA^{12}$ have the L-configuration and $AA^{13}$, if present, has the D-configuration. Alternatively, if the amino acids represented by $AA^{11}$ have the L-configuration then amino acids represented by $AA^{12}$ have the D-configuration and $AA^{13}$, if present, has the L-configuration.

In some embodiments, the hydrophobic peptidyl segment comprises a sequence of 2 to 10 alternating D- and L-amino acids selected from the group consisting of alanine, valine, isoleucine, leucine (Leu), phenylalanine, tyrosine, tryptophan (Trp) and any combinations thereof.

As used herein, the term "hydrophobic amino acid" refers to an amino acid exhibiting a hydrophobicity of greater than zero according to the normalized consensus hydrophobicity scale of Eisenberg, 1984, J. Mol. Biol. 179:125-142 (1984). Exemplary hydrophobic amino acids include, but are not limited to, Ala, Val, Ile, Leu, Phe, Tyr, Trp, Pro, Met, Gly and derivatives thereof.

In some embodiments, a hydrophobic amino acid is an aromatic amino acid. As used herein, the term "aromatic amino acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO2, —NO, —NH$_2$, —NHR, —NRR, —C(O)R, —C(O)OH, —C(O)OR, —C(O)NH$_2$, —C(O)NHR, —C(O)NRR and the like where each R is independently (C1-C6) alkyl, substituted (C2-C6)alkyl, (C2-C6)alkenyl, substituted (C2-C6)alkenyl, (C2-C6)alkynyl, substituted (C2-C6)alkynyl, (C5-C20)aryl, substituted (C5-C20)aryl, (C6-C26) alkaryl, substituted (C6-C26)alkaryl, 5-20 membered heteroaryl, substituted 5-20 membered heteroaryl, 6-26 membered alkheteroaryl or substituted 6-26 membered alkheteroaryl. Exemplary aromatic amino acids include, but are not limited to, Phe, Tyr and Trp.

In some embodiments, a hydrophobic amino acid is an aliphatic amino acid. As used herein, the term "aliphatic amino acid" refers to a hydrophobic amino acid having an aliphatic hydrocarbon side chain. Exemplary aliphatic amino acids include, but are not limited to, Ala, Val, Leu and Ile.

In some embodiments, a hydrophobic amino acid is a nonpolar amino acid. As used herein, the term "nonpolar amino acid" refers to a hydrophobic amino acid having a side chain that is uncharged at physiological pH and which has bonds in which the pair of electrons shared in common by two atoms is generally held equally by each of the two atoms (i.e., the side chain is not polar). Exemplary nonpolar amino acids include, but are not limited to, Leu, Val, Ile, Met, Gly and Ala.

As will be appreciated by those of skill in the art, the categories of amino acids described herein are not mutually exclusive. Thus, amino acids having side chains exhibiting two or more physical-chemical properties can be included in multiple categories. For example, amino acid side chains having aromatic moieties that are further substituted with polar substituents, such as Tyr, can exhibit both aromatic hydrophobic properties and polar or hydrophilic properties, and can therefore be included in both the aromatic and polar categories. The appropriate categorization of any amino acid will be apparent to those of skill in the art, especially in light of the detailed disclosure provided herein.

In some embodiments, for each occurrence $AA^{11}$, $AA^{12}$ and $AA^{13}$ are selected independently from the group consisting of Pro, Ile, Phe, Val, Leu, Trp, Met, Ala, Gly, Tyr, and any combinations thereof.

Without limitation, all of the $AA^{11}$ and $AA^{12}$ can be the same, all different, or any combinations of same and different. Accordingly, in some embodiments, all of $AA^{11}$ are same. In some embodiments, all of $AA^{12}$ are same. In some embodiments, all of $AA^{11}$ are same, all of $AA^{12}$ are same, and $AA^{11}$ is different from $AA^{12}$.

In some embodiments, at least one of $AA^{11}$, $AA^{12}$ and $AA^{13}$ is not Tyr or Leu.

In some embodiments, at least one $AA^{11}$ is not Tyr.
In some embodiments, at least one of $AA^{12}$ is not Leu.
In some embodiments, $AA^{13}$ is not Tyr or Leu.
In some embodiments, $AA^{11}$ is Tyr.
In some embodiments, $AA^{12}$ is Leu.

In some embodiments, the hydrophobic peptidyl segment comprises an amino acid sequence $(Trp-Leu)_m-(Trp)_n$ (SEQ ID NO: 13) or $(Leu-Trp)_p-(Leu)_q$ (SEQ ID NO: 14), wherein m and p are independently an integer from 3 to 20, and n and q are independently 0 or 1. Each Trp can be D-Trp or L-Trp, and each Leu can be D-Leu or L-Leu. When Trp is D-Trp, then Leu is L-Leu, and when Trp is L-Trp, then Leu is D-Leu. Similarly, when Leu is L-Leu, then Trp is D-Trp, and when Leu is D-Leu, then Trp is L-Trp.

In some embodiment, m and p are independently an integer of 1, 2, 3, 4, 5, 6, 7, 8, 9, 10, 11, 12, 13, 14, or 15. In some embodiments, m and p are independently an integer from 1 to 5 (e.g., an integer of 1, 2, 3, 4, or 5). In some embodiments, m or p is an integer of 1, 2, or 3. In one embodiment, m or p is an integer of 3.

In one embodiment, the hydrophobic peptidyl segment comprises an amino acid sequence $((L-Trp)-(D-Leu))_3-(L-Trp)$ (SEQ ID NO: 15).

Hydrophilic Peptidyl Segment

As used herein, the term "hydrophilic peptidyl segment" refers to a peptidyl segment having hydrophilicity properties relative to a hydrocarbon moiety. In some embodiments, the hydrophilic peptidyl segment refers to a peptidyl segment having hydrophilicity properties relative to the hydrophobic peptidyl segment of an amphiphilic peptide described herein. Generally, the hydrophilic peptidyl segment comprises at least one hydrophilic amino acid. As used herein, the term "hydrophilic amino acid" refers to an amino acid residue exhibiting a hydrophobicity of less than zero according to the normalized consensus hydrophobicity scale of Eisenberg et al., J. Mol. Biol. 179:125-142 (1984), content of which is incorporated herein by reference. Exemplary hydrophilic amino acids include, but are not limited to Lys, Arg, His, Asp, Glu, Ser, Thr, Asn, Gln, and derivatives thereof.

In some embodiments, the hydrophilic amino acid is a charged or uncharged amino acid. As used herein, the term "charged amino acid" refers to an amino acid residue that has a net charge. Accordingly, a charged amino acid can be a cationic amino acid or an anionic amino acid. As used herein, the term "uncharged amino acid" refers to an amino acid residue that has no net charge. A charged amino acid residue can be modified into an uncharged amino acid by masking the charge of the amino acid, for example, by conjugating a protecting group to a charge-carrying atom. In one embodiment, a charged amino acid residue can be modified into an uncharged amino acid by acetylation.

In some embodiments, the hydrophilic amino acid is a polar amino acid. As used herein, the term "polar amino acid" refers to a hydrophilic amino acid having a side chain that is charged or uncharged at physiological pH, but which has at least one bond in which the pair of electrons shared in common by two atoms is held more closely by one of the atoms. Exemplary polar amino acids include, but are not limited to, Asn, Gln, Ser, Thr, and any combinations thereof.

In some embodiments, the hydrophilic amino acid is a charged or uncharged polar amino acid.

In some embodiments, the hydrophilic amino acid is a cationic amino acid. As used herein, the term "cationic amino acid" refers to an amino acid residue that comprises a positively charged side chain under normal physiological conditions. Thus, the term "cationic amino acid" includes any naturally occurring amino acid or mimetic therefore having a positively charged side chain under normal physiological conditions. Generally, amino acid residues comprising an amino group in their variable side chain are considered as cationic amino acids. Exemplary cationic amino acids include, but are not limited to, lysine, histidine, arginine, hydroxylysine, ornithine, and their respective derivatives, analogues, and stereoisomeric configurations thereof.

In some the hydrophilic amino acid is an anionic amino acid. As used herein, the term "anionic amino acid" refers to a hydrophilic amino acid having a negative charge. Exemplary anionic amino acids include, but are not limited to, Glu, Asp, and derivatives thereof.

In some embodiments, the hydrophilic amino acid is an acidic amino acid. As used herein, the term "acidic amino acid" refers to a hydrophilic amino acid having a side chain pK value of less than 7. Acidic amino acids typically have negatively charged side chains at physiological pH due to loss of a hydrogen ion. Exemplary acidic amino acids include, but are not limited to, Glu, Asp, and derivatives thereof.

In some the hydrophilic amino acid is a basic amino acid. As used herein, the term "basic amino acid" refers to a hydrophilic amino acid having a side chain pK value of greater than 7. Basic amino acids typically have positively charged side chains at physiological pH due to association with hydronium ion. Exemplary basic amino acids include, but are not limited to, His, Arg, Lys, and derivatives thereof.

In some embodiments, the hydrophilic peptidyl segment comprises at least one charged amino acid, or at least one uncharged polar amino acid, or a combination thereof. In some embodiments, the hydrophilic peptidyl segment comprises at least one amino acid selected from the group consisting of Lys, Arg, His, Asp and Glu, or at least one amino acid selected from the group consisting of Ser, Thr, Asn, and Gln, or a combination thereof. In some embodiments, the hydrophilic peptidyl segment can comprise one amino acid selected from the group consisting of Lys, Arg, and His.

In some embodiments, at least one amino group in the hydrophilic peptidyl segment is masked or conjugated with a nitrogen- or amino-protecting group.

In some embodiments, the hydrophilic peptidyl segment comprises the amino acid sequence $(AA^{21})_f$, wherein $AA^{21}$ is a hydrophilic amino acid selected independently for each occurrence and f is an integer from 1 to 21.

Without limitations, all of the $AA^{21}$ can be the same, all different, or any combination of same and different.

In some embodiments, f is 2, 3, 4, 5, 6, 7, 8, 9, 10, 11, 12, 13, 14, or 15.

In some embodiments, the hydrophilic peptidyl segment comprises an amino acid sequence $(Lys)_r$ (SEQ ID NO: 9), wherein r is an integer from 1 to 15. In some embodiments, r is an integer of 1, 2, 3, 4, 5, 6, 7, 8, 9, 10, 11, 12, 13, 14, or 15. In some embodiments, r is an integer from 2 to 5 (e.g., r is an integer of 2, 3, 4, or 5). In one embodiment, r is an integer of 3.

In some embodiments, the hydrophilic peptidyl segment comprises an amino acid sequence selected from the group consisting of (L-Lys)-(L-Lys)-(L-Lys), (L-Lys)-(L-Lys)-(L-Lys(Ac)), (L-Lys)-(L-Lys(Ac))-(L-Lys), (L-Lys(Ac))-(L-Lys)-(L-Lys), (L-Lys)-(L-Lys(Ac))-(L-Lys(Ac)), (L-Lys(Ac))-(L-Lys)-(L-Lys(Ac)), (L-Lys(Ac))-(L-Lys(Ac))-(L-Lys), L-Lys(Ac))-(L-Lys(Ac))-(L-Lys(Ac)), and any combinations thereof, wherein "Ac" refers to acetylation of the Lys amino acid residue.

In some embodiments, the hydrophilic peptide segment includes or is a hydrophilic polymer. As used herein, the term "hydrophilic polymer" refers to a polymer having hydrophilicity properties relative to a hydrocarbon moiety. In some embodiments, the term "hydrophilic polymer" refers to a polymer having hydrophilicity properties relative to the hydrophobic peptidyl segment of an amphiphilic peptide described herein. Hydrophilicity of a polymer can be determined by, for example, ASTM D570 testing. Generally, hydrophilic polymers are water-soluble. Exemplary hydrophilic polymers include, but are not limited to, poly(ethylene glycol), poly (ethylene oxide), poly(propylene glycol), poly (ethylene oxide-co-propylene oxide), hyaluronic acid, poly (2-hydroxyethyl methacrylate), heparin, polyvinyl(pyrrolidone), chondroitan sulfate, chitosan, glucosaminoglucans, dextran, dextrin, dextran sulfate, cellulose acetate, carboxymethyl cellulose, hydroxyethyl cellulose, cellulosics, poly(trimethylene glycol), poly(tetramethylene glycol), polypeptides, polyacrylamide, polyacrylimide, poly(ethylene amine), poly(allyl amine), and blends thereof.

Exemplary Peptide Modifications

In some embodiments, an amphiphilic peptide described herein can comprise at least one (e.g., 1, 2, 3, 4, 5, 6, 7, 8, 9, 10, 11, 12, 13, 14, 15, or more) amino acid selected from the group consisting of alanine; argnine; asparagine; aspartic acid; cysteine; glutamic acid; glutamine; glycine; histidine; isoleucine; leucine; lysine; methionine; phenylalanine; proline; serine; threonine; tryptophan; tyrosine; valine; homocysteine; phosphoserine; phosphothreonine; phosphotyrosine; hydroxyproline; γ-carboxyglutamate; hippuric acid; octahydroindole-2-carboxylic acid; statine; 1,2,3,4,-tetrahydroisoquinoline-3-carboxylic acid; penicillamine (3-mercapto-D-valine); ornithine (Orn); citruline; alpha-methyl-alanine; para-benzoylphenylalanine; para-aminophenylalanine; p-fluorophenylalanine; phenylglycine; propargylglycine; N-methylglycins (sarcosine, Sar); and tert-butylglycine; diaminobutyric acid; 7-hydroxy-tetrahydroisoquinoline carboxylic acid; naphthylalanine; biphenylalanine; cyclohexylalanine; amino-isobutyric acid (Aib); norvaline; norleucine (Nle); tert-leucine; tetrahydroisoquinoline carboxylic acid; pipecolic acid; phenylglycine; homophenylalanine; cyclohexylglycine; dehydroleucine; 2,2-diethylglycine; 1-amino-1-cyclopentanecarboxylic acid; 1-amino-1-cyclohexanecarboxylic acid; amino-benzoic acid; amino-naphthoic acid; gamma-aminobutyric acid; difluorophenylalanine; nipecotic acid; N-α-imidazole acetic acid (IMA); thienyl-alanine; t-butylglycine; desamino-Tyr; aminovaleric acid (Ava); pyroglutaminic acid (<Glu); α-aminoisobutyric acid (αAib); γ-aminobutyric acid (γAbu); α-aminobutyric acid (αAbu); αγ-aminobutyric acid (αγAbu); 3-pyridylalanine (Pal); Isopropyl-α-$N^∈$lysine (ILys); Napthyalanine (NaI); α-napthyalanine (α-Nal); β-napthyalanine (β-Nal); Acetyl-β-napthyalanine (Ac-β-napthyalanine); α,β-napthyalanine; $N^∈$-picoloyl-lysine (PicLys); 4-halo-Phenyl; 4-pyrolidylalanine; isonipecotic carboxylic acid (inip); beta-amino acids; and isomers, analogs and derivatives thereof. One of skill in the art would know that this definition includes, D- and L-amino acids; alpha-, beta- and gamma-amino acids; chemically modified amino acids; naturally occurring non-proteogenic amino acids; rare amino acids; and chemically synthesized compounds that have properties known in the art to be characteristic of an amino acid. Additionally, each embodiment can include any combinations of the groups.

Furthermore, as used herein, the term "amino acid" includes a compound or molecule which departs from the structure of the naturally occurring amino acids, but which have substantially the structure of an amino acid, such that they can be used for substitution of the naturally-occurring amino acids within a peptide, after which the peptide's activity, e.g., aggregate forming activity, is still retained. Thus, for example, in some embodiments amino acids can also include amino acids having side chain modifications or substitutions, and also include related organic acids, amides or the like. Without limitation, an amino acid can be a proteogenic or non-proteogenic amino acid. As used herein, the term "proteogenic" indicates that the amino acid can be incorporated into a protein in a cell through well-known metabolic pathways.

In some embodiments, an amphiphilic peptide comprises at least one (e.g., 1, 2, 3, 4, 5, 6, 7, 8, 9, 10, 11, 12, 13, 14, 15, or more) chemically modified amino acid. As used herein, the term "chemically modified amino acid" refers to an amino acid that has been treated with one or more reagents. A chemically modified amino acid can be present at any position in the amphiphilic peptide. When more than one chemically modified amino acids are present, they can be positioned next to or not next to each other. When three or more chemically modified amino acids are present some of the chemically modified amino acids can be present next to each other while some of the chemically modified amino are not next to another chemically modified amino acid.

In some embodiments, the hydrophilic peptidyl segment comprises a chemically modified amino acid. Without limitations, the chemically modified amino acid can be present at any position of the hydrophilic peptidyl segment, for example, reading from the N-terminal, at position 1, 2, 3, 4, 5, 6, 7, 8, 9, 10, and so on of the hydrophilic peptidyl segment.

In some embodiments, the hydrophobic peptidyl segment comprises a chemically modified amino acid. Without limitations, the chemically modified amino acid can be present at any position of the hydrophobic peptidyl segment, for example, reading from the N-terminal, at position 1, 2, 3, 4, 5, 6, 7, 8, 9, 10, and so on of the hydrophobic peptidyl segment.

In some embodiments, both the hydrophilic and hydrophobic peptidyl segments can each comprise at least one chemically modified amino acid. When both the hydrophilic and hydrophobic peptidyl segments comprise a chemically modified amino acid, the number of such chemically modified amino acids present in each segment can be the same or different.

In some embodiments, the amphiphilic peptide comprises at least one (e.g., 1, 2, 3, 4, 5, 6, 7, 8, 9, 10 or more) beta-amino acid. When more than one beta-amino acids are present, they can be positioned next to or not next to each other. When three or more beta-amino acids are present some of the beta-amino acids can be present next to another beta-amino acid while some of the beta-amino acids are not next to another beta-amino acid.

In some embodiments, the hydrophilic peptidyl segment comprises a beta-amino acid. Without limitations, the beta-amino acid can be present at any position of the hydrophilic peptidyl segment, for example, reading from the N-terminal, at position 1, 2, 3, 4, 5, 6, 7, 8, 9, 10, and so on of the hydrophilic peptidyl segment.

In some embodiments, the hydrophobic peptidyl segment comprises a beta-amino acid. Without limitations, the beta-amino acid can be present at any position of the hydrophobic peptidyl segment, for example, reading from the N-terminal, at position 1, 2, 3, 4, 5, 6, 7, 8, 9, 10, and so on of the hydrophobic peptidyl segment.

In some embodiments, both the hydrophilic and hydrophobic peptidyl segments can each comprise at least one beta-amino acid. When both the hydrophilic and hydrophobic peptidyl segments comprise a beta-amino acid, the number of such beta-amino acids in each segment can be the same or different.

Exemplary beta-amino acids include, but are not limited to, L-β-Homoproline hydrochloride; (±)-3-(Boc-amino)-4-(4-biphenylyl)butyric acid; (±)-3-(Fmoc-amino)-2-phenylpropionic acid; (1S,3R)-(+)-3-(Boc-amino)cyclopentanecarboxylic acid; (2R,3R)-3-(Boc-amino)-2-hydroxy-4-phenylbutyric acid; (2S,3R)-3-(Boc-amino)-2-hydroxy-4-phenylbutyric acid; (R)-2-[(Boc-amino)methyl]-3-phenylpropionic acid; (R)-3-(Boc-amino)-2-methylpropionic acid; (R)-3-(Boc-amino)-2-phenylpropionic acid; (R)-3-(Boc-amino)-4-(2-naphthyl)butyric acid; (R)-3-(Boc-amino)-5-phenylpentanoic acid; (R)-3-(Fmoc-amino)-4-(2-naphthyl)butyric acid; (R)-(−)-Pyrrolidine-3-carboxylic acid; (R)-Boc-3,4-dimethoxy-β-Phe-OH; (R)-Boc-3-(3-pyridyl)-β-Ala-OH; (R)-Boc-3-(trifluoromethyl)-β-Phe-OH; (R)-Boc-3-cyano-β-Phe-OH; (R)-Boc-3-methoxy-β-Phe-OH; (R)-Boc-3-methyl-β-Phe-OH; (R)-Boc-4-(4-pyridyl)-β-Homoala-OH; (R)-Boc-4-(trifluoromethyl)-β-Homophe-OH; (R)-Boc-4-(trifluoromethyl)-β-Phe-OH; (R)-Boc-4-bromo-β-Phe-OH; (R)-Boc-4-chloro-β-Homophe-OH; (R)-Boc-4-chloro-β-Phe-OH; (R)-Boc-4-cyano-β-Homophe-OH; (R)-Boc-4-cyano-β-Phe-OH; (R)-Boc-4-fluoro-β-Phe-OH; (R)-Boc-4-methoxy-β-Phe-OH; (R)-Boc-4-methyl-β-Phe-OH; (R)-Boc-β-Tyr-OH; (R)-Fmoc-4-(3-pyridyl)-β-Homoala-OH; (R)-Fmoc-4-fluoro-β-Homophe-OH; (S)-(+)-Pyrrolidine-3-carboxylic acid; (S)-3-(Boc-amino)-2-methylpropionic acid; (S)-3-(Boc-amino)-4-(2-naphthyl)butyric acid; (S)-3-(Boc-amino)-5-phenylpentanoic acid; (S)-3-(Fmoc-amino)-2-methylpropionic acid; (S)-3-(Fmoc-amino)-4-(2-naphthyl)butyric acid; (S)-3-(Fmoc-amino)-5-hexenoic acid; (S)-3-(Fmoc-amino)-5-phenyl-pentanoic acid; (S)-3-(Fmoc-amino)-6-phenyl-5-hexenoic acid; (S)-Boc-2-(trifluoromethyl)-β-Homophe-OH; (S)-Boc-2-(trifluoromethyl)-β-Homophe-OH; (S)-Boc-2-(trifluoromethyl)-β-Phe-OH; (S)-Boc-2-cyano-β-Homophe-OH; (S)-Boc-2-methyl-β-Phe-OH; (S)-Boc-3,4-dimethoxy-β-Phe-OH; (S)-Boc-3-(trifluoromethyl)-β-Homophe-OH; (S)-Boc-3-(trifluoromethyl)-β-Phe-OH; (S)-Boc-3-methoxy-β-Phe-OH; (S)-Boc-3-methyl-β-Phe-OH; (S)-Boc-4-(4-pyridyl)-β-Homoala-OH; (S)-Boc-4-(trifluoromethyl)-β-Phe-OH; (S)-Boc-4-bromo-β-Phe-OH; (S)-Boc-4-chloro-β-Homophe-OH; (S)-Boc-4-chloro-β-Phe-OH; (S)-Boc-4-cyano-β-Homophe-OH; (S)-Boc-4-cyano-β-Phe-OH; (S)-Boc-4-fluoro-β-Phe-OH; (S)-Boc-4-iodo-β-Homophe-OH; (S)-Boc-4-methyl-β-Homophe-OH; (S)-Boc-4-methyl-β-Phe-OH; (S)-Boc-β-Tyr-OH; (S)-Boc-γ,γ-diphenyl-β-Homoala-OH; (S)-Fmoc-2-methyl-β-Homophe-OH; (S)-Fmoc-3,4-difluoro-β-Homophe-OH; (S)-Fmoc-3-(trifluoromethyl)-β-Homophe-OH; (S)-Fmoc-3-cyano-β-Homophe-OH; (S)-Fmoc-3-methyl-β-Homophe-OH; (S)-Fmoc-γ,γ-diphenyl-β-Homoala-OH; 2-(Boc-aminomethyl) phenylacetic acid; 3-Amino-3-(3-bromophenyl)propionic acid; 3-Amino-4,4,4-trifluorobutyric acid; 3-Aminobutanoic acid; DL-3-Aminoisobutyric acid; DL-β-Aminoisobutyric acid puriss; DL-β-Homoleucine; DL-β-Homomethionine; DL-β-Homophenylalanine; DL-β-Leucine; DL-β-Phenylalanine; L-β-Homoalanine hydrochloride; L-β-Homoglutamic acid hydrochloride; L-β-Homoglutamine hydrochloride; L-β-Homohydroxyproline hydrochloride; L-β-Homoisoleucine hydrochloride; L-β-Homoleucine hydrochloride; L-β-Homolysine dihydrochloride; L-β-Homomethionine hydrochloride; L-β-Homophenylalanine allyl ester hydrochloride; L-β-Homophenylalanine hydrochloride; L-β-Homoserine; L-β-Homothreonine; L-β-Homotryptophan hydrochloride; L-β-Homotyrosine hydrochloride; L-β-Leucine hydrochloride; Boc-D-β-Leu-OH; Boc-D-β-Phe-OH; Boc-β$^3$-Homopro-OH; Boc-β-Glu(OBzl)-OH; Boc-β-Homoarg(Tos)-OH; Boc-β-Homoglu(OBzl)-OH; Boc-β-Homohyp(Bzl)-OH (dicyclohexylammonium) salt technical; Boc-β-Homolys(Z)-OH; Boc-β-Homoser(Bzl)-OH; Boc-β-Homothr(Bzl)-OH; Boc-β-Homotyr(Bzl)-OH; Boc-β-Ala-OH; Boc-β-Gln-OH; Boc-β-Homoala-OAll; Boc-β-Homoala-OH; Boc-β-Homogln-OH; Boc-β-Homoile-OH; Boc-β-Homoleu-OH; Boc-β-Homomet-OH; Boc-β-Homophe-OH; Boc-β-Homotrp-OH; Boc-β-Homotrp-OMe; Boc-β-Leu-OH; Boc-β-Lys(Z)-OH (dicyclohexylammonium) salt; Boc-β-Phe-OH; Ethyl 3-(benzylamino)propionate; Fmoc-D-β-Homophe-OH; Fmoc-L-β$^3$-homoproline; Fmoc-β-D-Phe-OH; Fmoc-β-Gln(Trt)-OH; Fmoc-β-Glu(OtBu)-OH; Fmoc-β-Homoarg(Pmc)-OH; Fmoc-β-Homogln(Trt)-OH; Fmoc-13-Homoglu(OtBu)-OH; Fmoc-β-Homohyp(tBu)-OH; Fmoc-β-Homolys(Boc)-OH; Fmoc-β-Homoser(tBu)-OH; Fmoc-β-Homothr(tBu)-OH; Fmoc-β-Homotyr(tBu)-OH; Fmoc-β-Ala-OH; Fmoc-β-Gln-OH; Fmoc-β-Homoala-OH; Fmoc-β-Homogln-OH; Fmoc-β-Homoile-OH; Fmoc-β-Homoleu-OH; Fmoc-β-Homomet-OH; Fmoc-β-Homophe-OH; Fmoc-β-Homotrp-OH; Fmoc-β-Leu-OH; Fmoc-β-Phe-OH; N-Acetyl-DL-β-phenylalanine; Z-D-β-Dab(Boc)-OH; Z-D-β-Dab(Fmoc)-OH purum; Z-DL-β-Homoalanine; Z-β-D-Homoala-OH; Z-β-Glu(OtBu)-OH technical; Z-β-Homotrp(Boc)-OH; Z-β-Ala-OH purum; Z-β-Ala-ONp purum; Z-β-Dab(Boc)-OH; Z-β-Dab(Fmoc)-OH; Z-β-Homoala-OH; β-Alanine; β-Alanine BioXtra; β-Alanine ethyl ester hydrochloride; β-Alanine methyl ester hydrochloride; β-Glutamic acid hydrochloride; cis-2-Amino-3-cyclopentene-1-carboxylic acid hydrochloride; cis-3-(Boc-amino)cyclohexanecarboxylic acid; and cis-3-(Fmoc-amino)cyclohexanecarboxylic acid.

In some embodiments, an amphiphilic peptide described herein can comprise at least one (e.g., 1, 2, 3, 4, 5, 6, 7, 8, 9, 10, 11, 12, 13, 14, 15 or more) modified amide linkage, e.g., an amide bond in the backbone replaced by a linkage selected from the group consisting of reduced psi peptide bond, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group. The amide replacement linkage can be present at any position in the amphiphilic peptide. When two or more amide replacement linkages are present, they can be positioned next to (e.g., on both sides of a given amino acid) or not next to each other (e.g., only one side of a given amino acid is linked via a peptide replacement linkage to the next amino acid).

In some embodiments, the amide replacement linkage is present in the hydrophilic peptidyl segment. Without limitations, the amide replacement linkage can be present at any position of the hydrophilic peptidyl segment, for example, reading from the N-terminal, at position 1, 2, 3, 4, 5, 6, 7, 8, 9, 10, and so on of the hydrophilic peptidyl segment.

In some embodiments, the amide replacement linkage is present in the hydrophobic peptidyl segment. Without limitations, the amide replacement linkage can be present at any position of the hydrophobic peptidyl segment, for example, reading from the N-terminal, at position 1, 2, 3, 4, 5, 6, 7, 8, 9, 10, and so on of the hydrophobic peptidyl segment.

In some embodiments, both the hydrophilic and hydrophobic peptidyl segments can each comprise at least one amide replacement linkage. When both the hydrophilic and hydrophobic peptidyl segments comprise an amide replacement linkage, the number of such amide replacement linkages in each segment can be the same or different.

The C-terminus of an amphiphilic peptide described herein can be unmodified or modified by conjugating a carboxyl protecting group or an amide group. Exemplary carboxyl protecting groups include, but are not limited to, esters such as methyl, ethyl, t-butyl, methoxymethyl, 2,2,2-trichloroethyl and 2-haloethyl; benzyl esters such as triphenylmethyl, diphenylmethyl, p-bromobenzyl, o-nitrobenzyl and the like; silyl esters such as trimethylsilyl, triethylsilyl, t-butyldimethylsilyl and the like; amides; and hydrazides. Other carboxylic acid protecting groups can include optionally protected alpha-amino acids which are linked with the amino moiety of the alpha-amino acids. In some embodiments, the C-terminus of an amphiphilic peptide is conjugated with $NH_2$, NH-alkyl, or $N(alkyl)_2$.

Linkage Between Hydrophilic and Hydrophobic Segments

Without limitations, the hydrophilic peptidyl segment can be linked to either the N-terminus or the C-terminus of the hydrophobic peptidyl segment. Accordingly, an amphiphilic peptide can be (hydrophilic peptidyl segment)-linker-(hydrophobic peptidyl segment) or (hydrophobic peptidyl segment)-linker-(hydrophilic peptidyl segment). In one embodiment, the hydrophilic peptidyl segment is linked to N-terminus of the hydrophobic peptidyl segment. Stated another way, in one embodiment, the hydrophobic peptidyl segment is linked to the C-terminus of the hydrophilic peptidyl segment. The linkage between the hydrophilic and hydrophobic peptidyl segments can be an amide linkage, an amide replacement linkage, or a linker as defined herein.

In some embodiments, the linkage between the hydrophilic and hydrophobic peptidyl segments is an amide linkage (e.g., —NHC(O)—) or an amide replacement linkage.

In some embodiments, the linkage between the hydrophilic and hydrophobic peptidyl segments includes an amino acid, two amino acids, or a peptide comprising from 3 to 15 amino acids. It is to be understood that when the hydrophilic and hydrophobic peptidyl segments are linked by a chain of amino acids, the linker can comprise one or more of the peptide modifications described herein, e.g., amide replacement linkage, beta-amino acids, D-amino acids, chemically modified amino acids etc.

Exemplary Amphiphilic Peptides and Uses Thereof.

In some embodiments, an amphiphilic peptide comprises an amino acid sequence $(L-AA^{21})_{f'}-((L-AA^{11})-(D-AA^{12}))_{b'}-(L-AA^{13})$, wherein $AA^{21}$ is a Lys residue or a substitution thereof; $AA^{11}$ and $AA^{13}$ is each independently a Trp residue or a substitution thereof, $AA^{12}$ is a Leu residue or a substitution thereof, and wherein f' is an integer from 3-21 and b' is an integer from 3-20, and wherein at least one of N-terminus amino group or a side chain amino group of at least one $AA^{21}$ residue is conjugated with a nitrogen- or amino-protecting group.

The term "substitution" when referring to a peptide, refers to a change in an amino acid for a different entity, for example another amino acid or amino-acid moiety. Substitutions can be conservative or non-conservative substitutions. In some embodiments, the substitution is a conservative substitution. As used herein, the term "conservative substitution" refers to an amino acid substitution in which the substituted amino acid residue is of similar charge, and/or similar hydrophobicity as the replaced residue. The substituted residue can be of similar size as, or smaller size or larger size than, the replaced residue, provided that the substituted residue has similar biochemical properties as the replaced residue. Conservative substitutions of amino acids include, but are not limited to, substitutions made amongst amino acids within the following groups: (i) the small non-polar amino acids: alanine (Ala), methionine (Met), isoleucine (Ile), leucine (Leu), and valine (Val); (ii) the small polar amino acids: glycine (Gly), serine (Ser), threonine (Thr) and cysteine (Cys); (iii) the amido amino acids: glutamine (Gln) and asparagine (Asn); (iv) the aromatic amino acids: phenylalanine (Phe), tyrosine (Tyr) and tryptophan (Trp); (v) the basic amino acids: lysine (Lys), arginine (Arg) and histidine (His); and (vi) the acidic amino acids: glutamine acid (Glu) and aspartic acid (Asp). Substitutions which are charge-neutral and which replace a residue with a smaller residue can also be considered "conservative substitutions" even if the residues are in different groups (e.g., replacement of phenylalanine with the smaller isoleucine). The term "conservative substitution" also encompasses the use of amino acid mimetics, analogs, variants, or non-proteinogenic or non-standard amino acid. By way of example only, AdaA or AdaG can be substituted for valine (Val); L-I-thioazolidine-4-carboxylic acid or D- or -L-1-oxazolidine-4-carboxylic acid (See Kauer, U.S. Pat. No. 4,511,390) can be substituted for proline; and Aib, β-Ala, or Acp can be substituted for glycine (Gly).

Accordingly, in some embodiments, $AA^{21}$ can be a Lys residue, or a conservative substitution thereof, e.g., Arg or His. In one embodiment, $AA^{21}$ is a Lys residue or a derivative thereof.

In some embodiments, $AA^{11}$ and $AA^{13}$ can each be independently a Trp residue, or a conservative substitution thereof, e.g., Phe, or Tyr. In one embodiment, $AA^{11}$ and $AA^{13}$ is each independently a Trp residue or a derivative thereof.

In some embodiments, $AA^{12}$ can be a Leu residue, or a conservative substitution thereof, e.g., Ala, Met, Ile, or Val. In one embodiment, $AA^{12}$ is a Leu residue or a derivative thereof.

In some embodiments, an amphiphilic peptide comprises an amino acid sequence $(L-Lys)_{r'}-((L-Trp)-(D-Leu))_{m'}-(L-Trp)$ (SEQ ID NO: 16), wherein r' is an integer from 3-21 and m' is an integer from 3-20, and wherein at least one of N-terminus amino group or a side chain amino group of at least one Lys residue is conjugated with a nitrogen- or amino-protecting group.

In some embodiment, r' and m' are independently 3, 4, 5, 6, 7, 8, 9, 10, 11, 12, 13, 14, or 15. In some embodiments, both of r' and m' are the same. In one embodiment, both r' and m' are 3.

In some embodiments, the amphiphilic peptide comprises the amino acid sequence selected from the group consisting of: Ac-(L-Lys(Ac))-(L-Lys(Ac))-(L-Lys(Ac))-((L-Trp)-(D-Leu))$_3$-(L-Trp)-NH$_2$ (SEQ ID NO: 17) (also referred to as CD3ac herein, wherein the abbreviation "ac" or "Ac" refers to acetylation of either N-terminus amino group of an amphiphilic peptide or an amino group of a Lys residue in the hydrophilic peptidyl segment); Ac-(L-Lys)-(L-Lys)-(L-Lys)-((L-Trp)-(D-Leu))$_3$-(L-Trp)-NH$_2$ (SEQ ID NO: 18); (L-Lys)-(L-Lys)-(L-Lys(Ac))-((L-Trp)-(D-Leu))$_3$-(L-Trp)-NH$_2$ (SEQ ID NO: 19); (L-Lys)-(L-Lys(Ac))-(L-Lys)-((L-Trp)-(D-Leu))$_3$-(L-Trp)-NH$_2$ (SEQ ID NO: 20); (L-Lys(Ac))-(L-Lys)-(L-Lys)-((L-Trp)-(D-Leu))$_3$-(L-Trp)-NH$_2$ (SEQ ID NO: 21); (L-Lys)-(L-Lys(Ac))-(L-Lys(Ac))-((L-Trp)-(D-Leu))$_3$-(L-Trp)-NH$_2$ (SEQ ID NO: 22); (L-Lys(Ac))-(L-Lys)-(L-Lys(Ac))-((L-Trp)-(D-Leu))$_3$-(L-Trp)-NH$_2$ (SEQ ID NO: 23); (L-Lys(Ac))-(L-Lys(Ac))-(L-Lys)-((L-Trp)-(D-Leu))$_3$-(L-Trp)-NH$_2$ (SEQ ID NO: 24); (L-Lys(Ac))-(L-Lys(Ac))-(L-Lys(Ac))-((L-Trp)-(D-Leu))$_3$-(L-Trp)-NH$_2$ (SEQ ID NO: 25); Ac-(L-Lys(Ac))-(L-Lys(Ac))-(L-Lys(Ac))-((L-Trp)-(D-Leu))$_3$-(L-Trp)-NH$_2$ (SEQ ID NO: 26); Ac-(L-Lys)-(L-Lys)-(L-Lys)-((L-Trp)-(D-Leu))$_3$-(L-Trp) (SEQ ID NO: 27); (L-Lys)-(L-Lys)-(L-Lys(Ac))-((L-Trp)-(D-Leu))$_3$-(L-Trp) (SEQ ID NO: 28); (L-Lys)-(L-Lys(Ac))-(L-Lys)-((L-Trp)-(D-Leu))$_3$-(L-Trp) (SEQ ID NO: 29); (L-Lys(Ac))-(L-Lys)-(L-Lys)-((L-Trp)-(D-Leu))$_3$-(L-Trp) (SEQ ID NO: 30); (L-Lys)-(L-Lys(Ac))-(L-Lys(Ac))-((L-Trp)-(D-Leu))$_3$-(L-Trp) (SEQ ID NO: 31); (L-Lys(Ac))-(L-Lys)-(L-Lys(Ac))-((L-Trp)-(D-Leu))$_3$-(L-Trp) (SEQ ID NO: 32); (L-Lys(Ac))-(L-Lys(Ac))-(L-Lys)-((L-Trp)-(D-Leu))$_3$-(L-Trp) (SEQ ID NO: 33); (L-Lys(Ac))-(L-Lys(Ac))-(L-Lys(Ac))-((L-Trp)-(D-Leu))$_3$-(L-Trp) (SEQ ID NO: 34); Ac-(L-Lys)-(L-Lys)-(L-Lys(Ac))-((L-Trp)-(D-Leu))$_3$-(L-Trp)-NH$_2$ (SEQ ID NO: 35); Ac-(L-Lys)-(L-Lys(Ac))-(L-Lys)-((L-Trp)-(D-Leu))$_3$-(L-Trp)-NH$_2$ (SEQ ID NO: 36); Ac-(L-Lys(Ac))-(L-Lys)-(L-Lys)-((L-Trp)-(D-Leu))$_3$-(L-Trp)-NH$_2$ (SEQ ID NO: 37); Ac-(L-Lys)-(L-Lys(Ac))-(L-Lys(Ac))-((L-Trp)-(D-Leu))$_3$-(L-Trp)-NH$_2$ (SEQ ID NO: 38); Ac-(L-Lys(Ac))-(L-Lys)-(L-Lys(Ac))-((L-Trp)-(D-Leu))$_3$-(L-Trp)-NH$_2$ (SEQ ID NO: 39); Ac-(L-Lys(Ac))-(L-Lys(Ac))-(L-Lys)-((L-Trp)-(D-Leu))$_3$-(L-Trp)-NH$_2$ (SEQ ID NO: 40); Ac-(L-Lys)-(L-Lys)-(L-Lys(Ac))-((L-Trp)-(D-Leu))$_3$-(L-Trp) (SEQ ID NO: 41); Ac-(L-Lys)-(L-Lys(Ac))-(L-Lys)-((L-Trp)-(D-Leu))$_3$-(L-Trp) (SEQ ID NO: 42); Ac-(L-Lys(Ac))-(L-Lys)-(L-Lys)-((L-Trp)-(D-Leu))$_3$-(L-Trp) (SEQ ID NO: 43); Ac-(L-Lys)-(L-Lys(Ac))-(L-Lys(Ac))-((L-Trp)-(D-Leu))$_3$-(L-Trp) (SEQ ID NO: 44); Ac-(L-Lys(Ac))-(L-Lys)-(L-Lys(Ac))-((L-Trp)-(D-Leu))$_3$-(L-Trp) (SEQ ID NO: 45); Ac-(L-Lys(Ac))-(L-Lys(Ac))-(L-Lys)-((L-Trp)-(D-Leu))$_3$-(L-Trp) (SEQ ID NO: 46); Ac-(L-Lys(Ac))-(L-Lys(Ac))-(L-Lys(Ac))-((L-Trp)-(D-Leu))$_3$-(L-Trp) (SEQ ID NO: 47); and any combinations thereof.

In some embodiments, the hydrophilic peptidyl segment of the amphiphilic peptide can comprise a cysteine. In some embodiments, the cysteine can be present on the N-terminus of the hydrophilic peptidyl segment.

The inventor has discovered that some embodiments of the amphiphilic peptides described herein can have cell penetration ability. Thus, in some embodiments, amphiphilic peptides described herein can be used as cell penetration and/or transfection agents. In these embodiments, the amphiphilic peptides can be designed to be positively-charged. Accordingly, use of a composition comprising a positively-charged amphiphilic peptide as a cell-penetrating agent or transfection agent is provided herein, wherein the positive-charged amphiphilic peptide comprises a hydrophobic peptidyl segment and a hydrophilic peptidyl segment. The hydrophobic peptidyl segment of the positive-charged amphiphilic peptide comprises an amino acid sequence of (Trp-Leu)$_m$-(Trp)$_n$ (SEQ ID NO: 7) or (Leu-Trp)$_p$-(Leu)$_q$ (SEQ ID NO: 8), wherein each Trp is D-Trp or L-Trp and each Leu is D-Leu or L-Leu, m and p are independently an integer from 1 to 5, and n and q are independently 0 or 1, provided that when Trp is D-Trp then Leu is L-Leu, and when Trp is L-Trp then Leu is D-Leu, or vice versa; while the hydrophilic peptidyl segment comprises an amino acid sequence of (Lys)$_r$ (SEQ ID NO: 9), wherein r is an integer from 1 to 15. Additionally, in the positively-charged amphiphilic peptide, at least one of the Lys residues or the N-terminus amino group of the amphiphilic peptide is not acetylated. In some embodiments, all of the Lys residues and the N-terminus amino group of the positively-charged amphiphilic peptide are not acetylated.

In some embodiments, the positively-charged amphiphilic peptide can comprise an amino acid sequence of (L-Lys)-(L-Lys)-(L-Lys)-(L-Trp)-(D-Leu)-(L-Trp)-(D-Leu)-(L-Trp)-(D-Leu)-(L-Trp)-X (SEQ ID NO: 10), wherein X is absent or NH$_2$.

In some embodiments, the composition can further comprise a nucleic acid molecule or oligonucleotide (e.g., DNA or RNA) to be delivered into a cell. In some embodiments, the composition can further comprise a plurality (e.g., at least 2 or more) of nucleic acid molecules or oligonucleotides (e.g., DNA or RNA including, but not limited to, siRNA, shRNA, miRNA). In some embodiments, the nucleic acid molecules or oligonucleotides can be designed for use in therapeutic intervention, e.g., gene therapy or siRNA therapy.

Peptide Synthesis

The amphiphilic peptides described herein can be synthesized according to the usual methods of solution and solid phase peptide chemistry, or by classical methods known in the art. Purification of peptides is well known in the art and can be, for example, HPLC. Methods describing useful peptide synthesis and purification methods can be found, for example, in U.S. Pat. App. Pub. No. 20060084607, content of which is incorporated herein by reference.

Peptides described herein can be synthetically constructed by suitable known peptide polymerization techniques, such as exclusively solid phase techniques, partial solid-phase techniques, fragment condensation or classical solution couplings. For example, the peptides of the invention can be synthesized by the solid phase method using standard methods based on either t-butyloxycarbonyl (BOC) or 9-fluorenylmethoxy-carbonyl (FMOC) protecting groups. This methodology is described by G. B. Fields et al. in Synthetic Peptides: A User's Guide, W. M. Freeman & Company, New York, N.Y., pp. 77-183 (1992) and in the textbook "Solid-Phase Synthesis", Stewart & Young, Freemen & Company, San Francisco, 1969, and are exemplified by the disclosure of U.S. Pat. No. 4,105,603, issued Aug. 8, 1979. Classical solution synthesis is described in detail in "Methoden der Organischen Chemic (Houben-Weyl): Synthese von Peptiden", E. Wunsch (editor) (1974) Georg Thieme Verlag, Stuttgart West Germany. The fragment condensation method of synthesis is exemplified in U.S. Pat. No. 3,972,859. Other available syntheses are exemplified in U.S. Pat. No. 3,842,067, U.S. Pat. No. 3,872,925, issued Jan. 28, 1975, Merrifield B, Protein Science (1996), 5: 1947-1951; The chemical synthesis of proteins; Mutter M, Int J Pept Protein Res 1979 March; 13 (3): 274-7 Studies on the coupling rates in liquid-phase peptide synthesis using competition experiments; and Solid Phase Peptide Synthesis in the series Methods in Enzymology (Fields, G. B. (1997) Solid-Phase Peptide Synthesis. Academic Press, San Diego. #9830). Content of all of the foregoing disclosures is incorporated herein by reference.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic inhibitor.

Modifications of peptides to produce peptide mimetics are described, for example, in U.S. Pat. No. 5,643,873 and No. 5,654,276, content of both of which is incorporated herein by reference.

Peptide Mimetics

In some embodiment, the amphiphilic peptide is a peptide mimetic. For example, the hydrophilic peptide segment can be peptide mimetic, the hydrophobic peptidyl segment can be a peptide mimetic, or both can be peptide mimetics.

Methods of designing peptide mimetics and screening of functional peptide mimetics are well known to those skilled in the art. One basic method of designing a molecule which mimics a known protein or peptide is first to identify the active region(s) of the known protein (for example, in the case of an antibody-antigen interaction, one identifies which region(s) of the antibody that permit binding to the antigen), and then searches for a mimetic which emulates the active region. If the active region of a known protein is relatively small, it is anticipated that a mimetic will be smaller (e.g. in molecular weight) than the protein, and correspondingly easier and cheaper to synthesize. Such a mimetic could be used as a convenient substitute for the protein, as an agent for interacting with the target molecule.

Methods for preparing peptide mimetics include modifying the N-terminal amino group, the C-terminal carboxyl group, and/or changing one or more of the amide linkages in the peptide to a non-amide or a modified amide linkage. Two or more such modifications can be coupled in one peptide mimetic. Modifications of peptides to produce peptide mimetics are described, for example, in U.S. Pat. No. 5,643,873 and No. 5,654,276, content of both of which is incorporated herein by reference.

For example, Reineke et al. (1999, Nature Biotechnology, 17; 271-275, content of which is herein incorporated by reference) designed a mimic molecule which mimics a binding site of the interleukin-10 protein using a large library of short synthetic peptides, each of which corresponded to a short section of interleukin 10. The binding of each of these peptides to the target (in this case an antibody against interleukin-10) was then tested individually by an assay technique, to identify potentially relevant peptides. Phage display libraries of peptides and alanine scanning method can be used.

Other methods for designing peptide mimetics to a particular peptide or protein include those described in European Patent EP1206494, the SuperMimic program by Andrean Goede et. al. 2006 BMC Bioinformatics, 7:11; and MIMETIC program by W. Campbell et. al., 2002, Microbiology and Immunology 46:211-215. The SuperMimic program is designed to identify compounds that mimic parts of a protein, or positions in proteins that are suitable for inserting mimetics. The application provides libraries that contain peptidomimetic building blocks on the one hand and protein structures on the other. The search for promising peptidomimetic linkers for a given peptide is based on the superposition of the peptide with several conformers of the mimetic. New synthetic elements or proteins can be imported and used for searching. The MIMETIC computer program, which generates a series of peptides for interaction with a target peptide sequence is taught by W. Campbell et. al., 2002. In depth discussion of the topic is reviewed in "Peptide Mimetic Design with the Aid of Computational Chemistry" by James R. Damewood Jr. in Reviews in Computational Chemistry Reviews in Computational Chemistry, January 2007, Volume 9 Book Series: Reviews in Computational Chemistry, Editor(s): Kenny B. Lipkowitz, Donald B. BoydPrint ISBN: 9780471186397 ISBN: 9780470125861 Published by John Wiley &Sons, Inc.; and in T. Tselios, et. al., Amino Acids, 14: 333-341, 1998. Content of all of the references described in this paragraph is herein incorporated by reference.

Methods for preparing libraries containing diverse populations of peptides, peptoids and peptidomimetics are well known in the art and various libraries are commercially available (see, for example, Ecker and Crooke, Biotechnology 13:351-360 (1995), and Blondelle et al., Trends Anal. Chem. 14:83-92 (1995), and the references cited therein, each of which is incorporated herein by reference; see, also, Goodman and Ro, Peptidomimetics for Drug Design, in "Burger's Medicinal Chemistry and Drug Discovery" Vol. 1 (ed. M. E. Wolff; John Wiley & Sons 1995), pages 803-861, and Gordon et al., J. Med. Chem. 37:1385-1401 (1994), each of which is incorporated herein by reference). One skilled in the art understands that a peptide can be produced in vitro directly or can be expressed from a nucleic acid, which can be produced in vitro. Methods of synthetic peptide and nucleic acid chemistry are well known in the art. Content of all of the references described in this paragraph is herein incorporated by reference.

A library of peptide molecules also can be produced, for example, by constructing a cDNA expression library from mRNA collected from a tissue of interest. Methods for producing such libraries are well known in the art (see, for example, Sambrook et. al., Molecular Cloning: A laboratory manual (Cold Spring Harbor Laboratory Press 1989), which is incorporated herein by reference). Preferably, a peptide encoded by the cDNA is expressed on the surface of a cell or a virus containing the cDNA.

Ligands and Active Agents

A wide variety of entities, e.g., ligands, can be coupled to an amphiphilic peptide described herein or a peptide particle described later. Ligands can include naturally occurring molecules, or recombinant or synthetic molecules. In some embodiments, a ligand can alter the distribution, targeting or lifetime of an amphiphilic peptide described herein or a peptide particle made therefrom. In some embodiments, a ligand can provide an enhanced affinity (e.g., increased binding strength) for a selected target, e.g., molecule, cell or cell type, compartment, e.g., a cellular or organ compartment, tissue, organ or region of the body, as, e.g., compared to a species absent such a ligand. In some embodiments, a ligand can provide an enhanced specificity of an amphiphilic peptide described herein or a peptide particle made therefrom for a selected target, as, e.g., compared to an amphiphilic peptide without such a ligand. The term "specificity" as used herein refers to the ability of an amphiphilic peptide or a peptide particle to preferentially bind to a selected target over any other entities. For example, the presence of a ligand on an amphiphilic peptide and/or a peptide particle described herein can enable the amphiphilic peptide or peptide particle to preferentially bind to a selected target over any other entities, as compared to an amphiphilic peptide or peptide particle without such a ligand.

Without limitation, a ligand can be selected from the group consisting of polymers, peptides, polypeptides, proteins, peptidomimetics, glycoproteins, lectins, nucleosides, nucleotides, nucleic acids, monosaccharides, disaccharides, trisaccharides, oligosaccharides, polysaccharides, lipopolysaccharides, vitamins, lipids, steroids, hormones, cofactors, receptors, receptor ligands, and any combinations thereof.

In some embodiments of this and other aspects described herein, the ligand is selected from the group consisting of polyethylene glycol (PEG, e.g., PEG-2K, PEG-5K, PEG-10K, PEG-12K, PEG-15K, PEG-20K, PEG-40K), MPEG, [MPEG]$_2$, poly (ethylene oxide) (PEO), poly(propylene glycol) (PPG), poly (ethylene oxide-co-propylene oxide), hyaluronic acid, poly(2-hydroxyethyl methacrylate), heparin, polyvinyl(pyrrolidone), chondroitan sulfate, chitosan, glucosaminoglucans, dextran, dextrin, dextran sulfate, cellulose acetate, carboxymethyl cellulose, hydroxyethyl cellulose, cellulosics, poly(trimethylene glycol), poly(tetramethylene glycol), polypeptides, polyacrylamide, polyacrylimide, poly (ethylene amine), poly(allyl amine), styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyvinyl alcohol (PVA), polyurethane, poly(2-ethylacryllic acid), N-isopropylacrylamide polymers, polyphosphazine, polyethylenimine, spermine, spermidine, polyamine, pseudopeptide-polyamine, peptidomimetic polyamine, dendrimer polyamine, arginine, amidine, protamine, thyrotropin, melanotropin, lectin, surfactant protein A, mucin, transferrin, bisphosphonate, polyglutamate, polyaspartate, an aptamer, asialofetuin, hyaluronan, procollagen, insulin, transferrin, albumin, acridines, cross-psoralen, mitomycin C, TPPC4, texaphyrin, Sapphyrin, polycyclic aromatic hydrocarbons (e.g., phenazine, dihydrophenazine), bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), RGD peptide, radiolabeled markers, haptens, naproxen, aspirin, dinitrophenyl, HRP, AP, lectins, vitamin A, vitamin E, vitamin K, vitamin B, folic acid, B12, riboflavin, biotin, pyridoxal, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, GalNAc, galactose, mannose, mannose-6P, clusters of sugars such as GalNAc cluster, mannose cluster, galactose cluster, an aptamer, integrin receptor ligands, chemokine receptor ligands, serotonin receptor ligands, PSMA, endothelin, GCPII, somatostatin, bacterial cell wall permeating peptide, GALA peptide, EALA peptide, INF-7 peptide, Inf HA-2 peptide, diINF-7 peptide, diINF-3peptide, GLF peptide, GALA-INF3 peptide, INF-5 peptide, penetratin peptide, Tat fragment 48-60, PVEC peptide, transportan peptide, LL-37 peptide, cecropin P1 peptide, α-defensin peptide, β-defensin peptide, PR-39 peptide, indolicidin peptide, RFGF peptide, RFGF analogue, bactenecin, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, caerins, and any combinations thereof.

In some embodiments, a ligand can include an active agent. As used herein, an "active agent" refers to a molecule that is to be delivered to a cell. Accordingly, without limitation, an active agent can be selected from the group consisting of small organic or inorganic molecules, monosaccharides, disaccharides, trisaccharides, oligosaccharides, polysaccharides, biological macromolecules, e.g., peptides, proteins, peptide analogs and derivatives thereof, peptidomimetics, nucleic acids, nucleic acid analogs and derivatives, polynucleotides, oligonucleotides, enzymes, an extract made from biological materials such as bacteria, plants, fungi, or animal cells or tissues, naturally occurring or synthetic compositions, particulates, or any combinations thereof. An active agent can be charge neutral or comprise a net charge, e.g., active agent is anionic or cationic. Furthermore, an active agent can be hydrophobic, hydrophilic, or amphiphilic. In some embodiments, the active agent comprises at least one aryl or heteroaryl group.

As used herein, the term "particulate" refers to a particle, powder, flake, etc., that inherently exists in a relatively small form and may be formed by, for example, grinding, shredding, fragmenting, pulverizing, atomizing, or otherwise subdividing a larger form of the material into a relatively small form.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is highly preferred that a small molecule have a molecular mass equal to or less than 700 Daltons.

In some embodiments, the active agent can be a peptide or a protein. As used herein, the term "peptide" is used in its broadest sense to refer to compounds containing two or more amino acids, amino acid equivalents or other non-amino groups joined to each other by peptide bonds or modified peptide bonds. Peptide equivalents can differ from conventional peptides by the replacement of one or more amino acids with related organic acids (such as PABA), amino acids or the like or the substitution or modification of side chains or functional groups. A peptide can be of any size so long; however, in some embodiments, peptides having twenty or fewer total amino acids are preferred. Additionally, the peptide can be linear or cyclic. Peptide sequences specifically recited herein are written with the amino terminus on the left and the carboxy terminus on the right. In addition, the term "peptide" broadly includes proteins, which generally are polypeptides. As used herein, the term "protein" is used to describe proteins as well as fragments thereof. Thus, any chain of amino acids that exhibits a three dimensional structure is included in the term "protein", and protein fragments are accordingly embraced.

A peptidomimetic is a molecule capable of folding into a defined three-dimensional structure similar to a natural peptide.

As used herein, the term "nucleic acid" refers to a polymers (polynucleotides) or oligomers (oligonucleotides) of nucleotide or nucleoside monomers consisting of naturally occurring bases, sugars and intersugar linkages. The term "nucleic acid" also includes polymers or oligomers comprising non-naturally occurring monomers, or portions thereof, which function similarly. Such modified or substituted nucleic acids are often preferred over native forms because of properties such as, for example, enhanced cellular uptake and increased stability in the presence of nucleases.

A nucleic acid can be single-stranded or double-stranded. A single-stranded nucleic acid can have double-stranded regions and a double-stranded nucleic acid can have single-stranded regions. Exemplary nucleic acids include, but are not limited to structural genes, genes including control and termination regions, self-replicating systems such as viral or plasmid DNA, single-stranded and double-stranded siRNAs and other RNA interference reagents (RNAi agents or iRNA agents), short-hairpin RNAs (shRNA), antisense oligonucleotides, ribozymes, microRNAs, microRNA mimics, aptamers, antimirs, antagomirs, triplex-forming oligonucleotides, RNA activators, immuno-stimulatory oligonucleotides, and decoy oligonucleotides.

In some embodiments, the active agent is biologically active or has biological activity. As used herein, the term "biological activity" or "bioactivity" refers to the ability of a compound to affect a biological sample. Biological activity can include, without limitation, elicitation of a stimulatory, inhibitory, regulatory, toxic or lethal response in a biological assay at the molecular, cellular, tissue or organ levels. For example, a biological activity can refer to the ability of a compound to exhibit or modulate the effect/activity of an enzyme, block a receptor, stimulate a receptor, modulate the expression level of one or more genes, modulate cell proliferation, modulate cell division, modulate cell morphology, or any combination thereof. In some instances, a biological activity can refer to the ability of a compound to produce a toxic effect in a biological sample, or it can refer to an ability to chemical modify a target molecule or cell.

In some embodiments the active agent is a therapeutic agent. As used herein, the term "therapeutic agent" refers to a biological or chemical agent used for treatment, curing, mitigating, or preventing deleterious conditions in a subject. The term "therapeutic agent" also includes substances and agents for combating a disease, condition, or disorder of a subject, and includes drugs, diagnostics, and instrumentation. "Therapeutic agent" also includes anything used in medical diagnosis, or in restoring, correcting, or modifying physiological functions. The terms "therapeutic agent" and "pharmaceutically active agent" are used interchangeably herein.

A therapeutic agent can be selected according to the treatment objective and biological action desired. Thus, a therapeutic agent can be selected from any class suitable for the therapeutic objective. Further, the therapeutic agent may be selected or arranged to provide therapeutic activity over a period of time.

Exemplary pharmaceutically active compound include, but are not limited to, those found in *Harrison's Principles of Internal Medicine*, 13$^{th}$ Edition, Eds. T. R. Harrison McGraw-Hill N.Y., NY; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

Exemplary pharmaceutically active agents include, but are not limited to, steroids and nonsteroidal anti-inflammatory agents, antirestenotic drugs, antimicrobial agents, angiogenic factors, calcium channel blockers, thrombolytic agents, antihypertensive agents, anti-coagulants, antiarrhythmic agents, cardiac glycosides, and the like.

In some embodiments, the therapeutic agent is selected from the group consisting of salicylic acid and derivatives (aspirin), para-aminophenol and derivatives (acetaminophen), arylpropionic acids (ibuprofen), corticosteroids, histamine receptor antagonists and bradykinin receptor antagonists, leukotriene receptor antagonists, prostaglandin receptor antagonists, platelet activating factor receptor antagonists, sulfonamides, trimethoprim-sulfamethoxazole, quinolones, penicillins, cephalosporin, basic fibroblast growth factor (FGF), acidic fibroblast growth factor, vascular endothelial growth factor, angiogenic transforming growth factor alpha and beta, tumor necrosis factor, angiopoietin, platelet-derived growth factor, dihydropyridines (e.g., nifedipine, benzothiazepines such as dilitazem, and phenylalkylamines such as verapamil), urokinase plasminogen activator, urokinase, streptokinase, angiotensin converting enzyme (ACE) inhibitors, spironolactone, tissue plasminogen activator (tPA), diuretics, thiazides, antiadrenergic agents, clonidine, propanolol, angiotensin-converting enzyme inhibitors, captopril, angiotensin receptor antagonists, losartan, calcium channel antagonists, nifedine, heparin, warfarin, hirudin, tick anti-coagulant peptide, and low molecular weight heparins such as enoxaparin, lidocaine, procainamide, encamide, flecanide, beta adrenergic blockers, propranolol, amiodarone, verpamil, diltiazem, nickel chloride, cardiac glycosides, angiotensin converting enzyme inhibitors, angiotensin receptor antagonists, nitrovasodilators, hypolipidemic agents (e.g., nicotinic acid, probucol, etc.), bile acid-binding resins (e.g., cholestyramine, and fibric acid derivatives e.g., clofibrate), HMG CoA reductase inhibitors, HMG CoA synthase inhibitors, squalene synthase inhibitors, squalene epoxidase inhibitors, statins (e.g., lovastatin, cerivastatin, fluvastatin, pravastatin, simvaststin, etc.), anti-psychotics, SSRIs, antiseizure medication, contraceptives, systemic and local analgesics (chronic pain, bone growth/remodeling factors (osteoblast/osteoclast recruiting and stimulating factors), neurotransmitters (L-DOPA, Dopamine, neuropeptides), emphysema drugs, TGF-beta), rapamycin, naloxone, paclitaxel, amphotericin, Dexamethasone, flutamide, vancomycin, phenobarbital, cimetidine, atenolol, aminoglycosides, hormones (e.g., thyrotropin-releasing hormone, p-nitrophenyl beta-cellopentaosideand luteinizing hormone-releasing hormone), vincristine, amiloride, digoxin, morphine, procainamide, quinidine, quinine, ranitidine, triamterene, trimethoprim, vancomycin, aminoglycosides, and penicillin, and pharmaceutically acceptable salts thereof.

In some embodiments, the active agent is a siRNA, a short-hairpin RNA (shRNA), an antisense oligonucleotide, a ribozyme, a microRNA, a microRNA mimic, an aptamer, an antimir, an antagomir, a triplex-forming oligonucleotide, a RNA activator, an immunostimulatory oligonucleotide, a decoy oligonucleotide, a plasmid, or a DNA vector.

In some embodiments, the therapeutic agent is a radioactive material. Suitable radioactive materials include, for example, of $^{90}$yttrium, $^{912}$iridium, $^{198}$gold, $^{125}$iodine, $^{137}$cesium, $^{60}$cobalt, $^{55}$cobalt, $^{56}$cobalt, $^{57}$cobalt, $^{57}$magnesium, $^{55}$iron, $^{32}$phosphorous, $^{90}$strontium, $^{81}$rubidium, $^{206}$bismuth, $^{67}$gallium, $^{77}$bromine, $^{129}$cesium, $^{73}$selenium, $^{72}$selenium, $^{72}$arsenic, $^{103}$palladium, $^{123}$lead, $^{111}$Indium, $^{52}$iron, $^{167}$thulium, $^{57}$nickel, $^{62}$zinc, $^{62}$copper, $^{201}$thallium and $^{123}$iodine.

Without wishing to be bound by a theory, particles comprising a radioactive material can be used to treat diseased tissue such as tumors, arteriovenous malformations, and the like. In some embodiments, the active agent is an imaging agent. As used herein, the term "imaging agent" refers to an element or functional group in a molecule that allows for the detection, imaging, and/or monitoring of the presence and/or progression of a condition(s), pathological disorder(s), and/or disease(s). The imaging agent may be an echogenic substance (either liquid or gas), non-metallic isotope, an optical reporter, a boron neutron absorber, a paramagnetic metal ion, a ferromagnetic metal, a gamma-emitting radioisotope, a positron-emitting radioisotope, or an x-ray absorber. Without wishing to be bound by a theory, an imaging agent allows tracking of a composition comprising such an imaging agent.

Suitable optical reporters include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound.

Suitable fluorescent reporters include xanthene dyes, such as fluorescein or rhodamine dyes, including, but not limited to, Alexa Fluor® dyes (InvitrogenCorp.; Carlsbad, Calif.), fluorescein, fluorescein isothiocyanate (FITC), Oregon Green™, rhodamine, Texas red, tetrarhodamine isothiocynate (TRITC), 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N,N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylamino-naphthyl-5-sulfonate,1-anilino-8-naphthalene sulfonate, 2-p-toluidinyl-6-naphthalene sulfonate, and 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p(2-benzoxazolyl)phenyl)maleimide; cyanines, such as Cy2, indodicarbocyanine 3 (Cy3), indodicarbocyanine 5 (Cy5), indodicarbocyanine 5.5 (Cy5.5), 3-(-carboxy-pentyl)-3'ethyl-5,5'-dimethyloxacarbocyanine (CyA); 1H,5H,11H,15H-Xantheno[2,3,4-ij:5,6,7-i'j']diquinolizin-18-ium, 9-[2 (or 4)-[[[6-[2,5-dioxo-1-pyrrolidinyl)oxy]-6-oxohexyl]amino]sulfonyl]-4(or 2)-sulfophenyl]-2,3,6,7,12,13,16, 17octahydro-inner salt (TR or Texas Red); BODIPY™ dyes; benzoxadiazoles; stilbenes; pyrenes; and the like. Many suitable forms of these fluorescent compounds are available and can be used.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al, *Mol. Microbiol*, 55:1767-1781 (2005), the GFP variant described in Crameri et al, *Nat. Biotechnol.*, 14:315319 (1996), the cerulean fluorescent proteins described in Rizzo et al, *Nat. Biotechnol*, 22:445 (2004) and Tsien, *Annu. Rev. Biochem.*, 67:509 (1998), and the yellow fluorescent protein described in Nagal et al, *Nat. Biotechnol.*, 20:87-90 (2002). DsRed variants are described in, e.g., Shaner et al, *Nat. Biotechnol.*, 22:1567-1572 (2004), and include mStrawberry, mCherry, morange, mBanana, mHoneydew, and mTangerine. Additional DsRed variants are described in, e.g., Wang et al, *Proc. Natl. Acad. Sci. U.S.A.*, 101:16745-16749 (2004) and include mRaspberry and mPlum. Further examples of DsRed variants include mRFPmars described in Fischer et al, *FEBS Lett.*, 577:227-232 (2004) and mRFPruby described in Fischer et al, *FEBS Lett*, 580:2495-2502 (2006).

Suitable echogenic gases include, but are not limited to, a sulfur hexafluoride or perfluorocarbon gas, such as perfluoromethane, perfluoroethane, perfluoropropane, perfluorobutane, perfluorocyclobutane, perfluoropentane, or perfluorohexane.

Suitable non-metallic isotopes include, but are not limited to, $^{11}$C, $^{14}$C, $^{13}$N, $^{18}$F, $^{123}$I, $^{124}$I, and $^{125}$I. Suitable radioisotopes include, but are not limited to, $^{99m}$Tc, $^{95}$Tc, $^{111}$In, $^{62}$Cu, $^{64}$Cu, Ga, $^{68}$Ga, and $^{153}$Gd. Suitable paramagnetic metal ions include, but are not limited to, Gd(III), Dy(III), Fe(III), and Mn(II). Suitable X-ray absorbers include, but are not limited to, Re, Sm, Ho, Lu, Pm, Y, Bi, Pd, Gd, La, Au, Au, Yb, Dy, Cu, Rh, Ag, and Ir. In some embodiments, the radionuclide is bound to a chelating agent or chelating agent-linker attached to the aggregate. Suitable radionuclides for direct conjugation include, without limitation, $^{18}$F, $^{124}$I, $^{125}$I, $^{131}$I, and mixtures thereof. Suitable radionuclides for use with a chelating agent include, without limitation, $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, $^{212}$Bi, and mixtures thereof. Suitable chelating agents include, but are not limited to, DOTA, BAD, TETA, DTPA, EDTA, NTA, HDTA, their phosphonate analogs, and mixtures thereof. One of skill in the art will be familiar with methods for attaching radionuclides, chelating agents, and chelating agent-linkers to the particles.

A detectable response generally refers to a change in, or occurrence of, a signal that is detectable either by observation or instrumentally. In certain instances, the detectable response is fluorescence or a change in fluorescence, e.g., a change in fluorescence intensity, fluorescence excitation or emission wavelength distribution, fluorescence lifetime, and/or fluorescence polarization. One of skill in the art will appreciate that the degree and/or location of labeling in a subject or sample can be compared to a standard or control (e.g., healthy tissue or organ). In certain other instances, the detectable response the detectable response is radioactivity (i.e., radiation), including alpha particles, beta particles, nucleons, electrons, positrons, neutrinos, and gamma rays emitted by a radioactive substance such as a radionuclide.

Specific devices or methods known in the art for the in vivo detection of fluorescence, e.g., from fluorophores or fluorescent proteins, include, but are not limited to, in vivo near-infrared fluorescence (see, e.g., Frangioni, *Curr. Opin. Chem. Biol*, 7:626-634 (2003)), the Maestro™ in vivo fluorescence imaging system (Cambridge Research & Instrumentation, Inc.; Woburn, Mass.), in vivo fluorescence imaging using a flying-spot scanner (see, e.g., Ramanujam et al, *IEEE Transactions on Biomedical Engineering*, 48:1034-1041 (2001), and the like. Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes.

Any device or method known in the art for detecting the radioactive emissions of radionuclides in a subject is suitable for use in the present invention. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled aggregate. Positron emission tomography (PET) is another suitable technique for detecting radiation in a subject.

In some embodiments, the ligand is a cell surface receptor ligand. As used herein, a "cell surface receptor ligand" refers to a molecule that can bind to the outer surface of a cell. Exemplary, cell surface receptor ligand includes, for example, a cell surface receptor binding peptide, a cell surface receptor binding glycopeptide, a cell surface receptor binding protein, a cell surface receptor binding glycoprotein, a cell surface receptor binding organic compound, and a cell surface receptor binding drug.

Cell surface receptor ligands include, but are not limited to, cytokines, growth factors, hormones, antibodies, and angiogenic factors.

In some embodiments, the cell surface receptor ligand is transferrin or EGF.

Ligands providing enhanced affinity for a selected target are also termed targeting ligands herein. As used herein, the term "targeting ligand" refers to a molecule that binds to or interacts with a target molecule. Typically the nature of the interaction or binding is noncovalent, e.g., by hydrogen, electrostatic, or van der Waals interactions, however, binding may also be covalent.

As used herein, the term "endosomolytic ligand" refers to molecules having endosomolytic properties. Endosomolytic ligands promote the lysis of and/or transport of the composition of the invention, or its components, from the cellular compartments such as the endosome, lysosome, endoplasmic reticulum (ER), golgi apparatus, microtubule, peroxisome, or other vesicular bodies within the cell, to the cytoplasm of the cell. Some exemplary endosomolytic ligands include, but are not limited to, imidazoles, poly or oligoimidazoles, linear or branched polyethyleneimines (PEIs), linear and brached polyamines, e.g. spermine, cationic linear and branched polyamines, polycarboxylates, polycations, masked oligo or poly cations or anions, acetals, polyacetals, ketals/polyketals, orthoesters, linear or branched polymers with masked or unmasked cationic or anionic charges, dendrimers with masked or unmasked cationic or anionic charges, polyanionic peptides, polyanionic peptidomimetics, pH-sensitive peptides, natural and synthetic fusogenic lipids, natural and synthetic cationic lipids.

As used herein, the terms "PK modulating ligand" and "PK modulator" refers to molecules which can modulate the pharmacokinetics of the composition of the invention. Some exemplary PK modulator include, but are not limited to, lipophilic molecules, bile acids, sterols, phospholipid analogues, peptides, protein binding agents, vitamins, fatty acids, phenoxazine, aspirin, naproxen, ibuprofen, suprofen, ketoprofen, (S)-(+)-pranoprofen, carprofen, PEGs, biotin, and transthyretia-binding ligands (e.g., tetraiidothyroacetic acid, 2, 4, 6-triiodophenol and flufenamic acid).

In some embodiments, an amphiphilic peptide comprises at least one (e.g., 1, 2, 3, 4, 5 or more) ligand conjugate. When two or more ligands are present, the ligands can all have same properties, all have different properties or some ligands have the same properties while others have different properties. For example, a ligand can have targeting properties, have endosomolytic activity or have PK modulating properties. Accordingly, the two or more ligands can be same ligand, different ligands, same type of ligand (e.g., targeting ligand, endosomolytic ligand, PK modulator), different types of ligands, or any combinations thereof. In some embodiments, all the ligands have different properties.

In some embodiments, the amphiphilic peptide comprises a hydrophilic polymer selected from the group consisting of poly(ethylene glycol), poly (ethylene oxide), poly(propylene glycol), poly (ethylene oxide-co-propylene oxide), hyaluronic acid, poly(2-hydroxyethyl methacrylate), heparin, polyvinyl(pyrrolidone), chondroitan sulfate, chitosan, glucosaminoglucans, dextran, dextrin, dextran sulfate, cellulose acetate, carboxymethyl cellulose, hydroxyethyl cellulose, cellulosics, poly(trimethylene glycol), poly(tetramethylene glycol), polypeptides, polyacrylamide, polyacrylimide, poly (ethylene amine), poly(allyl amine), and blends thereof, and wherein the hydrophilic polymer is covalently linked with the hydrophobic peptidyl segment.

Linking to Peptides

A molecule (e.g. a ligand) can be conjugated to a peptide using any of a variety of methods known to those of skill in the art. The molecule can be coupled or conjugated to the peptide covalently or non-covalently. The covalent linkage between the molecule and the peptide can be mediated by a linker. The non-covalent linkage between the molecule and the peptide can be based on ionic interactions, van der Waals interactions, dipole-dipole interactions, hydrogen bonds, electrostatic interactions, and/or shape recognition interactions.

Without limitations, ligands can be coupled to a peptide at various places, for example, N-terminus, C-terminus, and/or at an internal position (e.g., side chain of an amino acid). When two or more ligands are present, the ligand can be on opposite ends of a peptide (e.g., N-terminus and C-terminus).

Generally, the ligand is located at the terminal end (e.g., at position 1, 2, 3, 4, 5, 6, 7, 8, 9, or 10 counting from the end) that is furthest away from the hydrophobic peptidyl segment. Without wishing to be bound by a theory, this allows the ligand to be position on or near the surface of a particle formed by self-aggregation of amphiphilic peptides.

In some embodiments, a ligand is located at the terminus of hydrophilic peptidyl segment that is not linked with the hydrophobic peptidyl segment. For example, if the N-terminus of the hydrophilic peptidyl segment is linked to the hydrophobic peptidyl segment, then the ligand is located at position 1, 2, 3, 4, 5, 6, 7, 8, 9, 10 counting from C-terminus of the hydrophilic peptidyl segment. Alternatively, if the C-terminus of the hydrophilic peptidyl segment is linked to the hydrophobic peptidyl segment, then the ligand is located at position 1, 2, 3, 4, 5, 6, 7, 8, 9, 10 counting from N-terminus of the hydrophilic peptidyl segment.

In some embodiments, the ligand is attached the peptide via a linker. The ligand can be present on a monomer when said monomer is incorporated into a peptide during synthesis. In some embodiments, the ligand can be incorporated via coupling to a "precursor" monomer after said "precursor" monomer has been incorporated into the peptide. For example, a monomer having, e.g., an amino-terminated linker (i.e., having no associated ligand), e.g., monomer-linker-$NH_2$ can be incorporated into peptide. In a subsequent operation, i.e., after incorporation of the precursor monomer into the peptide a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether. In another non-limiting example, a ligand having an electrophilic group can be attached to a N-terminus, C-terminus or an internal side chain amino group. In another example, a thiol comprising ligand can be linked to a peptide by a disulfide linker when the peptide comprises a cysteine.

Linkers

As used herein, the term "linker" means an organic moiety that connects two parts of a compound. Linkers typically comprise a direct bond or an atom such as oxygen or sulfur, a unit such as NH, C(O), C(O)NH, SO, $SO_2$, $SO_2$NH, SS, or a chain of atoms, such as substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{12}$ aryl, substituted or unsubstituted $C_5$-$C_{12}$ heteroaryl, substituted or unsubstituted $C_5$-$C_{12}$ heterocyclyl, substituted or unsubstituted $C_3$-$C_{12}$ cycloalkyl, where one or more methylenes can be interrupted or terminated by O, S, S(O), $SO_2$, NH, C(O).

In some embodiments, the linker is a branched linker. The branchpoint of the branched linker may be at least trivalent, but can be a tetravalent, pentavalent or hexavalent atom, or a group presenting such multiple valencies. In some embodiments, the branchpoint is —N, —N(R)—C, —O—C, —S—C, —SS—C, —C(O)N(R)—C, —OC(O)N(R)—C, —N(R)C(O)—C, or —N(R)C(O)O—C; wherein R is independently for each occurrence H or optionally substituted alkyl. In some embodiments, the branchpoint is glycerol or derivative thereof.

In some embodiments, linker comprises a cleavable linking group. As used herein, a "cleavable linking group" is a chemical moiety which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. For example, for liver targeting, cleavable linking groups can include an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid celavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleaveable in an acidic environment with a pH of about 6.5 or lower (e.g., about 6.0, 5.5, 5.0, or lower), or by agents such as enzymes that can act as a general acid.

In addition to covalent linkages, two parts of a compound can be linked together by an affinity binding pair. The term "affinity binding pair" or "binding pair" refers to first and second molecules that specifically bind to each other. One member of the binding pair is conjugated with first part to be linked while the second member is conjugated with the second part to be linked. As used herein, the term "specific binding" refers to binding of the first member of the binding pair to the second member of the binding pair with greater affinity and specificity than to other molecules.

Exemplary binding pairs include any haptenic or antigenic compound in combination with a corresponding antibody or binding portion or fragment thereof (e.g., digoxigenin and anti-digoxigenin; mouse immunoglobulin and goat anti-mouse immunoglobulin) and nonimmunological binding pairs (e.g., biotin-avidin, biotin-streptavidin, hormone [e.g., thyroxine and cortisol-hormone binding protein, receptor-receptor agonist, receptor-receptor antagonist (e.g., acetylcholine receptor-acetylcholine or an analog thereof), IgG-protein A, lectin-carbohydrate, enzyme-enzyme cofactor, enzyme-enzyme inhibitor, and complementary oligonucleoitde pairs capable of forming nucleic acid duplexes), and the like. The binding pair can also include a first molecule which is negatively charged and a second molecule which is positively charged.

One example of using binding pair conjugation is the biotin-avidin or biotin-streptavidin conjugation. In this approach, one of the molecule or the peptide is biotinylated and the other is conjugated with avidin or streptavidin. Many commercial kits are also available for biotinylating molecules, such as proteins.

Another example of using binding pair conjugation is the biotin-sandwich method. See, e.g., example Davis et al., Proc. Natl. Acad. Sci. USA, 103: 8155-60 (2006). The two molecules to be conjugated together are biotinylated and then conjugated together using tetravalent streptavidin as a linker.

Still another example of using binding pair conjugation is double-stranded nucleic acid conjugation. In this approach, the first part to be linked is conjugated is with linked a first strand first strand of the double-stranded nucleic acid and the second part to be linked is conjugated with the second strand of the double-stranded nucleic acid. Nucleic acids can include, without limitation, defined sequence segments and sequences comprising nucleotides, ribonucleotides, deoxyribonucleotides, nucleotide analogs, modified nucleotides and nucleotides comprising backbone modifications, branchpoints and normucleotide residues, groups or bridges.

Peptide Particles

The inventor has also discovered that the amphiphilic peptides described herein undergo self-aggregation to form supramolecular aggregates. Thus, in another aspect the invention provides peptide particles comprising an amphiphilic peptide described herein. In some embodiments, the peptide particle comprises a plurality of amphiphilic peptides described herein. For example, a peptide particle can comprise at least about 2, at least about 3, at least about 4, at least about 5, at least about 6, at least about 7, at least about 8, at least about 9, at least about 10, at least about 20, at least about 25, at least about 50, at least about 75, at least about 100, at least about 150, at least about 200, at least about 250, at least about 500, at least about 750, at least about 1000, at least about 2500, at least about 5000, at least about 10,000 or more amphiphilic peptides described herein. The plurality of amphiphilic peptides present in a peptide particle can comprise one embodiment of an amphiphilic peptide described herein, or at least two different embodiments of an amphiphilic peptide described herein.

The term "particle" includes spheres; nanorods; and prisms. The peptide particles described herein differ from micelles, liposomes, and other particles that comprise a distinct shell (e.g., a lipid layer), which serves as a wall-forming material, surrounding encapsulated media located within the shell. The particles described here in are solid particles. The particles can be, e.g., monodisperse or polydisperse and the variation in diameter of the particles of a given dispersion may vary. However, because amphiphilic peptides of a uniform size can be obtained, the particles described herein generally are monodisperse. Accordingly, in some embodiments, the diameter of a particle described herein is within ±2.5%, within ±5%, within ±10%, within ±15%, within ±20%, within ±25%, within ±30%, or within ±35% of the average diameter.

In some embodiments, a peptide particle described herein is a nanoparticle. As used herein, the term "nanoparticle" refers to particles that are on the order of $10^{-9}$ or one billionth of a meter and below $10^{-6}$ or 1 millionth of a meter in size.

Generally, the peptide particles have an average diameter of from about 5 nm to about 5000 nm. In some embodiments, the particles have an average diameter of from about 50 nm to about 2500 nm. In some embodiments, the particles have an average diameter of from about 100 nm to about 2000 nm. In some embodiments, the particles have an average diameter of from about 150 nm to about 1700 nm. In some embodiments, the particles have an average diameter of from about 200 nm to about 1500 nm. In some embodiment, the particles have an average diameter of about 260 nm. In one embodiment, the particles have an average diameter of about 30 nm to about 150 nm. Without wishing to be bound by a theory, particle size can be modulated by changing the concentration of the amphiphilic peptide in the solution used for fabricating the peptide particles.

In some embodiments, a peptide particle described herein comprises a mixture of fully masked amphiphilic peptides and partially or non-masked amphiphilic peptides. As used herein a "non-masked peptide" refers to an amphiphilic peptide in which none of the N-terminus amino group and the side chain amino groups in the hydrophilic peptidyl segment is conjugated with a nitrogen- or amino-protecting group.

By changing the ratio of fully masked to partially masked or non-masked peptides, net charge of the peptide particle can be varied. Without wishing to be bound by a theory, higher ratios of fully masked peptides can increase particle stability, while higher ratios of partially and/or non-masked peptides can increase loading of molecules carrying anionic charges (e.g., nucleic acids, such as DNA or RNA including siRNA) and a higher capacity to penetrate a cell membrane.

In some embodiments, the peptide particle can comprise a fully-masked amphiphilic peptide (e.g., a fully-acetylated amphiphilic peptide). The term "fully-acetylated amphiphilic peptide" as used herein refers to an amphiphilic peptide in which all of the N-terminus amino group and the side chain amino groups in the hydrophilic peptidyl segment is acetylated.

In some embodiments, the peptide particle can comprise a mixture of fully-masked (e.g., fully-acetylated) and partially masked (e.g., partially-acetylated) peptides. As used herein, the term "partially-acetylated amphiphilic peptide" refers to an amphiphilic peptide in which at least one of the N-terminus amino group and the side chain amino groups in the hydrophilic peptidyl segment is acetylated, but not all of them. In some embodiments a partially-acetylated amphiphilic peptide can have the N-terminus amino group of the amphiphilic peptide acetylated, but not any of the side chain amino groups in the hydrophilic peptidyl segment. In some embodiments, a partially-acetylated amphiphilic peptide can have at least one (including at least two or more) of the side chain amino groups in the hydrophilic peptidyl segment acetylated, but not the N-terminus amino group of the amphiphilic peptide. In some embodiments, a partially-acetylated amphiphilic peptide can have both the N-terminus amino group of the amphiphilic peptide and at least one (including at least two or more), but not all, of the side chain amino groups in the hydrophilic peptidyl segment acetylated.

In some embodiments, the peptide particle can comprise a mixture of fully-masked (e.g., fully-acetylated) and non-masked (e.g., non-acetylated) amphiphilic peptides. As used herein, the term "non-acetylated amphiphilic peptide" refers to an amphiphilic peptide in which none of the N-terminus amino group and the side chain amino groups in the hydrophilic peptidyl segment is acetylated. In some embodiments, the peptide particle can comprise a mixture of fully-masked (e.g., fully-acetylated), partially-masked (e.g., partially-acetylated) and non-masked (e.g., non-acetylated) amphiphilic peptides.

In some embodiments, the peptide particle does not comprise a fully masked amphiphilic peptide, e.g., the particle comprises partially masked amphiphilic peptides or a mixture of partially masked peptides. In some embodiments, the peptide particle comprises a mixture of partially-masked and non-masked peptides.

Without limitations, ratio of fully-masked to partially-masked or non-masked peptides in the peptide particle can range from about 100:1 to about 1:100. In some embodiments, ratio of fully-masked to partially-masked or non-masked peptides in the peptide particle ranges from about 95:5 to about 1:1.

The particles described herein can be used for drug delivery. Thus, a wide variety of therapeutic agents can be included in the particles described herein. Accordingly, in some embodiments, a peptide particle described herein can comprise an active agent described herein. An active agent can be covalently linked with a component, e.g., amphiphilic peptide, of the peptide particle. In some embodiments, the active agent in the peptide particle described herein is not covalently linked to a component of the particle. Without limitations, the active agent can be absorbed/adsorbed on the surface of the particle, encapsulated in the particle, or distributed (homogenously or non-homogenously) throughout the particle.

Generally, any ratio of active agent to amphiphilic peptides can be present in the peptide particle described herein. Accordingly, in some embodiments, ratio of the active agent to the amphiphilic peptides ranges from about 100:1 to about 1:100,000. In some embodiments, ratio of the active agent to the amphiphilic peptides ranges from about 1:1 to about 1:100,000. In some embodiments, ratio of the active agent to the amphiphilic peptides ranges from about 1:1 to about 1:10,000. In some embodiments, ratio of the active agent to the amphiphilic peptides ranges from about 1:1 to about 1:1000. In some embodiments, ratio of the active agent to the amphiphilic peptides ranges from about 1:1 to about 1:100. In some embodiments, ratio of the active agent to the amphiphilic peptides ranges from about 1:1 to about 1:10. In some embodiments, ratio of the active agent to the amphiphilic peptides ranges from about 50:1 to about 1:500. In some embodiments, ratio of the active agent to the amphiphilic peptides ranges from about 10:1 to about 1:25.

In some embodiments, the peptide particle can comprise a ligand. Without limitations, a ligand can be covalently linked with a component, e.g., amphiphilic peptide, of the particles. In some embodiments, a ligand is not covalently linked to a component of the particle, e.g., the ligand is absorbed/adsorbed on the surface of the particle, the ligand is encapsulated in the particle, or the ligand is distributed (homogenously or non-homogenously) throughout the particle. In some embodiments, the ligand is a targeting ligand.

In some embodiments, the ligand forms a layer on the surface of the peptide particle, e.g., the ligand forms a corona around the particle. When the ligand forms a layer on the surface of particle, thickness of the layer can range from about 1 nm to about 100 nm. In some embodiments, thickness of the layer is about 10 nm.

Generally, any ratio of a ligand to amphiphilic peptides can be present in the particle. Accordingly, in some embodiments, ratio of the ligand to the amphiphilic peptides ranges from about 1000:1 to about 1:1,000,000. In some embodiments, ratio of the ligand to the amphiphilic peptides ranges from about 1:10 to about 1:1,000,000. In some embodiments, ratio of the ligand to the amphiphilic peptides ranges from about 500:1 to about 1:500. In some embodiments, ratio of the ligand to the amphiphilic peptides ranges from about 100:1 to about 1:250. In some embodiments, ratio of the ligand to the amphiphilic peptides ranges from about 1:10 to about 1:1000.

In some embodiments, a peptide particle can comprise both an active agent (e.g., a therapeutic agent) and a ligand. In some embodiments, a peptide particle can comprise an active agent (e.g., a therapeutic agent) distributed within the particle and a ligand on the outer surface of the particle.

Without limitations, different types of peptide particles can be fabricated, e.g., (1) particles formed from amphiphilic peptides only; (2) particles formed from the amphiphilic peptides to which a molecule of interest, e.g., an active agent or a ligand, absorbs/adsorbs or forms a coating on a core of amphiphilic peptides; (3) particles formed from a core formed by a molecules of interest, e.g., an active agent or a ligand, which is coated with a layer of amphiphilic peptides; (4) particles formed from amphiphilic peptides to which a molecule of interest, e.g., an active agent or a ligand, is covalently linked; (5) particles formed from a mixture of a molecule of interest (e.g., an active agent or a ligand) and amphiphilic peptides; and (6) particles formed so as to comprise a generally homogeneous mixture of a molecule of interest, e.g., an active agent or a ligand with amphiphilic peptides, or any combinations thereof. For example, a peptide particle can be formed from the amphiphilic peptides to which a first molecule of interest, e.g., an active agent or a ligand, absorbs/adsorbs or forms a coating on a core of amphiphilic peptides, wherein the core of amphiphilic peptides further comprises a second molecule of interest, e.g., an active agent. In these embodiments, the second molecule of interest can be the same as or different from the first molecule of interest.

In some embodiments, a peptide particle can further comprise a polymer, e.g., a biocompatible polymer. As used herein, the term "biocompatible" means exhibition of essentially no cytotoxicity or immunogenicity while in contact with body fluids or tissues. As used herein, the term "polymer" refers to oligomers, co-oligomers, polymers and co-polymers, e.g., random block, multiblock, star, grafted, gradient copolymers and combination thereof.

The term "biocompatible polymer" refers to polymers which are non-toxic, chemically inert, and substantially non-immunogenic when used internally in a subject and which are substantially insoluble in blood. The biocompatible polymer can be either non-biodegradable or preferably biodegradable. Preferably, the biocompatible polymer is also noninflammatory when employed in situ.

Biodegradable polymers are disclosed in the art. Examples of suitable biodegradable polymers include, but are not limited to, linear-chain polymers such as polylactides, polyglycolides, polycaprolactones, copolymers of polylactic acid and polyglycolic acid, polyanhydrides, polyepsilon caprolactone, polyamides, polyurethanes, polyesteramides, polyorthoesters, polydioxanones, polyacetals, polyketals, polycarbonates, polyorthocarbonates, polydihydropyrans, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, polymethyl methacrylate, chitin, chitosan, copolymers of polylactic acid and polyglycolic acid, poly(glycerol sebacate) (PGS), and copolymers, terpolymers, and copolymers including one or more of the foregoing. Other biodegradable polymers include, for example, gelatin, collagen, silk, chitosan, alginate, cellulose, poly-nucleic acids, etc.

Suitable non-biodegradable biocompatible polymers include, by way of example, cellulose acetates (including cellulose diacetate), polyethylene, polypropylene, polybutylene, polyethylene terphthalate (PET), polyvinyl chloride, polystyrene, polyamides, nylon, polycarbonates, polysulfides, polysulfones, hydrogels (e.g., acrylics), polyacrylonitrile, polyvinylacetate, cellulose acetate butyrate, nitrocellulose, copolymers of urethane/carbonate, copolymers of styrene/maleic acid, poly(ethylenimine), poloxomers (e.g. Pluronic such as Poloxamers 407 and 188), Hyaluron, heparin, agarose, Pullulan, and copolymers including one or more of the foregoing, such as ethylene/vinyl alcohol copolymers (EVOH).

The peptide particles can also comprise additional moieties that can extend the lifetime of the particles in vivo. For example, the peptide particles can comprise functional moieties that enhance the in vivo lifetime of the particles in the blood. One exemplary moiety for increasing the in vivo lifetime is polyethylene glycol. Accordingly, the peptide particles can comprise polyethylene glycol in addition to the amphiphilic peptide.

Additional Embodiments of Peptide Particles

In one embodiment, a peptide particle described herein comprises particular embodiments of an amphiphilic peptide described herein. The amphiphilic peptide present in this embodiment of the peptide particle comprises a hydrophobic peptidyl segment and a hydrophilic peptidyl segment, wherein the hydrophobic peptidyl segment comprises an amino acid sequence of (Trp-Leu)$_m$-(Trp)$_n$ (SEQ ID NO: 7) or (Leu-Trp)$_p$-(Leu)$_q$ (SEQ ID NO: 8), wherein each Trp is D-Trp or L-Trp and each Leu is D-Leu or L-Leu, m and p are independently an integer from 1 to 5, and n and q are independently 0 or 1, provided that when Trp is D-Trp then Leu is L-Leu, and when Trp is L-Trp then Leu is D-Leu, or vice versa; and wherein the hydrophilic peptidyl segment comprises an amino acid sequence of (Lys)$_r$ (SEQ ID NO: 9), wherein r is an integer from 1 to 15, and wherein the peptide particle further comprises on its outer surface a ligand described herein.

In some embodiments, the peptide particle can comprise one or more embodiments of an amphiphilic peptide described earlier in the "Exemplary amphiphilic peptides" section. In one embodiment, the peptide particle can comprise an amphiphilic peptide with an amino acid sequence of (L-Lys)-(L-Lys)-(L-Lys)-(L-Trp)-(D-Leu)-(L-Trp)-(D-Leu)-(L-Trp)-(D-Leu)-(L-Trp)-X (SEQ ID NO: 10), wherein X is absent or NH$_2$. As described earlier, in some embodiments, at least one of the Lys residues of the hydrophilic peptidyl segment or the N-terminus amino group of the amphiphilic peptide is acetylated. In some embodiments, all of the Lys residues of the hydrophilic peptidyl segment are acetylated. In some embodiments, the N-terminus amino group of the amphiphilic peptide and all of the Lys residues of the hydrophilic peptidyl segment are acetylated.

The ligand present on the outer surface of the peptide particle can be selected based on types of target molecules (e.g., but not limited to, cells, bacteria, proteins, and/or nucleic acids) to which the peptide particle will bind and/or interact. For example, to facilitate delivery of a peptide particle described herein to a cell, a ligand specific for the cell surface receptor can be selected, thus facilitating the uptake of the peptide particle by the cell, e.g., via endocytosis. Hence, some embodiments of the peptide particles described herein can be used for targeted delivery of any active agent described herein using the peptide particles as delivery carriers or vehicles. In one embodiment, the peptide particles can be used to deliver to a cell an active agent that is cell-impermeable when delivered by itself.

As described earlier, in some embodiments, the peptide particle can comprise a mixture of fully-masked (e.g., fully-acetylated) and partially-masked (e.g., partially-acetylated) amphiphilic peptides described herein. In those embodiments, the ratio of the fully-acetylated to the partially-masked amphiphilic peptides can range from about 95:5 to about 1:1. In certain embodiments, the particle can further comprise non-masked (e.g., non-acetylated) amphiphilic peptides.

Accordingly, a mixed peptide particle comprising a fully-acetylated amphiphilic peptide and a partially-acetylated or non-acetylated amphiphilic peptide is also provided herein. In specific embodiments, the mixed peptide particle comprises a first amphiphilic peptide and a second amphiphilic peptide, wherein the first and the second amphiphilic peptide each independently comprises a hydrophobic peptidyl segment and a hydrophilic peptidyl segment, wherein the hydrophobic peptidyl segment comprises an amino acid sequence of (Trp-Leu)$_m$-(Trp)$_n$ (SEQ ID NO: 7) or (Leu-Trp)$_p$-(Leu)$_q$ (SEQ ID NO: 8), wherein each Trp is D-Trp or L-Trp and each Leu is D-Leu or L-Leu, m and p are independently an integer from 1 to 5, and n and q are independently 0 or 1, provided that when Trp is D-Trp then Leu is L-Leu, and when Trp is L-Trp then Leu is D-Leu, or vice versa; while the hydrophilic peptidyl segment comprises an amino acid sequence of (Lys)$_r$ (SEQ ID NO: 9), wherein r is an integer from 1 to 15. Additionally, the N-terminus amino group and all of the Lys residues of the first amphiphilic peptide are acetylated; while at least the N-terminus amino group or one of the Lys residues of the second amphiphilic peptide is not acetylated. In some embodiments, none of the N-terminus amino group and the Lys residues of the second amphiphilic peptide is acetylated.

In some embodiments, the mixed peptide particle can comprise a plurality (e.g., at least 2, at least 3, at least 4, at least 5, or more) of the first amphiphilic peptides and a plurality (e.g., at least 2, at least 3, at least 4, at least 5, or more) of the second amphiphilic peptides.

In particular embodiments, the first amphiphilic peptide(s) and the second amphiphilic peptide(s) can be selected from any one or more embodiments of an amphiphilic peptide described earlier in the "Exemplary amphiphilic peptides" section. In some embodiments, the first and second amphiphilic peptide can each independently comprise an amino acid sequence of (L-Lys)-(L-Lys)-(L-Lys)-(L-Trp)-(D-Leu)-(L-Trp)-(D-Leu)-(L-Trp)-(D-Leu)-(L-Trp)-X (SEQ ID NO: 10), wherein X is absent or NH$_2$.

The ratio of the first amphiphilic peptide to the second amphiphilic peptide can be varied based on a number of factors, e.g., but not limited to, desirable solubility and/or stability of the peptide particle, and/or properties of the active agent to be loaded therein. In some embodiments, the ratio of the first amphiphilic peptide to the second amphiphilic peptide can be in a range of about 1:1000 to about 1000:1. In some embodiments, the ratio of the first amphiphilic peptide to the second amphiphilic peptide can be in a range of about 1:1 to about 1000:1. In some embodiments, the ratio of the first amphiphilic peptide to the second amphiphilic peptide can be in a range of about 2:1 to about 500:1. In some embodiments, the ratio of the first amphiphilic peptide to the second amphiphilic peptide can be in a range of about 3:1 to about 200:1. In other embodiments, the ratio of the first amphiphilic peptide to the second amphiphilic peptide can be in a range of about 5:1 to about 100:1.

In some embodiments, the mixed peptide particle can further comprise an active agent described herein. The active agent can be present in the mixed peptide particle in any amounts, e.g., depending on the loading capacity of the peptide particle and/or binding capacity of the first or second amphiphilic peptide. In some embodiments, the ratio of the active agent to the second amphiphilic peptides can be in a range of about 1:1000 to 1:1. In some embodiments, the ratio of the active agent to the second amphiphilic peptides can be or about 1:100 to about 1:10. In some embodiments, the ratio of the active agent to the second amphiphilic peptide can be in a range of about 1:50 to about 1:5. In some embodiments, the ratio of the active agent to the second amphiphilic peptide can be in a range of about 1:10 to about 1:2.

In some embodiments, the mixed peptide particle can further comprise on its outer surface a ligand described herein. As described earlier, selection of a ligand can be determined based on a target molecule (e.g., but not limited to, cells, bacteria, proteins, nucleic acids) to which the mixed peptide particle binds. Non-limiting examples of a ligand can include a cell surface receptor ligand or a protein such as an antibody. In some embodiments, the ligand can be covalently linked to at least one of the first and the second amphiphilic peptide, e.g., the hydrophilic peptidyl segment of at least one of the first and the second amphiphilic peptide.

The mixed peptide particle described herein can be used to encapsulate any active agent described herein. Without wishing to be bound by theory, the presence of the second amphiphilic peptide in the mixed peptide particle can provide a cationic charge for binding with anionic nucleic acid molecules. Thus, in some embodiments, the active agent can include a nucleic acid molecule.

A further aspect provided herein is directed to use of one or more embodiments of the mixed peptide particle comprising a first amphiphilic peptide and a second amphiphilic peptide described herein for delivery of a nucleic acid molecule to a cell. Accordingly, in some embodiments, the mixed peptide particle for use in delivery of a nucleic acid molecule to a cell comprises a first amphiphilic peptide, a second amphiphilic peptide, and a nucleic acid molecule. In some embodiments, the mixed peptide particle can comprise a plurality (e.g., at least 2 or more) of nucleic acid molecules or oligonucleotides (e.g., DNA or RNA including, but not limited to, siRNA, shRNA, miRNA, or any combinations thereof). In some embodiments, the nucleic acid molecules or oligonucleotides can be designed for use in therapeutic intervention, e.g., gene therapy or siRNA therapy.

Peptide Particle Assembly

The peptide particles described herein can be assembled by a one-step procedure. For example, peptide particles can be conveniently assembled from dissolved amphiphilic peptide by addition of water: an emulsion spontaneously formed as a ternary mixture (peptide, organic solvent, $H_2O$) is brought into the two-phase region (peptide, $H_2O$). While the emulsification process resembles the ouzo effect, amphiphilic peptide droplets harden to solid particles as the organic solvent is removed. Neutral as well as charged molecules efficiently migrate into the dispersed phase and get trapped during particle formation.

Generally, peptide particles comprising an active agent and a ligand can be assembled in about 15 minutes using the procedure outlined herein. Additionally, the system allows for straightforward adjustment of particle size and entraps active agents at very high density.

Without wishing to be bound by a theory, the simplicity of system and formation protocol originates in the concerted interaction of all involved components of a peptide particle: amphiphilic peptides are not only matrix material, but supersedes encapsulation routines due to their high affinity for other components such as a ligand and/or an active agent. The process of active agent encapsulation most likely resembles a two-phase liquid extraction where the active agent escapes the aqueous phase and accumulates in peptide droplets. Additionally, the peptide's solubility in mild organic solvents allows for concurrent dissolution and self-assembly of all involved components. The presence of a ligand during emulsification of the peptides can result in the formation of a ligand corona. Additionally, the presence of the ligand can allow for straightforward adjustment of particle size due to its surface activity and thus early stabilization of the peptide emulsion.

Pharmaceutical Compositions

For administration to a subject, peptide particles and active agent-amphiphilic peptide complexes described herein can be provided in pharmaceutically acceptable compositions. These pharmaceutically acceptable compositions comprise a particle or an active agent-amphiphilic peptide complex formulated together with one or more pharmaceutically acceptable carriers (additives) and/or diluents. As described in detail below, the pharmaceutical compositions described herein can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

As used herein, the term "administer" refers to the placement of a composition into a subject by a method or route which results in at least partial localization of the composition at a desired site such that desired effect is produced. Routes of administration include both local and systemic administration. Generally, local administration results in more of the therapeutic agent being delivered to a specific location as compared to the entire body of the subject, whereas, systemic administration results in delivery of the therapeutic agent to essentially the entire body of the subject.

Administration to a subject can be by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments of the aspects described herein, administration is by intravenous infusion or injection.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with autoimmune disease or inflammation. In addition, the methods and compositions described herein can be used to treat domesticated animals and/or pets.

Kits

A further aspect provided herein relates to a kit comprising a peptide particle, a formulation comprising a peptide particle, or components for making a peptide particle or a formulation comprising a peptide particle described herein.

In some embodiments, compositions or kits for making one or more embodiments of a peptide particle or a mixed peptide particle are provided herein. In some embodiments, the composition or kit can comprise an amphiphilic peptide described herein. The amphiphilic peptide supplied in the composition or kit can be provided in a container. Depending on a user's choice of a peptide particle or mixed particle described herein to be produced, in some embodiments, the composition or kit can comprise a first amphiphilic peptide and a second amphiphilic peptide described herein. The amphiphilic peptide can be provided in powder or lyophilized powder. In some embodiments, the composition or kit can further comprise at least one reagent, e.g., for reconstitution of the powdered amphiphilic peptide, for emulsification of a particle assembly mixture, or both. In some embodiments, the composition or kit can further comprise a ligand described herein, e.g., provided in a separate container. In some embodiments, the composition or kit can further comprise an active agent to be encapsulated into the peptide particle. The active agent can be provided in a separate container.

In addition to the above mentioned components, the kit can include informational material. The informational material can be descriptive, instructional, marketing or other material that relates to the methods described herein and/or the use of the aggregates for the methods described herein. For example, the informational material describes methods for administering the particle to a subject. The kit can also include a delivery device.

In one embodiment, the informational material can include instructions to administer the formulation in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., an adult human. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments the individual components of the formulation can be provided in one container. Alternatively, it can be desirable to provide the components of the formulation separately in two or more containers, e.g., one container for an amphiphilic peptide preparation, and at least another for a carrier compound. The different components can be combined, e.g., according to instructions provided with the kit. The components can be combined according to a method described herein, e.g., to prepare and administer a pharmaceutical composition.

In addition to the formulation, the composition of the kit can include other ingredients, such as a solvent or buffer, a stabilizer or a preservative, and/or a second agent for treating a condition or disorder described herein. Alternatively, the other ingredients can be included in the kit, but in different compositions or containers than the formulation. In such embodiments, the kit can include instructions for admixing the formulation and the other ingredients, or for using the oligonucleotide together with the other ingredients.

The formulation can be provided in any form, e.g., liquid, dried or lyophilized form. It is preferred that the formulation be substantially pure and/or sterile. When the formulation is provided in a liquid solution, the liquid solution preferably is an aqueous solution, with a sterile aqueous solution being preferred. When the formulation is provided as a dried form, reconstitution generally is by the addition of a suitable solvent. The solvent, e.g., sterile water or buffer, can optionally be provided in the kit.

In some embodiments, the kit contains separate containers, dividers or compartments for the formulation and informational material. For example, the formulation can be contained in a bottle, vial, or syringe, and the informational material can be contained in a plastic sleeve or packet. In other embodiments, the separate elements of the kit are contained within a single, undivided container. For example, the formulation is contained in a bottle, vial or syringe that has attached thereto the informational material in the form of a label.

In some embodiments, the kit includes a plurality, e.g., a pack, of individual containers, each containing one or more unit dosage forms of the formulation. For example, the kit includes a plurality of syringes, ampules, foil packets, or blister packs, each containing a single unit dose of the formulation. The containers of the kits can be air tight and/or waterproof.

Embodiments of the various aspects described herein can be illustrated by the following numbered paragraphs.

1. A peptide particle comprising an amphiphilic peptide, the amphiphilic peptide comprising a hydrophobic peptidyl segment and a hydrophilic peptidyl segment,
   wherein the hydrophobic peptidyl segment comprises an amino acid sequence of (Trp-Leu)$_m$-(Trp)$_n$ (SEQ ID NO: 7) or (Leu-Trp)$_p$-(Leu)$_q$ (SEQ ID NO: 8), wherein each Trp is D-Trp or L-Trp and each Leu is D-Leu or L-Leu, m and p are independently an integer from 1 to 5, and n and q are independently 0 or 1, provided that when Trp is D-Trp then Leu is L-Leu, and when Trp is L-Trp then Leu is D-Leu, or vice versa; and
   wherein the hydrophilic peptidyl segment comprises an amino acid sequence of (Lys)$_r$ (SEQ ID NO: 9), wherein r is an integer from 1 to 15, and
   wherein the peptide particle further comprises on its outer surface a ligand.
2. The peptide particle of paragraph 1, wherein r is an integer from 2 to 5.
3. The peptide particle of paragraph 1 or 2, wherein r is an integer of 3.
4. The peptide particle of any of paragraphs 1-3, wherein at least one Lys residue of the hydrophilic peptidyl segment or the N-terminus amino group of the amphiphilic peptide is acetylated.
5. The peptide particle of any of paragraphs 1-4, wherein all of the Lys residues of the hydrophilic peptidyl segment are acetylated.
6. The peptide particle of any of paragraphs 1-5, wherein the N-terminus amino group of the amphiphilic peptide is acetylated.
7. The peptide particle of any of paragraphs 1-6, wherein the hydrophobic peptidyl segment is linked to the C-terminus of the hydrophilic peptidyl segment.
8. The peptide particle of any of paragraphs 1-7, wherein Leu is D-Leu.
9. The peptide particle of any of paragraphs 1-8, wherein Trp is L-Trp.
10. The peptide particle of any of paragraphs 1-9, wherein Lys is L-Lys.
11. The peptide particle of any of paragraphs 1-10, wherein m or p is between 1 and 3.
12. The peptide particle of any of paragraphs 1-11, wherein m or p is 3.
13. The peptide particle of any of paragraphs 1-12, wherein n or q is 1.
14. The peptide particle of any of paragraphs 1-13, wherein the amphiphilic peptide comprises the amino acid sequence of (L-Lys)-(L-Lys)-(L-Lys)-(L-Trp)-(D-Leu)-(L-Trp)-(D-Leu)-(L-Trp)-(D-Leu)-(L-Trp)-X (SEQ ID NO: 10), wherein X is absent or NH$_2$.
15. The peptide particle of paragraph 14, wherein at least one of the L-Lys residues is acetylated.
16. The peptide particle of paragraph 14 or 15, wherein the N-terminus amino group of the amphiphilic peptide is acetylated.
17. The peptide particle of any of paragraphs 1-16, wherein the amphiphilic peptide has a length of about 5 to about 25 amino acid residues.
18. The peptide particle of any of paragraphs 1-17, wherein at least one backbone amide linkage of the amphiphilic peptide is an amide replacement linkage.
19. The peptide particle of any of paragraphs 1-18, wherein the amphiphilic peptide comprises a β-amino acid, a γ-amino acid, or a combination thereof
20. The peptide particle of any of paragraphs 1-19, wherein at least one of the hydrophobic peptidyl segment or the hydrophilic peptidyl segment comprises at least one point mutation.
21. The peptide particle of any of paragraphs 1-20, wherein the ligand includes a cell surface receptor ligand or an antibody.
22. The peptide particle of paragraph 21, wherein the cell surface receptor ligand includes transferrin, EGF, folate, or any combinations thereof.
23. The peptide particle of any of paragraphs 1-22, wherein the thickness of the ligand present on the outer surface of the peptide particle ranges from about 1 nm to about 100 nm
24. The peptide particle of any of paragraphs 23, wherein the thickness of the ligand present on the outer surface of the peptide particle is about 10 nm
25. The peptide particle of any of paragraphs 1-24, wherein the ligand is covalently linked to the amphiphilic peptide.
26. The peptide particle of any of paragraphs 1-25, wherein the ligand is covalently linked to the hydrophilic peptidyl segment of the amphiphilic peptide.
27. The peptide particle of any of paragraphs 1-26, wherein a ratio of the ligand to the amphiphilic peptide ranges from about 1:10 to about 1:1,000,000.
28. The peptide particle of any of paragraphs 1-27, wherein the particle has a size of about 5 nm to about 5,000 nm
29. The peptide particle of paragraph 28, wherein the particle has a size of about 30 nm to about 150 nm
30. The peptide particle of any of paragraphs 1-29, wherein the peptide particle comprises a mixture of a fully-acetylated amphiphilic peptide of any of paragraphs 1-29, and a partially-acetylated amphiphilic peptide of any of paragraphs 1-29.
31. The peptide particle of paragraph 30, wherein the ratio of the fully-acetylated to the partially-acetylated amphiphilic peptide ranges from about 95:5 to about 1:1.
32. The peptide particle of any of paragraphs 30-31, wherein the peptide particle further comprises a non-acetylated amphiphilic peptide.
33. The peptide particle of any of paragraphs 1-32, further comprising an active agent.
34. The peptide particle of paragraph 33, wherein the active agent is dispersed within the particle.
35. The peptide particle of any of paragraphs 33-34, wherein the active agent has no net charge.
36. The peptide particle of any of paragraphs 33-34, wherein the active agent has a net charge.
37. The peptide particle of any of paragraphs 33-36, wherein the active agent is selected from the group consisting of proteins, peptides, antigens, antibodies or portions thereof, antibody-like molecules, enzymes, nucleic acids, aptamers, small molecules, antibiotics, pharmaceutically active agents, therapeutic agents, contrast agents, and any combinations thereof 38. The peptide particle of any of paragraphs 33-37, wherein the active agent is a pharmaceutically active agent or a therapeutic agent.

39. The peptide particle of any of paragraphs 33-38, wherein the active agent is a nucleic acid molecule.

40. The peptide particle of paragraph 39, wherein the nucleic acid molecule includes siRNA, miRNA, shRNA, or any combinations thereof 41. The peptide particle of paragraph 39, wherein the nucleic acid molecule is DNA.

42. The peptide particle of any of paragraphs 33-41, wherein a ratio of the active agent to the amphiphilic peptide ranges from about 1:1 to about 1:10,000.

43. The peptide particle of paragraph 42, wherein the ratio of the active agent to the amphiphilic peptide ranges from about 1:1 to about 1:100, or from about 1:1 to about 1:10.

44. Use of the peptide particle of any of paragraphs 33-43 for targeted delivery of an active agent.

45. The use of paragraph 44, wherein the active agent is cell-impermeable when it is delivered to a cell by itself.

46. Use of a composition comprising a positively-charged amphiphilic peptide as a cell-penetrating agent or transfection agent, wherein the positive-charged amphiphilic peptide comprises a hydrophobic peptidyl segment and a hydrophilic peptidyl segment,
   wherein the hydrophobic peptidyl segment comprises an amino acid sequence of $(Trp-Leu)_m-(Trp)_n$ (SEQ ID NO: 7) or $(Leu-Trp)_p-(Leu)_q$ (SEQ ID NO: 8), wherein each Trp is D-Trp or L-Trp and each Leu is D-Leu or L-Leu, m and p are independently an integer from 1 to 5, and n and q are independently 0 or 1, provided that when Trp is D-Trp then Leu is L-Leu, and when Trp is L-Trp then Leu is D-Leu, or vice versa;
   wherein the hydrophilic peptidyl segment comprises an amino acid sequence of $(Lys)_r$ (SEQ ID NO: 9), wherein r is an integer from 1 to 15; and
   wherein at least one of the Lys residues or the N-terminus amino group of the amphiphilic peptide is not acetylated.

47. The use of paragraph 46, wherein all of the Lys residues and the N-terminus amino group of the amphiphilic peptide are not acetylated.

48. The use of paragraph 46 or 47, wherein r is an integer from 2 to 5.

49. The use of any of paragraphs 46-48, wherein r is an integer of 3.

50. The use of any of paragraphs 46-49, wherein the hydrophobic peptidyl segment is linked to the C-terminus of the hydrophilic peptidyl segment.

51. The use of any of paragraphs 46-50, wherein Leu is D-Leu.

52. The use of any of paragraphs 46-51, wherein Trp is L-Trp.

53. The use of any of paragraphs 46-52, wherein Lys is L-Lys.

54. The use of any of paragraphs 46-53, wherein m or p is between 1 and 3.

55. The use of any of paragraphs 46-54, wherein m or p is 3.

56. The use of any of paragraphs 46-55, wherein n or q is 1.

57. The use of any of paragraphs 46-56, wherein the amphiphilic peptide has a length of about 5 to about 25 amino acid residues.

58. The use of any of paragraphs 46-57, wherein at least one backbone amide linkage of the amphiphilic peptide is an amide replacement linkage.

59. The use of any of paragraphs 46-58, wherein the amphiphilic peptide comprises a 13-amino acid, a y-amino acid, or a combination thereof 60. The use of any of paragraphs 46-59, wherein at least one of the hydrophobic peptidyl segment or the hydrophilic peptidyl segment comprises at least one point mutation.

61. The use of any of paragraphs 46-60, wherein the particle has a size of about 5 nm to about 5,000 nm 62. The use of paragraph 61, wherein the particle has a size of about 30 nm to about 150 nm 63. The use of any of paragraphs 46-62, wherein the amphiphilic peptide comprises the amino acid sequence of (L-Lys)-(L-Lys)-(L-Lys)-(L-Trp)-(D-Leu)-(L-Trp)-(D-Leu)-(L-Trp)-(D-Leu)-(L-Trp)-X (SEQ ID NO: 10), wherein X is absent or $NH_2$.

64. The use of any of paragraphs 46-63, wherein the composition further comprises a nucleic acid molecule to be delivered into a cell.

65. A peptide particle comprising a first amphiphilic peptide and a second amphiphilic peptide, the first and the second amphiphilic peptide each independently comprising a hydrophobic peptidyl segment and a hydrophilic peptidyl segment,
   wherein the hydrophobic peptidyl segment comprises an amino acid sequence of $(Trp-Leu)_m-(Trp)_n$ (SEQ ID NO: 7) or $(Leu-Trp)_p-(Leu)_q$ (SEQ ID NO: 8), wherein each Trp is D-Trp or L-Trp and each Leu is D-Leu or L-Leu, m and p are independently an integer from 1 to 5, and n and q are independently 0 or 1, provided that when Trp is D-Trp then Leu is L-Leu, and when Trp is L-Trp then Leu is D-Leu, or vice versa; and
   wherein the hydrophilic peptidyl segment comprises an amino acid sequence of $(Lys)_r$ (SEQ ID NO: 9), wherein r is an integer from 1 to 15, and
   wherein the N-terminus amino group and all of the Lys residues of the first amphiphilic peptide are acetylated; and
   wherein at least the N-terminus amino group or one of the Lys residues of the second amphiphilic peptide is not acetylated.

66. The peptide particle of paragraph 65, wherein none of the N-terminus amino group and the Lys residues of the second amphiphilic peptide is acetylated.

67. The peptide particle of paragraph 65 or 66, further comprising an active agent.

68. The peptide particle of paragraph 67, wherein the active agent includes a nucleic acid molecule.

69. The peptide particle of any of paragraphs 65-68, wherein the ratio of the active agent to the second amphiphilic peptide is in a range of about 1:1000 to 1:1, or about 1:100 to about 1:10.

70. The peptide particle of paragraph 69, wherein the ratio of the active agent to the second amphiphilic peptide is in a range of about 1:10 to about 1:2.

71. The peptide particle of any of paragraphs 65-70, wherein the ratio of the first amphiphilic peptide to the second amphiphilic peptide is in a range of about 1:1 to about 1000:1, or about 5:1 to about 100:1.

72. The peptide particle of any of paragraphs 65-71, further comprising on its outer surface a ligand.

73. The peptide particle of paragraph 72, wherein the ligand includes a cell surface receptor ligand or an antibody.

74. The peptide particle of paragraph 73, wherein the cell surface receptor ligand includes transferrin, EGF, folate, or any combinations thereof 75. The peptide particle of any of paragraphs 65-74, wherein the thickness of the ligand present on the outer surface of the peptide particle ranges from about 1 nm to about 100 nm 76. The peptide particle of any of paragraphs 75, wherein the thickness of the ligand present on the outer surface of the peptide particle is about 10 nm 77. The peptide particle of any of paragraphs 65-76, wherein the ligand is covalently linked to at least one of the first and the second amphiphilic peptide.

78. The peptide particle of any of paragraphs 65-77, wherein the ligand is covalently linked to the hydrophilic peptidyl segment of at least one of the first and the second amphiphilic peptide.

79. The peptide particle of any of paragraphs 65-78, wherein a ratio of the ligand to the amphiphilic peptide ranges from about 1:10 to about 1:1,000,000.

80. The peptide particle of any of paragraphs 65-79, wherein r is an integer from 2 to 5.

81. The peptide particle of any of paragraphs 65-80, wherein r is an integer of 3.

82. The peptide particle of any of paragraphs 65-81, wherein the hydrophobic peptidyl segment is linked to the C-terminus of the hydrophilic peptidyl segment.

83. The peptide particle of any of paragraphs 65-82, wherein Leu is D-Leu.

84. The peptide particle of any of paragraphs 65-83, wherein Trp is L-Trp.

85. The peptide particle of any of paragraphs 65-84, wherein Lys is L-Lys.

86. The peptide particle of any of paragraphs 65-85, wherein m or p is between 1 and 3.

87. The peptide particle of any of paragraphs 65-86, wherein m or p is 3.

88. The peptide particle of any of paragraphs 65-87, wherein n or q is 1.

89. The peptide particle of any of paragraphs 65-88, wherein the first and the second amphiphilic peptide each independently has a length of about 5 to about 25 amino acid residues.

90. The peptide particle of any of paragraphs 65-89, wherein at least one backbone amide linkage of the first or the second amphiphilic peptide is an amide replacement linkage.

91. The peptide particle of any of paragraphs 65-90, wherein at least one of the first and the second amphiphilic peptide comprises a β-amino acid, a γ-amino acid, or a combination thereof 92. The peptide particle of any of paragraphs 65-91, wherein at least one of the hydrophobic peptidyl segment or the hydrophilic peptidyl segment comprises at least one point mutation.

93. The peptide particle of any of paragraphs 65-92, wherein the peptide particle has a size of about 5 nm to about 5,000 nm 94. The peptide particle of paragraph 93, wherein the peptide particle has a size of about 30 nm to about 150 nm 95. The peptide particle of any of paragraphs 65-94, wherein the first and second amphiphilic peptide each independently comprises the amino acid sequence of (L-Lys)-(L-Lys)-(L-Lys)-(L-Trp)-(D-Leu)-(L-Trp)-(D-Leu)-(L-Trp)-(D-Leu)-(L-Trp)-X (SEQ ID NO: 10), wherein X is absent or NH$_2$.

96. Use of the peptide particle of any of paragraphs 65-95 for delivery of a nucleic acid molecule to a cell.

97. The use of paragraph 96, wherein the nucleic acid molecule includes siRNA, miRNA, shRNA, or any combinations thereof 98. The use of paragraph 96, wherein the nucleic acid molecule includes DNA.

99. An amphiphilic peptide comprising a hydrophobic peptidyl segment and a hydrophilic peptidyl segment,
    wherein the hydrophobic peptidyl segment comprises an sequence of 2 to 10 alternating D- and L-amino acids selected from alanine, valine, isoleucine, leucine (Leu), phenylalanine, tyrosine or tryptophan (Trp), and
    wherein the hydrophilic peptidyl segment comprises charged, or uncharged but polar amino acids, or derivatives thereof.

100. The amphiphilic peptide of paragraph 99, wherein the hydrophobic peptidyl segment comprises an amino acid sequence of (Trp-Leu)$_m$-(Trp)$_n$ (SEQ ID NO: 1) or (Leu-Trp)$_p$-(Leu)$_q$ (SEQ ID NO: 2), wherein each Trp is D-Trp or L-Trp and each Leu is D-Leu or L-Leu, m and p are independently an integer from 1 to 20, and n and q are independently 0 or 1, provided that when Trp is D-Trp then Leu is L-Leu, and when Trp is L-Trp then Leu is D-Leu, or vice versa.

101. The amphiphilic peptide of paragraph 99 or 100, wherein the hydrophilic peptidyl segment comprises at least one charge present either on the N-terminus or an amino acid residue.

102. The amphiphilic peptide of paragraph 101, wherein the at least one charge is either a cationic or an anionic charge.

103. The amphiphilic peptide of paragraph 99 or 100, wherein the hydrophilic peptidyl segment comprises uncharged but polar amino acids.

104. The amphiphilic peptide of any of paragraphs 99 to 103, wherein the hydrophilic peptidyl segment comprises at least one charge and at least one uncharged but polar amino acid.

105. The amphiphilic peptide of any of paragraphs 99 to 104, wherein to the hydrophobic peptidyl segment a polymer is linked covalently.

106. The amphiphilic peptide of any of paragraphs 99-105, wherein at least one amino group in the amphiphilic peptide is acetylated.

107. The amphiphilic peptide of paragraph 102, wherein the at least one cationic charge is in an amino acid residue selected from the group consisting of Lys, Arg, His, and any combinations thereof 108. The amphiphilic peptide of paragraph 102, wherein the at least one anioic charge is in an amino acid residue selected from the group consisting of Asp or Glu, and any combinations thereof 109. The amphiphilic peptide of paragraph 103, wherein the at least one uncharged but polar amino acid residue is selected from the group consisting of Ser, Thr, Asn or Gln, and any combinations thereof 110. The amphiphilic peptide of paragraph 105, wherein the polymer is selected from the group consisting of PEG, PGG, PEO, polycaprolactone, polylactic acid, polyglycolic acid, polyhydroxyalkaboates, dextrans, polyanhydrides, PLA-PGA, polyorthoester, polyfuma- 111. The amphiphilic peptide of any of paragraphs 99 to 110, wherein the hydrophilic peptidyl segment comprises an amino acid sequence of (Lys)$_r$ (SEQ ID NO: 9), wherein r is an integer from 1 to 15.

112. The amphiphilic peptide of paragraph 111, where r is 3.

113. The amphiphilic peptide of any of paragraphs 99-112, wherein the at least one amino group is a N-terminus amino group of the amphiphilic peptide.

114. The amphiphilic peptide of any of paragraphs 99-113, wherein the at least one amino group is on a Lys residue of the hydrophilic peptidyl segment.

115. The amphiphilic peptide of any of paragraphs 99-114, wherein all of the amino groups in the hydrophilic peptidyl segment are acetylated.

116. The amphiphilic peptide of any of paragraphs 99-115, wherein the N-terminus amino group of the amphiphilic peptide and at least one of the amino groups in the hydrophilic peptidyl segment are acetylated.

117. The amphiphilic peptide of any of paragraphs 99-116, wherein the N-terminus amino group of the amphiphilic peptide and all of the amino groups in the hydrophilic peptidyl segment are acetylated.

118. The amphiphilic peptide of any of paragraphs 99-117 wherein the hydrophobic peptidyl segment is linked to the C-terminus of the hydrophilic peptidyl segment.

119. The amphiphilic peptide of any of paragraphs 99-118, wherein Leu is D-Leu.

120. The amphiphilic peptide of any of paragraphs 99-119, wherein Trp is L-Trp.

121. The amphiphilic peptide of any of paragraphs 99-120, wherein Lys is L-Lys.

122. The amphiphilic peptide of any of paragraphs 99-121, wherein m or p is between 1 and 3.

123. The amphiphilic peptide of paragraph 122, wherein m or p is 3.

124. The amphiphilic peptide of any of paragraphs 99-123, wherein n or q is 1.

125. The amphiphilic peptide of any of paragraphs 99-124, wherein the amphiphilic peptide comprises the amino acid sequence of (L-Lys)-(L-Lys)-(L-Lys)-(L-Trp)-(D-Leu)-(L-Trp)-(D-Leu)-(L-Trp)-(D-Leu)-(L-Trp) (SEQ ID NO: 3), wherein at least one of the L-Lys residues is acetylated.

126. The amphiphilic peptide of any of paragraphs 99-125, wherein the amphiphilic peptide comprises the amino acid sequence of Ac-(L-Lys)-(L-Lys)-(L-Lys)-(L-Trp)-(D-Leu)-(L-Trp)-(D-Leu)-(L-Trp)-(D-Leu)-(L-Trp) (SEQ ID NO: 4).

127. The amphiphilic peptide of paragraph 126, wherein at least one of the L-Lys residues is acetylated.

128. The amphiphilic peptide of any of paragraphs 99-127, wherein the amphiphilic peptide comprises the amino acid sequence of Ac-(L-Lys(Ac))-(L-Lys(Ac))-(L-Lys(Ac))-(L-Trp)-(D-Leu)-(L-Trp)-(D-Leu)-(L-Trp)-(D-Leu)-(L-Trp)-X (SEQ ID NO: 5), wherein X is absent or NH$_2$.

129. The amphiphilic peptide of any of paragraphs 99-128, wherein the amphiphilic peptide has a length of about 5 to about 25 amino acid residues.

130. The amphiphilic peptide of any of paragraphs 99-129, wherein at least one backbone amide linkage is an amide replacement linkage.

131. The amphiphilic peptide of any of paragraphs 99-130, wherein the amphiphilic peptide comprises at least one β-amino acid, γ-amino acid, or any combinations thereof 132. The amphiphilic peptide of any of paragraphs 99-131, wherein at least one of the hydrophobic peptidyl segment or the hydrophilic peptidyl segment comprises at least one point mutation.

133. A particle comprising one or more amphiphilic peptides of any of paragraphs 99-132.

134. The particle of paragraph 133, further comprising a ligand.

135. The particle of paragraph 133 or 134, wherein the ligand is a cell surface receptor ligand or an antibody.

136. The particle of paragraph 135, wherein the cell surface receptor ligand is transferrin, or EGF or folate.

137. The particles of any of paragraphs 133-136, wherein the ligand is present on an outer surface of the particle.

138. The particle of any of paragraphs 133-137, wherein the ligand is adsorbed on the outer surface of the particle.

139. The particle of paragraph 137 or 138, wherein a thickness of the ligand present on the outer surface of the particle ranges from about 1 nm to about 100 nm 140. The particle of paragraph 139, wherein the thickness of the ligand present on the outer surface of the particle is about 10 nm.

141. The particle of any of paragraphs 133-140, wherein the ligand is covalently linked to the amphiphilic peptide.

142. The particle of any of paragraphs 133-141, wherein the ligand is covalently linked to the hydrophilic peptidyl segment of the amphiphilic peptide.

143. The particle of any of paragraphs 133-142, further comprising an active agent.

144. The particle of paragraph 143, wherein the active agent is dispersed within the particle.

145. The particle of any of paragraphs 143-144, wherein the active agent has no net charge.

146. The particle of any of paragraphs 143-144, wherein the active agent has a net charge.

147. The particle of any of paragraphs 143-146, wherein the active agent comprises at least one aromatic group.

148. The particle of any of paragraphs 143-147, wherein the active agent is selected from the group consisting of proteins, peptides, antigens, antibodies or portions thereof, antibody-like molecules, enzymes, nucleic acids, aptamers, small molecules, antibiotics, pharmaceutically active agents, therapeutic agents, contrast agents, and any combinations thereof 149. The particle of any of paragraphs 143-148, wherein the active agent is a pharmaceutically active agent.

150. The particle of any of paragraphs 143-149, wherein the active agent is a nucleic acid molecule.

151. The particle of paragraph 150, wherein the nucleic acid molecule is siRNA miRNA or shRNA.

152. The particle of paragraph 150, wherein the nucleic acid molecule is DNA.

153. The particle of any of paragraphs 143-152, wherein a ratio of the active agent to the amphiphilic peptides ranges from 1:1 to 1:100,000.

154. The particle of paragraph 153, wherein the ratio of the active agent to the amphiphilic peptides ranges from 1:1 to about 1:1,000.

155. The particle of any of paragraphs 134-154, wherein a ratio of the ligand to the amphiphilic peptides ranges from about 1:10 to about 1:1,000,000.

156. The particle of any of paragraphs 133-155, wherein the particle has a size of about 5 nm to about 5,000 nm 157. The particle of paragraph 156, wherein the particle has a size of about 30 nm to about 150 nm
158. The particle of any of paragraphs 133-157, wherein the particle comprises a mixture of fully-acetylated and partially-acetylated amphiphilic peptides of any of paragraphs 99-132.
159. The particle of paragraph 158, wherein the ratio of the fully-acetylated to the partially-acetylated amphiphilic peptides ranges from about 95:5 to about 1:1.
160. The particle of any of paragraphs 133-159, wherein the particle further comprises non-acetylated amphiphilic peptides.
161. A method of using an amphiphilic peptide compound as a delivery system.
162. The method of paragraph 161, wherein the delivery system is a targeted delivery system.
163. The method of paragraph 161 or 162, wherein the delivery system is for therapeutic or diagnostic purposes.
164. Use of peptide compositions as cell penetration peptide or transfection agent, respectively.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not. Additionally, the term "comprising" or "comprises" includes "consisting essentially of" and "consisting of:"

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages can mean±1%.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The term "statistically significant" or "significantly" refers to statistical significance and generally means a two standard deviation (2SD) above or below a reference level. The term refers to statistical evidence that there is a difference. It is defined as the probability of making a decision to reject the null hypothesis when the null hypothesis is actually true. The decision is often made using the p-value.

The term "nanosphere" means a particle having an aspect ratio of at most 3:1. The term "aspect ratio" means the ratio of the longest axis of an object to the shortest axis of the object, where the axes are not necessarily perpendicular.

The term "longest dimension" of a particle means the longest direct path of the particle. The term "direct path" means the shortest path contained within the particle between two points on the surface of the particle. For example, a helical particle would have a longest dimension corresponding to the length of the helix if it were stretched out into a straight line.

The term "nanorod" means a particle having a longest dimension of at most 200 nm, and having an aspect ratio of from 3:1 to 20:1.

The term "nanoprism" means a particle having at least two non-parallel faces connected by a common edge.

The "length" of a particle means the longest dimension of the particle.

The "width" of a particle means the average of the widths of the particle; and the "diameter" of a particle means the average of the diameters of the particle.

The "average" dimension of a plurality of particles means the average of that dimension for the plurality. For example, the "average diameter" of a plurality of nanospheres means the average of the diameters of the nanospheres, where a diameter of a single nanosphere is the average of the diameters of that nanosphere.

As used herein, the term "pharmaceutically-acceptable salts" refers to the conventional nontoxic salts or quaternary ammonium salts of a compound, e.g., from non-toxic organic or inorganic acids. These salts can be prepared in situ in the administration vehicle or the dosage form manufacturing process, or by separately reacting a purified compound in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

As used herein, a ratio can be a mole ratio or weight ratio or molar ratio.

As used herein, a "cell penetration peptide" or "cell penetrating peptide" is defined as peptide that has membrane permeability and is capable of crossing biological membrane or a physiological barrier. Cell penetrating peptides (CPPs) are also called cell-permeable peptides, protein transduction domains (PTD) or membrane-translocation sequences (MTS). CPPs have the ability to translocate in vitro and/or in vivo the mammalian cell membranes and enter into cells, and directs a conjugated compound of interest, such as a drug or marker, to a desired cellular destination, e.g. into the cytoplasm (cytosol, endoplasmic reticulum, Golgi apparatus, etc.) or the nucleus. Accordingly, the CPP can direct or facilitate penetration of a compound of interest across a phospholipid, mitochondrial, endosomal or nuclear membrane. The CPP can also direct a compound of interest from outside the cell through the plasma membrane, and into the cytoplasm or to a desired location within the cell, e.g., the nucleus, the ribosome, the mitochondria, the endoplasmic reticulum, a lysosome, or a peroxisome. Alternatively or in addition, the CPP can direct a compound of interest across the blood-brain, trans-mucosal, hematoretinal, skin, gastrointestinal and/or pulmonary barriers.

Penetration across a biological membrane or a physiological barrier can be determined by various processes, for example by a cell penetration test having a first incubation step for the CPP conjugated to a marker in the presence of culture cells, followed by a fixating step, and then revelation of the presence of the marked peptide inside the cell. In another embodiment, the revelation step can be done with an incubation of the CPP in the presence of labeled antibodies and directed against the CPP, followed by detection in the cytoplasm or in immediate proximity of the cell nucleus, or even within it, of the immunologic reaction between the CPP's amino acid sequence and the labeled antibodies. Revelation can also be done by marking an amino acid sequence in the CPP and detecting the presence of the marking in the cell compartments. Cell penetration tests are well known to those skilled in the art. However, for example a cell penetration test was described in the above-mentioned patent application No WO 97/02840.

As used herein, the term "transfection agent" or "transfection reagent" refers to a compound that bind(s) to or complex(es) with a compound and enhances their entry into cells. Generally, the term transfection agent is used for compounds that enhance the delivery of nucleic acids into a cell.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Exemplary Materials and Methods (for Examples 1-2)

Exemplary Materials:

All chemicals and reagents including rose bengal (RB) (Aldrich 330000, 95%) and 5-carboxy-fluorescein (CF) (Sigma-Aldrich C0537, 99%) were obtained from Sigma-Aldrich and used without further purification unless otherwise noted below. Fmoc-protected amino acids and coupling reagents were purchased from IRIS Biotech and Novabiochem. 24-well crystallization plates were purchased from Hampton Research (Cryschem Plate).

Peptide Synthesis:

All peptides were synthesized on solid phase using Fmoc protection group chemistry. Individual steps of the synthesis are listed in Table 1. Rink Amide AM resin (200 mg, loading: 0.4 mmol/g-0.8 mmol/g) was used as solid phase in a 10 mL syringe. All reactions were carried out in dimethylformamide (DMF) previously treated with aluminum oxide to reduce the abundance of free amines. Fmoc-amino acids were dissolved in DMF (0.5M) prior to synthesis. Fmoc protection groups were cleft twice for each coupling step using piperidine in DMF (40%). 1H-benzotriazolium 1-[bis(dimethylamino) methylene]-5chloro-,hexafluorophosphate (1-),3-oxide (HCTU) was used as a coupling agent and N,N-diisopropylethylamine (DIPEA) dissolved in 1-methyl-2-pyrrolidinone (NMP) as a base. All couplings were executed with 4 equivalents (eq) amino acid, HCTU (4 eq) and DIPEA(12 eq) relative to the resin loading capacity. After each coupling step, the unreacted terminal amino group was capped by acetylation with a solution of acetic anhydride (5 eq) and DIPEA in DMF (5 eq).

TABLE 1

Automated steps of the Batch Fmoc solid phase peptide synthesis

| [Step] | Solvent/Reagent | Repetition | Time (min) | Description |
|---|---|---|---|---|
| 1 | 40% Piperidine/DMF | 1 | 5 | Fmoc deprotection |
| 2 | 40% Piperidine/DMF | 1 | 10 | Fmoc deprotection |
| 3 | DMF | 5 | 1 | Wash |
| 4 | 4 eq Fmoc protected amino acid, 4 eq HCTU, 12 eq DIPEA | 1 | 60 | Coupling [a] |
| 5 | DMF | 2 | 1 | Wash |
| 6 | 5 eq acetic anhydride, 5 eq DIPEA | 1 | 20 | End Capping [b] |
| 7 | DMF | 3 | 1 | Wash |

[a] In DMF Alox/NMP;
[b] In DMF Alox; wherein DMF Alox is DMF previously treated with aluminum oxide The same protocol was applied in a scaled up synthesis using Rink Amide AM resin (5 g) where the reaction was carried out in a 500 ml solid phase glass reactor using 3 eq of amino acids and coupling reagents. The pH was kept constant at 9 throughout the reaction and the resin was probed for free amino groups using a Kaiser- and trinitrobenzene sulfonate-test (TNBS) after each coupling and cleavage step. There was no need for NMP as a cosolvent.

Overall yields generally range between 10% and 15% at ~95% purity which is typical for solid phase peptide synthesis.

After synthesis, the peptide resin was washed with DMF, isopropyl alcohol, DMF, dichloromethane and diethyl ether before it was dried overnight on a vacuum line. Peptide cleavage from the resin and removal of protection groups was performed with cold TFA (95%), triethylsilane (2.5%) and $H_2O$ (2.5%). The ice cooled-cleavage mixture was added to the resin and incubated for 2 h-3 h at room temperature. The filtered cleavage cocktail was precipitated in and washed with cold diisopropyl ether (40 mL). The white solid was dried overnight on a vacuum line.

Figure 1B:
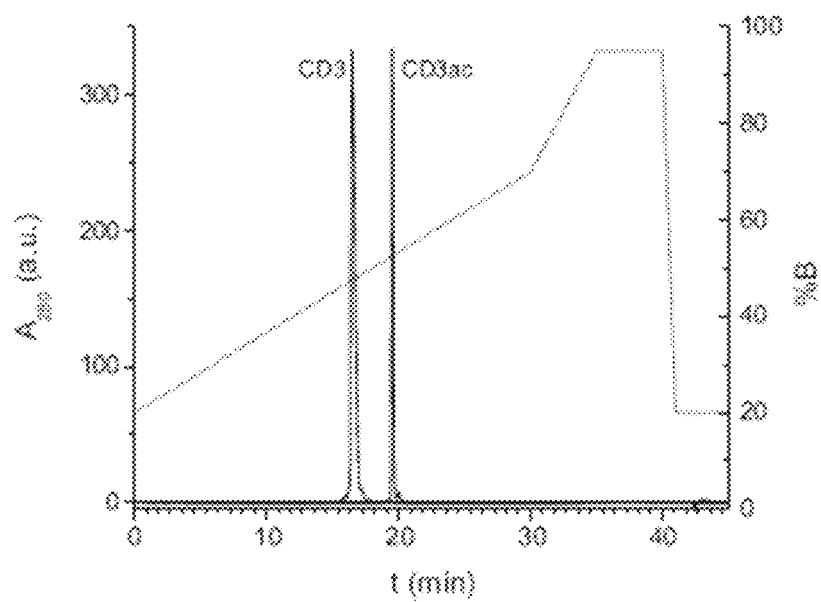

Peptide Purification:

All peptides were purified on a Shimadzu Prominence HPLC with parameters listed in Table 2. The crude peptides were ground and dissolved in a mixture of DMF and acetonitrile (4 mL, 1:1) and diluted with $H_2O$ (0.1% TFA) to a final volume of 20 mL. Gelation of crude product is eliminated under these solvent conditions. The sample was subsequently filtered through a 0.45 μm PTFE syringe filter and pumped onto a Merck LiChrospher 100, RP-18e column (5 μm, 250-10) at a flow rate of 4 mL/min and eluted with a linear gradient of water (0.1% TFA) to acetonitrile (MeCN). Sample elution was followed by absorption at 280 nm and collected according to fixed fraction volumes of 5 mL. The presence of product peptide was qualified by mass spectrometry (FIG. 1A) and quantified in analytical HPLC runs (FIG. 1B). Fractions containing more than 80% product ($A_{280}$) were applied to a second purification step on the same chromatography material carried out with acetic acid (2%) in the aqueous phase. Fractions containing more than 95% product were combined, neutralized with ammonia and lyophilized.

TABLE 2

Parameters of HPLC purification

| Feature | Preparative | Analytical |
|---|---|---|
| Solvent A | $H_2O$ bidist, 0.1% TFA or 2% AcOH | $H_2O$ bidist, 0.1% TFA |
| Solvent B | MeCN | MeCN |
| Column | LiChrospher 100, RP-18e (5 μm), 250-10 | LiChrospher 100, RP-18e (5 μm), 250-4.6 |
| Gradient | 5% B → 95% B, 120 min | 20% B → 70% B, 30 min |
| Injected volume | According to requirements | 25 μL |
| Flow rate | 5 mL/min | 1.5 mL/min |
| Detection | $A_{280}$ | $A_{280}$ |
| Fractionation | λ > 500 mAU | — |
| Fraction size | 5 mL | — |

Post Purification Modification:

Acetylation of primary amines on N-terminus and lysines was performed on purified peptide dissolved in DMF by applying a 40-fold excess of acetic anhydride and DIPEA. Completeness of the reaction was controlled by mass spectrometry before the reaction mixture was repurified according to the procedure described earlier.

Bead Formation and Co-Assembly:

CD3ac and rose bengal (RB) were dissolved in $H_2O$:EtOH at a ratio of 1:1 and mixed to yield final RB concentrations of $61.5 \times 10^{-6}$ M, $184.5 \times 10^{-6}$ M, $307.5 \times 10^{-6}$ M, $615 \times 10^{-6}$ M and $922.5 \times 10^{-6}$ M. The concentration of CD3ac was kept constant at $615 \times 10^{-6}$ M. Solvent exchange to $H_2O$ was carried out by counter-evaporation in 24-well sitting drop crystallization plates; 50 μL pre-mixed solution of CD3ac and RB was applied to a sitting drop well and counter-evaporated four times against 1 mL $H_2O$ during 16 h. All experiments were carried out in triplicates. CD3ac spheres precipitate after ca. 30 min and sediment during the next 5 h.

In order to quantify the amount of encapsulated RB, the bead pellet was resuspended after solvent equilibration and normalized with $H_2O$ to a final volume of 100 μL. Subsequently, all samples were centrifuged for 30 min at 20 000 g, before 80 mL of supernatant was separated. The remaining pellet fraction was diluted 1:1 with 20 μL DMSO to dissolve the peptide assemblies. The concentration of RB in pellet and supernatant fractions was determined by absorption measurements and corrected for RB in the remaining 20 μL of the pellet fraction.

Estimating Bead Volume and Partition Coefficient:

In order to estimate the density of CD3ac precipitates, beads ($307.5 \times 10^{-6}$ M CD3ac starting concentration) were prepared large enough to exceed the diffraction limit of visible light. A low concentration of RB ($10 \times 10^{-6}$ M) was co-precipitated to allow an estimate of the bead diameter by confocal fluorescence microscopy (1.35 μm) and facilitate counting on a hemacytometer (Hausser Scientific). An average of 72 beads were counted in an observed cell volume of 250,000 μm$^3$ that equals a bead volume fraction of $3.71 \times 10^{-4}$. A solution of 50 μL $307.5 \times 10^{-6}$ M CD3ac thus contains a total bead volume of 18.6 mL and the density of CD3ac can be determined ($\rho_{CD3ac} \approx 1.35$ g/cm$^3$). The logarithmic partition coefficient of RB in an aqueous solution of CD3ac beads was calculated according to $$\log P_{CD3ac/H_2O} = \log\left(\frac{[RB]_{CD3ac}}{[RB]_{H_2O}}\right) \quad (1)$$

Ultraviolet-Visible Spectroscopy:

Absorption measurements were carried out on a Nanodrop 1000 (Thermo Scientific). Extinction coefficients of CD3ac in $H_2O$:Ethanol:DMSO 1:1:2 (21,780 M$^{-1} \cdot$cm$^{-1}$, 280 nm) and rose bengal in $H_2O$:DMSO 1:1 (11,639 M$^{-1} \cdot$cm$^{-1}$, 562 nm) were obtained. DMSO was used to dissolve precipitated CD3ac after assembly and to reduce solvent evaporation during preparation time as the measured sample volume amounts for only 4 μL. If necessary, the sample was further diluted with $H_2O$:EtOH:DMSO 1:1:2 to yield absorption intensities in the linear range of the instrument. RB concentrations were determined by weigh-in prior to co-assembly. After co-precipitation of CD3ac and RB, pellet and supernatant fractions were diluted 1:1 with DMSO (assembled CD3ac dissolves in a solution of $H_2O$:DMSO 1:1).

Circular Dichroism (CD):

CD experiments were carried out on an Applied Photophysics Chirascan in QS cuvettes (1 mm path length). Sample concentrations were adjusted to yield dynode values between 300 V and 500 V in the measured wavelength range. Blank measurements were carried out with water immediately prior to sample measurements. Each spectrum was averaged from three scans in wavelength intervals of 1 nm, each of two independent sample preparations. All spectra were smoothed applying the 2nd-order Savitzky Golay algorithm. CD data are reported in molar units (deg cm$^2$ dmol$^{-1}$), shown as degrees molar ellipticity.

Scanning Electron Microscopy:

Scanning electron microscopy (SEM) was carried out on a Hitachi S-4800. SEM sample holders were cooled to −196° C. before a drop of the bead suspension was directly applied to the cold metal surface. The frozen sample on the plate was subsequently lyophilized, sputtered with platinum and analyzed.

Dynamic Light Scattering:

Dynamic light scattering was measured on an ALV/CGS-8F platform based goniometer system equipped with an ALV/-5000/E correlator and an Argon-Ion laser with a wavelength of 633 nm (35 mW) at scattering angles between 30° and 150°. An ALV-5000/E correlator calculates the photon intensity autocorrelation function g2(t). All experiments were performed at T=293 K and evaluated by second order cumulant fit (considering previously determined spherical particle shape by SEM). Polydispersities were determined by the contin-algorithm at all angles and never exceeded 0.11. Angular dependent measurements were carried out in steps of 10° from 30° to 150°. In order to avoid influence of multiple scattering, concentration dependent experiments were performed. For both angular and concentration dependence, a hydrodynamic radius was calculated from the Stokes-formula $$r_h = \frac{k_B T}{6\pi \eta D} \quad (2)$$

where $r_h$ is the hydrodynamic radius of spherical particles, D is the diffusion constant, $k_B$ is the Boltzmann constant, T is the absolute temperature and is the viscosity of water. A graph of $1/r_h$ versus angle (concentration) was plotted and the hydrodynamic radius ($r_{h0}$) was calculated by extrapolating both concentration and angle measurements to zero.

Mass Spectrometry:

Mass spectrometry was performed on an LTQ-Orbitrap (Thermo Scientific). 5 μL of a CD3ac solution ($10\times10^{-6}$ M, H$_2$O:MeCN 2:1) was loaded onto a 100 μm capillary column packed with Magic C18 AQ (3 μm particle diameter). The peptide was eluted in a 30 min gradient from H$_2$O (4% formic acid) to MeCN. The orbitrap was set to positive mode and a resolution of 10,000.

Confocal Microscopy:

Confocal microscopy images were obtained on a Nikon Ti motorized inverted microscope equipped with DIC, phase and epi-fluorescence optics, a Yokagawa CSU-10 spinning disc confocal with 488 nm, 568 nm and 647 nm laser lines. A Hamamatsu ORCA-AG cooled CCD camera was used for confocal, and a Hamamatsu ORCA-R2 was used for wide-field imaging. CD3ac ($615\times10^{-6}$ M) was co-dissolved with (a) RB ($10\times10^{-6}$ M), (b) CF ($10\times10^{-6}$ M) and (c) RB and CF (both $10\times10^{-6}$ M) in a volume of 50 μL 50% EtOH each and counter-evaporated against water. The resulting suspension was normalized with H$_2$O to a total volume of 50 μL per sample and subsequently applied to the confocal microscope.

Example 1

Solid Peptide CD3ac Nanoparticles—Structural Characterization

Figure 2A:
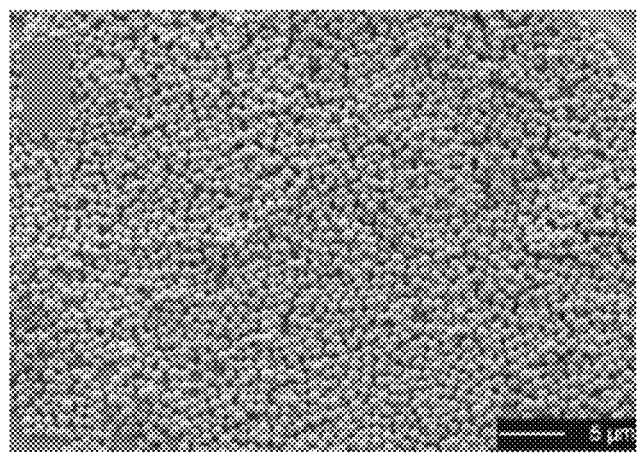
FIGS. 2A-2C show SEM images of CD3ac peptide nanoparticles in accordance with one or more embodiments of the invention.

Conventional hydrophobic peptides are generally difficult to get synthesized and purified, and they are also generally difficult to dissolve and tend to precipitate to amorphous structures in aqueous solution. In accordance with various aspects and embodiments described herein, a de novo designed peptide CD3ac consisting of ten amino acids:

Ac-(LK(Ac))$_3$-LW-DL-LW-DL-LW-DL-LW-NH$_2$
(SEQ ID NO: 17), where LK(Ac)=acetylated L-lysine; LW=L-tryptophan; DL=D-leucine, demonstrates different properties from other peptidic materials: CD3ac readily dissolves in most organic solvents (EtOH, iPrOH, DMSO, DMF, MeCN) and precipitates to evenly structured bead-like spheres upon solvent exchange to water (FIG. 2A).

The CD3ac peptide (mass 1652.910 g/mol; purity >95%, A280) can be considered amphiphilic as its sequence is divided into two sections: a hydrophobic block consisting of alternating L-tryptophane and D-leucine, and a hydrophilic one consisting of three acetylated L-lysines. The terms "hydrophilic" and "hydrophobic" as used herein are not absolute but describe the relative polarity within the amino acid sequence, e.g., of CD3ac. Although the CD3ac peptide is hydrophobic, it can be synthesized at high yield and purified with standard procedures on reverse phase C18 chromatography material (see the Materials and Methods Section described earlier), as compared to conventional hydrophobic peptides.

Figure 2B:
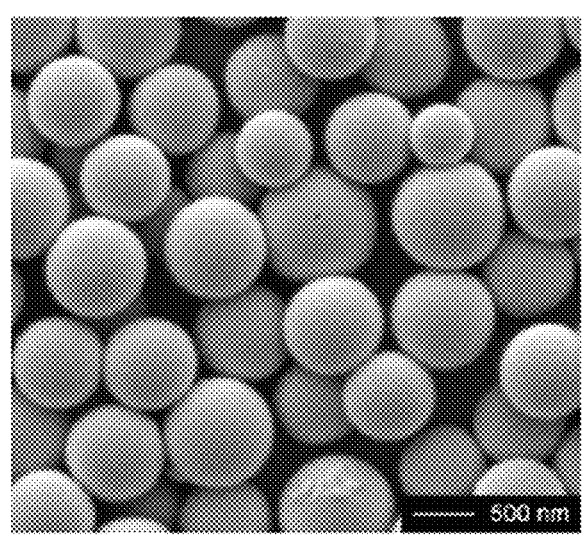
Figure 2C:
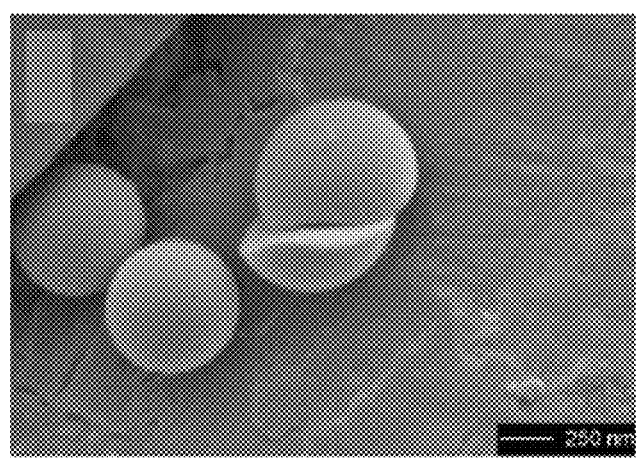
Figure 3A:
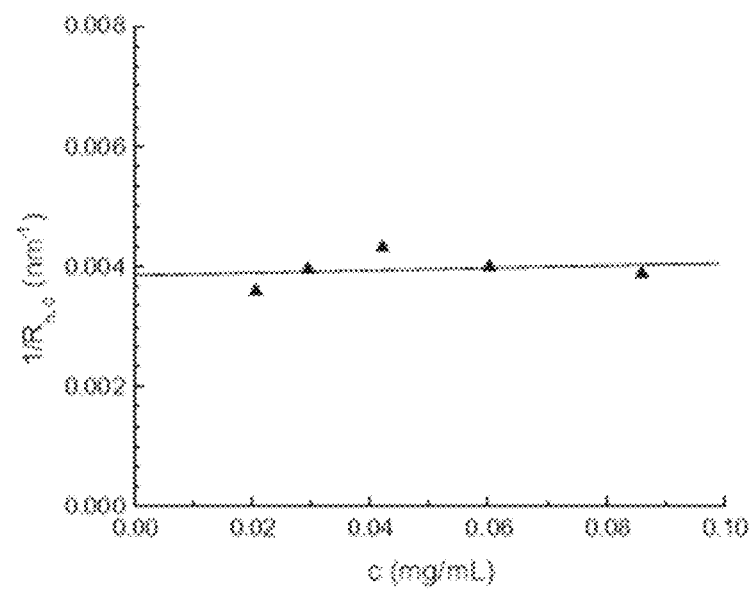
FIGS. 3A-3B show linear fits of dynamic light scattering (DLS) results. It is determined that both particle concentration (FIG. 3A) and detection angle (FIG. 3B) unlikely influence the diffusion properties of CD3ac beads in aqueous solution.
Figure 3B:
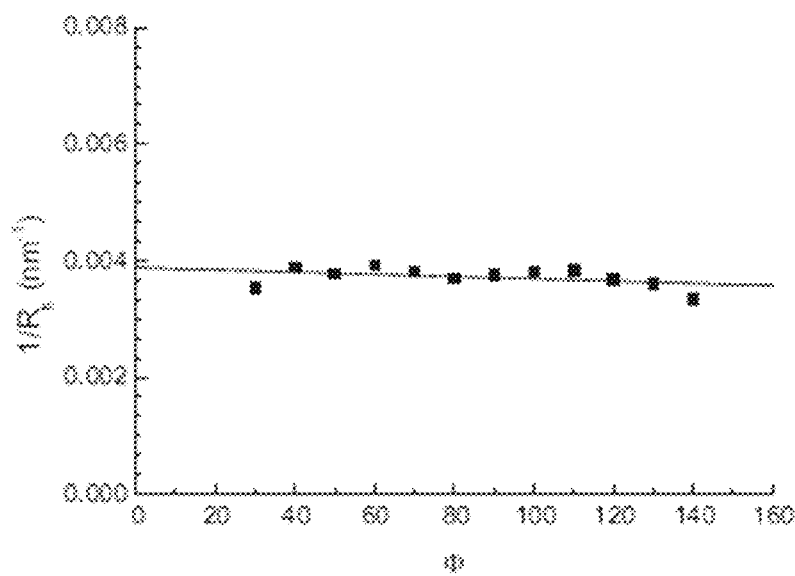

CD3ac is able to precipitate to spherical aggregates in the colloidal size range, and it can do so in a robust and reproducible manner. Solvent exchange was carried out by dialysis or, in order to reduce material consumption, by counter-evaporation against water in 24-well crystallization plates. The size distribution of the resulting peptide bead suspension was measured by scanning electron microscopy (SEM, FIGS. 2A-2C), and concentration- and angle-dependent dynamic light scattering (DLS, FIGS. 3A-3B). Both methods reveal a particle radius of about 260 nm. The sphere's radius can be influenced by the concentration of initially dissolved CD3ac (before solvent exchange) and lies in the size range between about 200 nm and about 1500 nm corresponding to initial CD3ac concentrations between $61.5\times10^{-6}$ M to $923\times10^{-6}$ M. The DLS data shown in FIGS. 3A-3B refer to CD3ac particles formed from initially dissolved CD3ac at $123\times10^{-6}$ M. The obtained peptide particles (beads) have low polydispersity without a need for sizing procedures such as sonication or extrusion, which are commonly applied to achieve a narrow size distribution in e.g., lipid suspensions.

Secondary structure can play, in part, a crucial role in the assembly of CD3ac beads. Without wishing to be bound by theory, due to light scattering, it can be difficult to obtain quantifiable circular dichroism data of colloidal suspensions containing particles larger than 50 nm in diameter. Thus, four structural derivatives of CD3ac (CD1, CD2, CD3 and CD4), which are not acetylated, and therefore are charged and water soluble (see Table 3) were synthesized.

TABLE 3

Amino acid sequences and molecular weight of exemplary synthesized peptides and derivatives thereof

| [Name] | Sequence SEQ ID NOS 48-49, 11, 50, 17 and 51-52, respectively in order of apperance) | MW (Da) |
|---|---|---|
| CD1 | H-LK-LW-DL-LW-DL-LW-DL-LW-NH$_2$ | 1228.680 |
| CD2 | H-LK-LK-LW-DL-LW-DL-LW-DL-LW-NH$_2$ | 1356.775 |
| CD3 | H-LK-LK-LK-LW-DL-LW-DL-LW-DL-LW-NH$_2$ | 1484.870 |
| CD4 | H-LK-LK-LK-LK-LW-DL-LW-DL-LW-DL-LW-NH$_2$ | 1612.965 |
| CD3ac | Ac-LK(Ac)-LK(Ac)-LK(Ac)-LW-DL-LW-DL-LW-DL-LW-NH$_2$ | 1652.910 |
| LCD3 | H-LK-LK-LK-LW-LL-LW-LL-LW-LL-LW-NH$_2$ | 1484.870 |
| LCD3ac | Ac-LK(Ac)-LK(Ac)-LK(Ac)-LW-LL-LW-LL-LW-LL-LW-NH$_2$ | 1652.910 |

Figure 4:
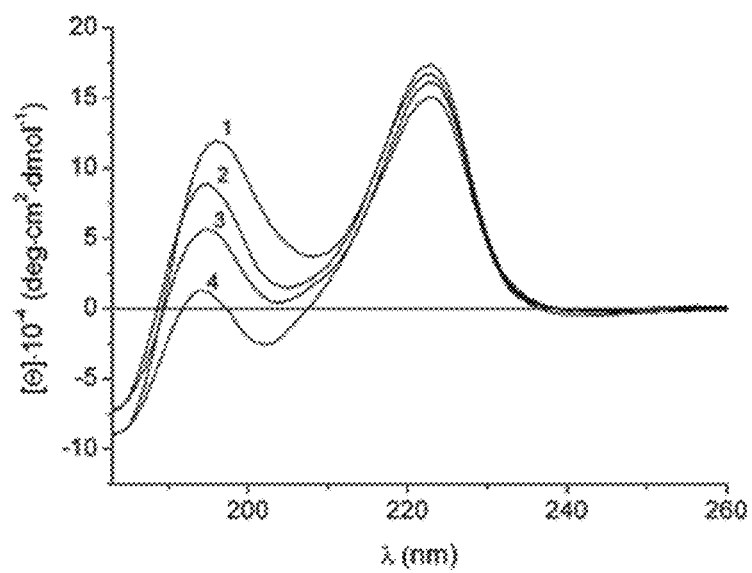
FIG. 4 shows a set of circular dichroism spectra of CD3ac derivatives CD1, CD2, CD3 and CD4. Displayed numbers equal the number of N-terminally attached lysine residues.

FIG. 4 shows circular dichroism spectra of CD1 to CD4 in water. Generally, charged poly-L-lysine peptides adopt a random coil secondary structure and exhibit negative ellipticities between 180 nm and 210 nm; presented herein shows that peptides with shorter oligo-lysine sequences show increasing ellipticities in this wavelength range. Also, a typical random coil spectrum has little to no influence on ellipticities above 210 nm; thus, the wavelength range between 210 nm and 260 nm can be assigned almost entirely to the influence of the alternating sequence of L-Trp and D-Leu. For example, the intensity and position of the peak at 223 nm remains nearly unchanged as the number of attached lysine residues is varied, indicating that the secondary structure of repeating units of LW-DL is little or not affected by the length of N-terminally attached oligo-lysine—possibly not even influenced by the presence of multiple cationic charges on the attached lysine residues.

The circular dichroism spectra of the CD4-CD1 series can be theoretically extrapolated to an imaginary CD0, which would not contain any lysine, to obtain a spectrum with maxima at about 196 nm and 223 nm. Similar spectra have not been observed in prior synthetic hydrophobic peptides, but were reported previously in structural studies of gramicidin A, a 15 amino acid antibiotic peptide derived from the soil living bacterium *Bacillus brevis* [16, 17].

The secondary structure motif of gramicidin is a wide helix rarely observed in nature and versatile in terms of helical pitch, handedness and dimeric configuration (quaternary structure) [17c,18], depending on the dielectric constant of its environment [19]. While gramicidin A contains an alternating motif of L-Trp and D-Leu, CD3ac presented herein is distinct from gramicidin in various aspects, e.g., peptide sequence and length, significant modifications of terminally attached formyl and ethanolamine present in gramicidin. For example, the gramicidin sequence is hydrophobic throughout its length, but CD3ac presented herein is amphiphilic due to N-terminal addition of at least one L-lysine (e.g., 1 L-lysine, 2 L-lysines, or 3 L-lysines) and acetylation of at least one amino group of the amphiphilic peptide.

Without wishing to be bound by theory, a repeated sequence of LW-DL can lead to a set of phi- and psi-angles distinctly different from the ones observed in isolated alpha-helices, beta-sheets and random coils, and be most likely governed by steric hindrance; stable intramolecular hydrogen bonds can be occasionally observed in comparatively short peptides [20]. While such secondary structures and intramolecular hydrogen bonds can exist in CD3ac, CD3ac is most likely too short to fold back on itself.

Figure 5A:
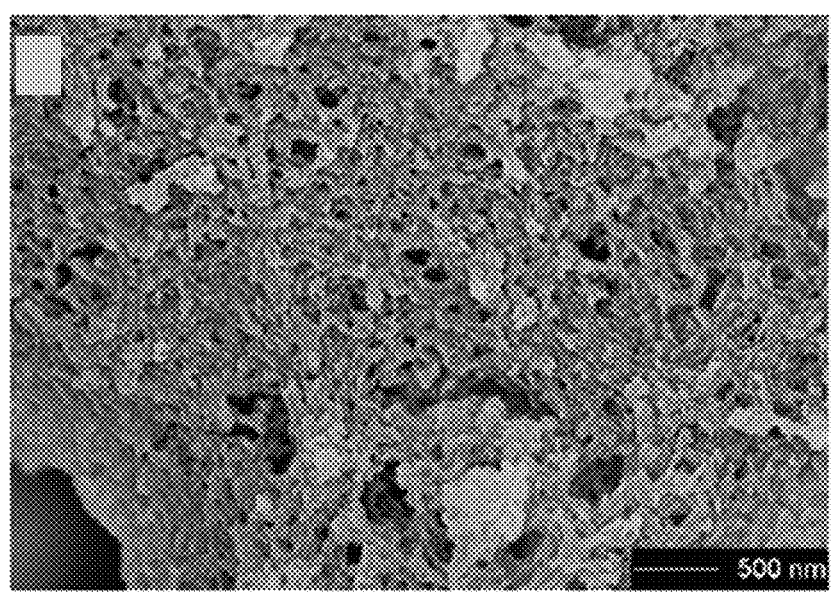
FIGS. 5A-5B show the effects of solely L-amino acids on properties of peptide nanoparticles.
Figure 5B:
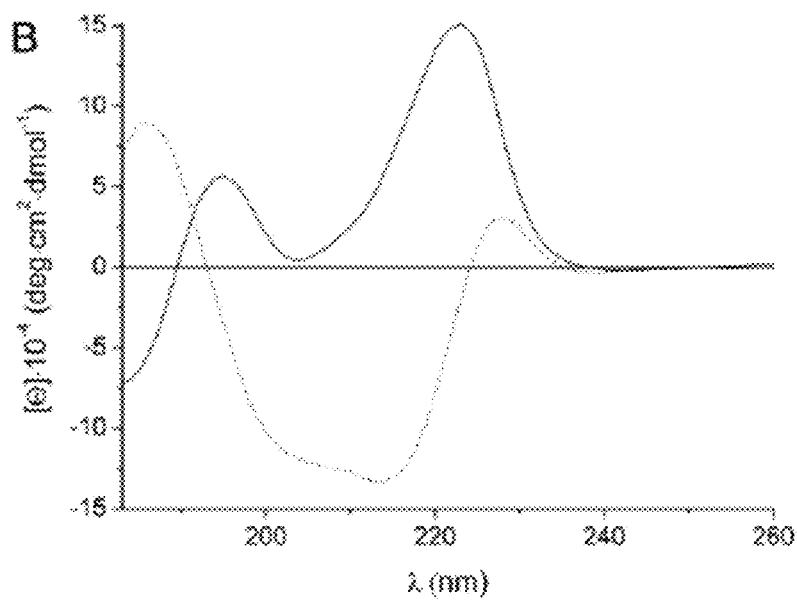

The importance of secondary structure in regard of the bead-like assembly was demonstrated by LCD3ac, a peptide of identical constitution (amino acid sequence) but entirely composed of L-amino acids. LCD3ac precipitates to amorphous structure in the size range of micrometers (FIG. 5A) and the circular dichroism spectrum of charged LCD3 has dominant α-helical characteristics (FIG. 5B). Combined data of SEM and circular dichroism indicate that the feature of spherical precipitation depends, at least in part, on the presence of D-Leu and the specific secondary structure induced by it.

Example 2

Solid Peptide CD3ac Nanoparticles—Cargo Encapsulation

CD3ac is the first peptide synthesized by Fmoc chemistry which forms solid particles in the nano- and micrometer size range and holds promise for drug delivery applications. Although precipitated CD3ac spheres, in some embodiments, do not generally adhere to each other and have no observable affinity to glass or plastic surfaces, they can encapsulate cargo molecules during their formation. CD3ac were co-dissolved with $10 \times 10^{-6}$ M 5-carboxyfluorescein (CF), $10 \times 10^{-6}$ M 4,5, 6,7-tetrachloro-2',4',5',7'-tetraiodofluorescein (RB) and an equimolar mixture of both dyes, respectively. The experiment was carried out at pH 5 where RB is charged but CF is largely protonated exhibiting low solubility in aqueous solution. The solvent volume was re-adjusted to 50 μL after counter-evaporation, so that the fluorescence contrast between background and peptide beads can at least qualitatively determine cargo accumulation within the spheres.

Figure 6A:
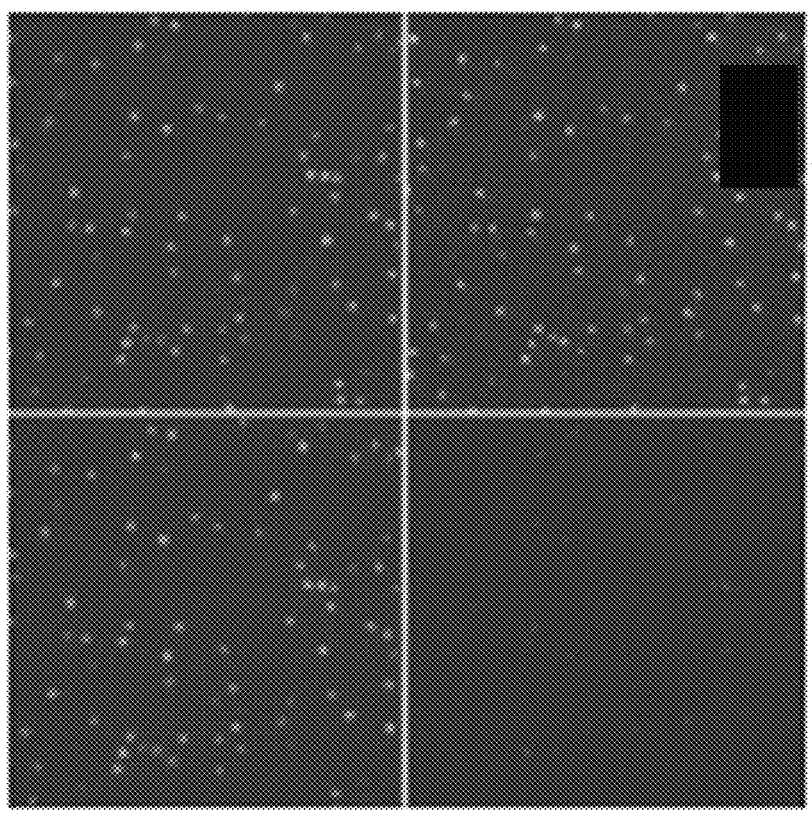
FIGS. 6A-6C show confocal microscopy images of CD3ac beads co-assembled with rose bengal (RB), 5-carboxy-fluorescein (CF), or a mixture of both.
Figure 6B:
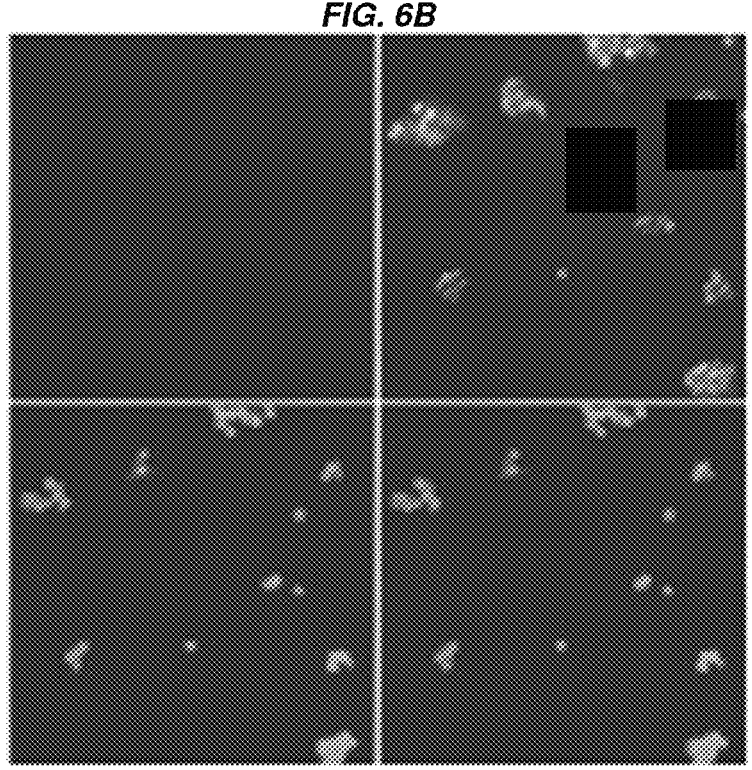
Figure 6C:
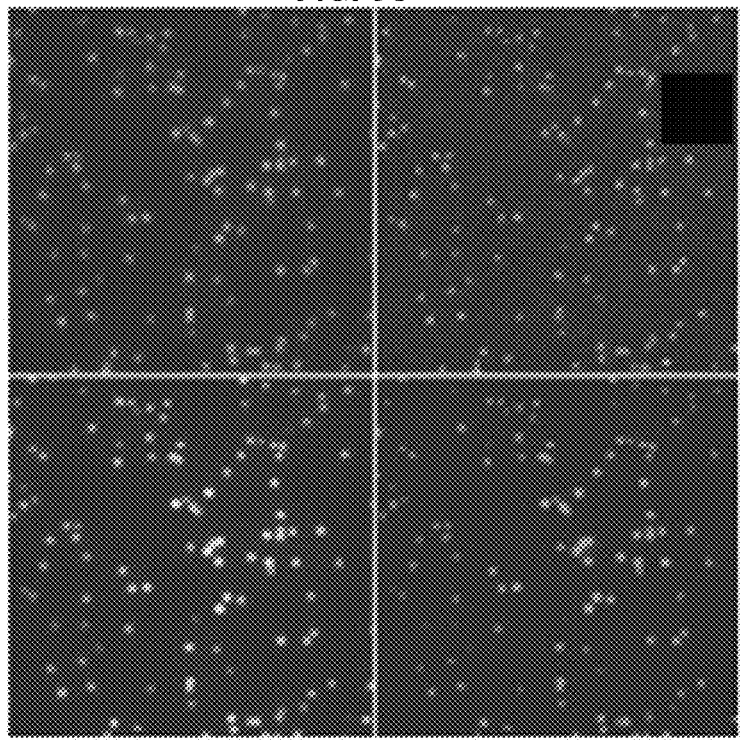

CF as well as RB is taken up by CD3ac-beads, rather independent of the dye's charge state (FIGS. 6A-6C). However, CF-loaded beads aggregate to grape-like assemblies (FIG. 6B) whereas RB-loaded spheres do not adhere to each other (FIG. 6A), most likely due to the display of charged RB on or close to the bead surface.

Hydrophobic dye such as CF and relatively hydrophilic dye such as RB can be both encapsulated by CD3ac-beads. Without wishing to be bound by theory, guest molecules can pre-associate with CD3ac early (in solution) and assemble upon removal of ethanol. The extent of pre-association, and thus coassembly efficiency, would depend on the affinity of host and guest compounds; in the case of xanthene-derivatives such as CF and RB, the interaction of delocalized ring-structures could contribute to their pre-association with CD3ac.

To analyze the molar composition of loaded CD3ac beads, the dye content of RB loaded CD3ac beads was quantified. RB is readily available and soluble in ethanol as well as water. While not wishing to be bound by theory, solubility in water is mandatory to avoid cargo precipitation outside the peptide beads upon solvent exchange. In addition, light absorption of RB is not strongly quenched in mixtures of water and DMSO, which allows for convenient and precise quantification by optical density.

Briefly, CD3ac and RB were co-dissolved at various concentration ratios in 50% EtOH. 50 μL each were applied to 24-well crystallization plates and counter-evaporated against four times 1 mL $H_2O$ during 16 h. All experiments were carried out in triplicates. CD3ac spheres usually precipitate after about 30 min, depending on the concentration of RB. After solvent equilibration, the formed bead pellet was re-suspended and normalized with $H_2O$ to a final volume of 100 μL. Samples were centrifuged for 30 min at 20,000 g, before 80 μL of supernatant was separated. Subsequently, the remaining pellet fraction was diluted 1:1 with 20 μL DMSO to dissolve the peptide assemblies. Contrary to ethanol, the use of DMSO helps to reduce sample evaporation and yields stable absorption values over at least 5 min (the sample volume for a UV-V is experiment is 4 μL, see the Exemplary Materials and Method section described earlier).

Figure 7A:
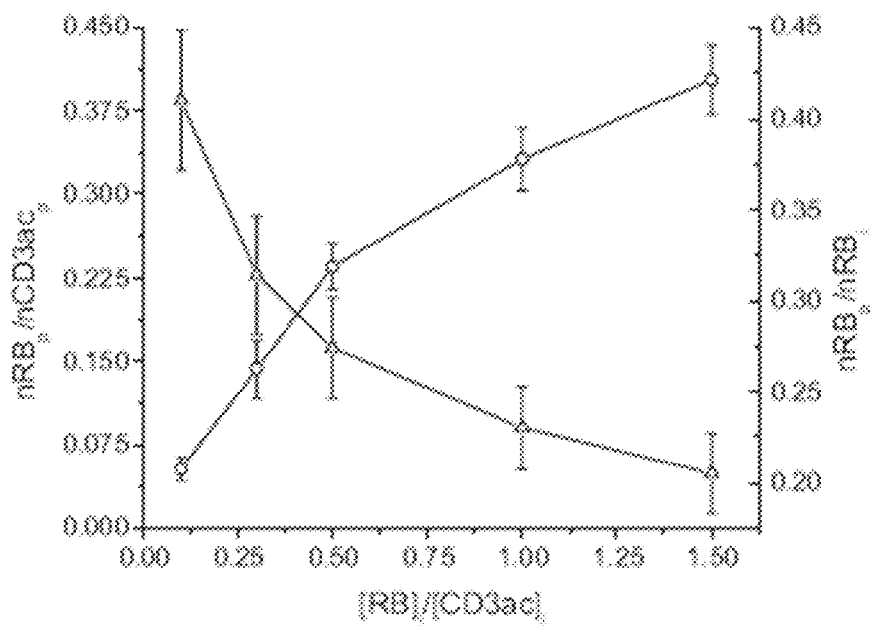
FIGS. 7A-7B show encapsulation efficiency of rose bengal (RB) in CD3ac nanoparticles.
Figure 7B:
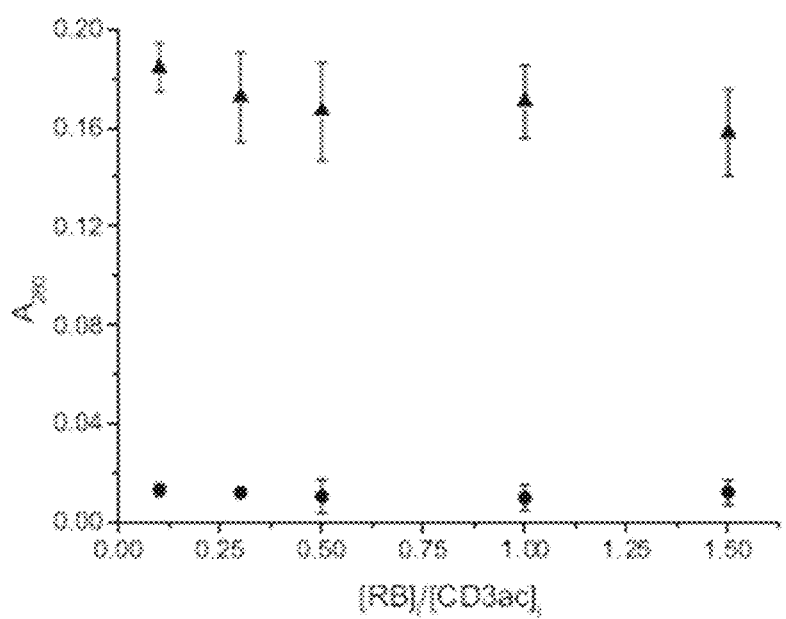

The co-assembly quantification data are summarized in FIG. 7A. The concentration of CD3ac was kept constant at $615 \times 10^{-6}$ M in the experiments described herein. Initially dissolved molar ratio of dye to peptide is given as $[RB]_i/[CD3ac]_i$. For example, at $[RB]_i/[CD3ac]_i=1$ as the experimental starting condition, after bead formation, about one-third of the sphere's molar composition ($nRB_p/nCD3ac_p$) is RB (open circles as shown in FIG. 7A) and roughly 25% of initially dissolved dye was loaded into CD3ac beads ($nRB_p/nRB_i$, open triangles as shown in FIG. 7A). As shown in FIG. 7B, absorption of pellet and supernatant fractions at 280 nm (absorption maximum of tryptophans) indicates that CD3ac precipitates almost quantitatively in the presence of a wide concentration range of RB (the molar ratio of RB to CD3ac $[RB]_i/[CD3ac]_i$ in the experiments described herein spans 1.5 orders of magnitude). Addition of higher RB concentrations can lead to more dye molecules co-assembled within CD3ac beads; however, the relation of initially dissolved and co-assembled RB is not linearly proportional, and the efficiency of co-assembly (nRBp/nRBi) will reach a saturation limit.

The encapsulation efficiency of RB in CD3ac beads can amount for at least about 30% w/w or at least about 40 mol-% or higher in analyzed concentration ratios, which corresponds to an about 900-fold increase of RB concentration or a logarithmic partition coefficient of RB in CD3ac/$H_2O$ of 2.95. Similar or even higher efficiencies are contemplated for hydrophobic cargo molecules; however, accurate quantification of water-insoluble compounds can be prone to artifacts due to cargo precipitation outside the peptide beads upon solvent exchange.

The ability of CD3ac to efficiently pre-associate and co-precipitate RB is remarkable, at least partly because RB is doubly charged and water soluble. In fact, its solubility in water is about five times higher than in ethanol. As presented herein, bead assembly of CD3ac is not inhibited by the presence of equimolar concentrations of RB, and it is contemplated that, not to be bound by theory, peptide and dye interact mainly on aromatic interactions leading to rather unspecific binding (as compared to e.g., avidin/biotin). This functionality can complement the encapsulation properties of solid lipid nanoparticles as well as vesicular systems.

Presented herein is a highly hydrophobic sequence of 10 amino acids synthesized and purified at high yields and preparative quantities. The peptide (CD3ac) can assemble into evenly-shaped beads of low size polydispersity in the absence of any templating strategies. Circular dichroism measurements of charged derivatives of CD3ac indicate a structural relation to D,L-helical gramicidin and the essential role of D-Leu in regard of its specific secondary structure. LCD3, which exclusively contains L-amino acids, exhibits α-helical characteristics and precipitates amorphously in its acetylated state. CD3ac can encapsulate both hydrophilic and hydrophobic compounds with efficiencies exceeding existing encapsulation strategies [15], for example, resulting in logarithmic partition coefficients of at least 2.95, and the encapsulation efficiency is not limited by the concentration of the hydrophilic species in solution, unless it reaches a saturation limit.

In accordance with various aspects and embodiments described herein, the solid peptide particle state in conjunction with a highly efficient cargo encapsulation can be utilized to decrease degradation of sensitive and cost intensive pharmaceuticals and applied to deliver high payloads into cells. Such peptide drug delivery system can entrap and accumulate guest molecules (e.g., active agents) in a convenient one-step procedure. Therefore, presented herein is non-polymeric drug delivery system based on natural amino acid building blocks and synthesis by Fmoc chemistry, which can augment the current toolbox of colloidal species and holds promise for medical applications.

Example 3

CD3ac Nanoparticles with a Protein Corona for Drug Delivery into Cells

As described in Examples 1 and 2, CD3ac peptide nanoparticles can be assembled from dissolved CD3ac by addition of water: an emulsion spontaneously forms as the ternary mixture (CD3ac, organic solvent, H2O) is brought into the two-phase region (CD3ac, H2O). The emulsification process resembles the ouzo effect (8), however, CD3ac droplets harden to solid particles as the organic solvent is removed. Examples 1 and 2 demonstrate that neutral as well as charged aromatic molecules can migrate into the dispersed phase and get trapped during particle formation (5).

Figure 8A:
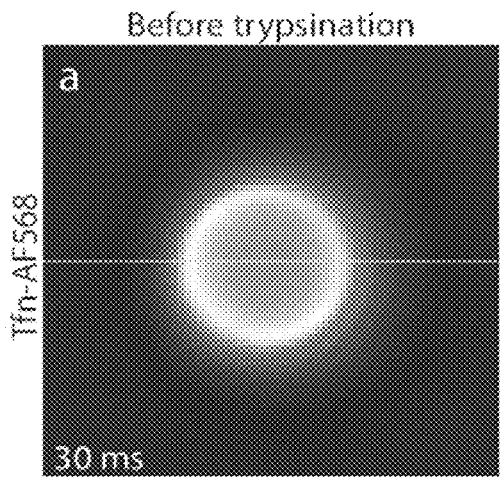
FIGS. 8A-8I show results of characterization of CD3ac peptide particles assembled in the presence of transferrin labeled with AF568 (Tfn-AF568) and Flutax-2 and transferrin (Tfn).
Figure 8D:
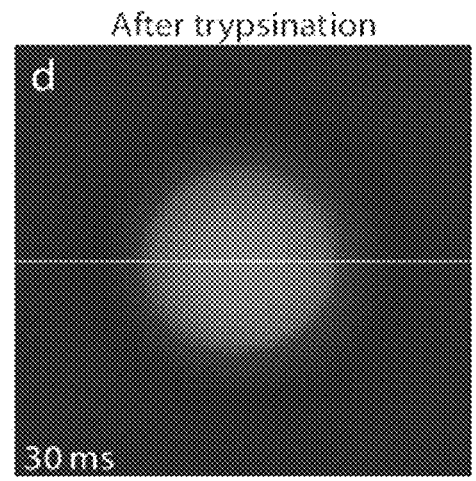
Figure 8B:
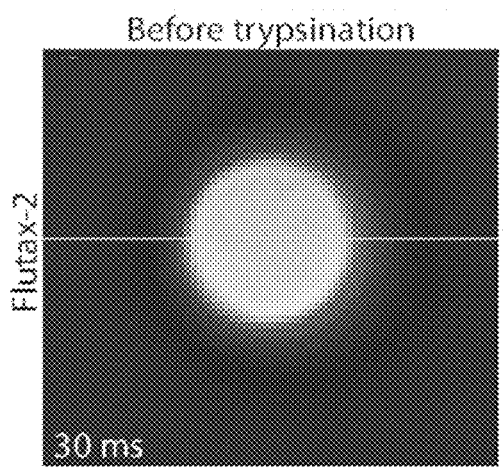
Figure 8E:
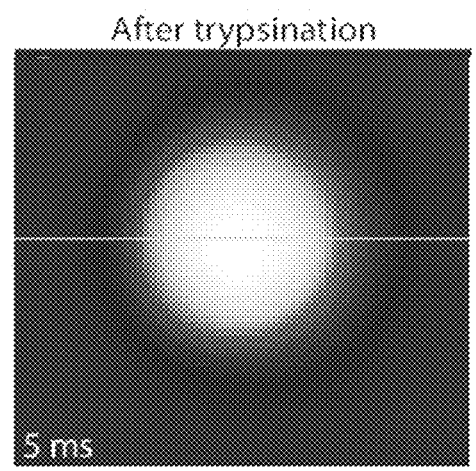
Figure 8C:
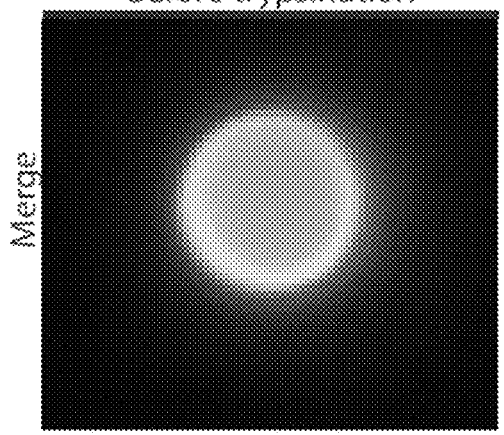

In Example 3, presented herein is a new drug delivery system consists of the CD3ac peptide matrix, entrapped cargo (Flutax-2) and a corona of transferrin, optionally labeled with Alexa Fluor 568 (Tfn-AF568) for visualization purposes. To evaluate the spatial arrangement of the reagents in self-assembled CD3ac particles, CD3ac peptides were dissolved along with Flutax-2 and Tfn-AF568 in 50% EtOH and the EtOH content was reduced in steps as shown in the Exemplary Materials and Methods later. FIGS. 8A-8I shows fluorescence images of the resulting CD3ac peptide drug carrier nanoparticles. In this embodiment, the CD3ac nanoparticles were about 3 μm in diameter, the size designed to be large enough to distinguish the distribution of fluorescence in the core and at the surface by conventional light microscopy. Without wishing to be bound, smaller or larger CD3ac peptide nanoparticles can be produced. Tfn-AF568 shows a bright ring of fluorescence at the particle periphery whereas Flutax-2 fluorescence is equally distributed throughout the particle (FIGS. 8A-8C). The entrapment efficiency was measured by determining the partition coefficient of Flutax-2 between peptide particles and water (FIGS. 9A-9D). The partition coefficient of Flutax-2 between peptide particles and water was determined to be 5.25, i.e., under applied experimental conditions, more than 80% of co-dissolved Flutax-2 escapes the aqueous phase and gets entrapped in particles. Such partition coefficient value is remarkably high for a water soluble compound.

Figure 8F:
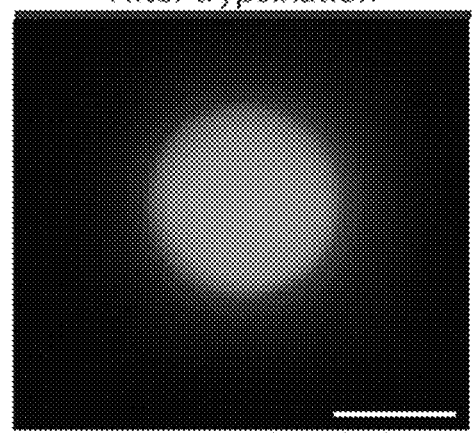
Figure 8G:
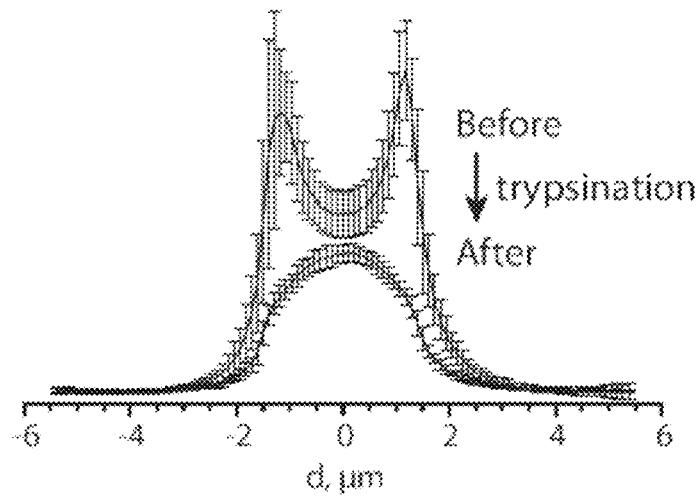
Figure 8H:
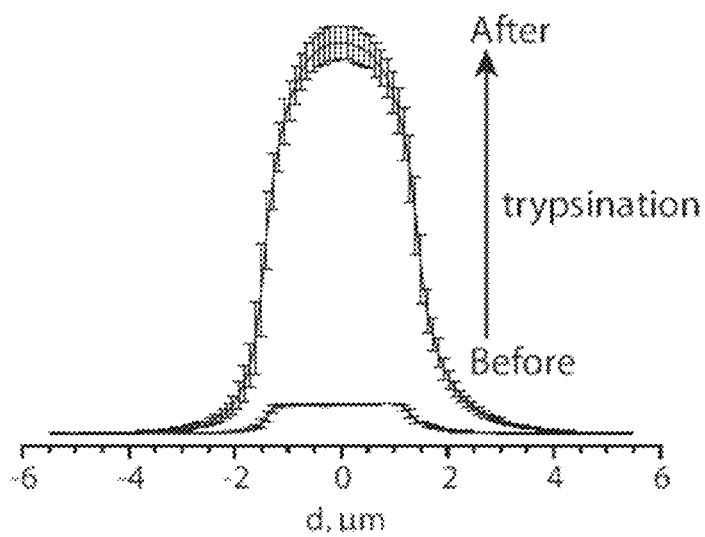
Figure 8I:
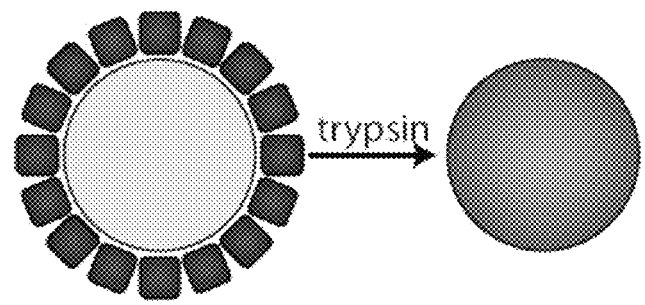

Proteins are generally surface-active and can adsorb onto solid-liquid interfaces. Accordingly, it was sought to determine whether particles in contact with protein solutions can get covered with a layer of proteins referred to as "protein corona" (10). As such, it was assessed whether the pronounced rim of red fluorescence represents a corona consisting of Tfn-AF568. To assess this, the particles described herein were incubated for 6 hours in 50 μg/mL trypsin. The rim disappeared while the spatial distribution of the Flutax-2 cargo remained unaltered (FIGS. 8D-8F). Quantification of gray-level profiles indicated that the intensity of the Tfn-AF568 rim was reduced by 3-fold after trypsin incubation (FIG. 8G). At the same time, removal of the Tfn-AF568 corona resulted in an increase of green fluorescence of Flutax-2 up to a factor of 13 (FIG. 8H), originating in the spectral overlap of Tfn-AF568-absorption and Flutax-2-emission. Together, these experiments indicate that self-assembly of CD3ac, Flutax-2 and Tfn-AF568 leads to the formation of particles with entrapped Flutax-2 and a corona of surface-adsorbed Tfn-AF568. Trypsination of the self-assembled particles can result in proteolytic degradation of Tfn-AF568 followed by surface desorption of the fragments (FIG. 8I).

Figure 10A:
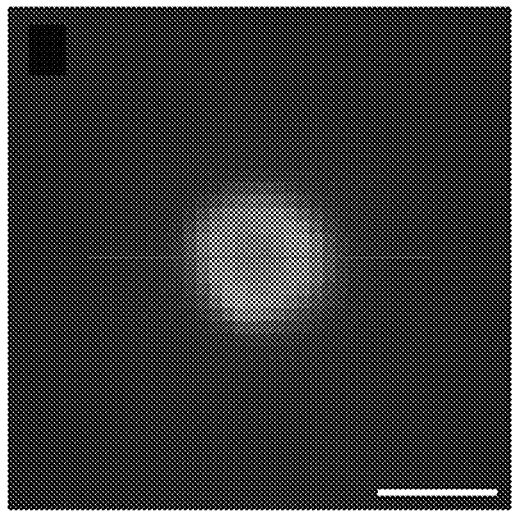
FIGS. 10A-10K show control of particle diameter and characterization of nanoparticle morphology by TEM.
Figure 10B:
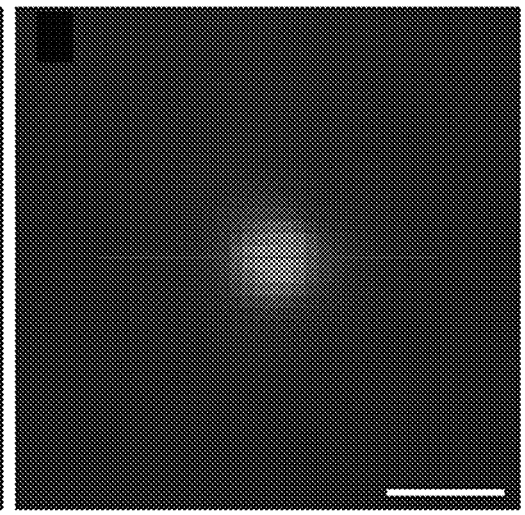
Figure 10C:
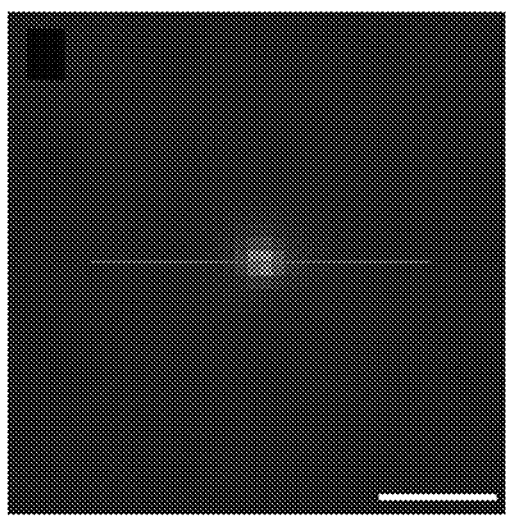
Figure 10D:
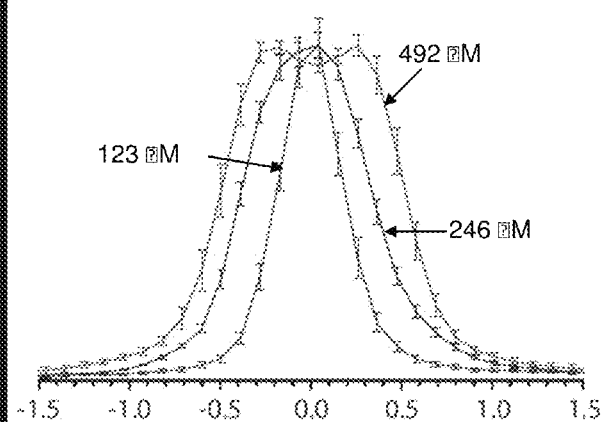
Figure 10E:
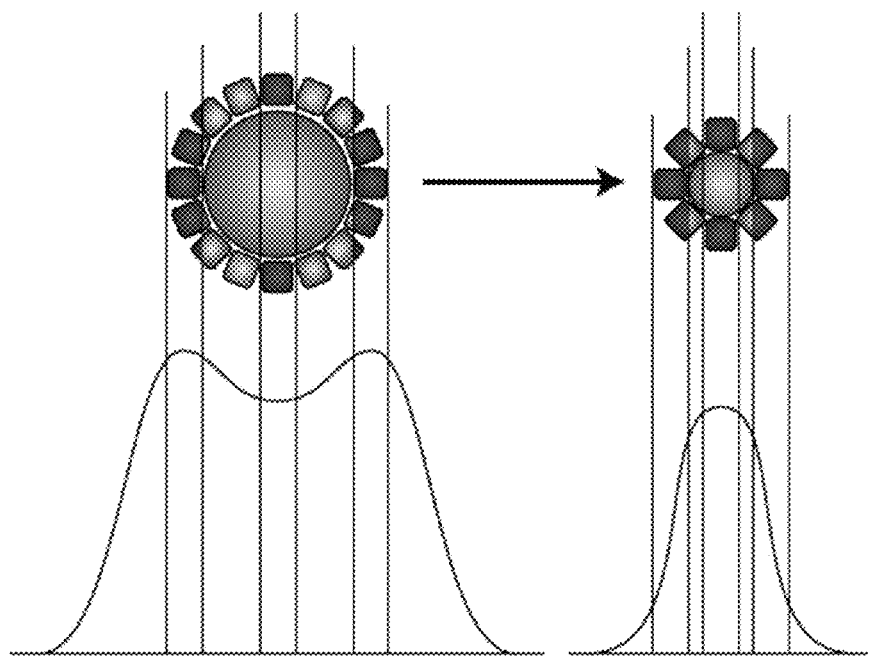

Particles for drug delivery are generally between 8 nm and 200 nm in diameter as this size range is less likely to be cleared by kidney and liver (4). Also, receptor mediated endocytosis, a possible mechanism for the uptake of targeted drug-containing particles, is size-dependent and more efficient for particles smaller than about 150 nm (11). In order to reduce CD3ac particle size, lower peptide concentrations were dissolved prior to emulsification: FIGS. 10A-10C show fluorescence microscopy images of peptide particles prepared from 492 μM, 246 μM and 123 μM CD3ac, assembled in the presence of 10 μg/mL Tfn-AF568. The resulting size differences are summarized in FIG. 10D by intensity profiles of particle-associated fluorescence. The characteristic ring, still visible at 492 µM, cannot be observed on smaller particles due to the diffraction limit of visible light, although light microscopy confirms the presence of Tfn-AF568 on particles smaller than 300 nm (FIG. 10E). To confirm corona formation of Tfn-AF568 on nanoparticles (d<100 nm), transmission electron microscopy (TEM) was applied.

Figure 10F:
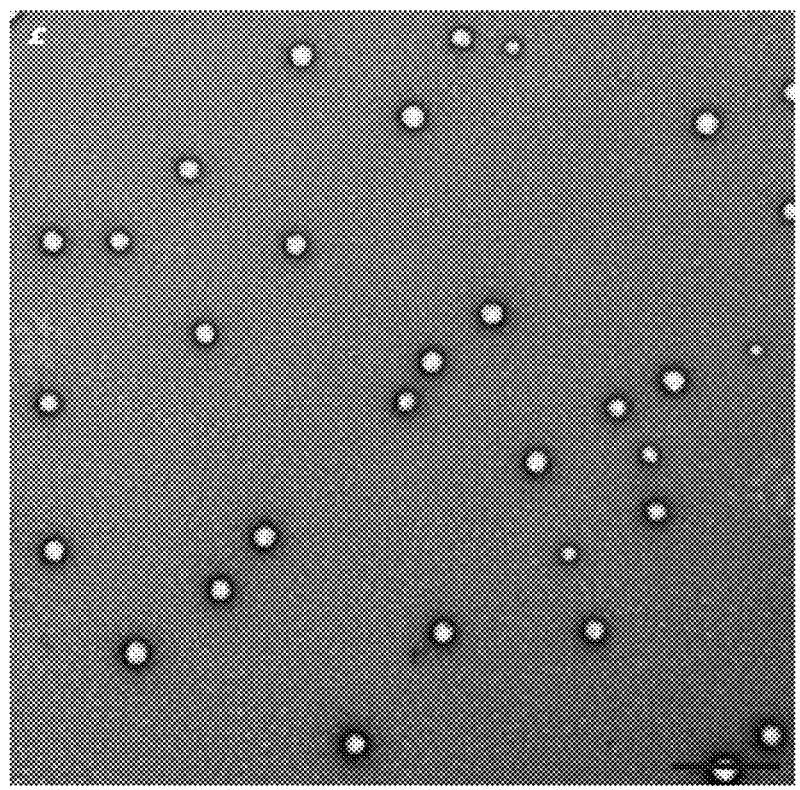
Figure 10G:
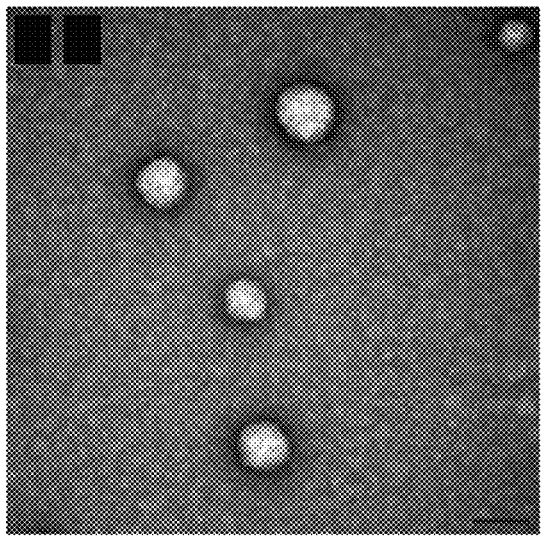
Figure 10H:
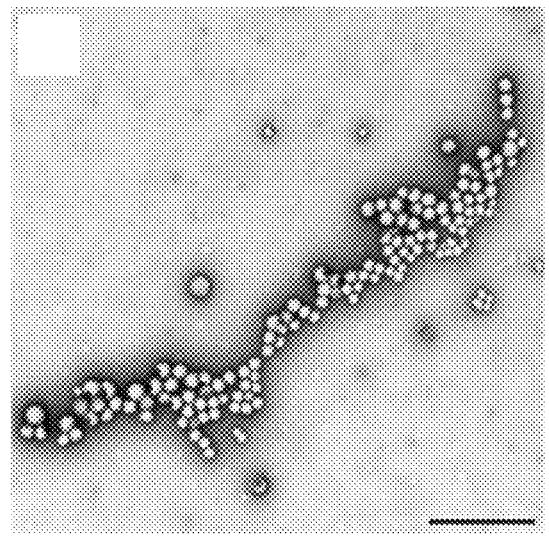
Figure 10I:
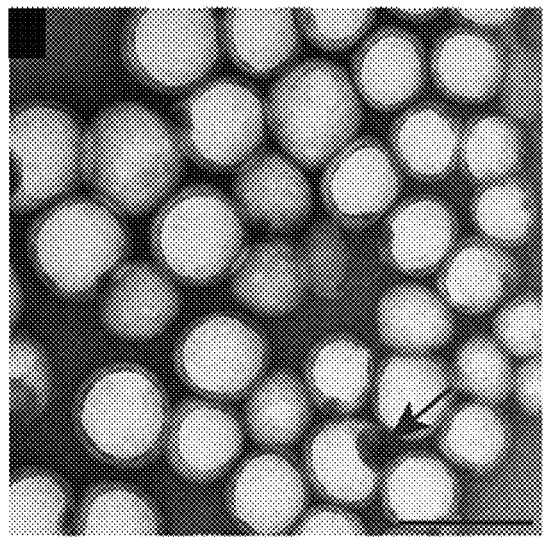
Figure 10J:
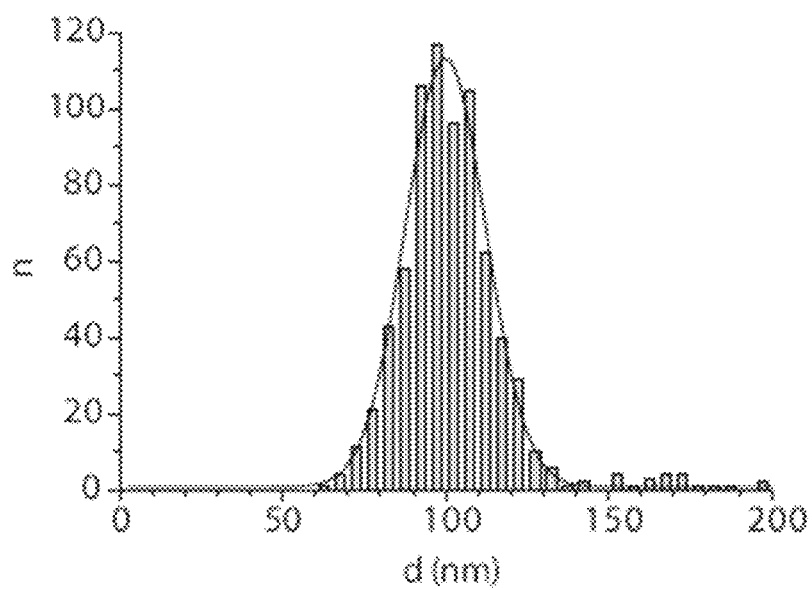
Figure 10K:
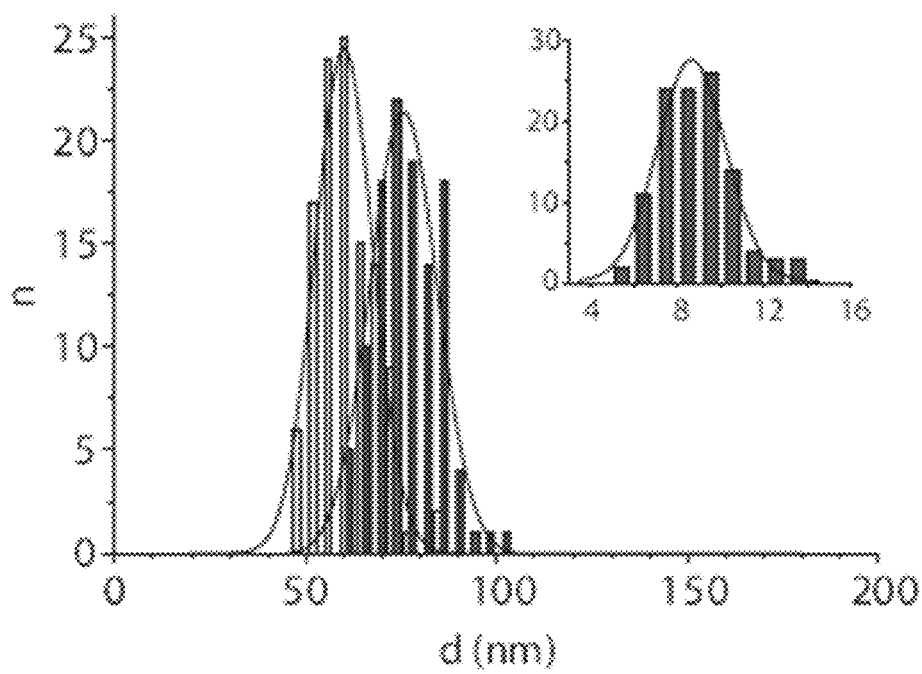

For the sake of brevity, $PNP_{Cargo}^{Corona}$ is used herein as an acronym for CD3ac peptide nanoparticles self-assembled in the presence of cargo (e.g., Flutax-2 used herein) and corona (e.g., Tfn-AF568 used herein). FIGS. 10E-10I show TEM images of PNP particles in various configurations: $PNP_{Flutax-2}$ (FIGS. 10F-10G) and $PNP_{Flutax-2}^{Tfn-AF568}$ (FIGS. 10H-10I). Both samples were stained with uranyl acetate, setting apart bright particles and dark background. $PNP_{Flutax-2}$ were detected in large numbers, and evenly distributed on the carbon film (FIG. 10F). By contrast, only few particles could be detected in the $PNP_{Flutax-2}^{Tfn-AF2568}$ sample; instead, they clustered together (FIG. 10H), indicating the process of de-wetting and residual water evaporation during sample preparation and thus differential affinity to the hydrophobic carbon support. Higher magnification (FIG. 10I) shows a rim of intermediate contrast on the nanoparticle interface. Its average thickness of 9.85 nm (st. dev.=2.1, n=99) is in agreement with the expected protein diameter (12). Although both samples were prepared by the same protocol, the average diameter of $PNP_{Flutax-2}$ (100 nm, FIG. 10J) was twice that of $PNP_{Flutax-2}^{Tfn-AF2568}$ (51 nm, excluding corona, FIG. 10K). Without wishing to be bound by theory, the average size of peptide particles depends not only partly on the peptide concentration but also partly on the presence of surface active molecules which stabilize the emulsion early in the process of phase separation (8). Thus, these electron microscopic analyses indicate that peptide particle diameters can be controlled down to a few ten nanometers, e.g., by modulating different processing parameters, for example, but not limited to, peptide concentration and/or concentration and/or types of surface active molecules. Together with the fluorescence microscopy images of FIGS. 8A-8F, the TEM images indicate the presence of a Tfn-AF568 corona on PNPs.

Example 4

Figure 9A:
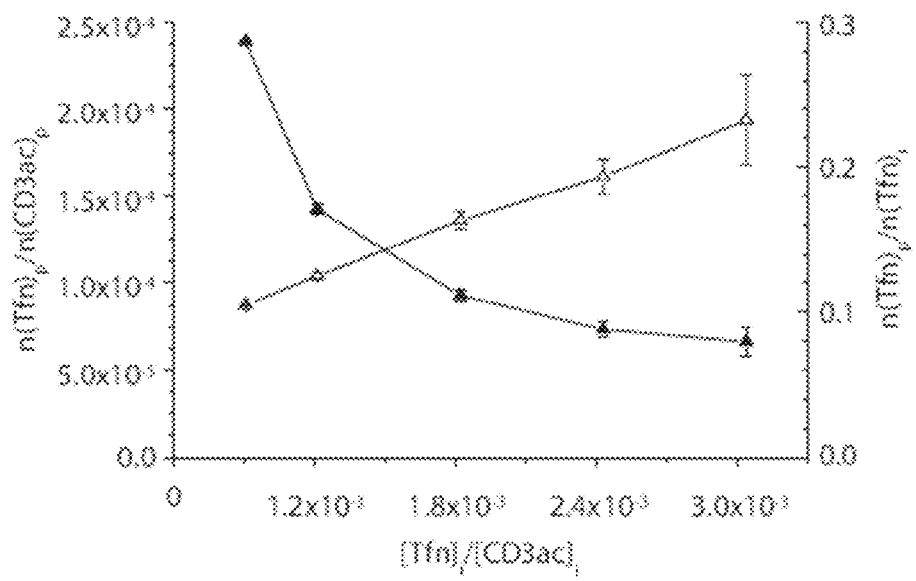
FIGS. 9A-9D show results of compositions of Flutax-2 and Tfn-AF568 within the CD3ac peptide nanoparticles.
Figure 9B:
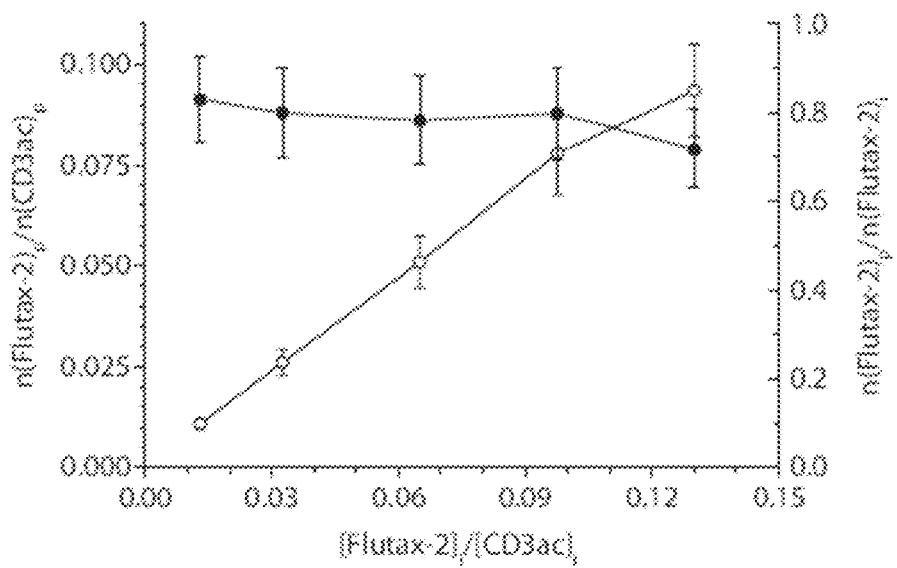
Figure 9C:
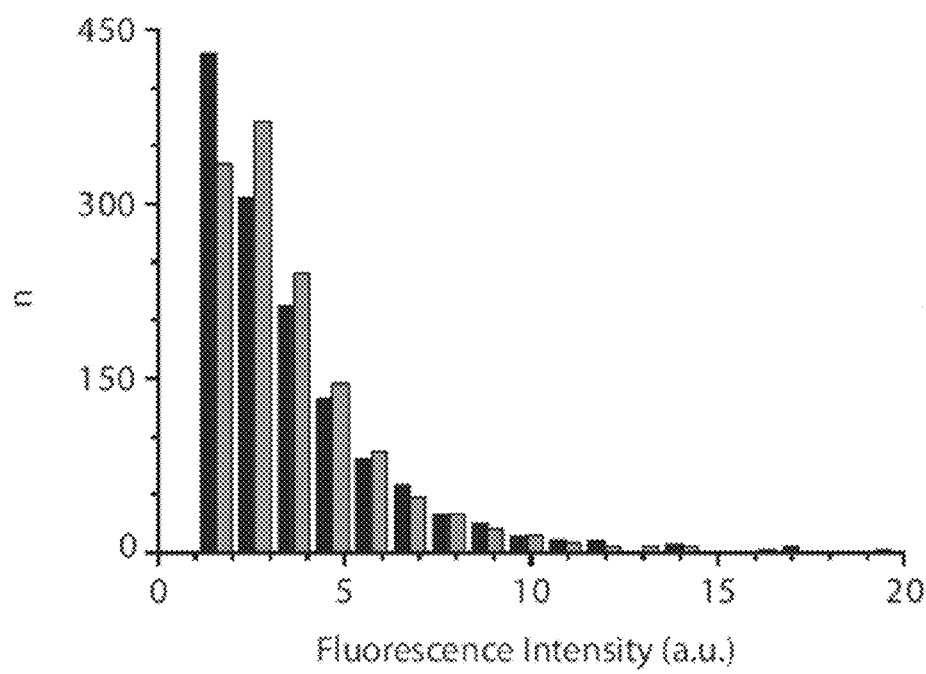
Figure 9D:
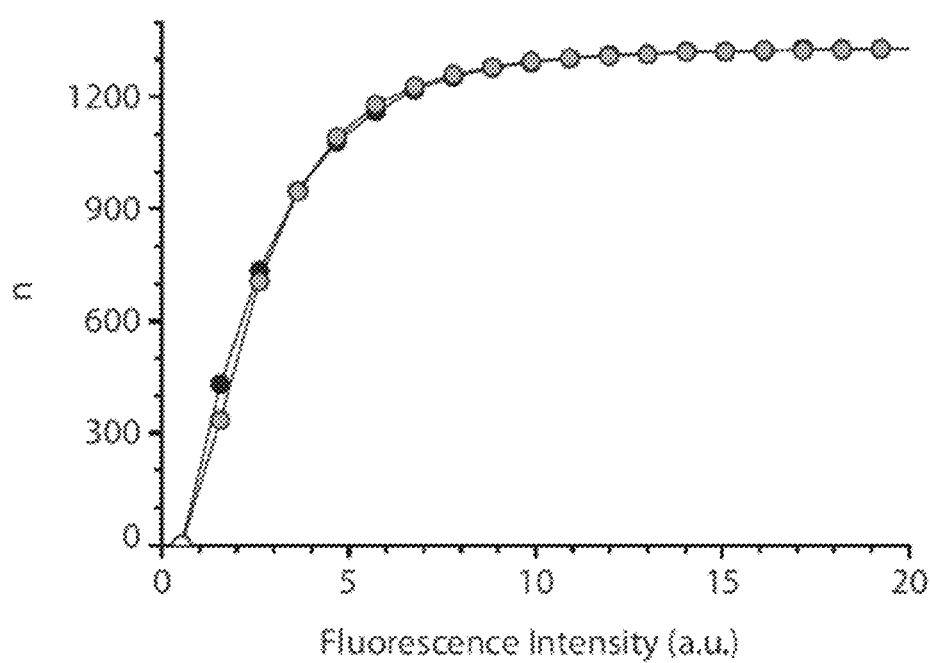
Figures 11A, 11B, 11C:
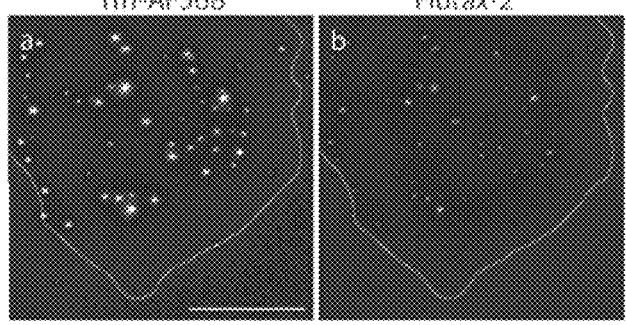
FIGS. 11A-11H show effects of Tfn competition on $PNP_{Flutax-2}^{Tfn-AF568}$ binding to CHO cells. $PNP_{Flutax-2}^{Tfn-AF568}$ is used herein as an acronym for CD3ac peptide nanoparticles self-assembled in the presence of cargo (e.g., Flutax-2 used herein) and corona (e.g., Tfn-AF568 used herein).
Figures 11D, 11E, 11F:
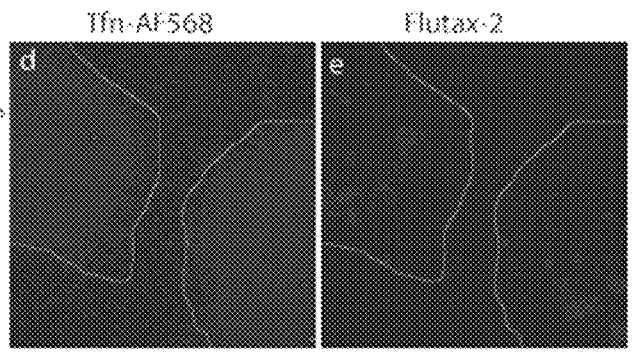
Figure 11G:
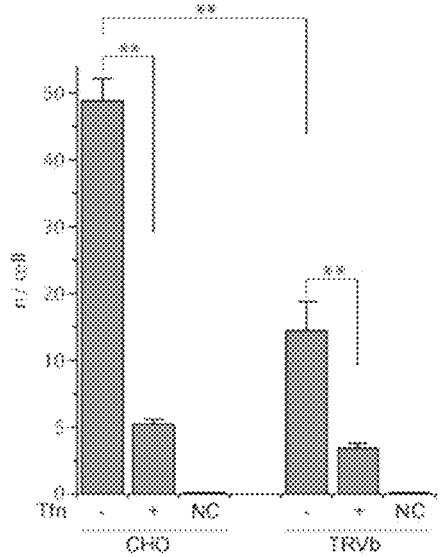
Figure 11H:
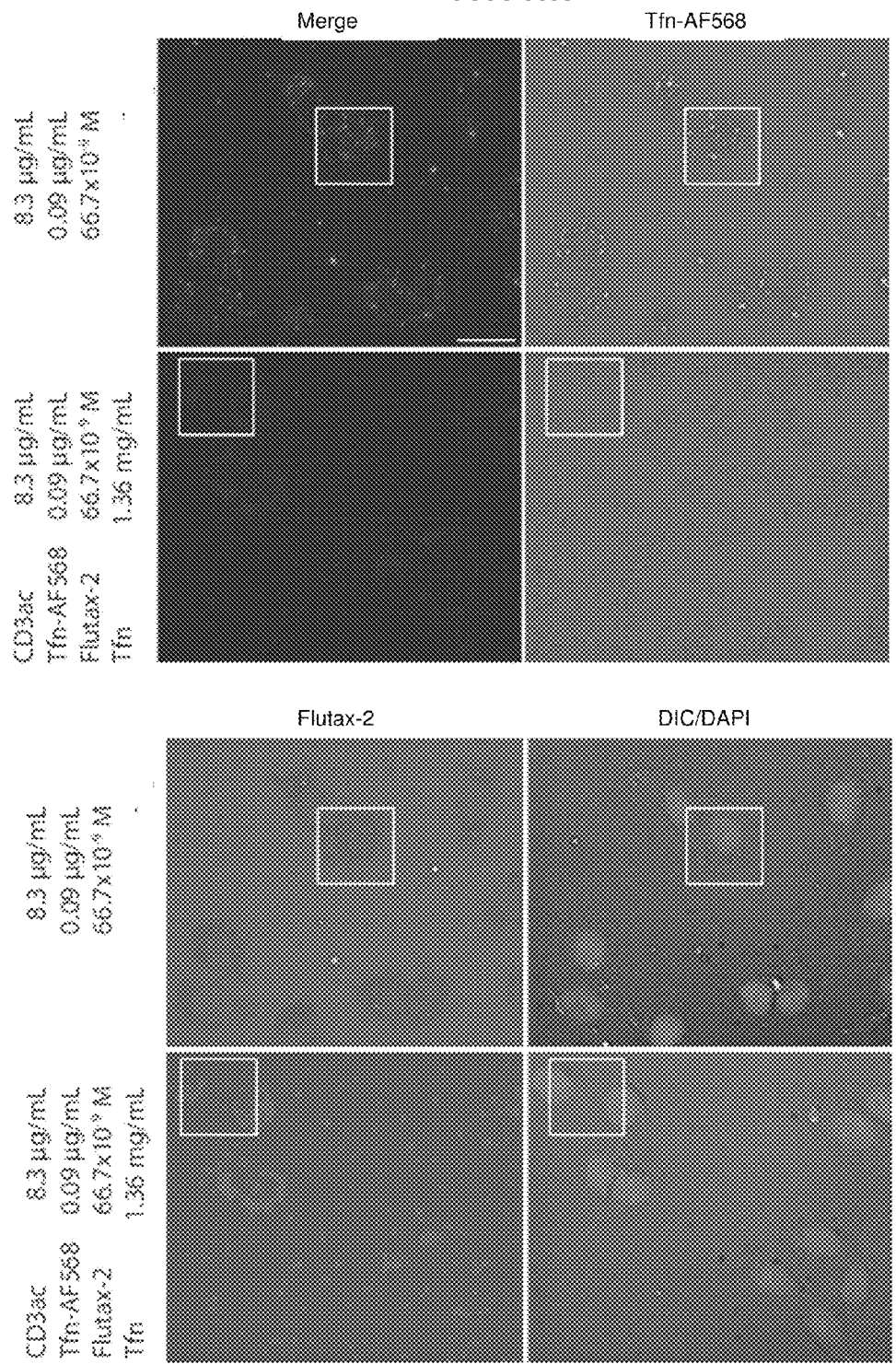

Delivery of Flutax-2 into CHO Cells by CD3ac Nanoparticles with a Protein Corona Selective binding to transferrin receptors (TfR) depends on the functionality of the protein corona: its function can be compromised by protein denaturation, steric hindrance (crowding) or unfavorable orientation relative to the PNPs' surface. Accumulation of PNPs on cell surfaces can be attributed to specific corona-receptor interactions and/or unspecific associations. For example, electrostatic (Coulomb) and electrodynamic (Van der Waals) forces can contribute to unspecific association (13-15). In order to test functionality of the detected corona in mediating specific binding, the number of cell surface-associated PNPs was correlated to the density of available TfR using two independent experimental protocols: a) PNP binding by Tfn in solution; and b) comparison of PNP binding between TfR-expressing Chinese hamster ovary (CHO) cells and TRVb cells, which are derived from Chinese hamster ovary tissue that lacks endogenous TfR but expresses TfR2 (16). FIGS. 11A-11H show microscopy images of CHO cells incubated for one hour with $PNP_{Flutax-2}^{Tfn-AF568}$. A significant accumulation of PNPs was detected within the projected cell perimeter (FIGS. 11A-C) which could be blocked by incubating CHO cells with 17 µM unlabeled Tfn (FIG. 11D-11F). This indicates that PNP interactions with the cell surface depend on freely valent TfR. FIG. 11G shows that the lower TfR density in TRVb leads to a significantly reduced association rate of $PNP_{Flutax-2}^{Tfn-AF568}$. Incubation of TRVb with 17 µM unlabeled Tfn blocks binding of $PNP_{Flutax-2}^{Tfn-AF568}$, indicating that in these cells $PNP_{Flutax-2}^{Tfn-AF568}$ interact mostly via the low-abundant receptor TfR2. Application of excess Tfn might not only compete with the PNPs for TfR but may also exchange fluorescent Tfn-AF568 in the particle corona with non-fluorescent Tfn. To assess this possibility, the fluorescence intensity distribution of $PNP^{Tfn-AF568}$ incubated at 37° C. in the presence and absence of 17 µM Tfn after 24 hours were compared and there were insignificant differences (FIGS. 9C-9D). This indicates that the rate of TfR-mediated binding of PNPs to the cell surface is much faster than the protein exchange on the PNP surface. Together with the results presented in FIGS. 11A-11H, PNPs are shown to bind to TfR specifically via the Tfn-AF568 corona.

Figure 12A:
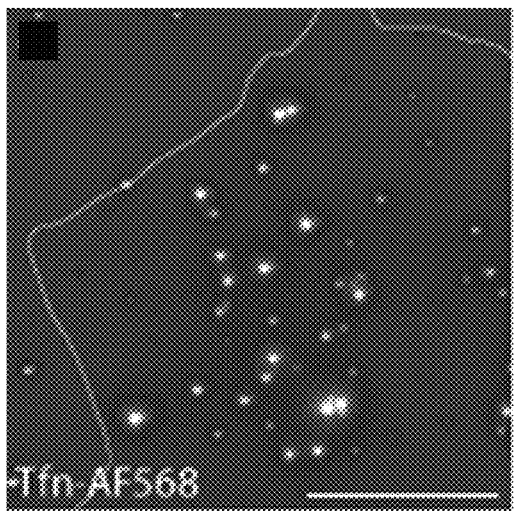
FIGS. 12A-12M show experimental results of internalization of nanoparticles.
Figure 12B:
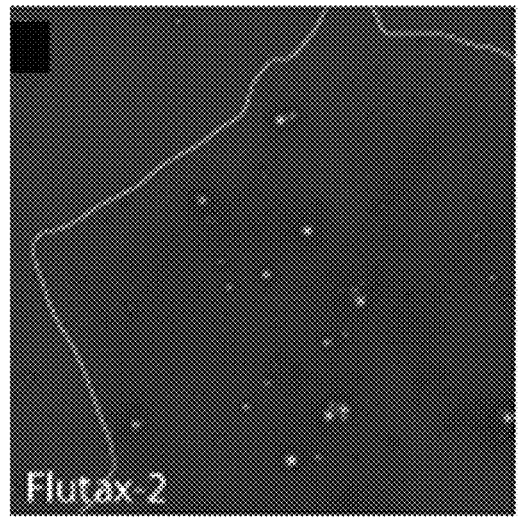
Figure 12C:
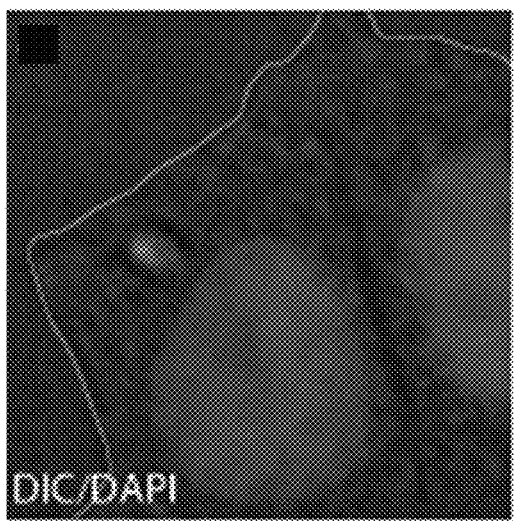
Figure 12D:
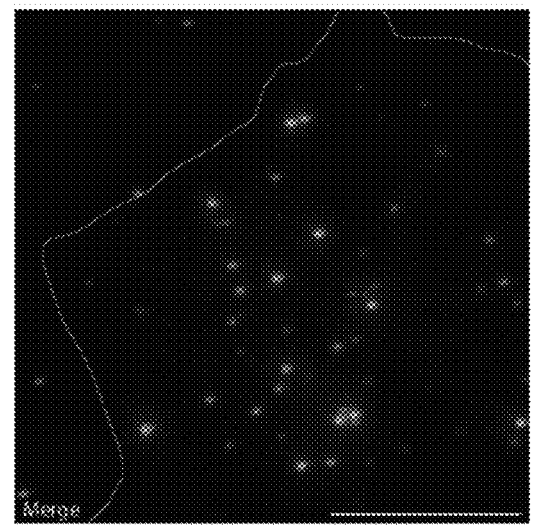
Figure 12E:
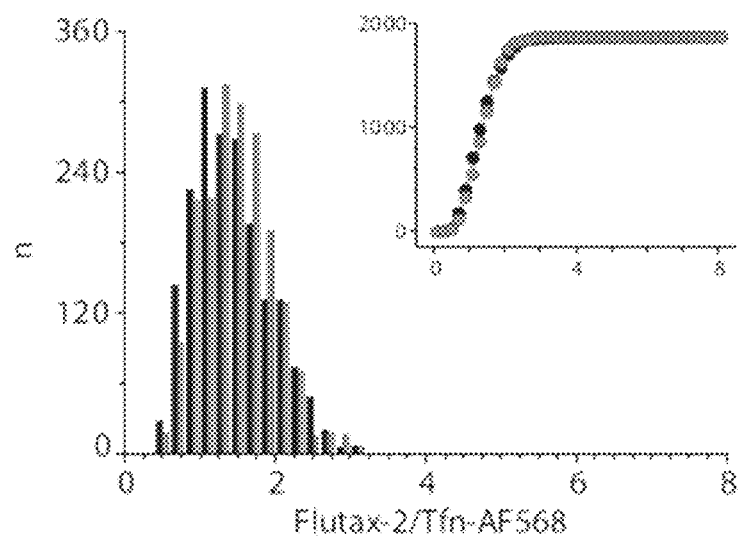
Figure 12F:
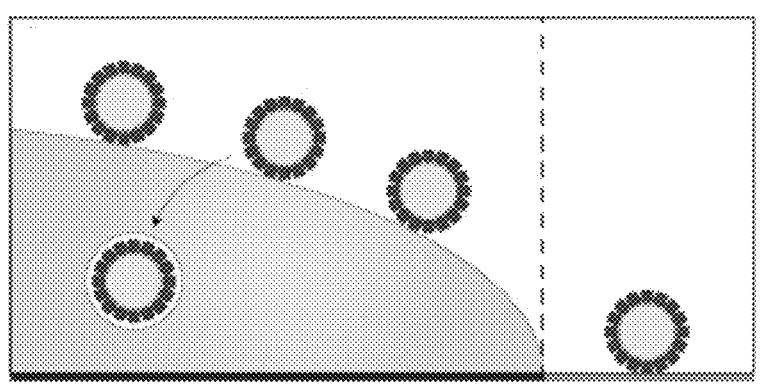
Figure 12G:
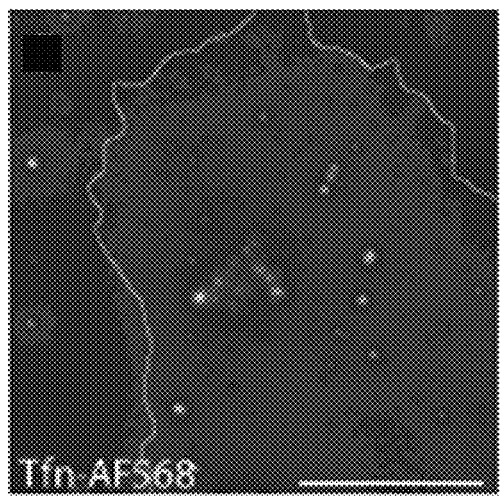
Figure 12H:
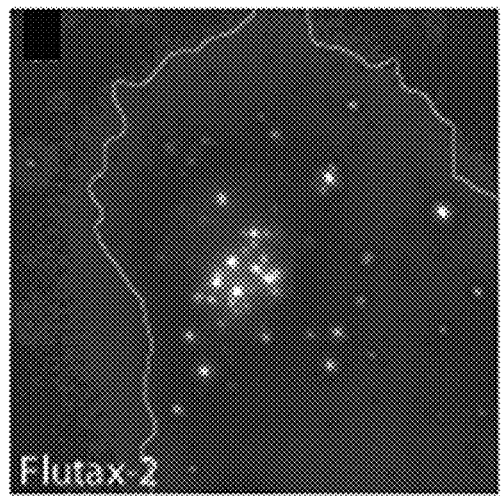
Figure 12I:
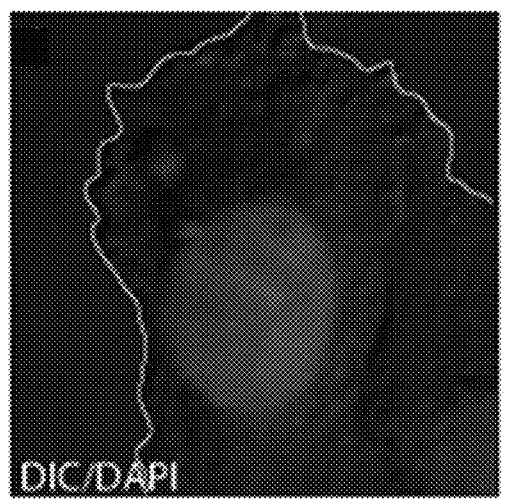
Figure 12J:
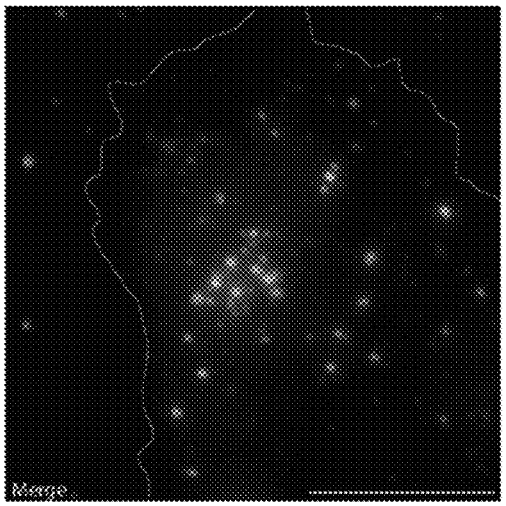
Figure 12K:
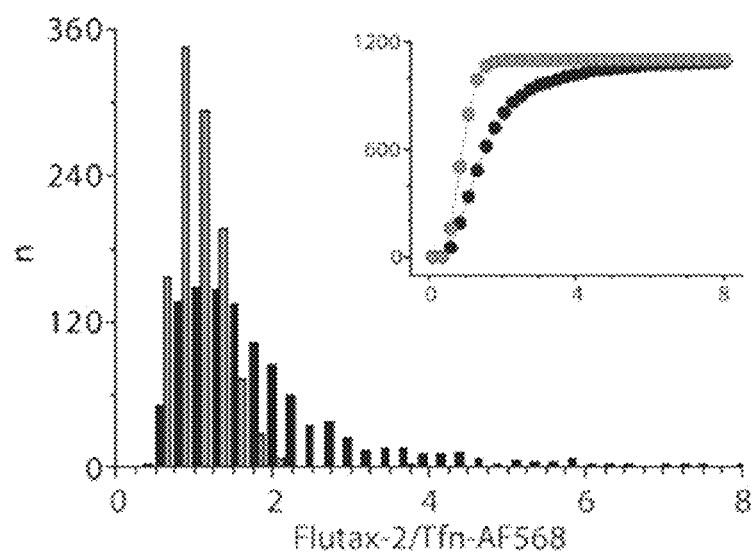
Figure 12L:
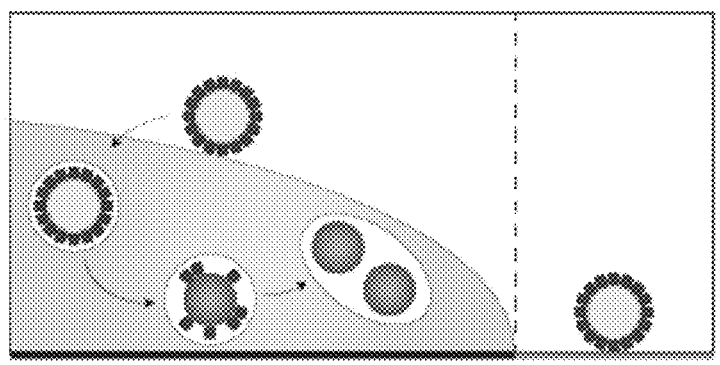
Figure 12M:
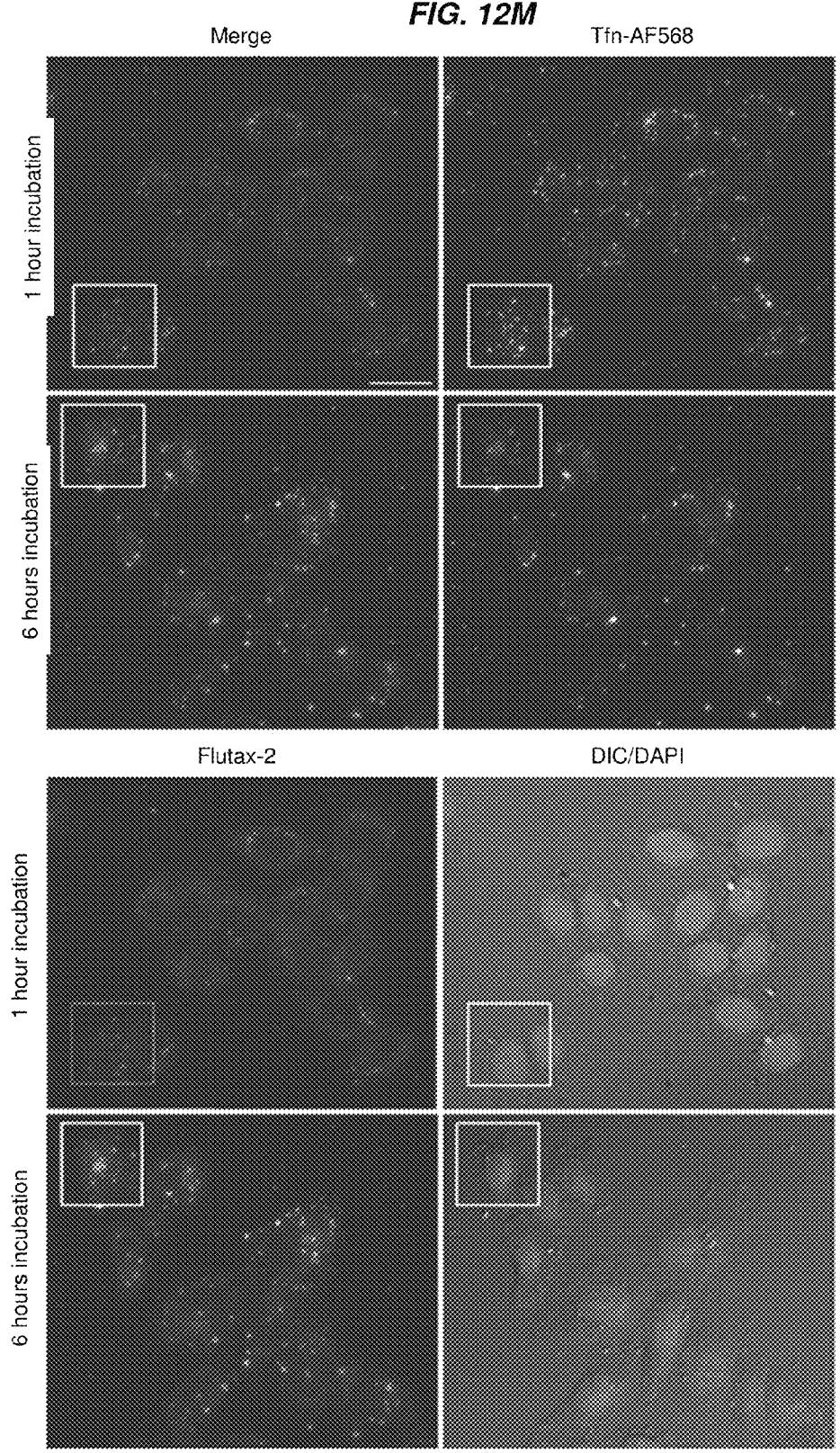

While $PNP_{Flutax-2}^{Tfn-AF568}$ can bind to cells via interactions with TfR, Tfn could dissociate from the PNP corona before internalization takes place, and/or the size difference between single Tfn proteins and a NP may affect cellular uptake. Thus, it was next sought to determine if the particles can be internalized by cells. Distinction between associated and internalized PNPs can be not straightforward due to the flat shape of surface-adherent cells and a limited z-resolution of light microscopy. As shown earlier, removal of Tfn-AF568 from the particle surface can be detected by a pronounced shift of green to red fluorescence ratio (G/R). As such, G/R distribution was measured to distinguish between PNPs associated and internalized into cells, as shown in FIGS. 12A-12M, respectively. CHO cells were fixed and imaged after 1 hour (FIGS. 12A-12E) and after 6 hours (FIGS. 12G-12K) of incubation with $PNP_{Flutax-2}^{Tfn-AF568}$. After 1 hour the G/R distribution showed a tight peak around 1.5 for both PNPs within (FIG. 12E, black bars) and outside (FIG. 12E, gray bars) the cell perimeter. As shown in FIG. 12K, after 6 hours, the population of PNPs within the cell perimeter (black bars) displayed a significant shift towards higher G/R values, while the G/R distribution of PNPs outside the cell perimeter (gray bars) remained confined around 1.5. Without wishing to be bound by theory, it is contemplated that after incubation for 1 hour, most PNPs have not yet reached a lysosomal compartment and those which have been internalized still have an intact corona containing Tfn-AF568; after six hours, the majority of PNPs have been transported into lysosomes and their protein coronas have been proteolytically digested. The smaller degradation products can dissociate from the particle surface due to weaker Van der Waals forces (17). In analogy to an increase in G/R after removal of the corona by trypsin (FIG. 8H), the proteolytic digestion of the PNP corona in lysosomes can yield an increase in the G/R values of internalized PNPs. This is corroborated by the unchanged G/R values of PNPs detected on the glass surface. Changes in G/R can be used herein as a qualitative indicator of internalized PNPs (because of the relatively slow digestion kinetics) to demonstrate that PNPs with a Tfn-AF568 corona can enter or be up-taken by the cells, for example, by clathrin-mediated endocytosis via TfR(18).

Figure 13I:
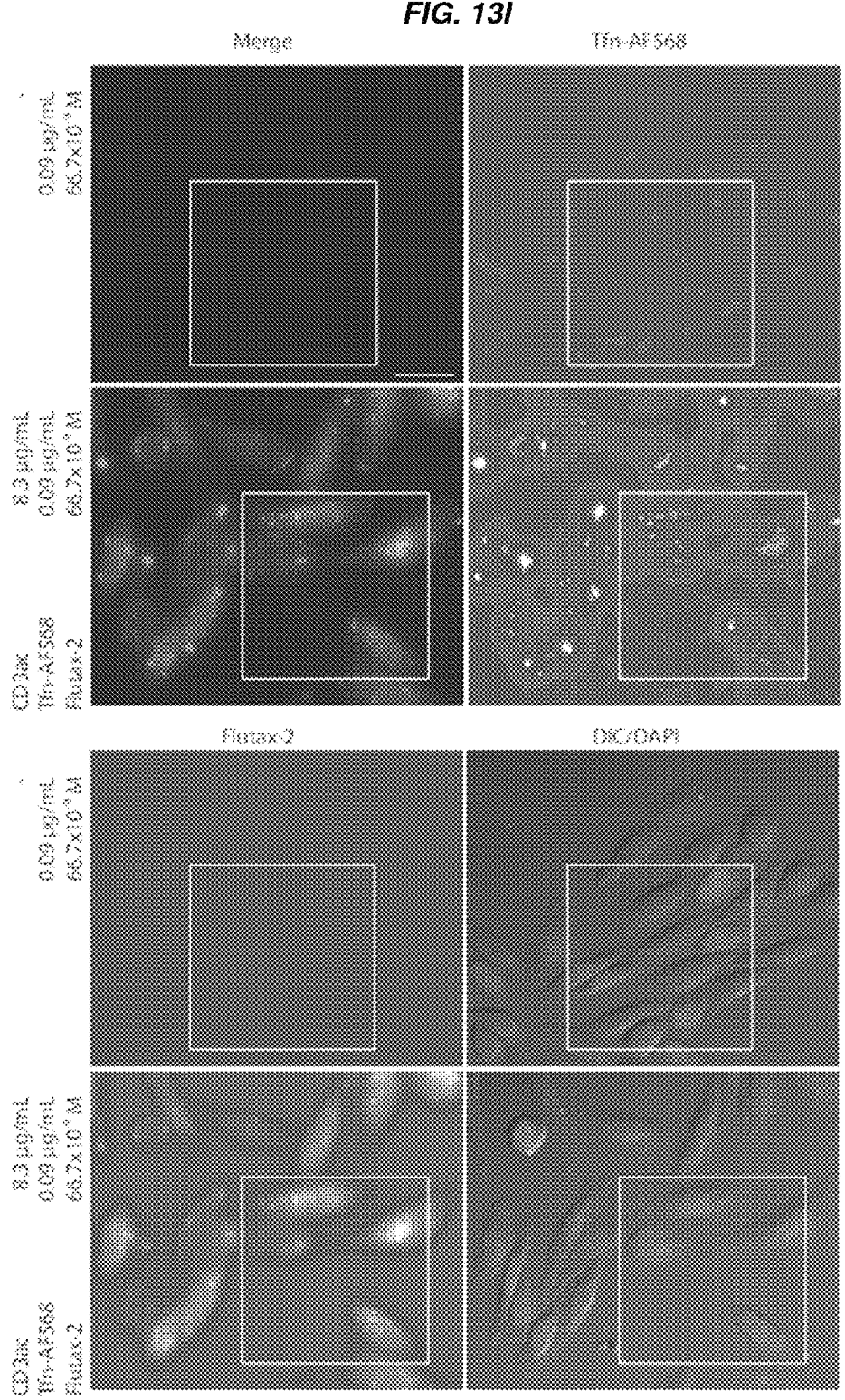
Figure 14:
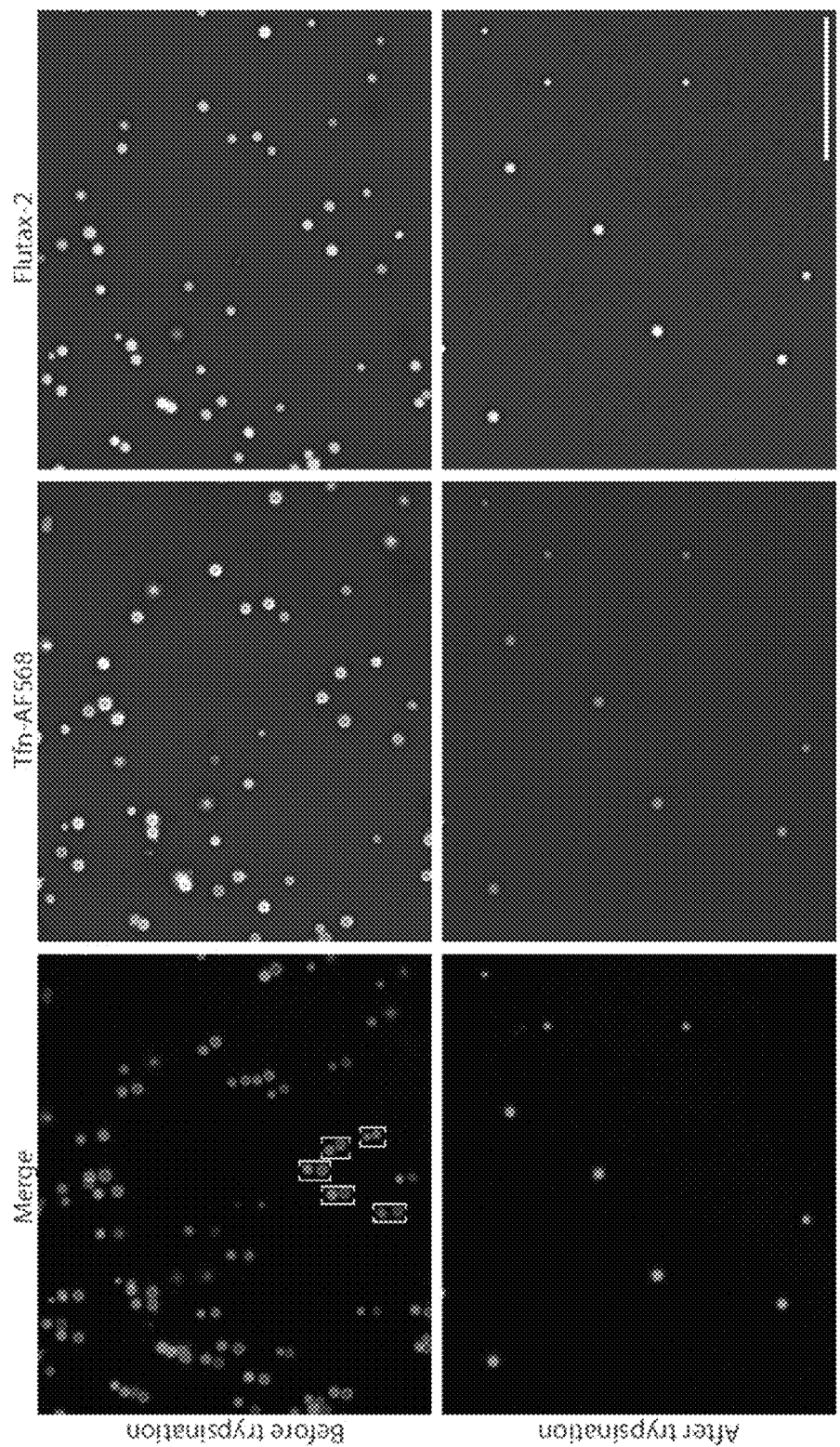
FIG. 14 shows a set of fluorescence microscopy images of peptide particles (e.g., CD3ac) assembled with Flutax-2 and Tfn-AF568. The upper row shows the sample prior to trypsination. Red and green channel are not congruent as the dispersed particles move and there is a time delay between the images caused by the change of excitation and emission filters. Identical particles are set in brackets and are superimposed in FIGS. 8A-8F. The lower row shows the same sample after 6 hours incubation with trypsin. The red corona disappears and the remaining particles adhere to the surface of the glass cover slide.
Figure 15A:
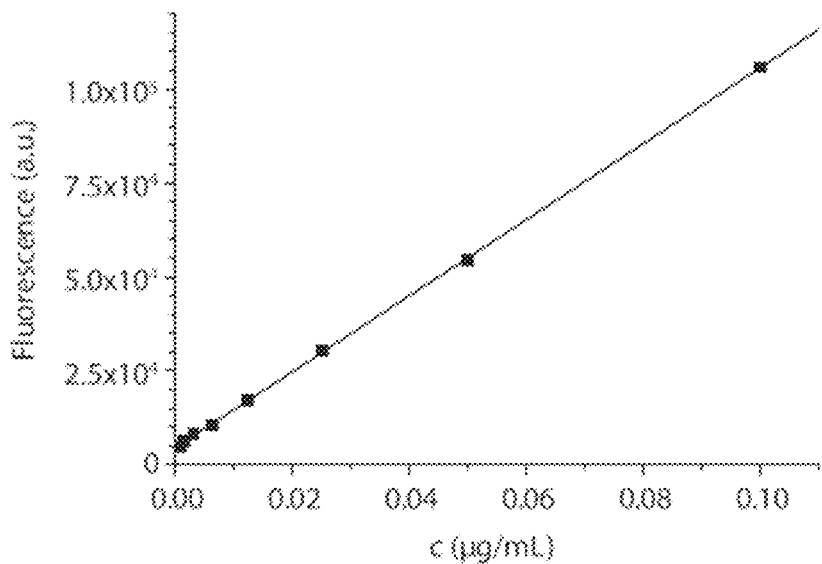
FIGS. 15A-15B show fluorescence calibration curves of Tfn-AF568 (FIG. 15A) and Flutax-2 (FIG. 15B). Both measured in a solution of 60% $H_2O$, 30% DMSO, 10% FBS. The organic solvent is required to dissolve the nanoparticles in the pellet fraction and the presence of FBS minimizes adsorption of labeled analytes to plastic surfaces, providing linearity between fluorophore concentration and measured fluorescence.
Figure 15B:
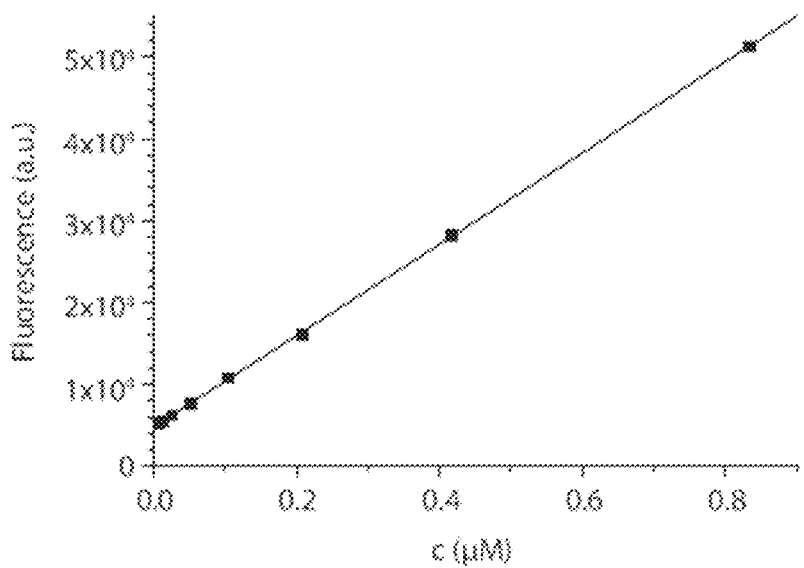

To assess whether binding and internalization of PNPs can result in the selective import of small molecule cargo, the release of encapsulated Flutax-2 into cells was analyzed 24 hours post addition of $PNP_{Flutax-2}^{Tfn-AF568}$ into the cells (FIGS. 13A-13I). Flutax-2 is an Oregon Green (OG) modified derivative of paclitaxel(19), a mitotic inhibitor applied in cancer therapy (20). Unlike its unlabeled form, Flutax-2 is charged and water-soluble at the applied concentration and does consequently not permeate cell membranes. Thus, it was used a model compound to investigate efficiency and specificity of small molecule delivery by PNPs to the cytosol. CHO cells were incubated for 24 hours with 0.67 µM Flutax-2, either dissolved in media (FIGS. 13A-13C) or entrapped in $PNP_{Flutax-2}^{Tfn-AF568}$ (FIGS. 13D-13G). Flutax-2 emission in the cytosol was averaged to quantify the amount of delivered compound into the cells. Direct permeation of dissolved Flutax-2 through cell membranes could not be detected as the resulting fluorescence did not exceed the level of autofluorescence (FIGS. 13B and 13I). On the other hand, incubation with $PNP_{Flutax-2}^{Tfn-AF568}$ resulted in a strong diffuse green fluorescence signal (FIGS. 13E and 13G), indicating the delivery of Flutax-2 to the cytosol. The delivery was significantly reduced by competition of PNP-cell interactions with 17 µM dissolved and unlabeled Tfn in cell culture medium (FIG. 13H). Also, the overall rate of delivery was significantly lower for TRVb cells, which express only TfR2 (FIG. 13H).

Presented herein is a targeted drug delivery system consisting of CD3ac peptide matrix, cell membrane-impermeable Flutax-2 as cargo and Tfn-AF568 as a specific cell surface receptor ligand, according to one or more embodiments described herein. All three components can self-assemble to form drug-loaded and functionalized particles by application of a one-step-procedure (e.g., a single step of about 15 minutes). Without wishing to be bound, the simplicity of system and formation protocol originates in the concerted interaction of all involved components: CD3ac is not only matrix material, but supersedes encapsulation routines due to its high affinity to small aromatic molecules. The process of cargo uptake most likely resembles a two-phase liquid extraction where Flutax-2 escapes the aqueous phase and accumulates in peptide droplets, probably due to high affinity between delocalized ring systems of tryptophanes and Flutax-2. Additionally, the peptide's solubility in mild organic solvents allows for concurrent dissolution and self-assembly of all involved components. The presence of Tfn-AF568 during emulsification of CD3ac results in the formation of a protein corona, targeting PNPs against TfR. Additionally, the presence of the protein on particle surface can allow for modulation of particle size due to its surface activity and thus early stabilization of the peptide emulsion. Upon internalization of PNPs into lysosomal compartments, proteolytic digestion on a time scale of a few hours can remove the corona, and in turn release the entrapped cargo into the cytosol on a time scale of days. The fluorescence ratio of encapsulated green (e.g., Flutax-2 used herein) and surface adherent red dyes (e.g., Tfn-AF568) can shift to a higher value (e.g., by a factor of 13) as the corona is removed and this shift can allow for a qualitative description of cellular particle uptake. PNP binding to TfR and size range of the particles indicate particle uptake, e.g., via clathrin mediated endocytosis. Without wishing to be bound by theory, cargo release can go back to the proteolytic degradation of PNPs in the lysosome. The structure of charged CD3ac degradation products is likely to penetrate lipid membranes and might lead to the disruption of lysosomes (21).

Exemplary Materials and Methods (for Examples 3-4)

Stock Solutions:

Synthesis and purification of CD3ac was described in Exemplary Materials and Methods for Examples 1-2 (See, e.g., Dittrich and Meier (2010) Macromolecular Bioscience 10: 1406). Briefly, the peptide was synthesized on a solid phase using Fmoc protection group chemistry and purified on C18 reverse phase (RP) chromatography material applying a gradient of acetonitrile and water. Purity was determined by peak integration of RP-HPLC elution profiles at $A^{280}$ and exceeds 95%. CD3ac stock solutions were prepared by dissolving the peptide in $EtOH:H_2O$ (1:1 v/v). The concentration was determined by absorption (Thermo Scientific Nanodrop 2000) at 280 nm in a mixture of $EtOH:H_2O:DMSO$ 1:1:2 considering $\epsilon_{280}$=21780. The peptide concentration was adjusted to 742 µM with $EtOH:H_2O$ (1:1 v/v), and aliquots of 200 µL were stored at −80° C. until further use. Tfn-AF568 (Invitrogen, T-23365) was dissolved at a concentration of 500 µg/mL and stored at +4° C. Flutax-2 (Invitrogen, P22310) was dissolved at a concentration of 40 µM in $H_2O:EtOH$ (1:1) and stored at −80° C.

Particle Assembly, Loading and Corona Formation:

PNPs were assembled by mixing stock solutions of CD3ac, Tfn-AF568 and Flutax-2 to yield final concentrations of 123 µM CD3ac, 6 µM Flutax-2 and 10 µg/mL Tfn-AF568 in $H_2O:EtOH$ (1:1, v/v). Emulsification was induced by a first dilution step (1:1, $H_2O$) followed by an equilibration period of 15 minutes before the ethanol content was further reduced to 25% by the second dilution step (1:1, $H_2O$). 50 µL aliquots of the resulting suspension were applied to 24-well sitting drop crystallization plates (Hampton Research, Cryschem) and counter-evaporated 3 times against 1 mL $H_2O$ during six hours.

Cultured Cell Experiments:

CHO cell lines were grown in F12:DMEM 1:1 (Cellgro, 10-090) plus 10% fetal bovine serum (Gibco). $2\times10^4$ cells in 0.5 mL media were seeded on cover glasses (VWR, 89015-724) in 24 well plates (Falcon, 353047) and incubated for 16 hours. Cells were washed 1× with PBS and incubated for an additional 30 min in Ham's F12 medium (Cellgro, 10-080) before 50 µL nanoparticle (NP)-solution (as prepared above) in 250 µL F12 was applied. The concentration of CD3ac used in cell incubation thus corresponds to 8.3 µg/mL, ignoring the weight of associated Flutax-2 and Tfn-AF568. In competition assays, cells were pre-incubated for 30 min in F12 medium containing 17 µM Tfn (Sigma, T1283) before a solution of 50 µL PNP in 250 µL F12 containing 17 µM Tfn was added. Samples were fixed with 3% paraformaldehyde (Sigma, P6148) in PBS, mounted on glass slides using fluorescent mounting medium (Dako, 53023) and analyzed within 24 hours.

Fluorimetry:

Fluorescence experiments were carried out on a BMG FLUOstar Omega plate reader on black 384 well-plates (MP100-1, Matrical). Dilution series of Tfn-AF568 and Flutax-2 were measured in $H_2O:DMSO:FBS$ 6:3:1 (V:V:V) and the data points were fitted linearly.

TABLE 4

Exemplary parameters determined from linear data regression

| | Tfn-AF568 | | Flutax-2 | |
|---|---|---|---|---|
| | Value | Std Error | Value | Std Error |
| Intercept | 4501.69 | 234.76 | 4809.00 | 85.56 |
| Slope | $1.011 \times 10^6$ | 5750.49 | $5.573 \times 10^{10}$ | $2.515 \times 10^8$ |
| $R^2$ | 0.99977 | | 0.99986 | |

To determine the encapsulation efficiencies of Flutax-2, PNPs were assembled with the procedure described above in the presence a fixed concentration of Tfn-AF568 (10 µg/mL)

and various amounts of Flutax-2 (1.6 µM, 4 µM, 8 µM, 12.5 µM and 16 µM). After assembly in crystallization plates (see above) PNP samples were normalized with H$_2$O to 100 µL and centrifuged for 1 hour at 16,000 g before 80 µL were separated from the pellet fraction. Both fractions were normalized to 133.3 µL in H$_2$O:DMSO:FBS 6:3:1 (v:v:v) before 120 µL were applied to the well-plate and the fluorescence intensity was measured.

Transmission Electron Microscopy:

PNP samples were prepared as described above. 5 µL of PNPs suspended in H$_2$O were applied to a carbon film coated copper grid (400 square mesh, Electron Microscopy Sciences) and dried. The sample was stained with 10 µL 1% uranyl acetate during one minute. Excess stain was removed with a filter paper and subsequently applied to a Tecnai G$^2$ Spirit BioTWIN.

Microscopy:

Fixed cells were analyzed on a Nikon Ti inverted microscope equipped with 60× Plan Apo NA 1.4 objective lens. DAPI fluorescence was excited with a 360/40 filter and collected with a 460/50 emission filter. Oregon Green fluorescence was excited with a 360/40 and collected with a 480/40 emission filter. AF568 fluorescence was excited with a 545/30 and collected with a 620/60 emission filter. Images were acquired with a Hamamatsu ORCA R2 cooled CCD camera controlled with MetaMorph 7 software. Gamma, brightness, and contrast were adjusted on displayed images (identically for compared image sets) using ImageJ software. z-Series optical sections were collected with a step size of 0.25 microns ranging from the glass slide to the highest detectable PNP using a Prior Proscan II focus motor. Samples observed after 1 hours and 6 hours of PNP-incubation are (merged) maximum stack-projections of AF568 and Oregon Green (OG) channels. The samples observed after 24 hours were obtained by average-projection of Oregon Green fluorescence and maximum-projection of AF-568 stacks. The average projection of OG was used to quantify differences in Flutax-2 fluorescence in the cytosol. Cell perimeters were segmented manually in DIC images. Fluorescence point maxima were extracted by ImageJ (v. 1.43u) using a noise tolerance of 50 in the public class MaximumFinder.

Example 5

Figure 16A:
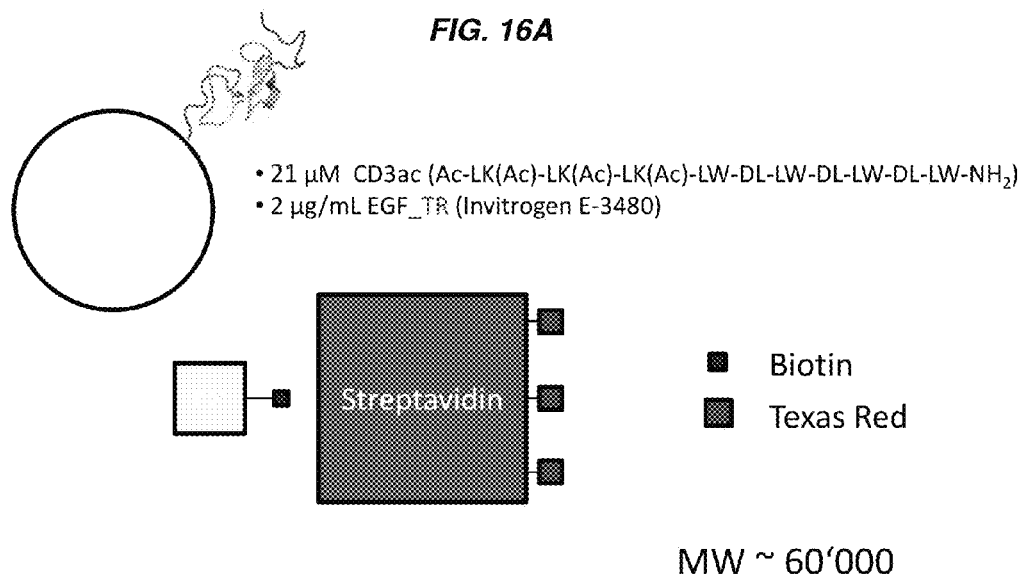
FIGS. 16A-16B show a peptide nanoparticle according to one or more embodiments of the invention.
Figure 16B:
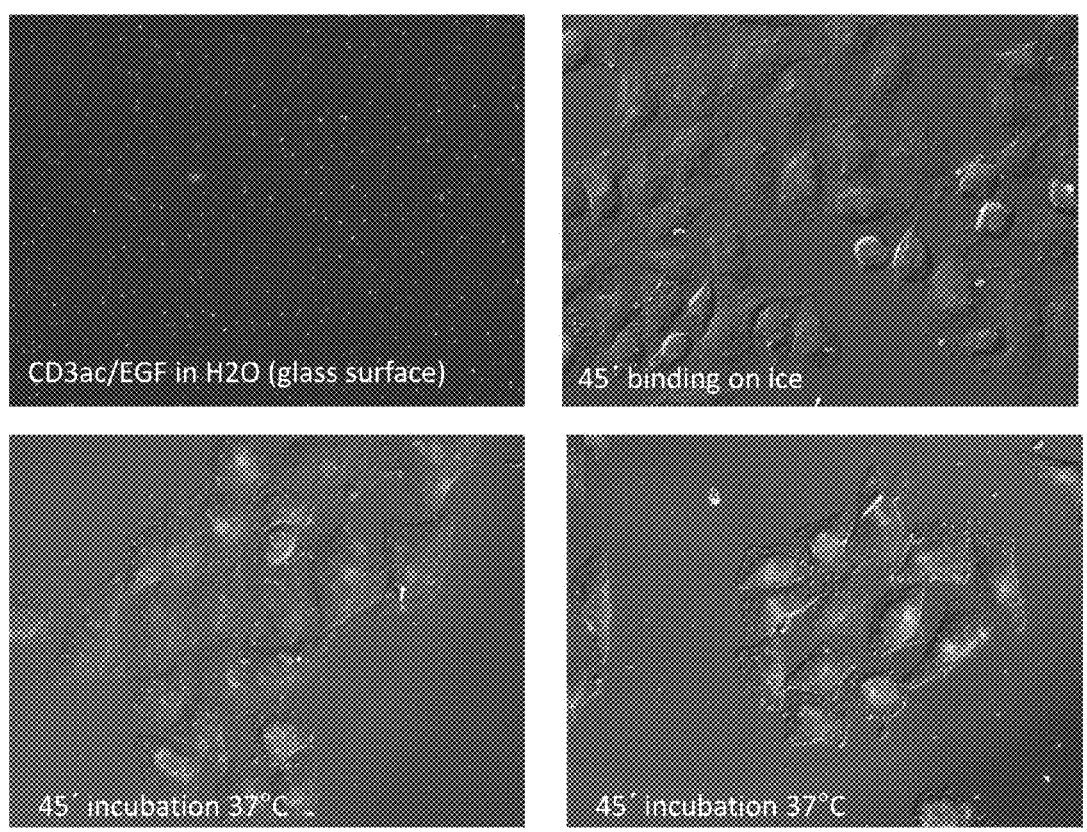
Figure 17A:
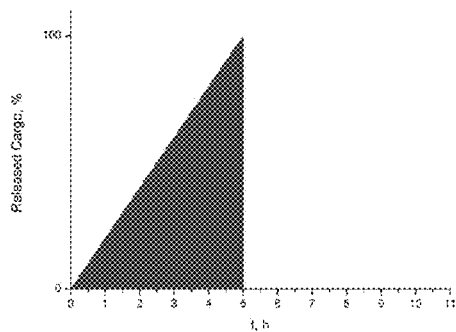
FIGS. 17A-17K show experimental results of cells (e.g., HeLa cells) treated with one embodiments of the peptide nanoparticles encapsulated with nocodazole (which is an chemical agent that can depolymerize microtubules and be used as an anti-neoplastic agent).
Figure 17A:
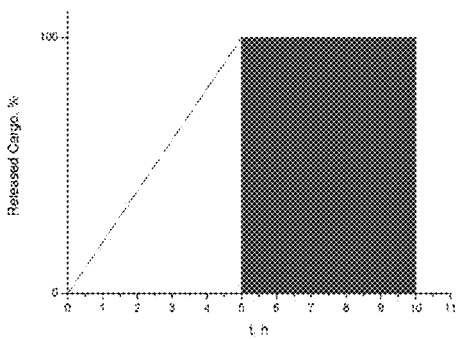
Figure 17B:
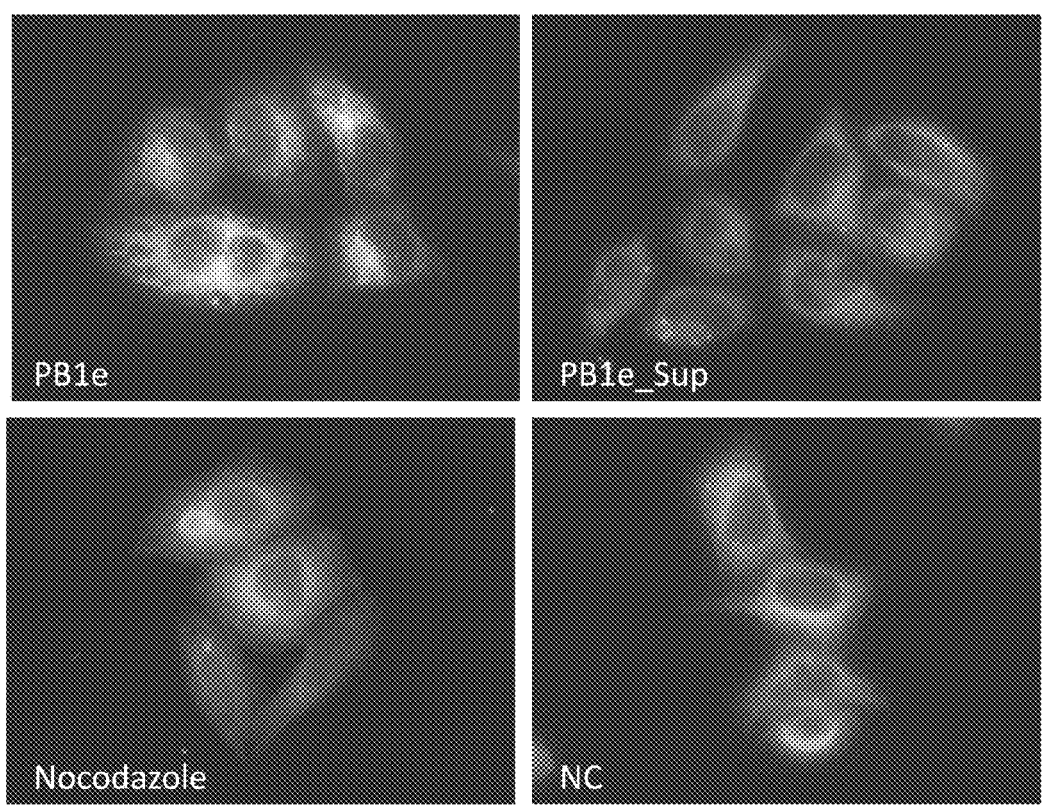
Figure 17C:
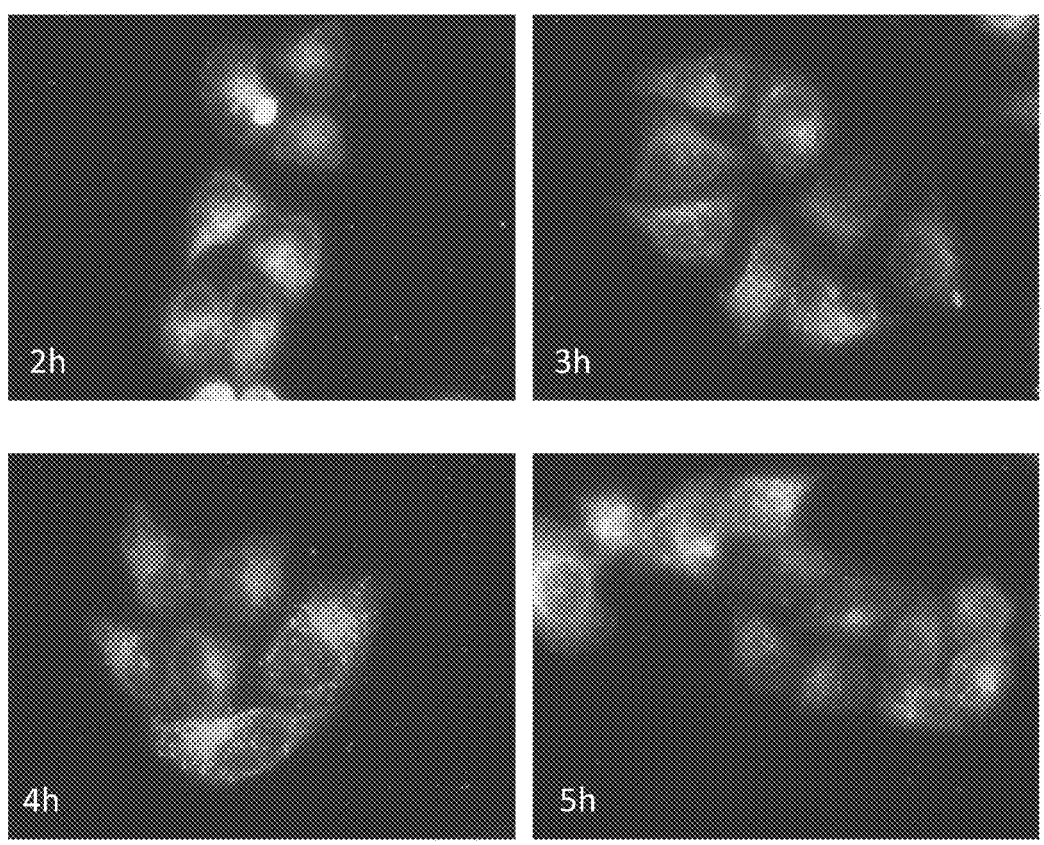
Figure 17D:
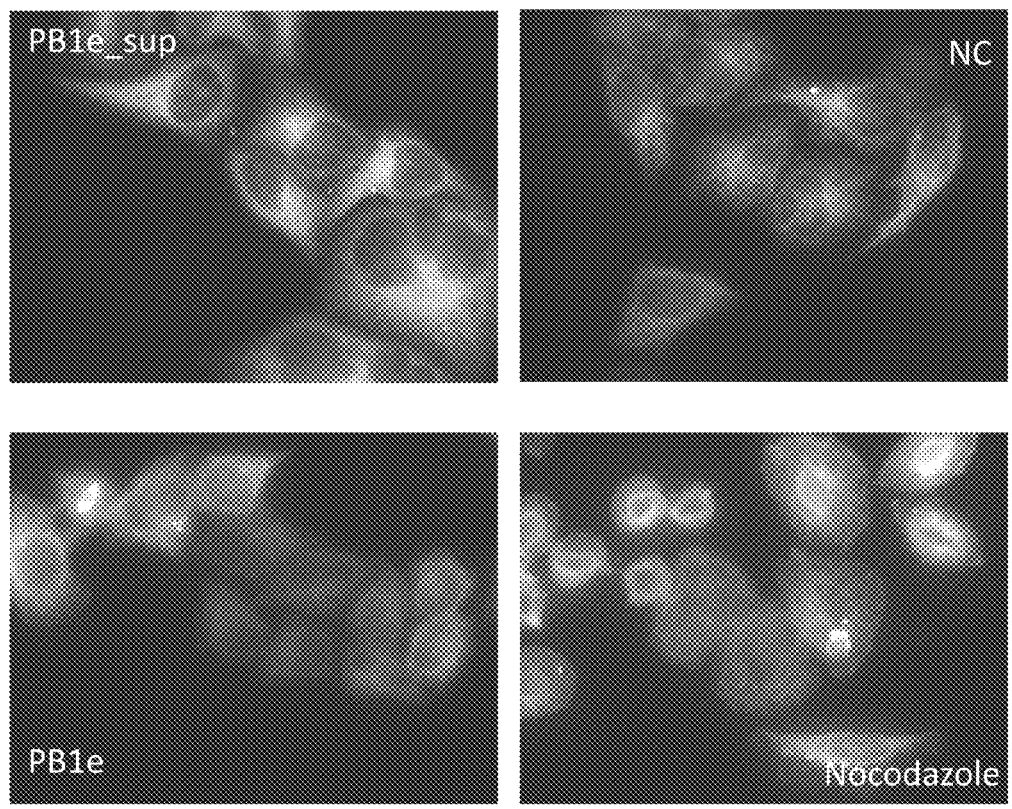
Figure 17E:
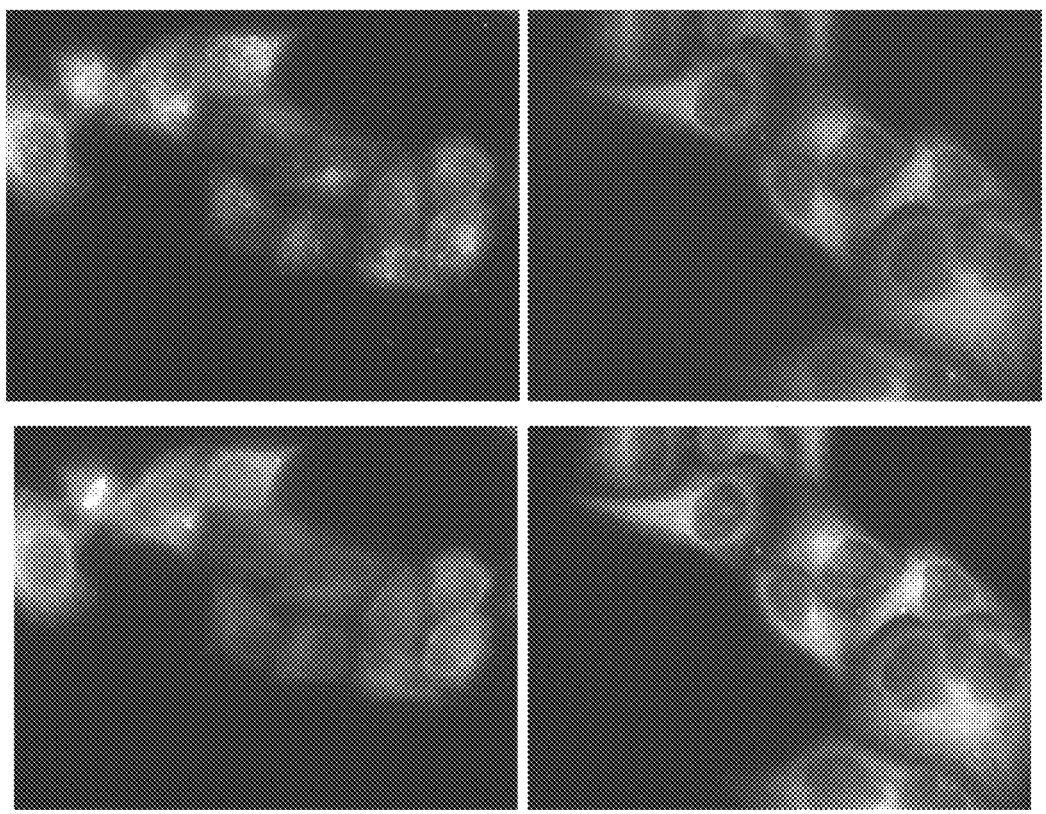
Figure 17F:
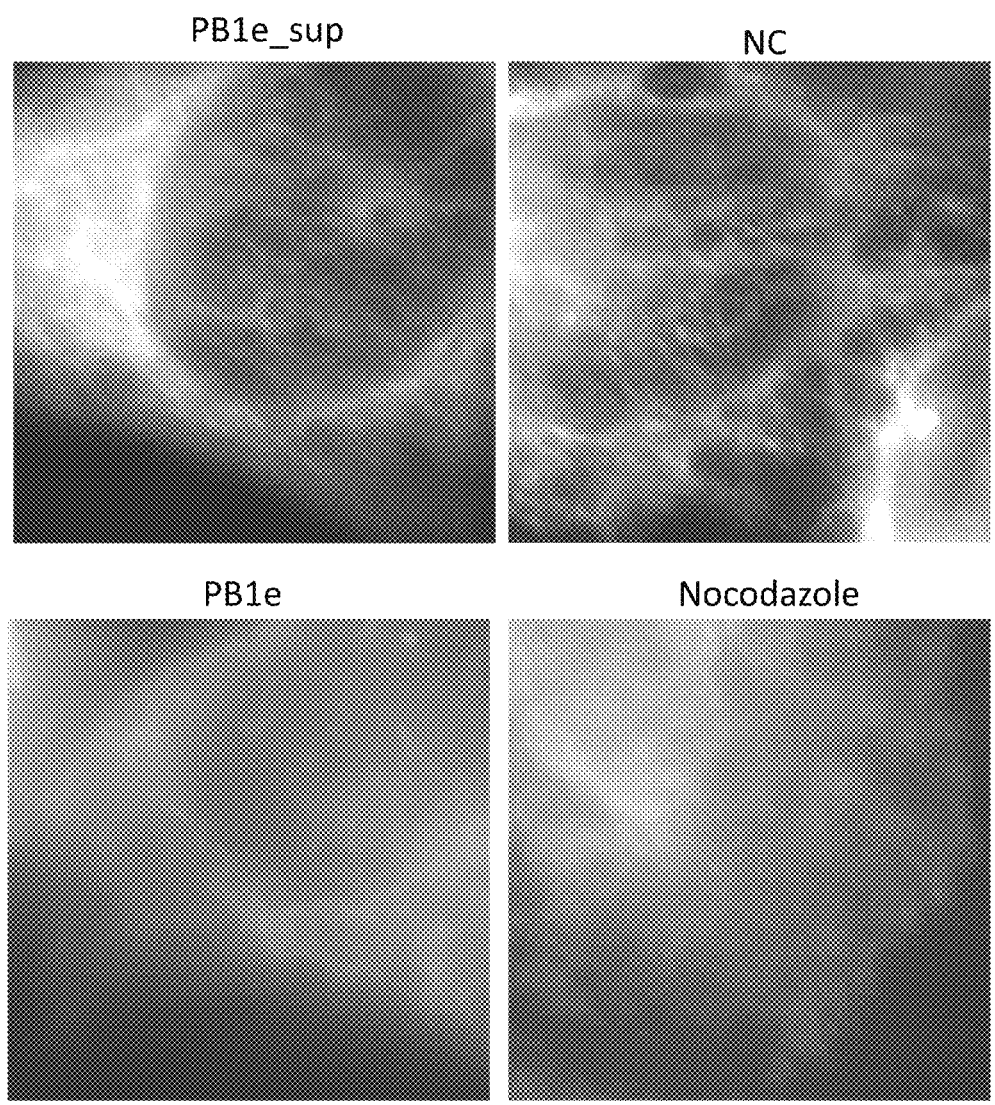
Figure 17G:
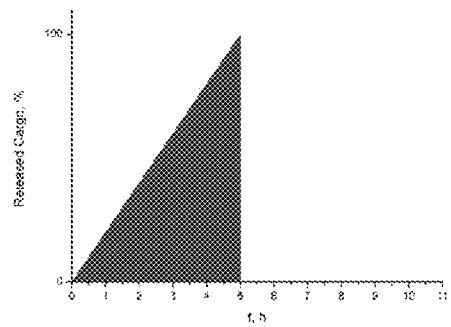
Figure 17G:
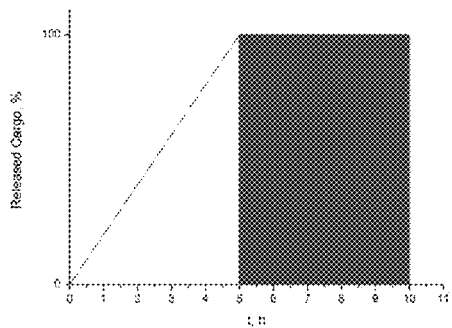
Figure 17H:
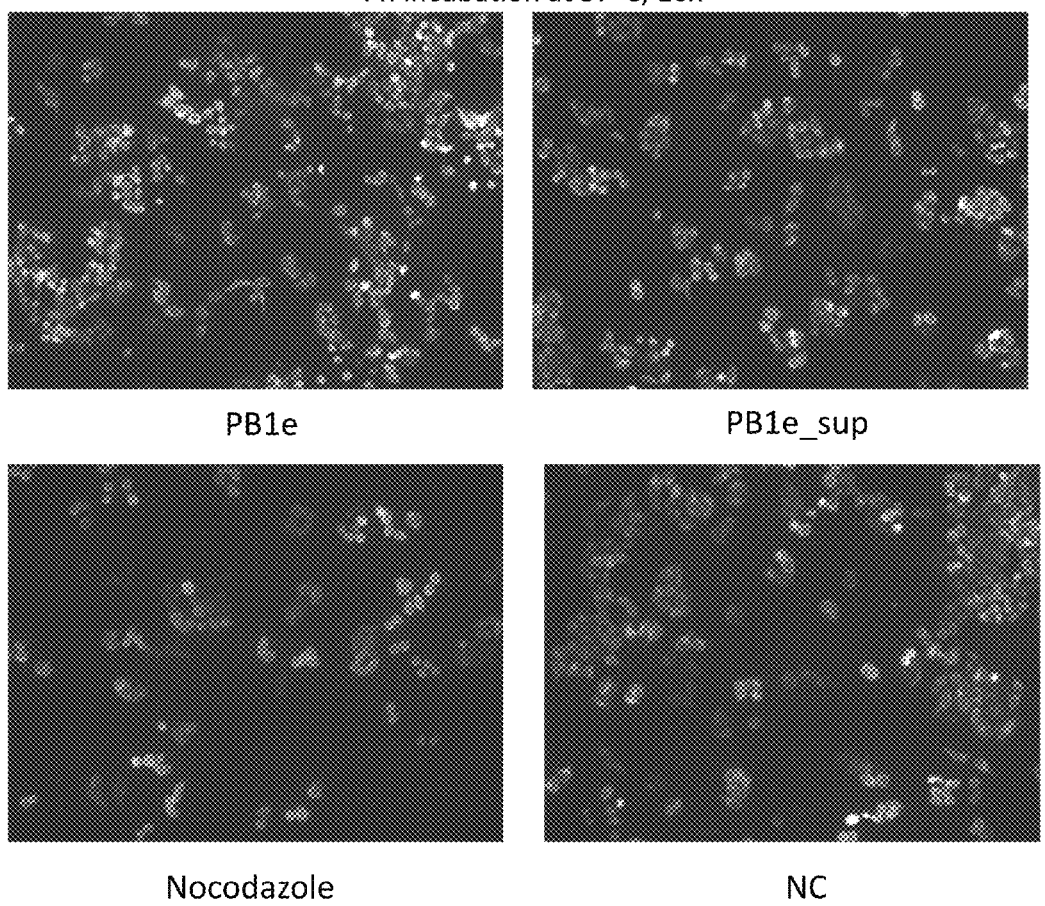
Figure 17I:
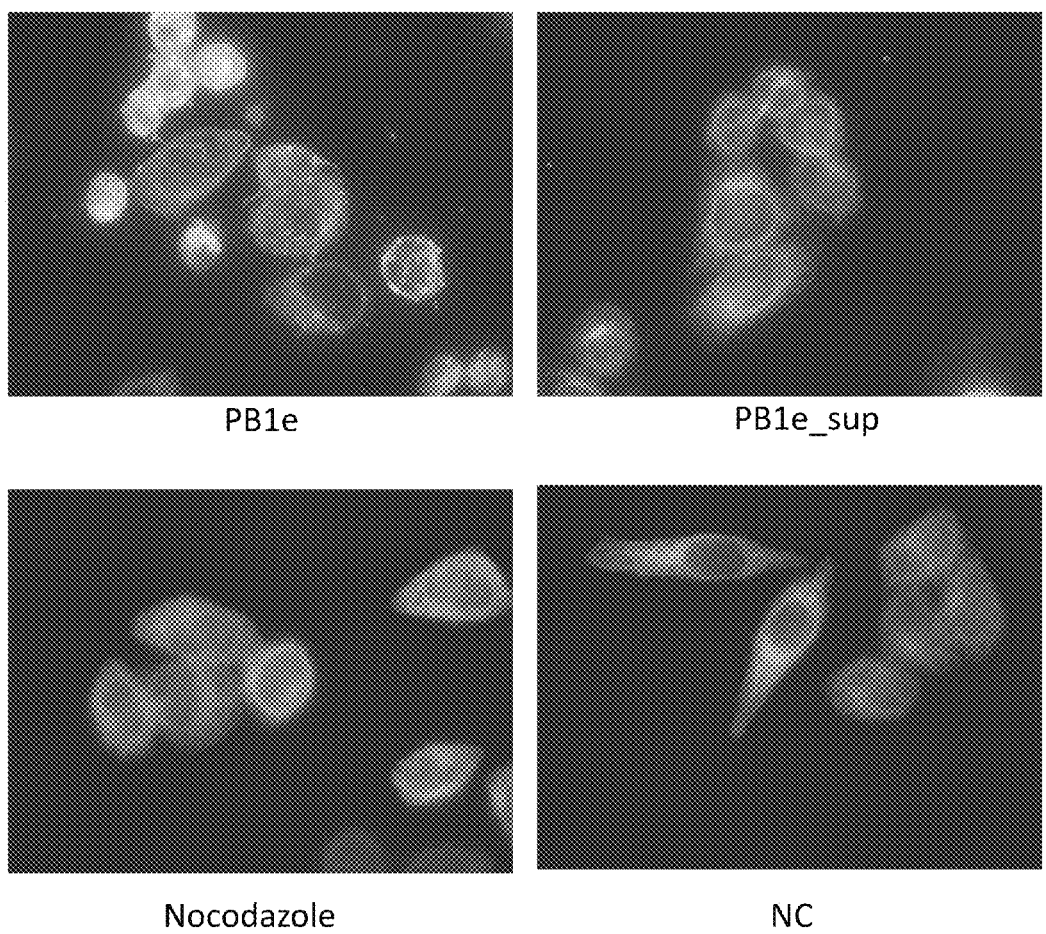
Figure 17J:
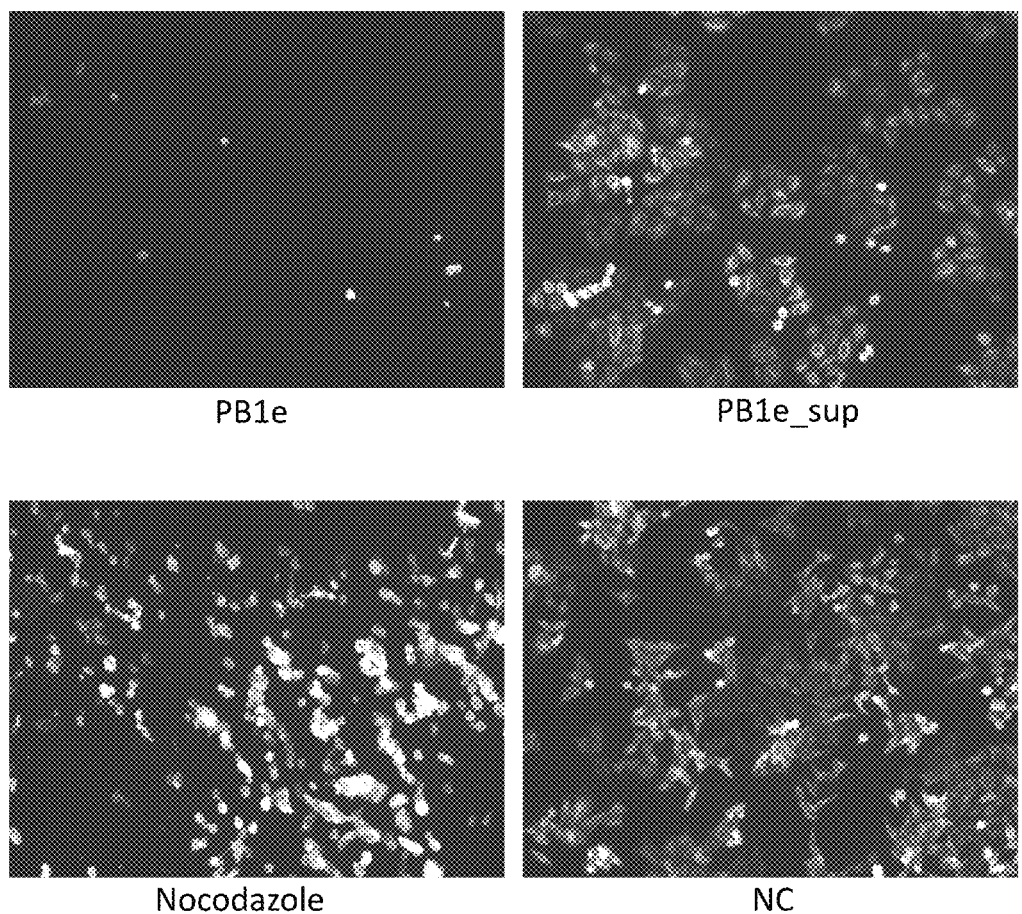
Figure 17K:
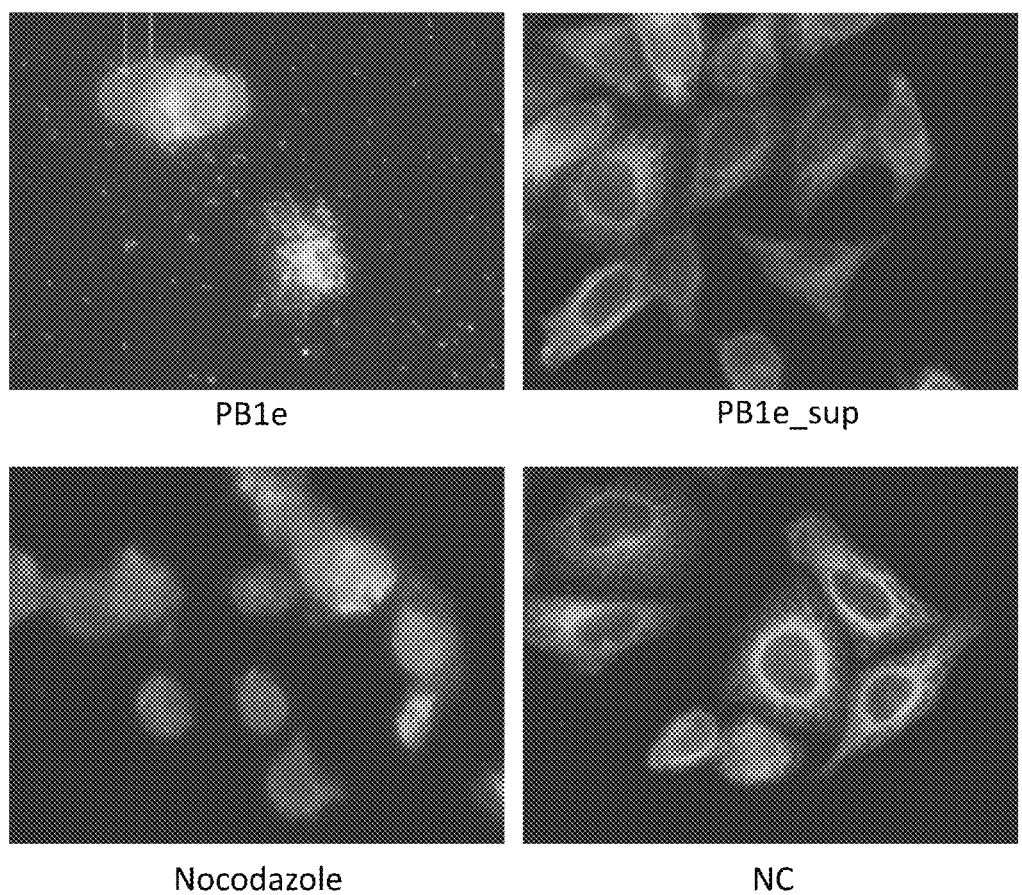

Delivery of Nocodazole into HeLa Cells with One or More Embodiments of CD3ac Nanoparticles FIG. 16A show one embodiment of the CD3ac nanoparticles, wherein EGF (optionally labeled with Texas red for visualization purposes) is a cell-targeting ligand. Such CD3ac nanoparticles with EGF as a ligand can be taken up by the cells, as shown in FIG. 16B. To produce CD3ac beads encapsulated with nocodazole, in some embodiments, 21 µM CD3ac, 2 µg/mL EGF (labeled with Texas Red for visualization purpose) and 20-40 µM nocodazole were dissolved in an organic solvent (FIG. 17A or 17G). Solvent exchange with water can result in formation of an emulsion and thus CD3ac solid nanoparticles containing nocodazole and EGF. In some embodiments, at least a portion of EGF was encapsulated into CD3ac beads. Additionally, EGF can adsorb on the outer surface of the CD3ac beads, resulting in EGF-functionalized CD3ac beads.

After incubation of HeLa cells in media containing such CD3ac particles encapsulated with two different concentrations of nocodazole (20 µM or 40 µM), fluorescent microscopic images (FIGS. 17B-17F, and 17H-17K) show the EGF-functionalized CD3ac particles were uptaken by the HeLa cells, and the microtubule in those HeLa cells treated with EGF-functionalized CD3ac particles were largely depolymerized. However, HeLa cells treated with the supernatant of pre-incubated and centrifuged CD3ac suspensions still contain intact microtubules. This indicates that nocodazole can be delivered into the cells by the EGF-functionalized CD3ac particles.

Without wishing to be bound by theory, the bead binding and uptake by the cells can occur through the interaction of EGF adsorbed on the surface of the CD3ac particles with EGFR present on the HeLa cells.

Example 6

CD3ac Nanoparticle Targeting with IgG

Figure 18A:
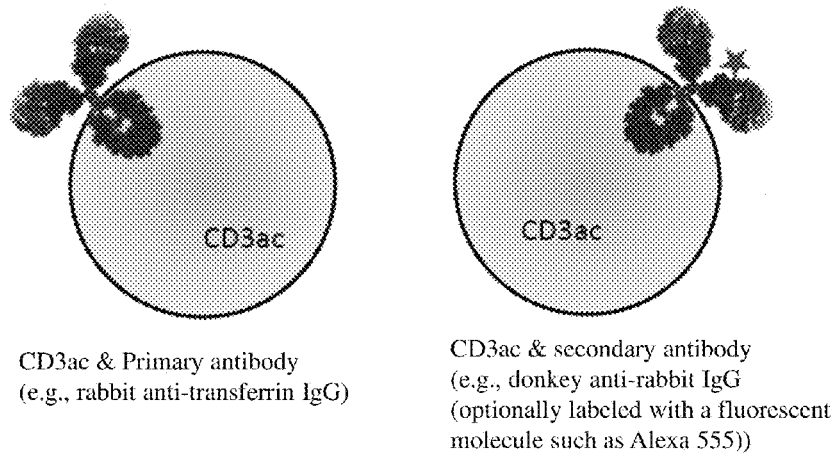
FIGS. 18A-18C show another embodiment of the peptide nanoparticles in accordance with the invention, wherein the CD3ac nanoparticles are functionalized with an antibody.
Figure 18B:
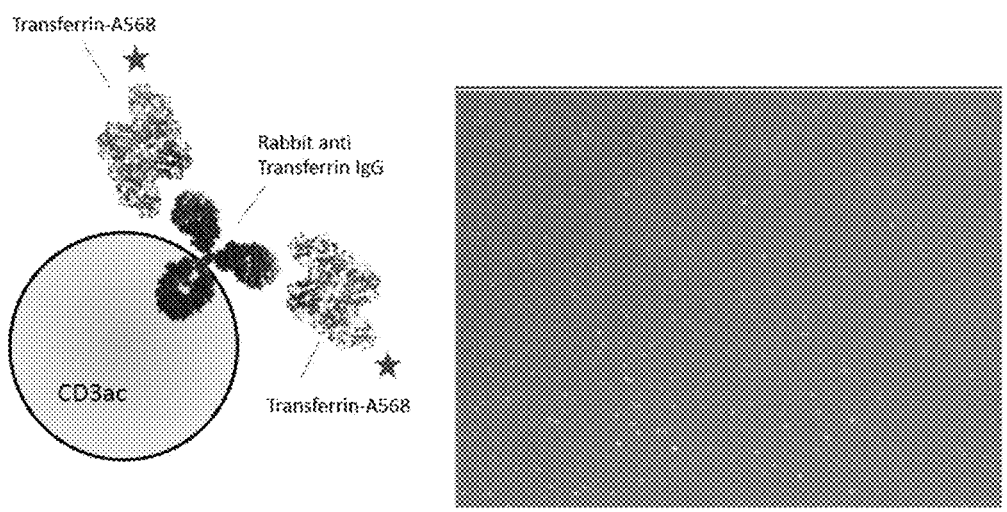
Figure 18C:
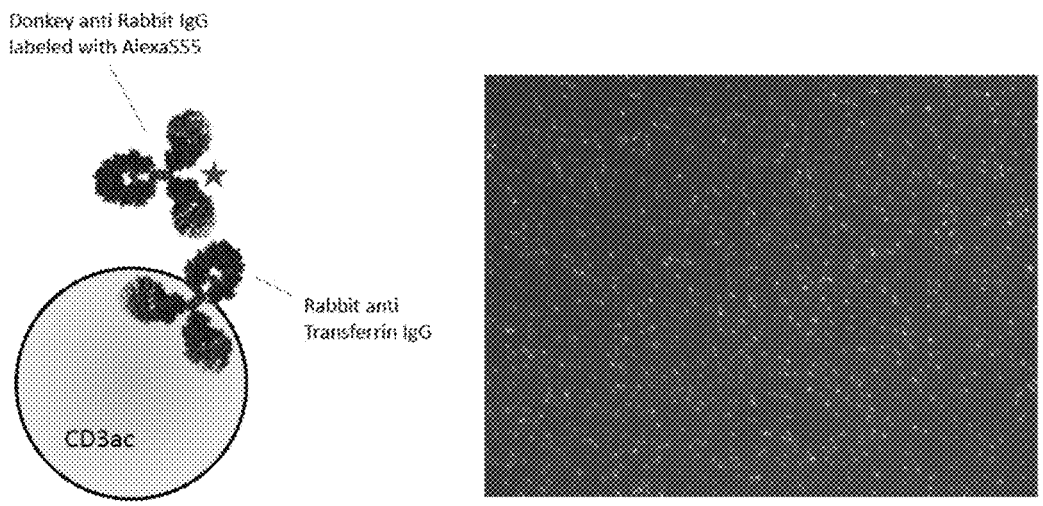

The CD3ac nanoparticles targeting with IgG can be prepared in one-step procedure as described herein. FIG. 18A shows that IgG antibodies (e.g., but not limited to, anti-transferrin IgG or anti-rabbit IgG) can be taken up by the CD3ac nanoparticles. In addition, as shown in FIG. 18B, incubation of the anti-transferrin IgG-functionalized CD3ac nanoparticles with transferrin A-546 generated fluorescence signals (indicated by white dots), indicating that the IgG is present on the CD3ac nanoparticle surface and enables binding of the IgG with transferrin A-546. Similarly, incubation of the anti-transferrin IgG-functionalized CD3ac nanoparticles with a secondary antibody (e.g., anti-rabbit IgG can be used if the anti-transferrin IgG is raised in rabbits) also resulted in binding of the IgG present on the CD3ac nanoparticle surface with the secondary antibodies (indicated by white dots in FIG. 18C). The IgG orientation at the interface of the nanoparticles is likely isotropic ("random"), e.g., the antigen binding site and/or the epitope for the secondary antibodies are exposed and accessible.

Example 7

Delivery of Nucleic Acid Molecules (e.g., DNA or RNA) by Peptide Particles (e.g., CD3 Peptide Particles or Mixed Peptide Particles Comprising CD3ac and CD3 Peptides)

DNA/siRNA transfection can be established by a peptide particle that is i) charged and ii) stable. While CD3ac particles (peptide sequence shown in Table 3) are insoluble in water, they are generally not charged and therefore unlikely bind to nucleic acid molecules (e.g., DNA or RNA including, but not limited to, siRNA). CD3 peptide (peptide sequence shown in Table 3) contains 4 primary amines (3 lysines+1 N-terminus) that can be either charged or acetylated.

Figure 19A:
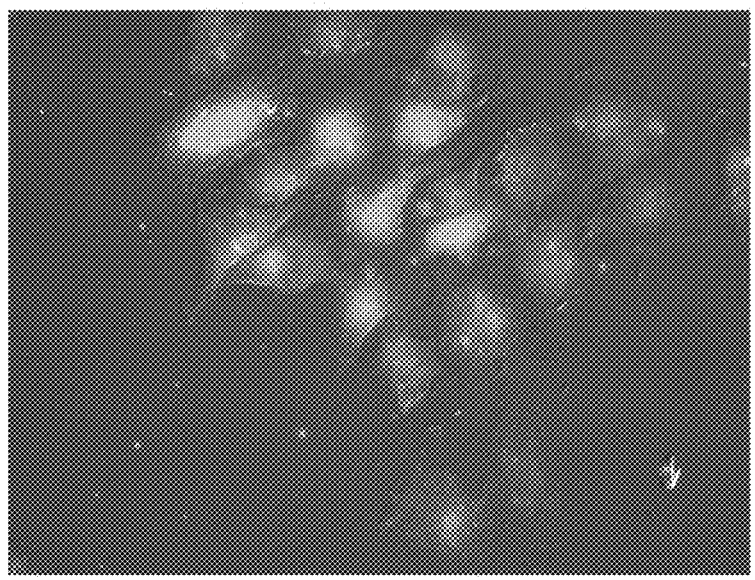
FIGS. 19A-19B show fluorescent images of non-acetylated peptide nanoparticles (CD3) for use as a transfection agent in vitro.
Figure 19B:

To evaluate cell transfection efficiency using CD3 peptides, HeLa cells were incubated with a mixture of CD3 peptides (with a peptide sequence shown in Table 3) and anionic nucleic acid molecules (e.g., single-stranded DNA), both dissolved in the cell culture medium at a molar ratio of about 3.7:1 (CD3:ssDNA). In order to easily visualize the presence of ssDNA inside a cell, a portion of the ssDNA added into the cell culture medium was labeled with a detectable label (e.g., Alexa Fluor 488; AF488). As shown in FIGS. 19A-19B, the presence of CD3 peptides in the cell culture media leads to increased fluorescence in the cytosol (FIG. 19A), as compared to the control (FIG. 19B). Thus, a mixture of positively-charged amphiphilic peptides described herein (e.g., CD3 peptides) and anionic nucleic acid molecules (e.g., DNA or RNA including, but not limited to, siRNA) can increase efficiency of transfecting cells with nucleic acid molecules, as compared to cell transfection in the absence of the positively-charged amphiphilic peptides described herein (e.g., CD3 peptides). Without wishing to be bound by theory, due to the amphiphilic structure and cationic head groups of the peptides described herein (e.g., CD3 peptides), some embodiments of the amphiphilic peptides described herein (e.g., CD3 peptides) can be used as cell-penetrating peptides or cell transfection agents.

Figure 20A:
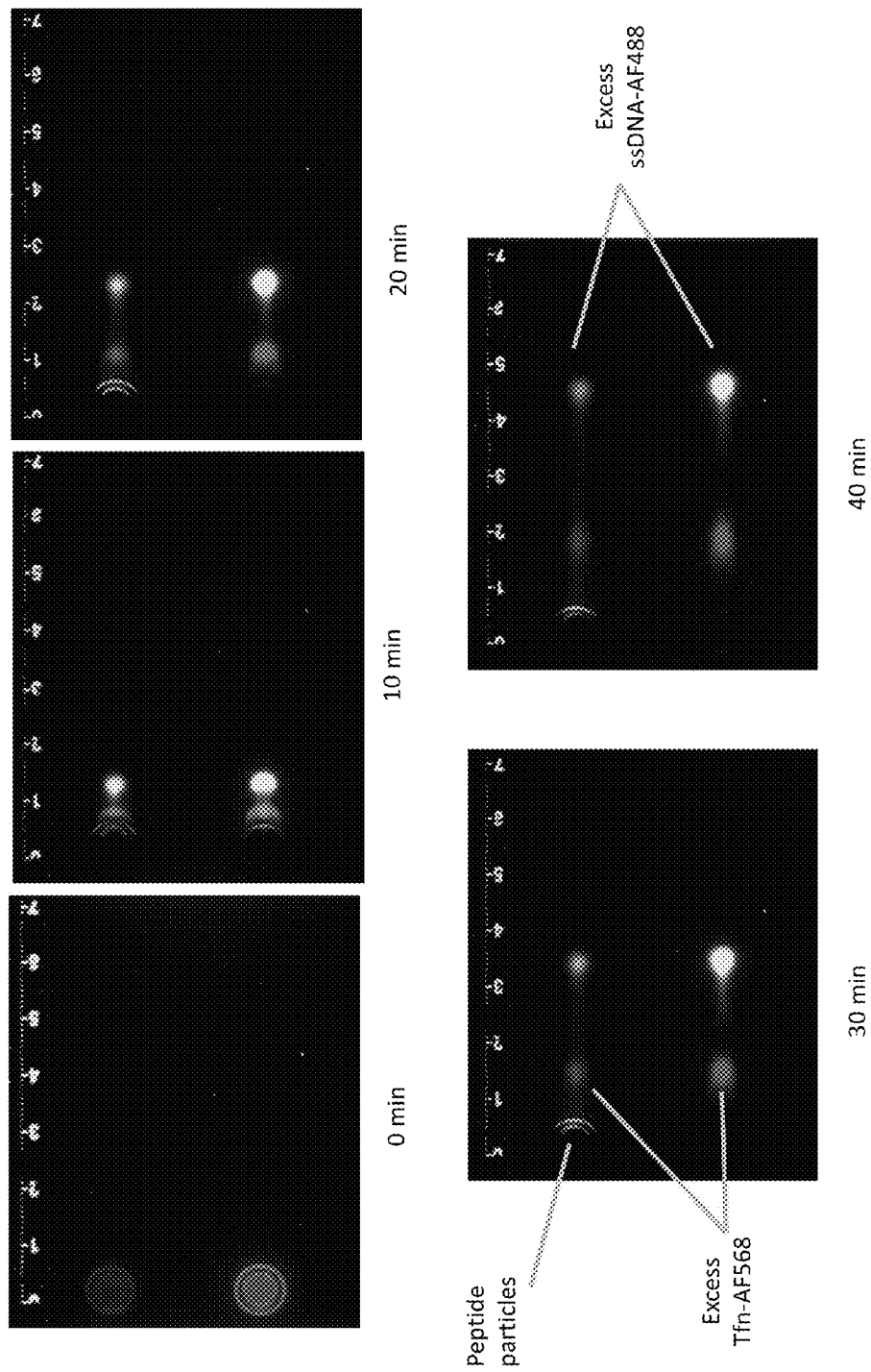
FIGS. 20A-20B show encapsulation efficiency of oligonucleotides in non-acetylated peptide particles.

It was next sought to determine if non-acetylated amphiphilic peptides (e.g., CD3 peptides) can self-assemble in the presence of nucleic acid molecules to form nucleic-acid containing peptide articles. To this end, a mixture of CD3 peptides, ssDNA, and transferrin was subjected to electrophoresis in agarose (as any formed peptide particles would be too large to migrate through the agarose gel). Some ssDNA in the mixture was labeled for visualization of its movement in agarose gel, while labeled transferrin (e.g., AF568-Tfn) was added into the peptide-nucleic acid mixture to monitor the presence of peptide particles. (As described earlier in Examples 3-6, a ligand (e.g., transferrin) added to a peptide mixture generally forms on the outer surface of the peptide particles.) As shown in FIG. 20A, co-localization of Tfn-AF568 signal and ssDNA-AF488 signal at the loading zone of the agarose after electrophoresis for about 40 mins indicates that peptide particles were formed from the mixture comprising CD3 peptides and nucleic acid molecules (e.g., AF488-ssDNA), and thus were unable to migrate into the agarose gel over time, while other excess protein molecules (e.g., ssDNA and Tfn) migrated toward the anode.

Figure 20B:
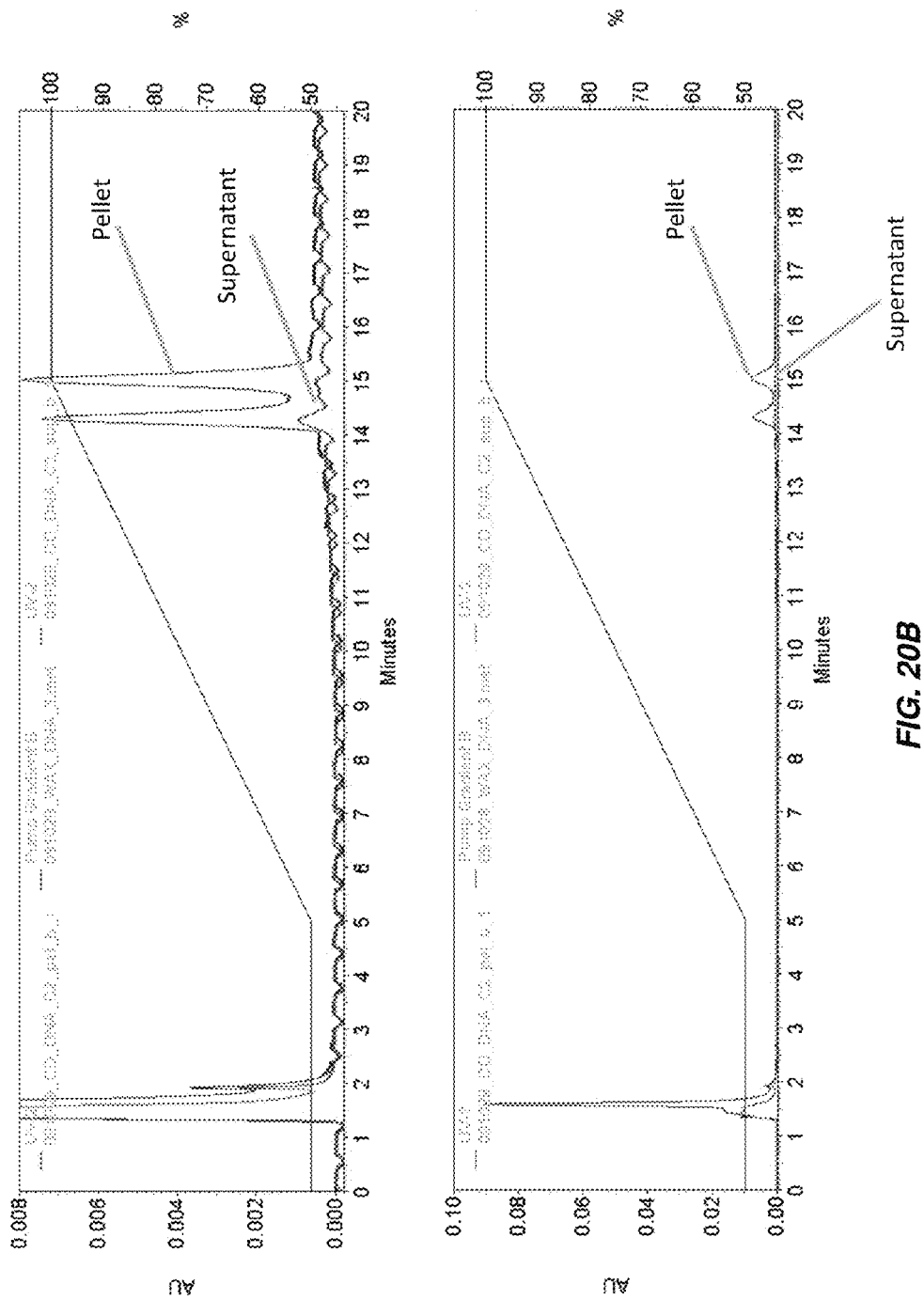

The efficiency of co-precipitation of non-acetylated amphiphilic peptides (e.g., CD3 peptides) and nucleic acid molecules (e.g., ssDNA) was also assessed and quantified, e.g., by a HP-WAX (weak anion exchange) chromatography method. For example, CD3 peptides and ssDNA were co-precipitated to form ssDNA-containing peptide particles prior to centrifugation and separation of supernatant and pellet, both of which were then subjected to a HP-WAX chromatography machine. As shown in FIG. 20B, a majority of the CD3 peptides and ssDNA were detected in the pellet of the peptide particles, as compared to the amounts in the supernatant, indicating that formation of ssDNA-containing peptide particles by the co-precipitation method is highly efficient.

It should be noted that a mixture of CD3 peptides and nucleic acid molecules can self-assemble to form stable particles in pure water; however, they are generally not stable and dissolve, responding to increasing salt strengths and higher temperatures.

Without limitations, there are two exemplary methods to decrease the solubility of nucleic acid (e.g., DNA or RNA including siRNA)-containing peptide nanoparticles. For example, the first approach can entail a mixture of fully-acetylated peptides (e.g., CD3ac with a peptide sequence as shown in Table 3) and partially and/or non-acetylated peptides (e.g., CD3 with a peptide sequence as shown in Table 3) during particle assembly. Even though CD3 is soluble in water, it can co-precipitate with CD3ac. Thus, a peptide nanoparticle's net charge can be easily modulated, e.g., by controlling the concentration or molar ratio of partially and/or non-acetylated peptides (e.g., CD3) and fully-acetylated peptides (e.g., CD3ac). By way of example only, more CD3ac can increase the particle stability while more CD3 can yield higher loading capacities for siRNA/DNA as well as a higher potential to penetrate cell membranes due to its net charges. One of skill in the art can determine the optimum ratio of CD3 to CD3ac in mixed peptide nanoparticles for particular applications, e.g., siRNA or DNA delivery. In some embodiments, the partially and/or non-acetylated peptides (e.g., CD3) can be present between 5 mole % and 50 mole % in mixed peptide nanoparticles. In some embodiments, the fully-acetylated peptides (e.g., CD3ac) can be present between 50 mole % and 95 mole % in mixed peptide nanoparticles. In various embodiments, the concentration or molar ratios of the partially and/or non-acetylated peptides (e.g., CD3) to fully-acetylated peptides (e.g., CD3ac) can range from about 1:100 to about 50:1; or from about 1:50 to about 10:1, or from about 1:20 to about 1:1.

Accordingly, in some embodiments, a mixture of fully-acetylated amphiphilic peptides (e.g., CD3ac peptides), partially-acetylated or non-acetylated amphiphilic peptides (e.g., CD3 peptides) and nucleic acid molecules can be prepared to form stable peptide particles containing nucleic acid molecules (e.g., DNA or RNA including siRNA). For example, to demonstrate formation of stable nucleic acid-containing peptide particles at physiological conditions, CD3ac peptides were added to a mixture of CD3 peptides and single-stranded DNA (ssDNA) at a molar ratio of about 11:1.8:1 (CD3ac:CD3:ssDNA). It was determined that the presence of CD3ac peptides stabilizes ssDNA-containing peptide particles at physiological conditions. All the three components co-precipitated to form ssDNA-containing peptide particles that were stable at the corresponding salt strength.

In some embodiments, a ligand (e.g., transferrin) can also be added into the mixture comprising fully-acetylated amphiphilic peptides (e.g., CD3ac peptides), partially-acetylated or non-acetylated amphiphilic peptides (e.g., CD3 peptides), and nucleic acid molecules (e.g., DNA or RNA including siRNA) to form nucleic acid-containing stable peptide particles against the protein to which the ligand binds (See, e.g., Examples 3-6 for some embodiments of the peptide particles described herein for use in targeted delivery of an active agent). For example, transferrin (Tfn labeled with AF568 for ease of visualization by imaging) was added to the mixture to form nucleic acid-containing stable peptide particles against transferrin receptors present on the cell surface. As discussed in Example 3, the ligand (e.g., Tfn) is generally present on the outer surface of the peptide particles.

Figure 21:
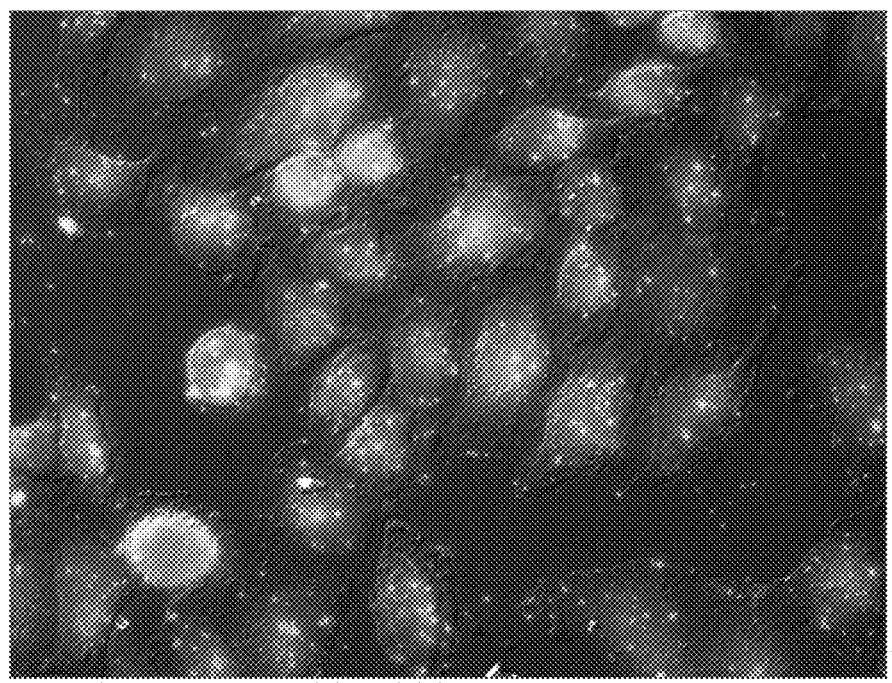
FIG. 21 is a microscopic fluorescent image showing uptake of nucleic acid-containing peptide particles by HeLa cells. In this embodiment, the peptide particles were formed from a mixture comprising CD3 peptides, CD3ac peptides, oligonucleotides (e.g., ssDNA) and trasferrin. The co-localization of the ssDNA-AF488 fluorescence signal with the peptide particles (as indicated by transferrin-AF568 fluorescence, where transferrin forms on the external surface of the particle) indicates the stability of the peptide particles at a physiological condition and the capability of such peptide particles to deliver nucleic acid molecules or oligonucleotides to cells.

To determine efficiency of delivering nucleic acid-containing peptide particles into cells, HeLa cells were incubated with nucleic acid-containing peptide particles (e.g., formed from a mixture of CD3ac peptides, CD3 peptides and ssDNA as described above). As discussed earlier, some ssDNA in the mixture were labeled with a detectable label (e.g., AF488) for ease of visualization by imaging. In addition, Tfn-AF568 was added to form nucleic-acid containing peptide particles as a means to visualize the formed peptide particles. As shown in FIG. 21, the Tfn-AF568 fluorescence signal from the formed peptide particles co-localized with the AF488-ssDNA fluorescence signal in the cytosol, indicating that ssDNA-containing peptide particles are stable at physiological conditions and delivered into the cells (e.g., HeLa cells).

It was next sought to determine the effect of net charges of nucleic acid-containing peptide articles on their stability at a physiological condition, e.g., in serum. As shown in Table 5 below, stable peptide particles are generally formed when the ratio of cationic charges to anionic charges of the nucleic acid-containing peptide particles is close to zero (e.g., between about 5 and about 0, or between about 3 and about 0). The charge ratio can be adjusted by molar ratios of anionic nucleic acid molecules (e.g., ssDNA), and cationic amphiphilic peptides described herein (e.g., partially-acetylated or non-acetylated amphiphilic peptides such as CD3) in a peptide assembly mixture. Without wishing to be bound by theory, a negative net charge of peptide particles (e.g., a ratio of cationic charges to anionic charges less than 1) can help to prevent particle aggregation.

Without wishing to be bound by theory, while the net charges of nucleic acid-containing peptide articles can influence the particle stability at physiological conditions, the amount of fully-acetylated amphiphilic peptides (e.g., CD3ac peptides) relative to non-acetylated amphiphilic peptides (e.g., CD3 peptides) can also contribute to the particle stability. For example, as discussed earlier, a mixture of non-acetylated amphiphilic peptides (e.g., CD3 peptides) and nucleic acid molecules can self-assemble to form particles; however, they are generally not stable and dissolve, responding to increasing salt strengths and higher temperatures. In contrast, peptide particles formed from fully-acetylated amphiphilic peptides (e.g., CD3ac peptides) are more stable. Accordingly, increasing the molar ratio of fully-acetylated amphiphilic peptides (e.g., CD3ac) to non-acetylated amphiphilic peptides (e.g., CD3) can increase stability of the resultant peptide particles at a physiological condition, e.g., in serum, which is in agreement with the data shown in Table 5.

TABLE 5

Effects of charge ratios (or molar ratios) in a peptide mixture on stability of resultant peptide particles in serum

| Peptide assembly mixture composition | Molar ratio (ssDNA:CD3ac: CD3) | Charge ratio (cation: anion) | Stability in serum |
|---|---|---|---|
| CD3<br>CD3ac<br>ssDNA | 1.23e−04M<br>1.23e−04M<br>6.20e−07M | 1:200:200 | 33.065 | Less stable |
| CD3<br>CD3ac<br>ssDNA | 1.23e−05M<br>1.23e−04M<br>6.20e−07M | 1:200:20 | 3.306 | Stable |
| CD3<br>CD3ac<br>ssDNA | 1.23e−06M<br>1.23e−04M<br>6.20e−07M | 1:200:2 | 0.331 | Stable | yield the amphiphilic character of the molecule. For example, at least one amino group (e.g., 1, 2, 3, 4, 5 or more amino groups, depending on the number of amino groups present in the hydrophilic peptidyl segment) of the hydrophilic peptidyl segment of the amphiphilic peptide described can remain non-acetylated, and at least one amino group (e.g., 1, 2, 3, 4, 5 or more amino groups, depending on the number of amino groups present in the hydrophilic peptidyl segment) of the hydrophilic peptidyl segment of the amphiphilic peptide described can be acetylated. In certain embodiments, such amphiphilic peptide can comprise an amino acid sequence of H-LK(Ac)-LK(Ac)-LK(Ac)-LW-DL-LW-DL-LW-DL-LW-NH$_2$ (SEQ ID NO: 53). In some embodiments, the amphiphilic peptide can comprise an amino acid sequence of H-LK-LK(Ac)-LK(Ac)-LW-DL-LW-DL-LW-DL-LW-NH$_2$ (SEQ ID NO: 54). In alternative embodiments, the amphiphilic peptide can comprise an amino acid sequence of H-LK-LK-LK(Ac)-LW-DL-LW-DL-LW-DL-LW-NH$_2$ (SEQ ID NO: 55) The ratio of acetylated amino groups to non-acetylated amino groups in an amphiphilic peptide can control the cationic and anionic properties of the amphiphilic peptides described herein. In some embodiments, the ratio of acetylated amino groups to non-acetylated amino groups in an amphiphilic peptide can be smaller than 1, about 1, or larger than 1.

Example 8

Stability of Nucleic Acid-Containing Peptide Particles (e.g., CD3 Peptide Particles or Mixed Peptide Particles Comprising CD3Ac and CD3 Peptides)

The stability of nucleic acid-containing CD3 peptide particles was characterized in pure water. Below is an exemplary CD3 peptide particle formulation further comprising nucleic acid molecules (e.g., ssDNA) and a ligand (e.g., transferrin, Tfn):

---
Peptide particle formulation 1 (CD3 + ssDNA + Tfn)

21 µM CD3 (H-LK-LK-LK-LW-DL-LW-DL-LW-DL-LW-NH$_2$) (SEQ ID NO: 11)$^{4+}$ 5.4 µM (5'-TTGTGCCGCCTTTGCAGGTGTATC-3') (SEQ ID NO: 12)$^{24-}$ 0.24 µM (AF488-5'-TTGTGCCGCCTTTGCAGGTGTATC-3') (SEQ ID NO: 12)$^{24-}$ 4.14 ug/mL Tfn-AF568
---

Figure 22A:
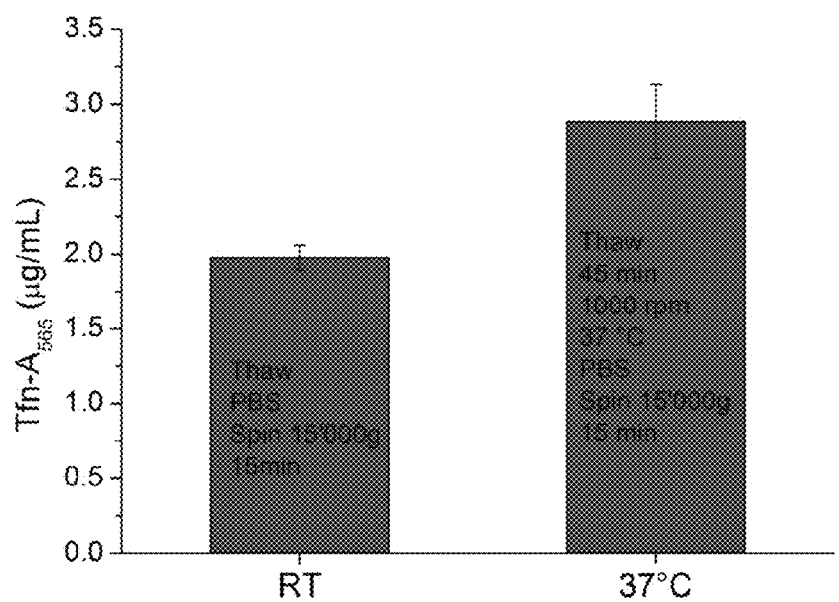
FIGS. 22A-22D show data for stability of ssDNA-containing peptide particles in serum (e.g., ~10% serum) and efficiency of cell transfection using the peptide particles.

The second approach to decrease the solubility of DNA/siRNA-containing peptide nanoparticles can involve custom synthesis of a single peptide with an acetylation degree, e.g., varying from acetylation of at least one amino group in the hydrophilic peptidyl segment of the amphiphilic peptide described herein to complete acetylation of all amino groups in the hydrophilic peptidyl segment of the amphiphilic peptide described herein. By way of example only, an amphiphilic peptide can be custom synthesized with an acetylation degree between CD3 and CD3ac. For example, an amphiphilic peptide can be custom synthesized with at least one charged or non-acetylated group, e.g., at the N-terminus, including at least one two charged or non-acetylated groups or at least three charged or non-acetylated groups. In one embodiment, the amphiphilic peptide can be designed to be cationic (e.g., for siRNA or DNA delivery) by modulating charges toward or on its N-terminus (e.g., with acetylation) to To evaluate the stability of peptide particles formed from formulation 1 (PNP1) in water, a sample of the peptide particles PNP1 was shaken in an eppendorf tube containing water for about 15 mins either at about room temperature or at about 37° C. The PNP1 sample was then centrifuged to spin down the peptide particles and the supernatant was collected for further analysis. The Tfn-AF568 concentration in the supernatant was measured and quantified by fluorescence intensity. As shown in FIG. 22A, a higher concentration of Tfn-AF568 was detected in the supernatant from the PNP1 sample shaken at a temperature of about 37° C. than at about room temperature, indicating that the stability of PNP1 particles in water is temperature-dependent and more PNP1 particles tend to dissociate at a higher temperature, thus releasing a greater amount of Tfn-AF568 into the supernatant.

Figure 22B:
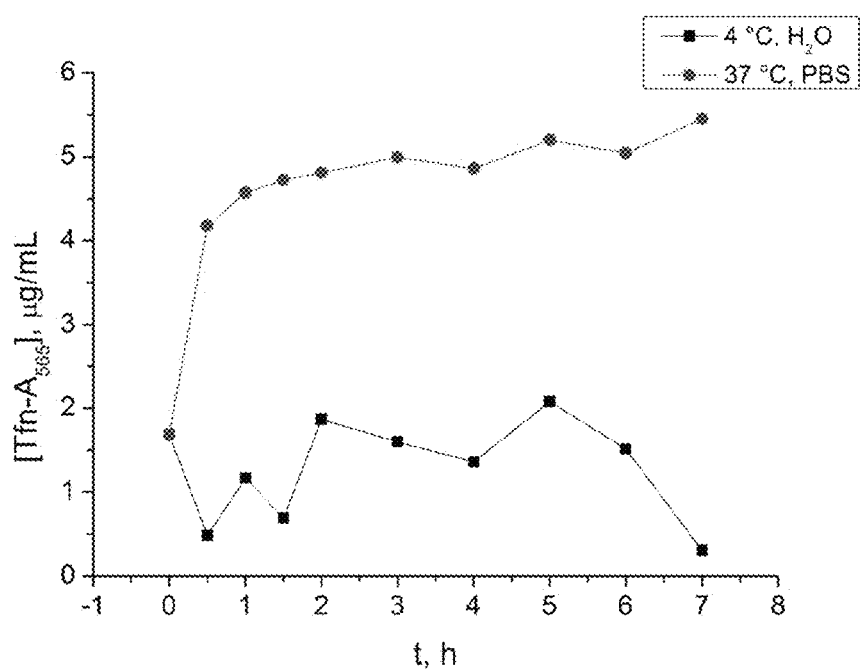

A time-course study of the PNP1 stability in water was also performed. Samples of the PNP1 particles were shaken in eppendorf tubes containing water at a temperature of either about 4° C. or about 37° C. At each pre-determined time point (as indicated in FIG. 22B), a PNP1 sample was then centrifuged to spin down the peptide particles and the supernatant was collected for further analysis. The Tfn-AF568 concentration in the supernatant was measured and quantified by fluorescence intensity. Similar to FIG. 22A, FIG. 22B shows that the stability of PNP1 particles in water is temperature-dependent and the PNP1 particles tend to dissociate faster at a higher temperature, e.g., at a temperature higher than 4° C.

It was next sought to compare the stability of PNP1 particles and peptide particles formed from formulation 2 (PNP2), as shown below, in cell culture media, e.g., containing about 10% serum.

| Peptide particle formulation 2 (CD3ac + CD3 ssDNA Tfn) |
|---|
| 123 µM CD3ac (Ac-LK(Ac)-LK(Ac)-LK(Ac)-LW-DL-LW-DL-LW-DL-LW-NH$_2$) (SEQ ID NO: 17) |
| 21 µM CD3 (H-LK-LK-LK-LW-DL-LW-DL-LW-DL-LW-NH$_2$) (SEQ ID NO: 11)$^{4+}$ |
| 5.4 µM (5'-TTGTGCCGCCTTTGCAGGTGTATC-3') (SEQ ID NO: 12)$^{24-}$ |
| 0.24 µM (AF488-5'-TTGTGCCGCCTTTGCAGGTGTATC-3') (SEQ ID NO: 12)$^{24-}$ |
| 4.14 ug/mL Tfn-AF568 |

HeLa cells were incubated with either PNP1 or PNP2 particles for about 30 minutes at temperatures of about 4° C. and 37° C. As HeLa cells generally perform clathrin-mediated endocytosis at about 37° C., but not at about 4° C., any Tfn-AF 568 dissolved in the media will be internalized by the cells. Thus, after the incubation, the cells were fixed with paraformaldehyde for imaging and detecting the fluorescence intensity. As shown in the upper panels of FIG. 22C, a diffuse and stronger Tfn-AF568 fluorescence signal was detected in the cytosol when the cells were incubated with the PNP1 particles at about 37° C., as compared to more punctated Tfn-AF568 fluorescence detected in the cells incubated at about 4° C. However, this contrast was not observed in the cells incubated with the PNP2 particles, as shown in the lower panels of FIG. 22C. Instead, punctated and comparable Tfn-AF568 fluorescence signals were observed in both the cells incubated at about 4° C. and about 37° C., in the presence of the PNP2 particles. These findings indicate that the PNP1 particles tend to dissociate at about 37° C., thus releasing into the culture media Tfn-AF568, which is then internalized by the cells; while the PNP2 particles appear to be more stable in serum (e.g., about 10% serum) at about 37° C. for at least about 30 mins, thus retaining most of the Tfn-AF568 in the PNP2 particles and/or on the surface of the PNP2 particles.

Figure 22C:
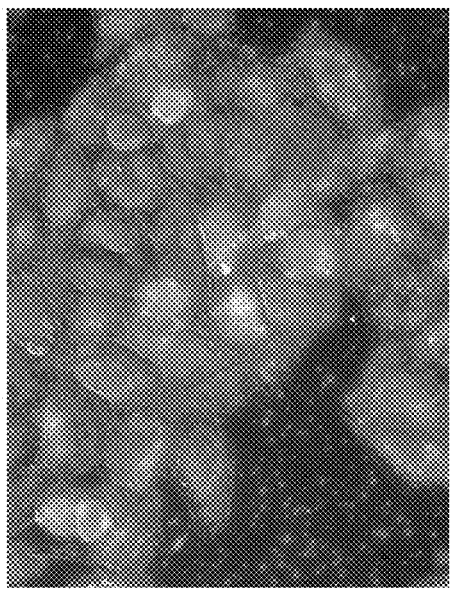
Figure 22C:
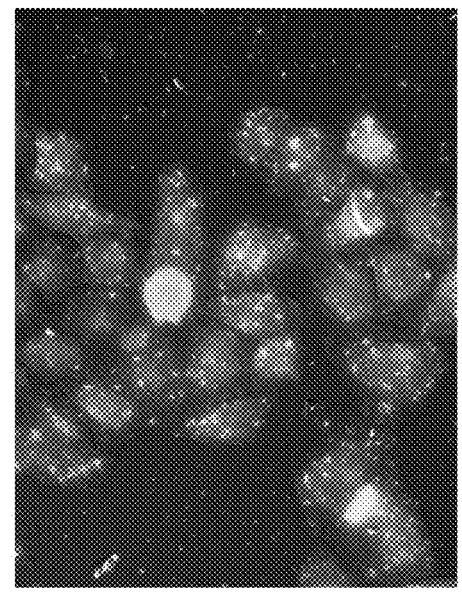
Figure 22C:
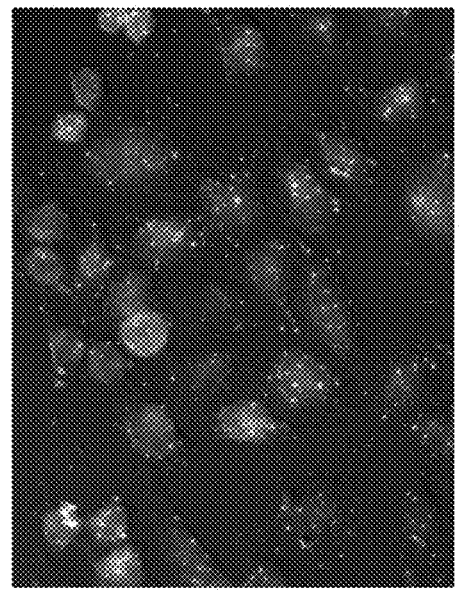
Figure 22C:
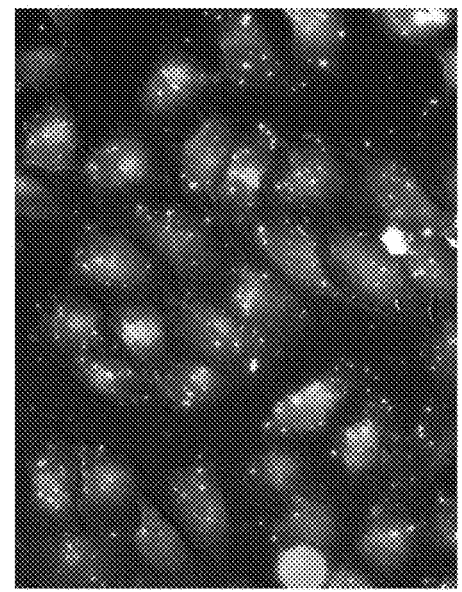
Figure 22D:
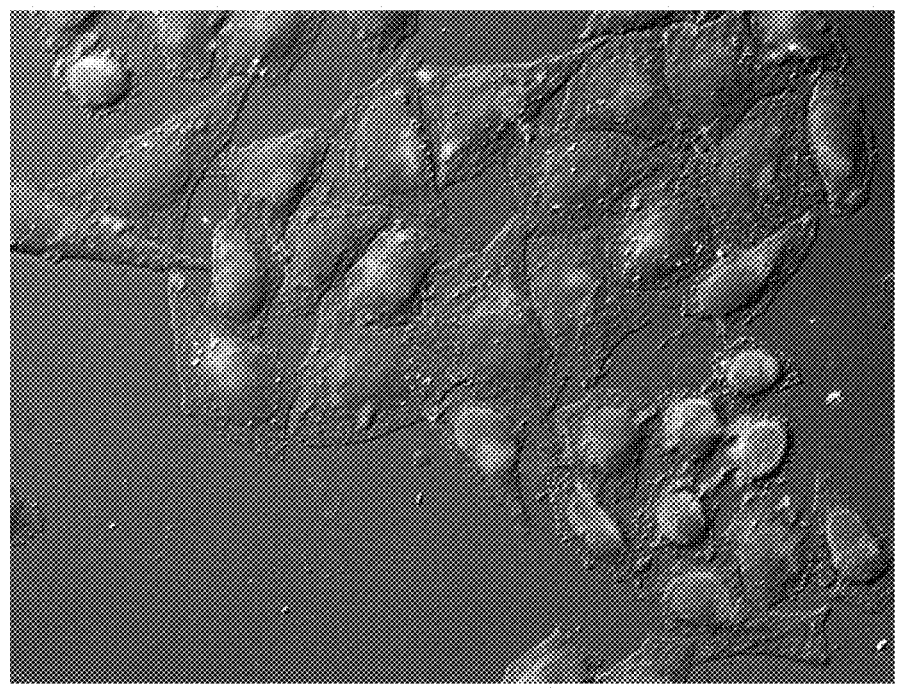

Comparing the cells in FIG. 22C with the negative control (i.e., cells incubated in the presence of ssDNA without CD3 or CD3ac peptides) shown in FIG. 22D, the fluorescence intensity of AF488-ssDNA in the negative control is significantly lower than that in the cells incubated with ssDNA-containing PNP1 or PNP2 particles. This indicates that the PNP1 or PNP2 particles can be used to facilitate cell transfection, and deliver a nucleic acid molecule (e.g., DNA or RNA) to a cell. It is noted that AF488-ssDNA fluorescence was also detected in the cells incubated in the presence of PNP1 or PNP2 particles at about 4° C. Without wishing to be bound by theory, while cell transfection in the presence of PNP1 or PNP2 particles at about 4° C. is unlikely to be TfR (transferrin receptor)-dependent, it is probably caused by passive transport through the cell membrane in the presence of CD3 peptides as discussed in Example 7.

REFERENCES (FOR EXAMPLES 1-2)

[1] H. Goesmann, C. Feldmann, Angew. Chem., Int. Ed., 2010, 49, 1362.

[2] [2a] Y. Kakizawa, R. Nishio, T. Hirano, Y. Koshi, M. Nukiwa, M. Koiwa, J. Michizoe, N. Ida, J. Control Release 142, 8; [2b] K. Kita-Tokarczyk, J. Grumelard, T. Haefele, W. Meier, Polymer 2005, 46, 3540; [2c] L. Zhang, J. M. Chan, F. X. Gu, J.-W. Rhee, A. Z. Wang, A. F. Radovic-Moreno, F. Alexis, R. Langer, O. C. Farokhzad, ACS Nano 2008, 2, 1696; [2d] A. Blanazs, S. P. Armes, A. J. Ryan, Macromol. Rapid Commun. 2009, 30, 267; [2e] T. Smart, H. Lomas, M. Massignani, M. V. Flores-Merino, L. R. Perez, G. Battaglia, Nano Today 2008, 3, 38.

[3] J. N. Israelachvili, Intermolecular and Surface Forces: With Applications to Colloidal and Biological Systems, American Chemical Society, 1985, p. 296.

[4] [4a] S. Rai, R. Paliwal, P. N. Gupta, K. Khatri, A. K. Goyal, B. Vaidya, S. P. Vyas, Curr. Nanosci. 2008, 4, 30; [4b] Y. Liu, K. Li, J. Pan, B. Liu, S.-S. Feng, Biomaterials 2009, 31, 330.

[5] D. Nishit, M. Samir, Adv. Funct. Mater. 2009, 9999, NA-NA.

[6] C. Lo Presti, H. Lomas, M. Massignani, T. Smart, G. Battaglia, J. Mater. Chem. 2009, 19, 3576.

[7] U. K. Slotta, S. Rammensee, S. Gorb, T. Scheibel, Angew. Chem., Int. Ed. 2008, 47, 4592.

[8] S. Raman, G. Machaidze, A. Lustig, U. Aebi, P. Burkhard, Nanomedicine 2006, 2, 95.

[9] [9a] M. Nigen, C. Gaillard, T. Croguennec, M.-N. Madec, S. Bouhallab, Biophys. Chem. 2009, 146, 30; [9b] M. Nigen, T. Croguennec, D. Renard, S. Bouhallab, Biochemistry 2007, 46, 1248.

[10] T. E. Rajapaksa, M. Stover-Hamer, X. Fernandez, H. A. Eckelhoefer, D. D. Lo, T. E. Rajapaksa, J. Control Release 2009.

[11] [11a]Q. Sun, S. Cai, B. R. Peterson, Q. Sun, J. Am. Chem. Soc. 2008, 130, 10064. [11b]S. Yang, D. J. Coles, A. Esposito, D. J. Mitchell, I. Toth, R. F. Minchin, S. Yang, J. Controlled Release 2009, 135, 159.

[12] M. G. Ryadnov, A. Bella, S. Timson, D. N. Woolfson, J. Am. Chem. Soc. 2009, 131, 13240.

[13] [13a] L. Aulisa, H. Dong, J. D. Hartgerink, Biomacromolecules 2009, 10, 2694; [13b] K. J. Channon, G. L. Devlin, C. E. MacPhee, J. Am. Chem. Soc. 2009, 131, 12520; [13c] J. Ryu, C. B. Park, Angew. Chem., Int. Ed. 2009, 48, 4820, S4820/4821-S4820/4826; [13d] H. Dong, S. E. Paramonov, J. D. Hartgerink, J. Am. Chem. Soc. 2008, 130, 13691; [13e] Y. Zimenkov, S. N. Dublin, R. Ni, R. S. Tu, V. Breedveld, R. P. Apkarian, V. P. Conticello, J. Am. Chem. Soc. 2006, 128, 6770.

[14] Vydac, http://www.nestgrp.com/pdf/Vapp/AN9802.pdf 2010.

[15] [15a] H. M. Redhead, S. S. Davis, L. Illum, J. Controlled Release 2001, 70, 353; [15b] W. Lin, M. C. Garnett, S. S. Davis, E. Schacht, P. Ferruti, L. Illum, J. Controlled Release 2001, 71, 117.

[16] W. R. Veatch, E. T. Fossel, E. R. Blout, Biochemistry 1974, 13, 5249.

[17] [17a] D. A. Kelkar, A. Chattopadhyay, Biochim. Biophys. Acta, Biomembr. 2007, 1768, 2011; [17b] R. D. Hotchkiss, R. Dubos, J. Biol. Chem. 1940, 132, 791; [17c] R. D. Hotchkiss, R. Dubos, J. Biol. Chem. 1940, 132, 793.

[18] [18a] D. W. Urry, D. F. Mayers, J. Haider, Biochemistry 1972, 11, 487; [18b] Y. Chen, A. Tucker, B. A. Wallace, J. Mol. Biol. 1996, 264, 757; [18c] D. A. Doyle, B. A. Wallace, J. Mol. Biol. 1997, 266, 963.

[19] [19a] F. Heitz, A. Heitz, Y. Trudelle, Biophys. Chem. 1986, 24, 149; [19b] S. V. Sychev, N. A. Nevskaya, S. Iordanov, E. N. Shepel, A. I. Miroshnikov, V. T. Ivanov, Bioorg. Chem. 1980, 9, 121.

[20] L. Eidenschink, B. L. Kier, K. N. L. Huggins, N. H. Andersen, Proteins: Struct., Funct., Bioinf. 2009, 75, 308.

REFERENCES (FOR EXAMPLES 3-4)

(1) Multifunctional nanocarriers. Adv Drug Deliv 58, 1532-1555 (2006).

(2) Stark. Nanoparticles in Biological Systems. Angew Chem Int Ed, n-a, doi:10.1002/anie.200906684 (2011).

(3) Soussan, E., Cassel, S., Blanzat, M. & Rico-Lattes, I. Drug delivery by soft matter: matrix and vesicular carriers. ACIE 48, 274-288, doi:10.1002/anie.200802453 (2009).

(4) Nel, A. E. et al. Understanding biophysicochemical interactions at the nano-bio interface. Nat Mater 8, 543-557, doi:10.1038/nmat2442 (2009).

(5) Dittrich, C. & Meier, W. Solid Peptide Nanoparticles: Structural Characterization and Quantification of Cargo Encapsulation. Macromolecular Bioscience 10, 1406-1415, doi:10.1002/mabi.201000221 (2010).

(6) Merrifield, R. B. Solid Phase Peptide Synthesis. I. The Synthesis of a Tetrapeptide. J Am 85, 2149-2154, doi:10.1021/ja00897a025 (1963).

(7) Nilsson, B. L., Soellner, M. B. & Raines, R. T. Chemical synthesis of proteins. Annu Rev Bioph Biom 34, 91-118, doi:10.1146/annurev.biophys.34.040204.144700 (2005).

(8) Sitnikova, N. L., Sprik, R., Wegdam, G. & Eiser, E. Spontaneously formed trans-anethol/water/alcohol emulsions: mechanism of formation and stability. LAGMUIR 21, 7083-7089, doi:10.1021/la0468161 (2005).

(9) Ashley, C. E. et al. The targeted delivery of multicomponent cargos to cancer cells by nanoporous particle-supported lipid bilayers. Nature, doi:10.1038/nmat2992 (2011).

(10) Monopoli, M. P. et al. Physical-Chemical Aspects of Protein Corona: Relevance to in Vitro and in Vivo Biological Impacts of Nanoparticles. J. Am. Chem. Soc. 133, 2525-2534, doi:10.1021/ja107583h (2011).

(11) Ehrlich, M. et al. Endocytosis by random initiation and stabilization of clathrin-coated pits. CEL 118, 591-605, doi:10.1016/j.cell.2004.08.017 (2004).

(12) MacGillivray, R. T. A. et al. Two High-Resolution Crystal Structures of the Recombinant N-Lobe of Human Transferrin Reveal a Structural Change Implicated in Iron Release. Biochemistry 37, 7919-7928, doi:10.1021/bi980355j (1998).

(13) Min, Y., Akbulut, M., Kristiansen, K., Golan, Y. & Israelachvili, J. The role of interparticle and external forces in nanoparticle assembly. Nat. Mater. 7, 527-538, doi:10.1038/nmat2206 (2008).

(14) Fleck, C. C. & Netz, R. R. Electrostatic colloid-membrane binding. Europhys. Lett. 67, 314-320, doi:10.1209/epl/i2004-10068-x (2004).

(15) Dagastine, R. R. et al. Dynamic Forces Between Two Deformable Oil Droplets in Water. Science (Washington, D.C., United States) 313, 210-213, doi:10.1126/science.1125527 (2006).

(16) McGraw, T. E., Greenfield, L. & Maxfield, F. R. Functional expression of the human transferrin receptor cDNA in Chinese hamster ovary cells deficient in endogenous transferrin receptor. JCB 105, 207-214, doi:10.2307/1612534 (1987).

(17) Parhi, P., Golas, A., Barnthip, N., Noh, H. & Vogler, E. A. Volumetric interpretation of protein adsorption: Capacity scaling with adsorbate molecular weight and adsorbent surface energy. Biomaterials 30, 6814-6824, doi:10.1016/j.biomaterials.2009.09.005 (2009).

(18) Harding, C., Heuser, J. & Stahl, P. Receptor-mediated endocytosis of transferrin and recycling of the transferrin receptor in rat reticulocytes. JCB 97, 329-339, doi:10.2307/1610388 (1983).

(19) Lillo, M. P., Cañadas, O., Dale, R. E. & Acuña, A. U. Location and properties of the taxol binding center in microtubules: a picosecond laser study with fluorescent taxoids. Biochemist 41, 12436-12449 (2002).

(20) Jordan, M. A. & Wilson, L. Microtubules as a target for anticancer drugs. Nat Rev Can 4, 253-265, doi:10.1038/nrc1317 (2004).

(21) Stewart, K. M., Horton, K. L. & Kelley, S. O. Cell-penetrating peptides as delivery vehicles for biology and medicine. Org Biomol Chem 6, 2242-2255, doi:10.1039/b719950c (2008).

(22) Hyuk, I. S., Jeong, U. & Xia, Y. Polymer hollow particles with controllable holes in their surfaces. Nat. Mater. 4, 671-675, doi:10.1038/nmat1448 (2005).

Content of all patents and other publications identified herein is expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

We claim:

1. An amphiphilic peptide comprising a hydrophobic peptidyl segment and a hydrophilic peptidyl segment,
   wherein the hydrophobic peptidyl segment comprises a sequence of 2 to 10 alternating D- and L-amino acids selected from alanine, valine, isoleucine, leucine (Leu), phenylalanine, tyrosine or tryptophan (Trp), and
   wherein the hydrophilic peptidyl segment comprises charged, or uncharged but polar amino acids, or derivatives thereof.

2. The amphiphilic peptide of claim 1, wherein the hydrophobic peptidyl segment comprises an amino acid sequence of $(Trp-Leu)_m$-$(Trp)_n$ (SEQ ID NO: 1) or $(Leu-Trp)_p$-$(Leu)_q$ (SEQ ID NO: 2), wherein each Trp is D-Trp or L-Trp and each Leu is D-Leu or L-Leu, m and p are independently an integer from 1 to 20, and n and q are independently 0 or 1, provided that when Trp is D-Trp then Leu is L-Leu, and when Trp is L-Trp then Leu is D-Leu, or vice versa.

3. The amphiphilic peptide of claim 2, wherein the amphiphilic peptide comprises at least one of the following characteristics:
i. Trp is L-Trp;
ii. m or p is between 1 and 3; or m or p is 3; and
iii. n or q is 1.

4. The amphiphilic peptide of claim 1, wherein the hydrophilic peptidyl segment comprises at least one cationic or anionic charge present either on the N-terminus or an amino acid residue.

5. The amphiphilic peptide of claim 4, wherein the at least one cationic charge is in an amino acid residue selected from the group consisting of Lys, Arg, His, and any combinations thereof; or wherein the at least one anionic charge is in an amino acid residue selected from the group consisting of Asp or Glu, and any combinations thereof.

6. The amphiphilic peptide of claim 1, wherein at least one of the uncharged but polar amino acid residues is selected from the group consisting of Ser, Thr, Asn or Gln, and any combinations thereof.

7. The amphiphilic peptide of claim 1, wherein the hydrophilic peptidyl segment comprises an amino acid sequence of $(Lys)_r$ (SEQ ID NO: 9), wherein r is an integer from 1 to 15; or r is 3.

8. The amphiphilic peptide of claim 7, wherein Lys is L-Lys.

9. The amphiphilic peptide of claim 1, wherein no amino group in the amphiphilic peptide is acetylated.

10. The amphiphilic peptide of claim 1, wherein at least one amino group in the amphiphilic peptide is acetylated.

11. The amphiphilic peptide of claim 10, wherein said at least one amino group includes a N-terminus amino group of the amphiphilic peptide, one or more amino acid residues of the hydrophilic peptidyl segment, or a combination thereof.

12. The amphiphilic peptide of claim 1, wherein the hydrophobic peptidyl segment is linked to the C-terminus of the hydrophilic peptidyl segment.

13. The amphiphilic peptide of claim 2, wherein the amphiphilic peptide comprises the amino acid sequence of (L-Lys)-(L-Lys)-(L-Lys)-(L-Trp)-(D-Leu)-(L-Trp)-(D-Leu)-(L-Trp)-(D-Leu)-(L-Trp)-X (SEQ ID NO: 10), or Ac-(L-Lys)-(L-Lys)-(L-Lys)-(L-Trp)-(D-Leu)-(L-Trp)-(D-Leu)-(L-Trp)-(D-Leu)-(L-Trp)-X (SEQ ID NO: 5), wherein X is absent or $NH_2$, and Ac is acetylation of the N-terminus amino group of the amphiphilic peptide.

14. The amphiphilic peptide of claim 13, wherein at least one or all of the Lys residues are acetylated.

15. The amphiphilic peptide of claim 1, wherein the amphiphilic peptide comprises at least one amino acid modification selected from the group consisting of substitution of one backbone amide linkage with an amide replacement linkage, inclusion of a β-amino acid, γ-amino acid, or any combinations thereof, inclusion of a point mutation, and any combinations thereof.

16. A peptide particle comprising an amphiphilic peptide of claim 1.

17. The peptide particle of claim 16, wherein the amphiphilic peptide is fully-acetylated, wherein the N-terminus amino group of the amphiphilic peptide and all of the amino acid resides of the hydrophilic peptidyl segment are acetylated.

18. The peptide particle of claim 17, further comprises a partially-acetylated or non-acetylated amphiphilic peptide, wherein a ratio of the partially acetylated or non-acetylated amphiphilic peptide to the fully-acetylated amphiphilic peptide ranges from about 1:1000 to about 1:1, or from about 1:100 to about 1:5.

19. The peptide particle of claim 16, further comprising a ligand.

20. The peptide particle of claim 19, wherein the ligand is present on an outer surface of the peptide particle.

21. The peptide particle of claim 20, wherein a thickness of the ligand present on the outer surface of the particle ranges from about 1 nm to about 100 nm, or is about 10 nm.

22. The peptide particle of claim 19, wherein the ligand is covalently linked to the amphiphilic peptide.

23. The particle of claim 22, wherein the ligand is covalently linked to the hydrophilic peptidyl segment of the amphiphilic peptide.

24. The peptide particle of claim 19, wherein the ligand is a cell surface receptor ligand or an antibody.

25. The peptide particle of claim 19, wherein a ratio of the ligand to the amphiphilic peptide ranges from about 1:10 to about 1:1,000,000.

26. The peptide particle of claim 16, further encapsulating an active agent therein.

27. The peptide particle of claim 26, wherein the active agent has no net charge or a net charge, and wherein the active agent is selected from the group consisting of proteins, peptides, antigens, antibodies or portions thereof, enzymes, nucleic acids, aptamers, small molecules, antibiotics, pharmaceutically active agents, therapeutic agents, contrast agents, and any combinations thereof.

28. The peptide particle of claim 24, wherein the active agent is cell-impermeable when it is delivered to a cell by itself.

29. The peptide particle of claim 26, wherein a ratio of the active agent to the amphiphilic peptide ranges from about 1:1 to about 1:100,000, or from about 1:1 to about 1:1,000, or from about 1:1 to about 1:100, or from about 1:1 to about 1:10.

30. The peptide particle of claim 26, wherein the active agent includes a nucleic acid molecule, and a ratio of the nucleic acid molecule to the partially acetylated or non-acetylated amphiphilic peptide ranges from about 1:10 to about 1:2.

31. The peptide particle of claim 16, wherein the peptide particle has a size of about 5 nm to about 5,000 nm, or about 30 nm to about 150 nm.

* * * * *

SEQUENCE LISTING

<160> NUMBER OF SEQ ID NOS: 55

<210> SEQ ID NO 1

-continued

```
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This region may encompass 1 to 20 "Trp Leu"
      repeating units
<220> FEATURE:
<221> NAME/KEY: MOD_RES
<222> LOCATION: (1)..(1)
<223> OTHER INFORMATION: D-Trp or L-Trp
<220> FEATURE:
<221> NAME/KEY: MOD_RES
<222> LOCATION: (2)..(2)
<223> OTHER INFORMATION: D-Leu or L-Leu
<220> FEATURE:
<221> NAME/KEY: MOD_RES
<222> LOCATION: (3)..(3)
<223> OTHER INFORMATION: D-Trp or L-Trp
<220> FEATURE:
<221> NAME/KEY: MOD_RES
<222> LOCATION: (4)..(4)
<223> OTHER INFORMATION: D-Leu or L-Leu
<220> FEATURE:
<221> NAME/KEY: MOD_RES
<222> LOCATION: (5)..(5)
<223> OTHER INFORMATION: D-Trp or L-Trp
<220> FEATURE:
<221> NAME/KEY: MOD_RES
<222> LOCATION: (6)..(6)
<223> OTHER INFORMATION: D-Leu or L-Leu
<220> FEATURE:
<221> NAME/KEY: MOD_RES
<222> LOCATION: (7)..(7)
<223> OTHER INFORMATION: D-Trp or L-Trp
<220> FEATURE:
<221> NAME/KEY: MOD_RES
<222> LOCATION: (8)..(8)
<223> OTHER INFORMATION: D-Leu or L-Leu
<220> FEATURE:
<221> NAME/KEY: MOD_RES
<222> LOCATION: (9)..(9)
<223> OTHER INFORMATION: D-Trp or L-Trp
<220> FEATURE:
<221> NAME/KEY: MOD_RES
<222> LOCATION: (10)..(10)
<223> OTHER INFORMATION: D-Leu or L-Leu
<220> FEATURE:
<221> NAME/KEY: MOD_RES
<222> LOCATION: (11)..(11)
<223> OTHER INFORMATION: D-Trp or L-Trp
<220> FEATURE:
<221> NAME/KEY: MOD_RES
<222> LOCATION: (12)..(12)
<223> OTHER INFORMATION: D-Leu or L-Leu
<220> FEATURE:
<221> NAME/KEY: MOD_RES
<222> LOCATION: (13)..(13)
<223> OTHER INFORMATION: D-Trp or L-Trp
<220> FEATURE:
<221> NAME/KEY: MOD_RES
<222> LOCATION: (14)..(14)
<223> OTHER INFORMATION: D-Leu or L-Leu
<220> FEATURE:
<221> NAME/KEY: MOD_RES
<222> LOCATION: (15)..(15)
<223> OTHER INFORMATION: D-Trp or L-Trp
<220> FEATURE:
<221> NAME/KEY: MOD_RES
<222> LOCATION: (16)..(16)
<223> OTHER INFORMATION: D-Leu or L-Leu
<220> FEATURE:
<221> NAME/KEY: MOD_RES
<222> LOCATION: (17)..(17)
<223> OTHER INFORMATION: D-Trp or L-Trp
```

-continued

```
<220> FEATURE:
<221> NAME/KEY: MOD_RES
<222> LOCATION: (18)..(18)
<223> OTHER INFORMATION: D-Leu or L-Leu
<220> FEATURE:
<221> NAME/KEY: MOD_RES
<222> LOCATION: (19)..(19)
<223> OTHER INFORMATION: D-Trp or L-Trp
<220> FEATURE:
<221> NAME/KEY: MOD_RES
<222> LOCATION: (20)..(20)
<223> OTHER INFORMATION: D-Leu or L-Leu
<220> FEATURE:
<221> NAME/KEY: MOD_RES
<222> LOCATION: (21)..(21)
<223> OTHER INFORMATION: D-Trp or L-Trp
<220> FEATURE:
<221> NAME/KEY: MOD_RES
<222> LOCATION: (22)..(22)
<223> OTHER INFORMATION: D-Leu or L-Leu
<220> FEATURE:
<221> NAME/KEY: MOD_RES
<222> LOCATION: (23)..(23)
<223> OTHER INFORMATION: D-Trp or L-Trp
<220> FEATURE:
<221> NAME/KEY: MOD_RES
<222> LOCATION: (24)..(24)
<223> OTHER INFORMATION: D-Leu or L-Leu
<220> FEATURE:
<221> NAME/KEY: MOD_RES
<222> LOCATION: (25)..(25)
<223> OTHER INFORMATION: D-Trp or L-Trp
<220> FEATURE:
<221> NAME/KEY: MOD_RES
<222> LOCATION: (26)..(26)
<223> OTHER INFORMATION: D-Leu or L-Leu
<220> FEATURE:
<221> NAME/KEY: MOD_RES
<222> LOCATION: (27)..(27)
<223> OTHER INFORMATION: D-Trp or L-Trp
<220> FEATURE:
<221> NAME/KEY: MOD_RES
<222> LOCATION: (28)..(28)
<223> OTHER INFORMATION: D-Leu or L-Leu
<220> FEATURE:
<221> NAME/KEY: MOD_RES
<222> LOCATION: (29)..(29)
<223> OTHER INFORMATION: D-Trp or L-Trp
<220> FEATURE:
<221> NAME/KEY: MOD_RES
<222> LOCATION: (30)..(30)
<223> OTHER INFORMATION: D-Leu or L-Leu
<220> FEATURE:
<221> NAME/KEY: MOD_RES
<222> LOCATION: (31)..(31)
<223> OTHER INFORMATION: D-Trp or L-Trp
<220> FEATURE:
<221> NAME/KEY: MOD_RES
<222> LOCATION: (32)..(32)
<223> OTHER INFORMATION: D-Leu or L-Leu
<220> FEATURE:
<221> NAME/KEY: MOD_RES
<222> LOCATION: (33)..(33)
<223> OTHER INFORMATION: D-Trp or L-Trp
<220> FEATURE:
<221> NAME/KEY: MOD_RES
<222> LOCATION: (34)..(34)
<223> OTHER INFORMATION: D-Leu or L-Leu
<220> FEATURE:
<221> NAME/KEY: MOD_RES
<222> LOCATION: (35)..(35)
<223> OTHER INFORMATION: D-Trp or L-Trp
<220> FEATURE:
<221> NAME/KEY: MOD_RES
<222> LOCATION: (36)..(36)
<223> OTHER INFORMATION: D-Leu or L-Leu
<220> FEATURE:
<221> NAME/KEY: MOD_RES
<222> LOCATION: (37)..(37)
```

-continued

```
<223> OTHER INFORMATION: D-Trp or L-Trp
<220> FEATURE:
<221> NAME/KEY: MOD_RES
<222> LOCATION: (38)..(38)
<223> OTHER INFORMATION: D-Leu or L-Leu
<220> FEATURE:
<221> NAME/KEY: MOD_RES
<222> LOCATION: (39)..(39)
<223> OTHER INFORMATION: D-Trp or L-Trp
<220> FEATURE:
<221> NAME/KEY: MOD_RES
<222> LOCATION: (40)..(40)
<223> OTHER INFORMATION: D-Leu or L-Leu
<220> FEATURE:
<221> NAME/KEY: MOD_RES
<222> LOCATION: (41)..(41)
<223> OTHER INFORMATION: D-Trp, L-Trp or absent
<220> FEATURE:
<223> OTHER INFORMATION: see specification as filed for detailed
      description of substitutions and preferred embodiments

<400> SEQUENCE: 1

Trp Leu Trp Leu Trp Leu Trp Leu Trp Leu Trp Leu Trp Leu Trp Leu
1               5                   10                  15

Trp Leu Trp Leu Trp Leu Trp Leu Trp Leu Trp Leu Trp Leu Trp Leu
                20                  25                  30

Trp Leu Trp Leu Trp Leu Trp Leu Trp
                35                  40

<210> SEQ ID NO 2
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This region may encompass 1 to 20 "Leu Trp"
      repeating units
<220> FEATURE:
<221> NAME/KEY: MOD_RES
<222> LOCATION: (1)..(1)
<223> OTHER INFORMATION: D-Leu or L-Leu
<220> FEATURE:
<221> NAME/KEY: MOD_RES
<222> LOCATION: (2)..(2)
<223> OTHER INFORMATION: D-Trp or L-Trp
<220> FEATURE:
<221> NAME/KEY: MOD_RES
<222> LOCATION: (3)..(3)
<223> OTHER INFORMATION: D-Leu or L-Leu
<220> FEATURE:
<221> NAME/KEY: MOD_RES
<222> LOCATION: (4)..(4)
<223> OTHER INFORMATION: D-Trp or L-Trp
<220> FEATURE:
<221> NAME/KEY: MOD_RES
<222> LOCATION: (5)..(5)
<223> OTHER INFORMATION: D-Leu or L-Leu
<220> FEATURE:
<221> NAME/KEY: MOD_RES
<222> LOCATION: (6)..(6)
<223> OTHER INFORMATION: D-Trp or L-Trp
<220> FEATURE:
<221> NAME/KEY: MOD_RES
<222> LOCATION: (7)..(7)
<223> OTHER INFORMATION: D-Leu or L-Leu
<220> FEATURE:
<221> NAME/KEY: MOD_RES
<222> LOCATION: (8)..(8)
<223> OTHER INFORMATION: D-Trp or L-Trp
<220> FEATURE:
<221> NAME/KEY: MOD_RES
```

```
<222> LOCATION: (9)..(9)
<223> OTHER INFORMATION: D-Leu or L-Leu
<220> FEATURE:
<221> NAME/KEY: MOD_RES
<222> LOCATION: (10)..(10)
<223> OTHER INFORMATION: D-Trp or L-Trp
<220> FEATURE:
<221> NAME/KEY: MOD_RES
<222> LOCATION: (11)..(11)
<223> OTHER INFORMATION: D-Leu or L-Leu
<220> FEATURE:
<221> NAME/KEY: MOD_RES
<222> LOCATION: (12)..(12)
<223> OTHER INFORMATION: D-Trp or L-Trp
<220> FEATURE:
<221> NAME/KEY: MOD_RES
<222> LOCATION: (13)..(13)
<223> OTHER INFORMATION: D-Leu or L-Leu
<220> FEATURE:
<221> NAME/KEY: MOD_RES
<222> LOCATION: (14)..(14)
<223> OTHER INFORMATION: D-Trp or L-Trp
<220> FEATURE:
<221> NAME/KEY: MOD_RES
<222> LOCATION: (15)..(15)
<223> OTHER INFORMATION: D-Leu or L-Leu
<220> FEATURE:
<221> NAME/KEY: MOD_RES
<222> LOCATION: (16)..(16)
<223> OTHER INFORMATION: D-Trp or L-Trp
<220> FEATURE:
<221> NAME/KEY: MOD_RES
<222> LOCATION: (17)..(17)
<223> OTHER INFORMATION: D-Leu or L-Leu
<220> FEATURE:
<221> NAME/KEY: MOD_RES
<222> LOCATION: (18)..(18)
<223> OTHER INFORMATION: D-Trp or L-Trp
<220> FEATURE:
<221> NAME/KEY: MOD_RES
<222> LOCATION: (19)..(19)
<223> OTHER INFORMATION: D-Leu or L-Leu
<220> FEATURE:
<221> NAME/KEY: MOD_RES
<222> LOCATION: (20)..(20)
<223> OTHER INFORMATION: D-Trp or L-Trp
<220> FEATURE:
<221> NAME/KEY: MOD_RES
<222> LOCATION: (21)..(21)
<223> OTHER INFORMATION: D-Leu or L-Leu
<220> FEATURE:
<221> NAME/KEY: MOD_RES
<222> LOCATION: (22)..(22)
<223> OTHER INFORMATION: D-Trp or L-Trp
<220> FEATURE:
<221> NAME/KEY: MOD_RES
<222> LOCATION: (23)..(23)
<223> OTHER INFORMATION: D-Leu or L-Leu
<220> FEATURE:
<221> NAME/KEY: MOD_RES
<222> LOCATION: (24)..(24)
<223> OTHER INFORMATION: D-Trp or L-Trp
<220> FEATURE:
<221> NAME/KEY: MOD_RES
<222> LOCATION: (25)..(25)
<223> OTHER INFORMATION: D-Leu or L-Leu
<220> FEATURE:
<221> NAME/KEY: MOD_RES
<222> LOCATION: (26)..(26)
<223> OTHER INFORMATION: D-Trp or L-Trp
<220> FEATURE:
<221> NAME/KEY: MOD_RES
<222> LOCATION: (27)..(27)
<223> OTHER INFORMATION: D-Leu or L-Leu
<220> FEATURE:
<221> NAME/KEY: MOD_RES
<222> LOCATION: (28)..(28)
<223> OTHER INFORMATION: D-Trp or L-Trp
<220> FEATURE:
```

```
<221> NAME/KEY: MOD_RES
<222> LOCATION: (29)..(29)
<223> OTHER INFORMATION: D-Leu or L-Leu
<220> FEATURE:
<221> NAME/KEY: MOD_RES
<222> LOCATION: (30)..(30)
<223> OTHER INFORMATION: D-Trp or L-Trp
<220> FEATURE:
<221> NAME/KEY: MOD_RES
<222> LOCATION: (31)..(31)
<223> OTHER INFORMATION: D-Leu or L-Leu
<220> FEATURE:
<221> NAME/KEY: MOD_RES
<222> LOCATION: (32)..(32)
<223> OTHER INFORMATION: D-Trp or L-Trp
<220> FEATURE:
<221> NAME/KEY: MOD_RES
<222> LOCATION: (33)..(33)
<223> OTHER INFORMATION: D-Leu or L-Leu
<220> FEATURE:
<221> NAME/KEY: MOD_RES
<222> LOCATION: (34)..(34)
<223> OTHER INFORMATION: D-Trp or L-Trp
<220> FEATURE:
<221> NAME/KEY: MOD_RES
<222> LOCATION: (35)..(35)
<223> OTHER INFORMATION: D-Leu or L-Leu
<220> FEATURE:
<221> NAME/KEY: MOD_RES
<222> LOCATION: (36)..(36)
<223> OTHER INFORMATION: D-Trp or L-Trp
<220> FEATURE:
<221> NAME/KEY: MOD_RES
<222> LOCATION: (37)..(37)
<223> OTHER INFORMATION: D-Leu or L-Leu
<220> FEATURE:
<221> NAME/KEY: MOD_RES
<222> LOCATION: (38)..(38)
<223> OTHER INFORMATION: D-Trp or L-Trp
<220> FEATURE:
<221> NAME/KEY: MOD_RES
<222> LOCATION: (39)..(39)
<223> OTHER INFORMATION: D-Leu or L-Leu
<220> FEATURE:
<221> NAME/KEY: MOD_RES
<222> LOCATION: (40)..(40)
<223> OTHER INFORMATION: D-Trp or L-Trp
<220> FEATURE:
<221> NAME/KEY: MOD_RES
<222> LOCATION: (41)..(41)
<223> OTHER INFORMATION: D-Leu, L-Leu or absent
<220> FEATURE:
<223> OTHER INFORMATION: see specification as filed for detailed
      description of substitutions and preferred embodiments

<400> SEQUENCE: 2

Leu Trp Leu Trp Leu Trp Leu Trp Leu Trp Leu Trp Leu Trp Leu Trp
1               5                   10                  15

Leu Trp Leu Trp Leu Trp Leu Trp Leu Trp Leu Trp Leu Trp Leu Trp
            20                  25                  30

Leu Trp Leu Trp Leu Trp Leu Trp Leu
            35                  40

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: May or may not be Lys(Ac)
<220> FEATURE:
```

```
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: see specification as filed for detailed
      description of substitutions and preferred embodiments

<400> SEQUENCE: 3

Lys Lys Lys Trp Leu Trp Leu Trp Leu Trp
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(3)
<223> OTHER INFORMATION: May or may not be Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: see specification as filed for detailed
      description of substitutions and preferred embodiments

<400> SEQUENCE: 4

Lys Lys Lys Trp Leu Trp Leu Trp Leu Trp
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
```

```
<222> LOCATION: (9)..(9)
<223> OTHER INFORMATION: D-Leu
<220> FEATURE:
<223> OTHER INFORMATION: C-term NH2 or absent
<220> FEATURE:
<223> OTHER INFORMATION: see specification as filed for detailed
      description of substitutions and preferred embodiments

<400> SEQUENCE: 5

Lys Lys Lys Trp Leu Trp Leu Trp Leu Trp
1               5                   10

<210> SEQ ID NO 6
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(21)
<223> OTHER INFORMATION: This region may encompass 3 to 21 "Lys"
      residues, wherein some residues may be absent
<220> FEATURE:
<221> NAME/KEY: misc_feature
<222> LOCATION: (22)..(61)
<223> OTHER INFORMATION: This region may encompass 3 to 20 "Trp Leu"
      repeating units
<220> FEATURE:
<221> NAME/KEY: MOD_RES
<222> LOCATION: (23)..(23)
<223> OTHER INFORMATION: D-Leu
<220> FEATURE:
<221> NAME/KEY: MOD_RES
<222> LOCATION: (25)..(25)
<223> OTHER INFORMATION: D-Leu
<220> FEATURE:
<221> NAME/KEY: MOD_RES
<222> LOCATION: (27)..(27)
<223> OTHER INFORMATION: D-Leu
<220> FEATURE:
<221> NAME/KEY: MOD_RES
<222> LOCATION: (29)..(29)
<223> OTHER INFORMATION: D-Leu
<220> FEATURE:
<221> NAME/KEY: MOD_RES
<222> LOCATION: (31)..(31)
<223> OTHER INFORMATION: D-Leu
<220> FEATURE:
<221> NAME/KEY: MOD_RES
<222> LOCATION: (33)..(33)
<223> OTHER INFORMATION: D-Leu
<220> FEATURE:
<221> NAME/KEY: MOD_RES
<222> LOCATION: (35)..(35)
<223> OTHER INFORMATION: D-Leu
<220> FEATURE:
<221> NAME/KEY: MOD_RES
<222> LOCATION: (37)..(37)
<223> OTHER INFORMATION: D-Leu
<220> FEATURE:
<221> NAME/KEY: MOD_RES
<222> LOCATION: (39)..(39)
<223> OTHER INFORMATION: D-Leu
<220> FEATURE:
<221> NAME/KEY: MOD_RES
<222> LOCATION: (41)..(41)
<223> OTHER INFORMATION: D-Leu
<220> FEATURE:
<221> NAME/KEY: MOD_RES
<222> LOCATION: (43)..(43)
<223> OTHER INFORMATION: D-Leu
<220> FEATURE:
<221> NAME/KEY: MOD_RES
<222> LOCATION: (45)..(45)
<223> OTHER INFORMATION: D-Leu
```

```
<220> FEATURE:
<221> NAME/KEY: MOD_RES
<222> LOCATION: (47)..(47)
<223> OTHER INFORMATION: D-Leu
<220> FEATURE:
<221> NAME/KEY: MOD_RES
<222> LOCATION: (49)..(49)
<223> OTHER INFORMATION: D-Leu
<220> FEATURE:
<221> NAME/KEY: MOD_RES
<222> LOCATION: (51)..(51)
<223> OTHER INFORMATION: D-Leu
<220> FEATURE:
<221> NAME/KEY: MOD_RES
<222> LOCATION: (53)..(53)
<223> OTHER INFORMATION: D-Leu
<220> FEATURE:
<221> NAME/KEY: MOD_RES
<222> LOCATION: (55)..(55)
<223> OTHER INFORMATION: D-Leu
<220> FEATURE:
<221> NAME/KEY: MOD_RES
<222> LOCATION: (57)..(57)
<223> OTHER INFORMATION: D-Leu
<220> FEATURE:
<221> NAME/KEY: MOD_RES
<222> LOCATION: (59)..(59)
<223> OTHER INFORMATION: D-Leu
<220> FEATURE:
<221> NAME/KEY: MOD_RES
<222> LOCATION: (61)..(61)
<223> OTHER INFORMATION: D-Leu
<220> FEATURE:
<223> OTHER INFORMATION: see specification as filed for detailed
      description of substitutions and preferred embodiments

<400> SEQUENCE: 6

Lys Lys Lys Lys Lys Lys Lys Lys Lys Lys Lys Lys Lys Lys Lys
1               5                   10                  15

Lys Lys Lys Lys Lys Trp Leu Trp Leu Trp Leu Trp Leu Trp
            20                  25                  30

Leu Trp Leu Trp Leu Trp Leu Trp Leu Trp Leu Trp Leu Trp Leu Trp
            35                  40                  45

Leu Trp Leu Trp Leu Trp Leu Trp Leu Trp Leu Trp Leu Trp
    50                  55                  60

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: This region may encompass 1 to 5 "Trp Leu"
      repeating units
<220> FEATURE:
<221> NAME/KEY: MOD_RES
<222> LOCATION: (1)..(1)
<223> OTHER INFORMATION: D-Trp or L-Trp
<220> FEATURE:
<221> NAME/KEY: MOD_RES
<222> LOCATION: (2)..(2)
<223> OTHER INFORMATION: D-Leu or L-Leu
<220> FEATURE:
<221> NAME/KEY: MOD_RES
<222> LOCATION: (3)..(3)
<223> OTHER INFORMATION: D-Trp or L-Trp
<220> FEATURE:
<221> NAME/KEY: MOD_RES
<222> LOCATION: (4)..(4)
<223> OTHER INFORMATION: D-Leu or L-Leu
```

```
<220> FEATURE:
<221> NAME/KEY: MOD_RES
<222> LOCATION: (5)..(5)
<223> OTHER INFORMATION: D-Trp or L-Trp
<220> FEATURE:
<221> NAME/KEY: MOD_RES
<222> LOCATION: (6)..(6)
<223> OTHER INFORMATION: D-Leu or L-Leu
<220> FEATURE:
<221> NAME/KEY: MOD_RES
<222> LOCATION: (7)..(7)
<223> OTHER INFORMATION: D-Trp or L-Trp
<220> FEATURE:
<221> NAME/KEY: MOD_RES
<222> LOCATION: (8)..(8)
<223> OTHER INFORMATION: D-Leu or L-Leu
<220> FEATURE:
<221> NAME/KEY: MOD_RES
<222> LOCATION: (9)..(9)
<223> OTHER INFORMATION: D-Trp or L-Trp
<220> FEATURE:
<221> NAME/KEY: MOD_RES
<222> LOCATION: (10)..(10)
<223> OTHER INFORMATION: D-Leu or L-Leu
<220> FEATURE:
<221> NAME/KEY: MOD_RES
<222> LOCATION: (11)..(11)
<223> OTHER INFORMATION: D-Trp, L-Trp or absent
<220> FEATURE:
<223> OTHER INFORMATION: see specification as filed for detailed
      description of substitutions and preferred embodiments

<400> SEQUENCE: 7

Trp Leu Trp Leu Trp Leu Trp Leu Trp Leu Trp
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: This region may encompass 1 to 5 "Leu Trp"
      repeating units
<220> FEATURE:
<221> NAME/KEY: MOD_RES
<222> LOCATION: (1)..(1)
<223> OTHER INFORMATION: D-Leu or L-Leu
<220> FEATURE:
<221> NAME/KEY: MOD_RES
<222> LOCATION: (2)..(2)
<223> OTHER INFORMATION: D-Trp or L-Trp
<220> FEATURE:
<221> NAME/KEY: MOD_RES
<222> LOCATION: (3)..(3)
<223> OTHER INFORMATION: D-Leu or L-Leu
<220> FEATURE:
<221> NAME/KEY: MOD_RES
<222> LOCATION: (4)..(4)
<223> OTHER INFORMATION: D-Trp or L-Trp
<220> FEATURE:
<221> NAME/KEY: MOD_RES
<222> LOCATION: (5)..(5)
<223> OTHER INFORMATION: D-Leu or L-Leu
<220> FEATURE:
<221> NAME/KEY: MOD_RES
<222> LOCATION: (6)..(6)
<223> OTHER INFORMATION: D-Trp or L-Trp
<220> FEATURE:
<221> NAME/KEY: MOD_RES
<222> LOCATION: (7)..(7)
<223> OTHER INFORMATION: D-Leu or L-Leu
<220> FEATURE:
```

```
<221> NAME/KEY: MOD_RES
<222> LOCATION: (8)..(8)
<223> OTHER INFORMATION: D-Trp or L-Trp
<220> FEATURE:
<221> NAME/KEY: MOD_RES
<222> LOCATION: (9)..(9)
<223> OTHER INFORMATION: D-Leu or L-Leu
<220> FEATURE:
<221> NAME/KEY: MOD_RES
<222> LOCATION: (10)..(10)
<223> OTHER INFORMATION: D-Trp or L-Trp
<220> FEATURE:
<221> NAME/KEY: MOD_RES
<222> LOCATION: (11)..(11)
<223> OTHER INFORMATION: D-Leu, L-Leu or absent
<220> FEATURE:
<223> OTHER INFORMATION: see specification as filed for detailed
      description of substitutions and preferred embodiments

<400> SEQUENCE: 8

Leu Trp Leu Trp Leu Trp Leu Trp Leu Trp Leu
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(15)
<223> OTHER INFORMATION: This region may encompass 1 to 15 "Lys"
      residues, wherein some residues may be absent
<220> FEATURE:
<223> OTHER INFORMATION: see specification as filed for detailed
      description of substitutions and preferred embodiments

<400> SEQUENCE: 9

Lys Lys Lys Lys Lys Lys Lys Lys Lys Lys Lys Lys Lys Lys Lys
1               5                   10                  15

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2 or absent
<220> FEATURE:
<223> OTHER INFORMATION: see specification as filed for detailed
      description of substitutions and preferred embodiments

<400> SEQUENCE: 10

Lys Lys Lys Trp Leu Trp Leu Trp Leu Trp
1               5                   10

<210> SEQ ID NO 11
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 11

Lys Lys Lys Trp Leu Trp Leu Trp Leu Trp
1               5                   10

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttgtgccgcc tttgcaggtg tatc                                          24

<210> SEQ ID NO 13
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This region may encompass 3 to 20 "Trp Leu"
      repeating units
<220> FEATURE:
<221> NAME/KEY: MOD_RES
<222> LOCATION: (1)..(1)
<223> OTHER INFORMATION: D-Trp or L-Trp
<220> FEATURE:
<221> NAME/KEY: MOD_RES
<222> LOCATION: (2)..(2)
<223> OTHER INFORMATION: D-Leu or L-Leu
<220> FEATURE:
<221> NAME/KEY: MOD_RES
<222> LOCATION: (3)..(3)
<223> OTHER INFORMATION: D-Trp or L-Trp
<220> FEATURE:
<221> NAME/KEY: MOD_RES
<222> LOCATION: (4)..(4)
<223> OTHER INFORMATION: D-Leu or L-Leu
<220> FEATURE:
<221> NAME/KEY: MOD_RES
<222> LOCATION: (5)..(5)
<223> OTHER INFORMATION: D-Trp or L-Trp
<220> FEATURE:
<221> NAME/KEY: MOD_RES
<222> LOCATION: (6)..(6)
<223> OTHER INFORMATION: D-Leu or L-Leu
<220> FEATURE:
```

```
<221> NAME/KEY: MOD_RES
<222> LOCATION: (7)..(7)
<223> OTHER INFORMATION: D-Trp or L-Trp
<220> FEATURE:
<221> NAME/KEY: MOD_RES
<222> LOCATION: (8)..(8)
<223> OTHER INFORMATION: D-Leu or L-Leu
<220> FEATURE:
<221> NAME/KEY: MOD_RES
<222> LOCATION: (9)..(9)
<223> OTHER INFORMATION: D-Trp or L-Trp
<220> FEATURE:
<221> NAME/KEY: MOD_RES
<222> LOCATION: (10)..(10)
<223> OTHER INFORMATION: D-Leu or L-Leu
<220> FEATURE:
<221> NAME/KEY: MOD_RES
<222> LOCATION: (11)..(11)
<223> OTHER INFORMATION: D-Trp or L-Trp
<220> FEATURE:
<221> NAME/KEY: MOD_RES
<222> LOCATION: (12)..(12)
<223> OTHER INFORMATION: D-Leu or L-Leu
<220> FEATURE:
<221> NAME/KEY: MOD_RES
<222> LOCATION: (13)..(13)
<223> OTHER INFORMATION: D-Trp or L-Trp
<220> FEATURE:
<221> NAME/KEY: MOD_RES
<222> LOCATION: (14)..(14)
<223> OTHER INFORMATION: D-Leu or L-Leu
<220> FEATURE:
<221> NAME/KEY: MOD_RES
<222> LOCATION: (15)..(15)
<223> OTHER INFORMATION: D-Trp or L-Trp
<220> FEATURE:
<221> NAME/KEY: MOD_RES
<222> LOCATION: (16)..(16)
<223> OTHER INFORMATION: D-Leu or L-Leu
<220> FEATURE:
<221> NAME/KEY: MOD_RES
<222> LOCATION: (17)..(17)
<223> OTHER INFORMATION: D-Trp or L-Trp
<220> FEATURE:
<221> NAME/KEY: MOD_RES
<222> LOCATION: (18)..(18)
<223> OTHER INFORMATION: D-Leu or L-Leu
<220> FEATURE:
<221> NAME/KEY: MOD_RES
<222> LOCATION: (19)..(19)
<223> OTHER INFORMATION: D-Trp or L-Trp
<220> FEATURE:
<221> NAME/KEY: MOD_RES
<222> LOCATION: (20)..(20)
<223> OTHER INFORMATION: D-Leu or L-Leu
<220> FEATURE:
<221> NAME/KEY: MOD_RES
<222> LOCATION: (21)..(21)
<223> OTHER INFORMATION: D-Trp or L-Trp
<220> FEATURE:
<221> NAME/KEY: MOD_RES
<222> LOCATION: (22)..(22)
<223> OTHER INFORMATION: D-Leu or L-Leu
<220> FEATURE:
<221> NAME/KEY: MOD_RES
<222> LOCATION: (23)..(23)
<223> OTHER INFORMATION: D-Trp or L-Trp
<220> FEATURE:
<221> NAME/KEY: MOD_RES
<222> LOCATION: (24)..(24)
<223> OTHER INFORMATION: D-Leu or L-Leu
<220> FEATURE:
<221> NAME/KEY: MOD_RES
<222> LOCATION: (25)..(25)
<223> OTHER INFORMATION: D-Trp or L-Trp
<220> FEATURE:
<221> NAME/KEY: MOD_RES
<222> LOCATION: (26)..(26)
<223> OTHER INFORMATION: D-Leu or L-Leu
```

```
<220> FEATURE:
<221> NAME/KEY: MOD_RES
<222> LOCATION: (27)..(27)
<223> OTHER INFORMATION: D-Trp or L-Trp
<220> FEATURE:
<221> NAME/KEY: MOD_RES
<222> LOCATION: (28)..(28)
<223> OTHER INFORMATION: D-Leu or L-Leu
<220> FEATURE:
<221> NAME/KEY: MOD_RES
<222> LOCATION: (29)..(29)
<223> OTHER INFORMATION: D-Trp or L-Trp
<220> FEATURE:
<221> NAME/KEY: MOD_RES
<222> LOCATION: (30)..(30)
<223> OTHER INFORMATION: D-Leu or L-Leu
<220> FEATURE:
<221> NAME/KEY: MOD_RES
<222> LOCATION: (31)..(31)
<223> OTHER INFORMATION: D-Trp or L-Trp
<220> FEATURE:
<221> NAME/KEY: MOD_RES
<222> LOCATION: (32)..(32)
<223> OTHER INFORMATION: D-Leu or L-Leu
<220> FEATURE:
<221> NAME/KEY: MOD_RES
<222> LOCATION: (33)..(33)
<223> OTHER INFORMATION: D-Trp or L-Trp
<220> FEATURE:
<221> NAME/KEY: MOD_RES
<222> LOCATION: (34)..(34)
<223> OTHER INFORMATION: D-Leu or L-Leu
<220> FEATURE:
<221> NAME/KEY: MOD_RES
<222> LOCATION: (35)..(35)
<223> OTHER INFORMATION: D-Trp or L-Trp
<220> FEATURE:
<221> NAME/KEY: MOD_RES
<222> LOCATION: (36)..(36)
<223> OTHER INFORMATION: D-Leu or L-Leu
<220> FEATURE:
<221> NAME/KEY: MOD_RES
<222> LOCATION: (37)..(37)
<223> OTHER INFORMATION: D-Trp or L-Trp
<220> FEATURE:
<221> NAME/KEY: MOD_RES
<222> LOCATION: (38)..(38)
<223> OTHER INFORMATION: D-Leu or L-Leu
<220> FEATURE:
<221> NAME/KEY: MOD_RES
<222> LOCATION: (39)..(39)
<223> OTHER INFORMATION: D-Trp or L-Trp
<220> FEATURE:
<221> NAME/KEY: MOD_RES
<222> LOCATION: (40)..(40)
<223> OTHER INFORMATION: D-Leu or L-Leu
<220> FEATURE:
<221> NAME/KEY: MOD_RES
<222> LOCATION: (41)..(41)
<223> OTHER INFORMATION: D-Trp, L-Trp or absent
<220> FEATURE:
<223> OTHER INFORMATION: see specification as filed for detailed
      description of substitutions and preferred embodiments

<400> SEQUENCE: 13

Trp Leu Trp Leu Trp Leu Trp Leu Trp Leu Trp Leu Trp Leu Trp Leu
1               5                   10                  15

Trp Leu Trp Leu Trp Leu Trp Leu Trp Leu Trp Leu Trp Leu Trp Leu
                20                  25                  30

Trp Leu Trp Leu Trp Leu Trp Leu Trp
                35                  40

<210> SEQ ID NO 14
<211> LENGTH: 41
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This region may encompass 3 to 20 "Leu Trp"
      repeating units
<220> FEATURE:
<221> NAME/KEY: MOD_RES
<222> LOCATION: (1)..(1)
<223> OTHER INFORMATION: D-Leu or L-Leu
<220> FEATURE:
<221> NAME/KEY: MOD_RES
<222> LOCATION: (2)..(2)
<223> OTHER INFORMATION: D-Trp or L-Trp
<220> FEATURE:
<221> NAME/KEY: MOD_RES
<222> LOCATION: (3)..(3)
<223> OTHER INFORMATION: D-Leu or L-Leu
<220> FEATURE:
<221> NAME/KEY: MOD_RES
<222> LOCATION: (4)..(4)
<223> OTHER INFORMATION: D-Trp or L-Trp
<220> FEATURE:
<221> NAME/KEY: MOD_RES
<222> LOCATION: (5)..(5)
<223> OTHER INFORMATION: D-Leu or L-Leu
<220> FEATURE:
<221> NAME/KEY: MOD_RES
<222> LOCATION: (6)..(6)
<223> OTHER INFORMATION: D-Trp or L-Trp
<220> FEATURE:
<221> NAME/KEY: MOD_RES
<222> LOCATION: (7)..(7)
<223> OTHER INFORMATION: D-Leu or L-Leu
<220> FEATURE:
<221> NAME/KEY: MOD_RES
<222> LOCATION: (8)..(8)
<223> OTHER INFORMATION: D-Trp or L-Trp
<220> FEATURE:
<221> NAME/KEY: MOD_RES
<222> LOCATION: (9)..(9)
<223> OTHER INFORMATION: D-Leu or L-Leu
<220> FEATURE:
<221> NAME/KEY: MOD_RES
<222> LOCATION: (10)..(10)
<223> OTHER INFORMATION: D-Trp or L-Trp
<220> FEATURE:
<221> NAME/KEY: MOD_RES
<222> LOCATION: (11)..(11)
<223> OTHER INFORMATION: D-Leu or L-Leu
<220> FEATURE:
<221> NAME/KEY: MOD_RES
<222> LOCATION: (12)..(12)
<223> OTHER INFORMATION: D-Trp or L-Trp
<220> FEATURE:
<221> NAME/KEY: MOD_RES
<222> LOCATION: (13)..(13)
<223> OTHER INFORMATION: D-Leu or L-Leu
<220> FEATURE:
<221> NAME/KEY: MOD_RES
<222> LOCATION: (14)..(14)
<223> OTHER INFORMATION: D-Trp or L-Trp
<220> FEATURE:
<221> NAME/KEY: MOD_RES
<222> LOCATION: (15)..(15)
<223> OTHER INFORMATION: D-Leu or L-Leu
<220> FEATURE:
<221> NAME/KEY: MOD_RES
<222> LOCATION: (16)..(16)
<223> OTHER INFORMATION: D-Trp or L-Trp
<220> FEATURE:
<221> NAME/KEY: MOD_RES
<222> LOCATION: (17)..(17)
<223> OTHER INFORMATION: D-Leu or L-Leu
<220> FEATURE:
<221> NAME/KEY: MOD_RES
```

```
<222> LOCATION: (18)..(18)
<223> OTHER INFORMATION: D-Trp or L-Trp
<220> FEATURE:
<221> NAME/KEY: MOD_RES
<222> LOCATION: (19)..(19)
<223> OTHER INFORMATION: D-Leu or L-Leu
<220> FEATURE:
<221> NAME/KEY: MOD_RES
<222> LOCATION: (20)..(20)
<223> OTHER INFORMATION: D-Trp or L-Trp
<220> FEATURE:
<221> NAME/KEY: MOD_RES
<222> LOCATION: (21)..(21)
<223> OTHER INFORMATION: D-Leu or L-Leu
<220> FEATURE:
<221> NAME/KEY: MOD_RES
<222> LOCATION: (22)..(22)
<223> OTHER INFORMATION: D-Trp or L-Trp
<220> FEATURE:
<221> NAME/KEY: MOD_RES
<222> LOCATION: (23)..(23)
<223> OTHER INFORMATION: D-Leu or L-Leu
<220> FEATURE:
<221> NAME/KEY: MOD_RES
<222> LOCATION: (24)..(24)
<223> OTHER INFORMATION: D-Trp or L-Trp
<220> FEATURE:
<221> NAME/KEY: MOD_RES
<222> LOCATION: (25)..(25)
<223> OTHER INFORMATION: D-Leu or L-Leu
<220> FEATURE:
<221> NAME/KEY: MOD_RES
<222> LOCATION: (26)..(26)
<223> OTHER INFORMATION: D-Trp or L-Trp
<220> FEATURE:
<221> NAME/KEY: MOD_RES
<222> LOCATION: (27)..(27)
<223> OTHER INFORMATION: D-Leu or L-Leu
<220> FEATURE:
<221> NAME/KEY: MOD_RES
<222> LOCATION: (28)..(28)
<223> OTHER INFORMATION: D-Trp or L-Trp
<220> FEATURE:
<221> NAME/KEY: MOD_RES
<222> LOCATION: (29)..(29)
<223> OTHER INFORMATION: D-Leu or L-Leu
<220> FEATURE:
<221> NAME/KEY: MOD_RES
<222> LOCATION: (30)..(30)
<223> OTHER INFORMATION: D-Trp or L-Trp
<220> FEATURE:
<221> NAME/KEY: MOD_RES
<222> LOCATION: (31)..(31)
<223> OTHER INFORMATION: D-Leu or L-Leu
<220> FEATURE:
<221> NAME/KEY: MOD_RES
<222> LOCATION: (32)..(32)
<223> OTHER INFORMATION: D-Trp or L-Trp
<220> FEATURE:
<221> NAME/KEY: MOD_RES
<222> LOCATION: (33)..(33)
<223> OTHER INFORMATION: D-Leu or L-Leu
<220> FEATURE:
<221> NAME/KEY: MOD_RES
<222> LOCATION: (34)..(34)
<223> OTHER INFORMATION: D-Trp or L-Trp
<220> FEATURE:
<221> NAME/KEY: MOD_RES
<222> LOCATION: (35)..(35)
<223> OTHER INFORMATION: D-Leu or L-Leu
<220> FEATURE:
<221> NAME/KEY: MOD_RES
<222> LOCATION: (36)..(36)
<223> OTHER INFORMATION: D-Trp or L-Trp
<220> FEATURE:
<221> NAME/KEY: MOD_RES
<222> LOCATION: (37)..(37)
<223> OTHER INFORMATION: D-Leu or L-Leu
<220> FEATURE:
```

```
<221> NAME/KEY: MOD_RES
<222> LOCATION: (38)..(38)
<223> OTHER INFORMATION: D-Trp or L-Trp
<220> FEATURE:
<221> NAME/KEY: MOD_RES
<222> LOCATION: (39)..(39)
<223> OTHER INFORMATION: D-Leu or L-Leu
<220> FEATURE:
<221> NAME/KEY: MOD_RES
<222> LOCATION: (40)..(40)
<223> OTHER INFORMATION: D-Trp or L-Trp
<220> FEATURE:
<221> NAME/KEY: MOD_RES
<222> LOCATION: (41)..(41)
<223> OTHER INFORMATION: D-Leu, L-Leu or absent
<220> FEATURE:
<223> OTHER INFORMATION: see specification as filed for detailed
      description of substitutions and preferred embodiments

<400> SEQUENCE: 14

Leu Trp Leu Trp Leu Trp Leu Trp Leu Trp Leu Trp Leu Trp Leu Trp
1               5                   10                  15

Leu Trp Leu Trp Leu Trp Leu Trp Leu Trp Leu Trp Leu Trp Leu Trp
            20                  25                  30

Leu Trp Leu Trp Leu Trp Leu Trp Leu
        35                  40

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: D-Leu

<400> SEQUENCE: 15

Trp Leu Leu Leu Trp
1               5

<210> SEQ ID NO 16
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(21)
<223> OTHER INFORMATION: This region may encompass 3 to 21 "Lys"
      residues, wherein some residues may be absent
<220> FEATURE:
<221> NAME/KEY: misc_feature
<222> LOCATION: (23)..(61)
<223> OTHER INFORMATION: This region may encompass 3 to 20 "Trp Leu"
      repeating units
<220> FEATURE:
<221> NAME/KEY: MOD_RES
<222> LOCATION: (23)..(23)
<223> OTHER INFORMATION: D-Leu
<220> FEATURE:
<221> NAME/KEY: MOD_RES
<222> LOCATION: (25)..(25)
<223> OTHER INFORMATION: D-Leu
<220> FEATURE:
<221> NAME/KEY: MOD_RES
<222> LOCATION: (27)..(27)
<223> OTHER INFORMATION: D-Leu
<220> FEATURE:
```

```
<221> NAME/KEY: MOD_RES
<222> LOCATION: (29)..(29)
<223> OTHER INFORMATION: D-Leu
<220> FEATURE:
<221> NAME/KEY: MOD_RES
<222> LOCATION: (31)..(31)
<223> OTHER INFORMATION: D-Leu
<220> FEATURE:
<221> NAME/KEY: MOD_RES
<222> LOCATION: (33)..(33)
<223> OTHER INFORMATION: D-Leu
<220> FEATURE:
<221> NAME/KEY: MOD_RES
<222> LOCATION: (35)..(35)
<223> OTHER INFORMATION: D-Leu
<220> FEATURE:
<221> NAME/KEY: MOD_RES
<222> LOCATION: (37)..(37)
<223> OTHER INFORMATION: D-Leu
<220> FEATURE:
<221> NAME/KEY: MOD_RES
<222> LOCATION: (39)..(39)
<223> OTHER INFORMATION: D-Leu
<220> FEATURE:
<221> NAME/KEY: MOD_RES
<222> LOCATION: (41)..(41)
<223> OTHER INFORMATION: D-Leu
<220> FEATURE:
<221> NAME/KEY: MOD_RES
<222> LOCATION: (43)..(43)
<223> OTHER INFORMATION: D-Leu
<220> FEATURE:
<221> NAME/KEY: MOD_RES
<222> LOCATION: (45)..(45)
<223> OTHER INFORMATION: D-Leu
<220> FEATURE:
<221> NAME/KEY: MOD_RES
<222> LOCATION: (47)..(47)
<223> OTHER INFORMATION: D-Leu
<220> FEATURE:
<221> NAME/KEY: MOD_RES
<222> LOCATION: (49)..(49)
<223> OTHER INFORMATION: D-Leu
<220> FEATURE:
<221> NAME/KEY: MOD_RES
<222> LOCATION: (51)..(51)
<223> OTHER INFORMATION: D-Leu
<220> FEATURE:
<221> NAME/KEY: MOD_RES
<222> LOCATION: (53)..(53)
<223> OTHER INFORMATION: D-Leu
<220> FEATURE:
<221> NAME/KEY: MOD_RES
<222> LOCATION: (55)..(55)
<223> OTHER INFORMATION: D-Leu
<220> FEATURE:
<221> NAME/KEY: MOD_RES
<222> LOCATION: (57)..(57)
<223> OTHER INFORMATION: D-Leu
<220> FEATURE:
<221> NAME/KEY: MOD_RES
<222> LOCATION: (59)..(59)
<223> OTHER INFORMATION: D-Leu
<220> FEATURE:
<221> NAME/KEY: MOD_RES
<222> LOCATION: (61)..(61)
<223> OTHER INFORMATION: D-Leu
<220> FEATURE:
<223> OTHER INFORMATION: see specification as filed for detailed
      description of substitutions and preferred embodiments

<400> SEQUENCE: 16

Lys Lys Lys Lys Lys Lys Lys Lys Lys Lys Lys Lys Lys Lys Lys
1               5                   10                  15

Lys Lys Lys Lys Lys Trp Leu Trp Leu Trp Leu Trp Leu Trp Leu Trp
            20                  25                  30
```

```
Leu Trp Leu Trp Leu Trp Leu Trp Leu Trp Leu Trp Leu Trp
        35                  40                  45

Leu Trp Leu Trp Leu Trp Leu Trp Leu Trp Leu Trp
        50                  55                  60

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 17

Lys Lys Lys Trp Leu Trp Leu Trp Leu Trp
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 18

Lys Lys Lys Trp Leu Trp Leu Trp Leu Trp
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
```

```
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 19

Lys Lys Lys Trp Leu Trp Leu Trp Leu Trp
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 20

Lys Lys Lys Trp Leu Trp Leu Trp Leu Trp
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2
```

<400> SEQUENCE: 21

Lys Lys Lys Trp Leu Trp Leu Trp Leu Trp
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 22

Lys Lys Lys Trp Leu Trp Leu Trp Leu Trp
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Ac)
<220> FEATURE:
<221> NAME/KEY: MOD_RES
<222> LOCATION: (3)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 23

Lys Lys Lys Trp Leu Trp Leu Trp Leu Trp
1               5                   10

<210> SEQ ID NO 24
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 24

Lys Lys Lys Trp Leu Trp Leu Trp Leu Trp
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 25

Lys Lys Lys Trp Leu Trp Leu Trp Leu Trp
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
```

<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 26

Lys Lys Lys Trp Leu Trp Leu Trp Leu Trp
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu

<400> SEQUENCE: 27

Lys Lys Lys Trp Leu Trp Leu Trp Leu Trp
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu

<400> SEQUENCE: 28

Lys Lys Lys Trp Leu Trp Leu Trp Leu Trp
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic

```
              peptide
<220> FEATURE:
<221> NAME/KEY: MOD_RES
<222> LOCATION: (2)..(2)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu

<400> SEQUENCE: 29

Lys Lys Lys Trp Leu Trp Leu Trp Leu Trp
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu

<400> SEQUENCE: 30

Lys Lys Lys Trp Leu Trp Leu Trp Leu Trp
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu

<400> SEQUENCE: 31
```

```
Lys Lys Lys Trp Leu Trp Leu Trp Leu Trp
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Ac)
<220> FEATURE:
<221> NAME/KEY: MOD_RES
<222> LOCATION: (3)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu

<400> SEQUENCE: 32

Lys Lys Lys Trp Leu Trp Leu Trp Leu Trp
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu

<400> SEQUENCE: 33

Lys Lys Lys Trp Leu Trp Leu Trp Leu Trp
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
```

```
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu

<400> SEQUENCE: 34

Lys Lys Lys Trp Leu Trp Leu Trp Leu Trp
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 35

Lys Lys Lys Trp Leu Trp Leu Trp Leu Trp
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
```

```
<220> FEATURE:
<223> OTHER INFORMATION: C-term NH2

<400> SEQUENCE: 36

Lys Lys Lys Trp Leu Trp Leu Trp Leu Trp
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 37

Lys Lys Lys Trp Leu Trp Leu Trp Leu Trp
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 38

Lys Lys Lys Trp Leu Trp Leu Trp Leu Trp
1               5                   10

<210> SEQ ID NO 39
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys(Ac)
<220> FEATURE:
<221> NAME/KEY: MOD_RES
<222> LOCATION: (3)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 39

Lys Lys Lys Trp Leu Trp Leu Trp Leu Trp
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(2)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 40

Lys Lys Lys Trp Leu Trp Leu Trp Leu Trp
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
```

```
<220> FEATURE:
<221> NAME/KEY: MOD_RES
<222> LOCATION: (3)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 41

Lys Lys Lys Trp Leu Trp Leu Trp Leu Trp
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 42

Lys Lys Lys Trp Leu Trp Leu Trp Leu Trp
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
```

```
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 43

Lys Lys Lys Trp Leu Trp Leu Trp Leu Trp
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 44

Lys Lys Lys Trp Leu Trp Leu Trp Leu Trp
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys(Ac)
<220> FEATURE:
<221> NAME/KEY: MOD_RES
<222> LOCATION: (3)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2
```

```
<400> SEQUENCE: 45

Lys Lys Lys Trp Leu Trp Leu Trp Leu Trp
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(2)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 46

Lys Lys Lys Trp Leu Trp Leu Trp Leu Trp
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 47

Lys Lys Lys Trp Leu Trp Leu Trp Leu Trp
1               5                   10

<210> SEQ ID NO 48
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<223> OTHER INFORMATION: C-term NH2

<400> SEQUENCE: 48

Lys Trp Leu Trp Leu Trp Leu Trp
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (4)..(4)
<223> OTHER INFORMATION: D-Leu
<220> FEATURE:
<221> NAME/KEY: MOD_RES
<222> LOCATION: (6)..(6)
<223> OTHER INFORMATION: D-Leu
<220> FEATURE:
<221> NAME/KEY: MOD_RES
<222> LOCATION: (8)..(8)
<223> OTHER INFORMATION: D-Leu
<220> FEATURE:
<223> OTHER INFORMATION: C-term NH2

<400> SEQUENCE: 49

Lys Lys Trp Leu Trp Leu Trp Leu Trp
1               5

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (6)..(6)
<223> OTHER INFORMATION: D-Leu
<220> FEATURE:
<221> NAME/KEY: MOD_RES
<222> LOCATION: (8)..(8)
<223> OTHER INFORMATION: D-Leu
<220> FEATURE:
<221> NAME/KEY: MOD_RES
<222> LOCATION: (10)..(10)
<223> OTHER INFORMATION: D-Leu
<220> FEATURE:
<223> OTHER INFORMATION: C-term NH2
```

```
<400> SEQUENCE: 50

Lys Lys Lys Lys Trp Leu Trp Leu Trp Leu Trp
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 51

Lys Lys Lys Trp Leu Trp Leu Trp Leu Trp
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(3)
<223> OTHER INFORMATION: Lys(Ac)
<220> FEATURE:
<223> OTHER INFORMATION: C-term NH2

<400> SEQUENCE: 52

Lys Lys Lys Trp Leu Trp Leu Trp Leu Trp
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (1)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 53

Lys Lys Lys Trp Leu Trp Leu Trp Leu Trp
1               5                   10
```

```
<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 54

Lys Lys Lys Trp Leu Trp Leu Trp Leu Trp
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (3)..(3)
<223> OTHER INFORMATION: Lys(Ac)
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(9)
<223> OTHER INFORMATION: D-Leu
<220> FEATURE:
<223> OTHER INFORMATION: C-term NH2

<400> SEQUENCE: 55

Lys Lys Lys Trp Leu Trp Leu Trp Leu Trp
1               5                   10
```